US009295260B2

(12) United States Patent
Zhang et al.

(10) Patent No.: US 9,295,260 B2
(45) Date of Patent: Mar. 29, 2016

(54) PESTICIDAL COMPOSITIONS AND RELATED METHODS

(71) Applicant: DOW AGROSCIENCES LLC, Indianapolis, IN (US)

(72) Inventors: Yu Zhang, Carmel, IN (US); Asako Kubota, Indianapolis, IN (US); Noormohamed M. Niyaz, Indianapolis, IN (US); Thomas Barton, Indianopolis, IN (US); Tony K. Trullinger, Westfield, IN (US); Christian T. Lowe, Westfield, IN (US); Paul R. LePlae, Brownsburg, IN (US); Ann M. Buysse, Carmel, IN (US); Martin J. Walsh, Carmel, IN (US); Negar Garizi, Westfield, IN (US); Ricky Hunter, Westfield, IN (US); Daniel Knueppel, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/517,590

(22) Filed: Oct. 17, 2014

(65) Prior Publication Data

US 2015/0111734 A1    Apr. 23, 2015

Related U.S. Application Data

(60) Provisional application No. 61/894,364, filed on Oct. 22, 2013.

(51) Int. Cl.
| A01N 47/16 | (2006.01) |
| C07D 401/14 | (2006.01) |
| A01N 43/56 | (2006.01) |
| C07D 401/04 | (2006.01) |
| C07D 413/14 | (2006.01) |
| A01N 43/76 | (2006.01) |
| C07D 417/14 | (2006.01) |
| A01N 43/78 | (2006.01) |
| A01N 47/12 | (2006.01) |
| C07D 405/14 | (2006.01) |
| C05G 3/02 | (2006.01) |

(52) U.S. Cl.
CPC ............... *A01N 47/16* (2013.01); *A01N 43/56* (2013.01); *A01N 43/76* (2013.01); *A01N 43/78* (2013.01); *A01N 47/12* (2013.01); *C05G 3/02* (2013.01); *C07D 401/04* (2013.01); *C07D 401/14* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| 4,080,457 | A | 3/1978 | Harrison et al. |
| 4,260,765 | A | 4/1981 | Harrison et al. |
| 4,536,506 | A | 8/1985 | Marcoux et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony |
| 5,869,681 | A | 2/1999 | Muller et al. |
| 6,218,418 | B1 | 4/2001 | Pevarello et al. |
| 6,274,536 | B1 | 8/2001 | Nebel et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 7,192,906 | B2 | 3/2007 | Hirohara et al. |
| 7,196,104 | B2 | 3/2007 | Askew, Jr. et al. |
| 7,319,108 | B2 | 1/2008 | Schwink et al. |
| 7,774,978 | B2 | 8/2010 | Ding et al. |
| 7,803,832 | B2 | 9/2010 | Critcher et al. |
| 7,910,606 | B2 | 3/2011 | Nazare et al. |

(Continued)

FOREIGN PATENT DOCUMENTS

| EP | 0097323 | 1/1984 |
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 153273 | 7/1987 |
| JP | 174905 | 7/1988 |
| JP | 226815 | 9/1989 |
| JP | 2003212864 | 7/2003 |
| JP | 2004051628 | 2/2004 |

(Continued)

OTHER PUBLICATIONS

PCT International Search Report; PCT/US2014/061120; dated Jan. 15, 2015.
PCT Written Opinion; PCT/US2014/061120; dated Jan. 15, 2015.

*Primary Examiner* — Timothy R Rozof
(74) *Attorney, Agent, or Firm* — Carl D. Corvin; Magleby Cataxinos & Greenwood PC

(57) ABSTRACT

A pesticidal composition comprises at least one compounds selected from a compound of formula, or any agriculturally acceptable salt thereof, wherein $R_1$, $R_2$, $R_3$, $R_4$, $R_5$, $R_6$, $R_7$, $R_8$, Q, Z, L, $L_a$, and x are as described herein. A method of controlling pests comprises applying the pesticidal composition near a population of pests.

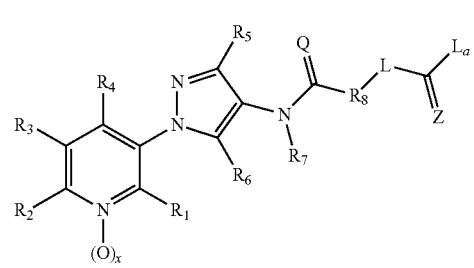

19 Claims, No Drawings

(56) References Cited

U.S. PATENT DOCUMENTS

| | | | |
|---|---|---|---|
| 7,923,573 | B2 | 4/2011 | Tamaki et al. |
| 8,163,756 | B2 | 4/2012 | Flynn et al. |
| 8,198,308 | B2 | 6/2012 | Steurer et al. |
| 8,222,280 | B2 | 7/2012 | Liu et al. |
| 2002/0013326 | A1 | 1/2002 | Tiebes et al. |
| 2003/0153464 | A1 | 8/2003 | Nakamura et al. |
| 2003/0213405 | A1 | 11/2003 | Harada et al. |
| 2004/0082629 | A1 | 4/2004 | Iwataki et al. |
| 2005/0038059 | A1 | 2/2005 | Mueller et al. |
| 2005/0176710 | A1 | 8/2005 | Schwink et al. |
| 2006/0160857 | A1 | 7/2006 | Buettelmann et al. |
| 2006/0160875 | A1 | 7/2006 | Gaines et al. |
| 2007/0167426 | A1 | 7/2007 | Siddiqui et al. |
| 2008/0004301 | A1 | 1/2008 | Tamaki et al. |
| 2008/0027046 | A1 | 1/2008 | Annan et al. |
| 2009/0069288 | A1 | 3/2009 | Breinlinger et al. |
| 2009/0137524 | A1 | 5/2009 | Billen et al. |
| 2009/0325956 | A1 | 12/2009 | Taniguchi et al. |
| 2010/0130474 | A1 | 5/2010 | Bothmann et al. |
| 2010/0204164 | A1 | 8/2010 | Crouse et al. |
| 2010/0222320 | A1 | 9/2010 | Fischer et al. |
| 2010/0292253 | A1 | 11/2010 | Trullinger et al. |
| 2010/0305200 | A1 | 12/2010 | Velicelebi et al. |
| 2011/0021771 | A1 | 1/2011 | Mallais et al. |
| 2011/0098287 | A1 | 4/2011 | Bretschneider et al. |
| 2011/0118290 | A1 | 5/2011 | Bretschneider et al. |
| 2011/0166129 | A1 | 7/2011 | Machacek et al. |
| 2011/0166143 | A1 | 7/2011 | Bretschneider et al. |
| 2011/0184188 | A1 | 7/2011 | Wada et al. |
| 2011/0201649 | A1 | 8/2011 | Matsuzaki et al. |
| 2011/0212949 | A1 | 9/2011 | Bretschneider et al. |
| 2011/0212999 | A1 | 9/2011 | Dahl et al. |
| 2011/0275583 | A1 | 11/2011 | Bretschneider et al. |
| 2011/0319428 | A1 | 12/2011 | Fu lein et al. |
| 2012/0053146 | A1 | 3/2012 | Parker et al. |
| 2012/0094837 | A1 | 4/2012 | Muhlthau et al. |
| 2012/0095023 | A1 | 4/2012 | Bretschneider et al. |
| 2012/0110701 | A1 | 5/2012 | Garizi et al. |
| 2012/0110702 | A1* | 5/2012 | Yap et al. ............... 800/298 |
| 2012/0115811 | A1 | 5/2012 | Du et al. |
| 2012/0165345 | A1 | 6/2012 | Bretschneider et al. |
| 2012/0220453 | A1 | 8/2012 | Lowe et al. |
| 2013/0072382 | A1 | 3/2013 | Trullinger et al. |
| 2013/0089622 | A1 | 4/2013 | Trullinger et al. |
| 2013/0109566 | A1 | 5/2013 | Niyaz et al. |
| 2013/0261141 | A1 | 10/2013 | Bretschneider et al. |
| 2013/0288893 | A1 | 10/2013 | Buysse et al. |
| 2013/0291227 | A1 | 10/2013 | Buysse et al. |
| 2013/0324736 | A1 | 12/2013 | Ross, Jr. et al. |
| 2013/0324737 | A1 | 12/2013 | Ross, Jr. et al. |

FOREIGN PATENT DOCUMENTS

| | | |
|---|---|---|
| JP | 2004292703 | 10/2004 |
| JP | 2012188418 | 10/2012 |
| JP | 2013075871 | 4/2013 |
| JP | 2013082699 | 5/2013 |
| JP | 2013082704 | 5/2013 |
| JP | 2013107867 | 6/2013 |
| JP | 2013129651 | 7/2013 |
| JP | 2013129653 | 7/2013 |
| WO | 9413644 | 6/1994 |
| WO | 9736897 | 10/1997 |
| WO | 9821199 | 5/1998 |
| WO | 9849166 | 11/1998 |
| WO | 0035919 | 6/2000 |
| WO | 0134127 | 5/2001 |
| WO | 0190078 | 11/2001 |
| WO | 02083111 | 10/2002 |
| WO | 03008405 | 1/2003 |
| WO | 03072102 | 9/2003 |
| WO | 2004041813 | 5/2004 |
| WO | 2005070925 | 8/2005 |
| WO | 2005074875 | 8/2005 |
| WO | 2006023462 | 3/2006 |
| WO | 2006033005 | 3/2006 |
| WO | 2006046593 | 5/2006 |
| WO | 2006103045 | 10/2006 |
| WO | 2007005838 | 1/2007 |
| WO | 2007087427 | 8/2007 |
| WO | 2007098826 | 9/2007 |
| WO | 2008005457 | 1/2008 |
| WO | 2008079277 | 7/2008 |
| WO | 2008090382 | 7/2008 |
| WO | 2008100426 | 8/2008 |
| WO | 2009149858 | 12/2009 |
| WO | 2010006713 | 1/2010 |
| WO | 2010009290 | 1/2010 |
| WO | 2010012442 | 2/2010 |
| WO | 2010048207 | 4/2010 |
| WO | 2010060379 | 6/2010 |
| WO | 2010075376 | 7/2010 |
| WO | 2010129497 | 11/2010 |
| WO | 2010133336 | 11/2010 |
| WO | 2010146236 | 12/2010 |
| WO | 2011003065 | 1/2011 |
| WO | 2011043371 | 4/2011 |
| WO | 2011045224 | 4/2011 |
| WO | 2011045240 | 4/2011 |
| WO | 2011091153 | 7/2011 |
| WO | 2011101229 | 8/2011 |
| WO | 2011126903 | 10/2011 |
| WO | 2011128304 | 10/2011 |
| WO | 2011134964 | 11/2011 |
| WO | 2011138285 | 11/2011 |
| WO | 2011163518 | 12/2011 |
| WO | 2012000896 | 1/2012 |
| WO | 2012004217 | 1/2012 |
| WO | 2012007500 | 1/2012 |
| WO | 2010033360 | 3/2012 |
| WO | 2012035011 | 3/2012 |
| WO | 2012052412 | 4/2012 |
| WO | 2012061290 | 5/2012 |
| WO | 2012070114 | 5/2012 |
| WO | 2012102387 | 8/2012 |
| WO | 2012108511 | 8/2012 |
| WO | 2012168361 | 12/2012 |
| WO | 2012175474 | 12/2012 |
| WO | 2013000931 | 1/2013 |
| WO | 2013001094 | 1/2013 |
| WO | 2013010946 | 1/2013 |
| WO | 2013062980 | 5/2013 |
| WO | 2013156431 | 10/2013 |
| WO | 2013156433 | 10/2013 |
| WO | 2013162715 | 10/2013 |
| WO | 2013162716 | 10/2013 |

* cited by examiner

PESTICIDAL COMPOSITIONS AND RELATED METHODS

CROSS-REFERENCE TO RELATED APPLICATION

This application claims the benefit of U.S. Provisional Patent Application Ser. No. 61/894,364, filed Oct. 22, 2013, the disclosure of which is hereby incorporated herein in its entirety by this reference.

TECHNICAL FIELD

This disclosure relates to the field of compounds having pesticidal utility against pests in Phyla Nematoda, Arthropoda, and/or Mollusca, processes to produce such compounds and intermediates used in such processes. These compounds may be used, for example, as nematicides, acaricides, pesticides, insecticides, miticides, and/or molluscicides.

BACKGROUND

Controlling pest populations is essential to human health, modern agriculture, food storage, and hygiene. There are more than ten thousand species of pests that cause losses in agriculture and the world-wide agricultural losses amount to billions of U.S. dollars each year. Accordingly, there exists a continuous need for new pesticides and for methods of producing and using such pesticides.

DETAILED DESCRIPTION

Definitions

The examples given in the definitions are non-exhaustive and must not be construed as limiting the present disclosure. It is understood that a substituent should comply with chemical bonding rules and steric compatibility constraints in relation to the particular molecule to which it is attached.

"Alkyl" means and includes an acyclic, saturated, branched or unbranched hydrocarbon. Non-limiting examples may include methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, or decyl.

"Cycloalkyl" means and includes a monocyclic or polycyclic saturated hydrocarbon. Non-limiting examples may include cyclopropyl, cyclobutyl, cyclopentyl, cyclohexyl, cycloheptyl, cyclooctyl, cyclodecyl, norbornyl, bicycle[2.2.2]octyl, or decahydronapthyl.

"Alkenyl" means and includes an acyclic, branched or unbranched hydrocarbon containing at least one carbon-carbon double bond. Non-limiting examples may include ethenyl, propenyl, butenyl, pentenyl, hexenyl, heptenyl, octenyl, nonenyl, or decenyl.

"Cycloalkenyl" means and includes a monocyclic or polycyclic hydrocarbon containing at least one carbon-carbon double bond. Non-limiting examples may include cyclopentenyl, cyclohexenyl, cycloheptenyl, cyclooctenyl, or cyclodecenyl.

"Alkynyl" means and includes acyclic, branched or unbranched hydrocarbon containing at least one carbon-carbon triple bond. Non-limiting examples may include ethynyl, propargyl, butynyl, pentynyl, hexynyl, heptynyl, octynyl, nonynyl, or decynyl.

"Cycloalkynyl" means and includes a monocyclic or polycyclic hydrocarbon containing at least one carbon-carbon triple bond. Non-limiting examples may include cycloheptynyl, cyclooctynyl, or cyclodecynyl.

"Aryl" means and includes an aromatic compound with or without any substitution. Non-limiting examples may include phenyl or naphthyl.

"Alkoxy" means and includes an alkyl group containing at least one carbon-oxygen single bond. Non-limiting examples may include methoxy, ethoxy, propoxy, butoxy, cyclopropoxy, cyclobutoxy, or cyclopentoxy.

"Alkenyloxy" means and includes an alkenyl containing at least one carbon-oxygen single bond. Non-limiting examples may include allyloxy, butenyloxy, pentenyloxy, hexenyloxy, heptenyloxy, octenyloxy, nonenyloxy, or decenyloxy.

"Alkynyloxy" means and includes an alkynyl containing at least one carbon-oxygen single bond. Non-limiting examples may include pentynyloxy, hexynyloxy, heptynyloxy, octynyloxy, nonynyloxy, or decynyloxy.

"Cycloalkoxy" means and includes a cycloalkyl containing at least one carbon-oxygen single bond. Non-limiting examples may include cyclopropyloxy, cyclobutyloxy, cyclopentyloxy, cyclohexyloxy, cycloheptyloxy, cyclooctyloxy, cyclodecyloxy, norbornyloxy, or bicyclo[2.2.2]octyloxy.

"Cyclohaloalkyl" means and includes a monocyclic or polycyclic, saturated substituent comprising carbon, halogen, and hydrogen. Non-limiting examples may include 1-chlorocyclopropyl, 1-chlorocyclobutyl, or 1-dichlorocyclopentyl.

"Cycloalkenyloxy" means and include a cycloalkenyl further consisting of a carbon-oxygen single bond. Non-limiting examples may include cyclobutenyloxy, cyclopentenyloxy, cyclohexenyloxy, cycloheptenyloxy, cyclooctenyloxy, cyclodecenyloxy, norbornenyloxy, or bicyclo[2.2.2]octenyloxy.

"Alkylthio" means and includes an alkyl group containing at least one carbon-sulfur single bond.

"Haloalkylthio" means and includes an alkyl group containing at least one carbon-sulfur single bond and halogen atom.

"Halo" or "halogen" means and includes fluorine, chlorine, bromine, or iodine.

"Haloalkyl" means and includes an alkyl group substituted with at least one halogen atom.

"Haloalkoxy" means and includes an alkoxy group substituted with at least one halogen atom.

"Heteroatom" means and includes sulfur (S), oxygen (O), or nitrogen (N) atom.

"Heteroalkyl" means and includes an alkyl containing at least one sulfur (S), oxygen (O), or nitrogen (N) atom.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. In the case of sulfur, that atom can be in other oxidation states such as a sulfoxide and sulfone. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, imidazolyl, indazolyl, indolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, oxetanyl, tetrahydrofuranyl, tetrahydrothienyl and tetrahydropyranyl. Examples of partially unsaturated heterocyclys include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl. Additional examples include the following

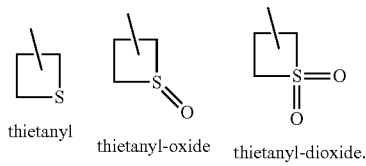

thietanyl   thietanyl-oxide   thietanyl-dioxide.

"Pesticidally effective amount" means and includes an amount of active material that causes an adverse effect to at least one insect, wherein the adverse effect may include deviations from natural development, killing, regulation, or the like.

"Control" or grammatical variations thereof means and includes regulating the number of living insects or regulating the number of viable eggs of the insects.

"Synergistic effect" or grammatical variations thereof means and includes a cooperative action encountered in a combination of two or more active agents in which the combined activity of the two or more active agents exceeds the sum of the activity of each active agent alone.

Pesticidal Compounds

In one particular embodiment, a pesticidal composition comprises at least one compound selected from compounds of formula I or any agriculturally acceptable salt thereof:

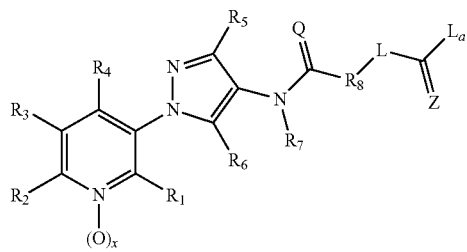

I wherein:

$R_1$, $R_2$, and $R_4$ are independently selected from hydrogen, F, Cl, Br, I, substituted or unsubstituted $C_1$-$C_6$ alkyl, or substituted or unsubstituted $C_1$-$C_6$ haloalkyl, wherein each said $R_1$, $R_2$, and $R_4$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_3$-$C_{10}$ cycloalkyl, or $C_3$-$C_{10}$ halocycloalkyl, (each of which that can be substituted, may optionally be substituted with $R_{10}$);

$R_3$ is selected from hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_1$-$C_6$ haloalkyl, substituted or unsubstituted $C_6$-$C_{20}$ aryl, substituted or unsubstituted $C_1$-$C_{20}$ heterocyclyl, $OR_{10}$, $C(=X_1)R_{10}$, $C(=X_1)OR_{10}$, $C(=X_1)N(R_{10})_2$, $N(R_{10})_2$, $N(R_{10})C(=X_1)R_{10}$, $SR_{10}$, $S(O)_nOR_{10}$, or $R_{10}S(O)_nR_{10}$, wherein each said $R_3$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, (each of which that can be substituted, may optionally be substituted with $R_{10}$);

$R_5$ is selected from H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, $C_3$-$C_{10}$ cycloalkyl, substituted or unsubstituted $C_6$-$C_{20}$ aryl, substituted or unsubstituted $C_1$-$C_{20}$ heterocyclyl, $OR_{10}$, $C(=X_1)R_{10}$, $C(=X_1)OR_{10}$, $C(=X_1)N(R_{10})_2$, $N(R_{10})_2$, $N(R_{10})C(=X_1)R_{10}$, $S(O)nR_{10}$, $S(O)_nOR_{10}$, or $R_{10}S(O)_nR_{10}$, wherein each said $R_5$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, (each of which that can be substituted, may optionally be substituted with $R_{10}$);

$R_6$ is selected from H, F, Cl, Br, I, substituted or unsubstituted $C_1$-$C_6$ alkyl, or $C_1$-$C_6$ haloalkyl, wherein each said $R_6$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, or $C_3$-$C_{10}$ halocycloalkenyl;

$R_7$ is selected from hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ alkoxy, substituted or unsubstituted $C_3$-$C_{10}$ cycloalkyl, $C_1$-$C_6$ alkyl $C_2$-$C_6$ alkynyl (wherein the alkyl and alkynyl may independently be substituted or unsubstituted), substituted or unsubstituted $C_6$-$C_{20}$ aryl, substituted or unsubstituted $C_1$-$C_{20}$ heterocyclyl, $C_1$-$C_6$ alkyl $C_6$-$C_{20}$ aryl (wherein the alkyl and aryl may independently be substituted or unsubstituted), $C_1$-$C_6$ alkyl-($C_3$-$C_{10}$ cyclohaloalkyl) wherein the alkyl and cyclohaloalkyl may independently be substituted, or $C_1$-$C_6$ alkyl-($C_3$-$C_{10}$ cycloalkyl) wherein the alkyl and cycloalkyl may independently be substituted, wherein each said $R_7$, when substituted, has one or more substituents selected from F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, $R_{10}$ aryl, (each of which that can be substituted, may optionally be substituted with $R_{10}$);

$R_8$ is selected from substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, or substituted or unsubstituted $C_1$-$C_{20}$ heterocyclyl, wherein each said $R_8$, when substituted, has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, oxo, $OR_{10}$, $S(O)_nR_{10}$, substituted or unsubstituted $C_6$-$C_{20}$ aryl, or substituted or unsubstituted $C_1$-$C_{20}$ heterocyclyl, (each of which, when substituted, is substituted with $R_{10}$);

L is selected from a bond, $R_9$, O, S, $N(R_9)$, $N(R_9)C(=X_1)$, $C(R_9)_2$, or $C(R_9)(R_{11})$;

$L_a$ is selected from $R_9$, $OR_9$, $N(R_9)_2$, $N(R_9)(R_{11})$, $N(R_9)(OR_{11})$, $N(R_9)C(=X_1)R_9$, $N(R_9)C(=X_1)(R_{11})$, $C(R_9)_3$, $C(R_9)(R_{11})(R_{12})$, or $SR_9$;

optionally L and $L_a$ is connected in a cyclic arrangement, which forms 3-8 membered heterocycles or carbocycles including L and $L_a$, wherein the cyclic arrangement contains none or at least one of O, S, or N heteroatoms, and the cyclic arrangement is unsubstituted or substituted, wherein when substituted, the cyclic arrangement has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, $N(R_9)S(O)_nR_{11}$, oxo, $OR_9$, $S(O)_nOR_9$, $R_9S(O)_nR_{11}$, $S(O)_nR_9$, substituted or unsubstituted $C_6$-$C_{20}$ aryl, or substituted or unsubstituted $C_1$-$C_{20}$ heterocyclyl (each of which, when substituted, is substituted with $R_{10}$);

$R_9$, $R_{11}$, $R_{12}$, and $R_{13}$ are independently selected from hydrogen, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl, substituted or unsubstituted $C_3$-$C_{10}$ cycloalkenyl, substituted or unsubstituted $C_6$-$C_{20}$ aryl, or substituted or unsubstituted $C_1$-$C_{20}$ heterocyclyl.

wherein each of said $R_9$, $R_{11}$, and $R_{12}$, when substituted, has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, oxo, $OR_{10}$, $C(=X_1)R_{10}$, $S(O)_nR_{10}$, substituted or unsubstituted $C_6$-$C_{20}$ aryl, or substituted or unsubstituted $C_1$-$C_{20}$ heterocyclyl, (each of which, when substituted, is substituted with $R_{10}$;

$R_{10}$ is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted $S(O)_nC_1$-$C_6$ alkyl, or substituted or unsubstituted $N(C_1$-$C_6$ alkyl$)_2$, wherein each said $R_{10}$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6$alkyl, $S(O)_nOC_1$-$C_6$ alkyl, $C_6$-$C_{20}$ aryl, or $C_1$-$C_{20}$ heterocyclyl;

Q is (each independently) O or S;
Z is (each independently) O, S, $CH_2$, $NR_{13}$ or $NOR_{13}$;
$X_1$ is (each independently) O or S;
n is 0, 1, or 2; and
x is 0 or 1.

The compound of formula I, when $R_7$ is H, may exist in various isomeric forms. Non-limiting examples of such isomeric forms may include, but are not limited to, compounds IA, or IB as shown below.

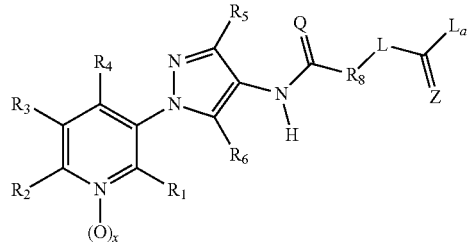

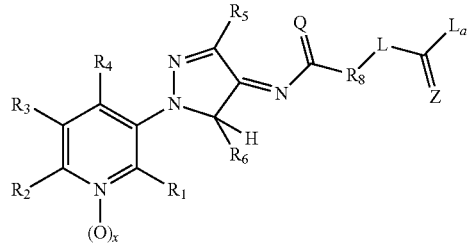

In one embodiment, compounds of formula I may be prepared using carboxylic acids as shown in Scheme 1.

Scheme 1

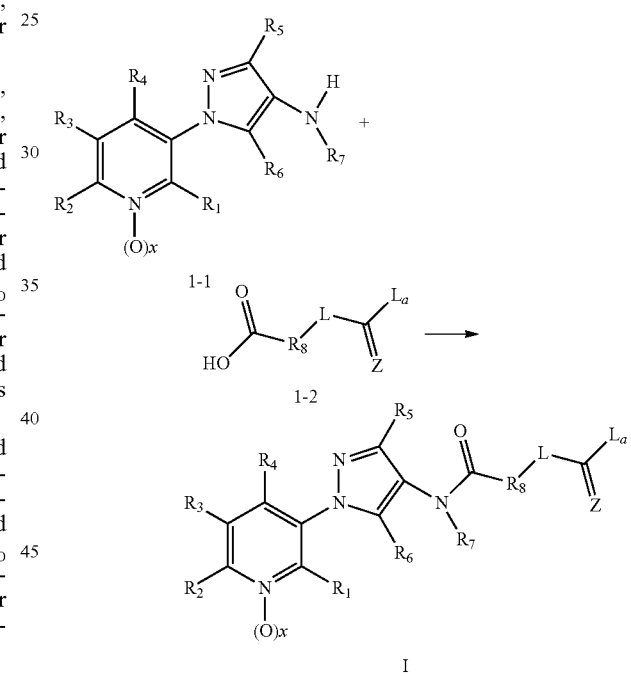

As shown in Scheme 1, compounds of formula I in which $R_1$, $R_2$, $R_3$, $R_4$, $R_5$, $R_6$, $R_7$, L, $L_a$ and x are as previously defined may be prepared from the reaction of the corresponding 1-(pyridin-3-yl)-1H-pyrazol-4-amine of formula 1-1 (prepared according to the U.S. Patent Publication No. 2012/0110702) and carboxylic acid 1-2. The 1-(pyridin-3-yl)-1H-pyrazol-4-amine (1-1) may be coupled to a carboxylic acid (1-2) with a coupling reagent, such as 1-ethyl-3-(3-dimethylaminopropyl) carbodiimide (EDC) or dicyclohexylcarbodiimide (DCC), in the presence of a base, such as 4-dimethylaminopyridine (DMAP) or diisopropylethylamine (DIPEA), in a polar aprotic solvent, such as N,N-dimethylformamide (DMF), dichloromethane ($CH_2Cl_2$), or 1,2-dichloroethane (DCE), at a temperature from about −10° C. to about 40° C. to produce compounds of formula I.

In another embodiment, compounds of formula I may be prepared using acid anhydride as shown in Scheme 2.

Scheme 2

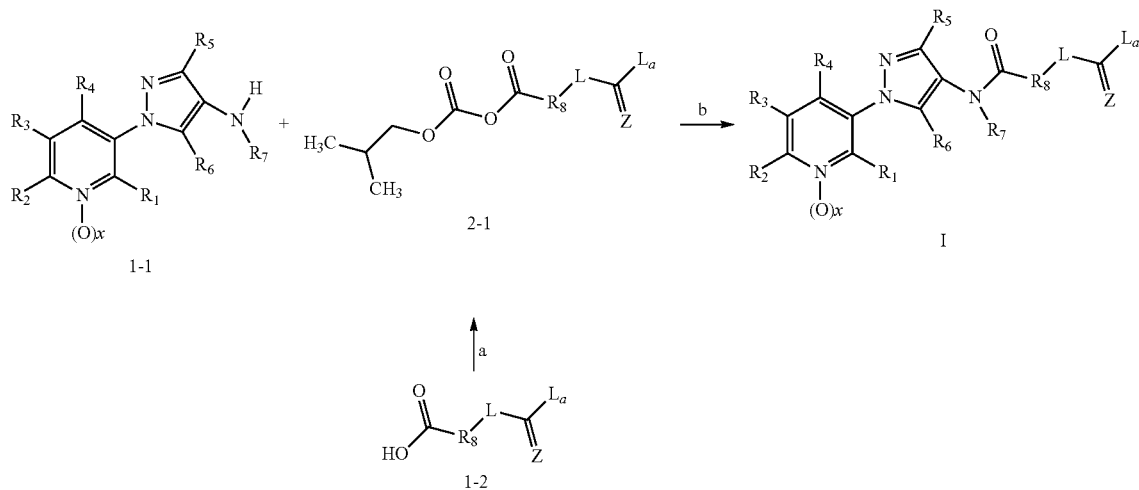

As shown in Scheme 2, compounds of formula I may be prepared from the reaction of the corresponding 1-(pyridin-3-yl)-1H-pyrazol-4-amine (1-1) and an acid anhydride (2-1). In step a of Scheme 2, the acid anhydride (2-1) may be generated from a carboxylic acid precursor (1-2) using a reagent such as isobutyl chloroformate and a base, such as DIPEA, in a polar aprotic solvent, such as $CH_2Cl_2$, at a temperature from about −78° C. to about 30° C. In step b of Scheme 2, the 1-(pyridin-3-yl)-1H-pyrazol-4-amine of formula 1-1 may be coupled with the acid anhydride (2-1) in a polar aprotic solvent, such as $CH_2Cl_2$, at a temperature from about −78° C. to about 30° C., to give compounds of formula I.

In yet another embodiment, compounds of formula I may be prepared using an acid chloride as shown in Scheme 3.

In step a of Scheme 3, the carboxylic acids of formula 1-2 may be treated with a reagent such as oxalyl chloride or thionyl chloride, in the presence of an initiator, such as dimethylformamide, in an aprotic solvent, such as $CH_2Cl_2$, at a temperature from about −20° C. to about 60° C. to give acid chlorides of the formula (3-1). In step b of Scheme 3, the acid chloride (3-1) may then be coupled with a 1-(pyridin-3-yl)-1H-pyrazol-4-amine of formula 1-1 in the presence of a base, such as diisopropylethylamine, and an aprotic solvent, such as dichloroethane, at a temperature from about −20° C. to about 60° C., to afford the compounds of formula I.

In one embodiment, compounds of formula 4-3 may be prepared as shown in Scheme 4.

Scheme 3

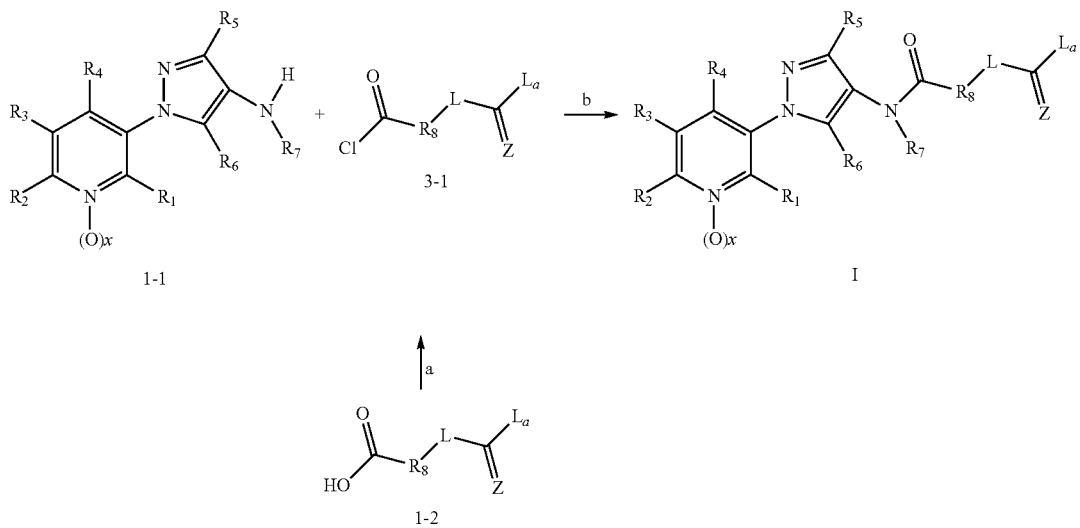

Scheme 4

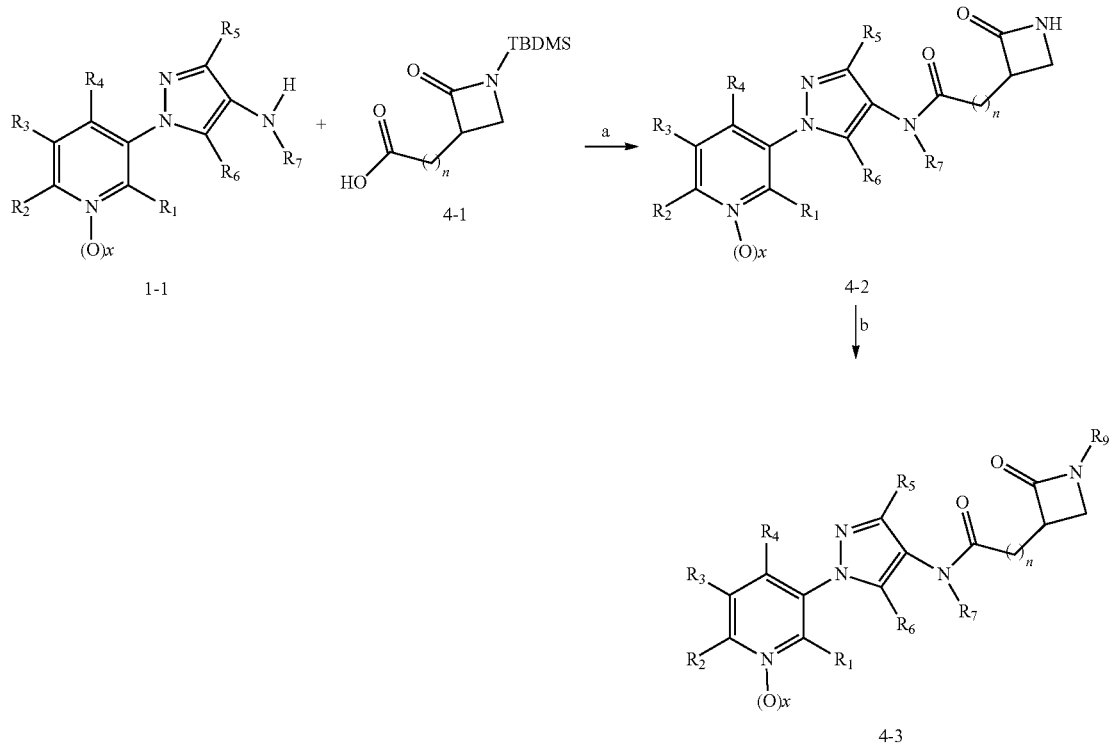

As shown in Scheme 4, compounds of formula 4-3 may be prepared from a reaction of a corresponding 1-(pyridin-3-yl)-1H-pyrazol-4-amine (1-1) (prepared according to the U.S. Publication No. 2012/0110702) and a known carboxylic acid (4-1) (*Bioorganic & Medicinal Chemistry Letters*, 2008, 18, 4163). In step a of Scheme 4, 1-(pyridin-3-yl)-1H-pyrazol-4-amine (1-1) may be coupled to a carboxylic acid (4-1) in a presence of a coupling reagent, such as n-propylphosphonic anhydride (T3P®), and a base, such as triethylamine, in a polar aprotic solvent, such as ethyl acetate (EtOAc), at a temperature from about −10° C. to about 80° C. to form compounds of formula 4-2. In step b of Scheme 4, the amide N—H group in compounds 4-2 may be further reacted with a base, such as sodium hydride (NaH), in the presence of a suitable electrophile, such as methyl iodide, in a polar aprotic solvent, such as DMF, at a temperature from about −30° C. to about 30° C. to provide the products 4-3.

In one embodiment, compounds of formula 5-4 may be prepared as shown in Scheme 5.

Scheme 5

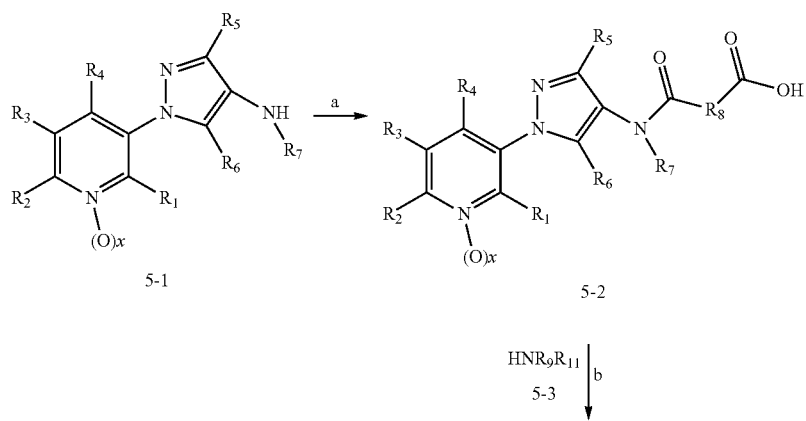

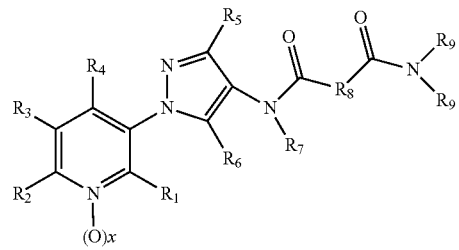

5-4

In step a of Scheme 5, 1-(pyridin-3-yl)-1H-pyrazol-4-amine of formula 5-1 may be treated with a suitable electrophile, such as succinic anhydride, in a presence of an amine, such as triethylamine, and a catalyst, such as DMAP, in a polar aprotic solvent, such as DCE, at a temperature from about 0° C. to about 80° C. to produce compounds of formula 5-2. In step b of Scheme 5, compounds of formula 5-2 may be treated with a suitable amine of formula 5-3 (which may be in the form of an salt), in the presence of a coupling reagent, such as N,N'-dicyclohexylcarbodiimide (DCC) or 1-(3-dimethylaminopropyl)-3-ethylcarbodiimide hydrochloride (EDCI), and a base, such as DMAP, in a polar aprotic solvent, such as diethyl ether or $CH_2Cl_2$, at a temperature of about 0° C. to about 25° C. to provide the products 5-4.

In one embodiment, compounds of formula 6-5 may be prepared as shown in Scheme 6.

In step a of Scheme 6, the N-Boc protected bis-heterocyclic amide of formula 6-1 may be treated with an acid, such as trifluoroacetic acid (TFA), in a polar aprotic solvent, such as $CH_2Cl_2$, at a temperature from about 0° C. to about 30° C. to yield bis-heterocyclic amine of formula 6-2. In step b, the bis-heterocyclic amine (6-2) may be treated with an acid of formula 6-3, in the presence of a coupling reagent, such as DCC or EDCI, and a base, such as DMAP, in a solvent, such as diethyl ether or $CH_2Cl_2$, at a temperature from about 0° C. to about 25° C. to provide the products 6-5. Alternatively, as shown in step c, bis-heterocyclic amine (6-2) may be treated with an acyl chloride of formula 6-4 in the presence of base, such as DMAP and/or pyridine, in a polar aprotic solvent, such as $CH_2Cl_2$, at a temperature from about 0° C. to about 30° C. to provide the products 6-5.

Scheme 6

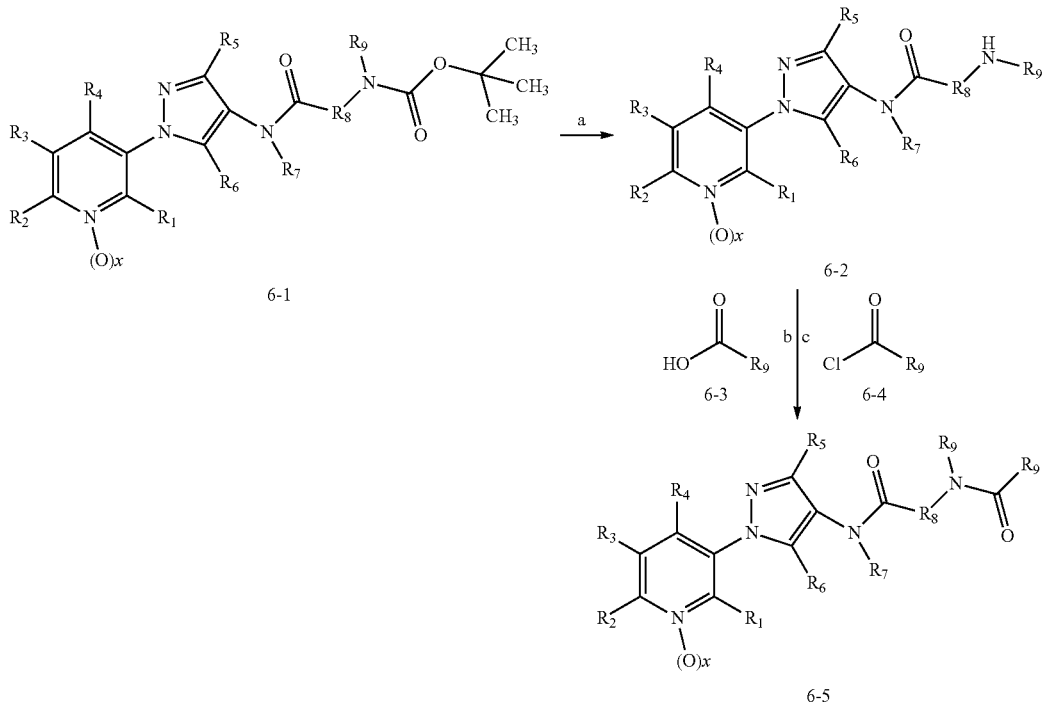

In one embodiment, compounds of formula 7-4 and 7-7 may be prepared as shown in Scheme 7.

In one embodiment, compounds of formula 8-3 may be prepared as shown in Scheme 8.

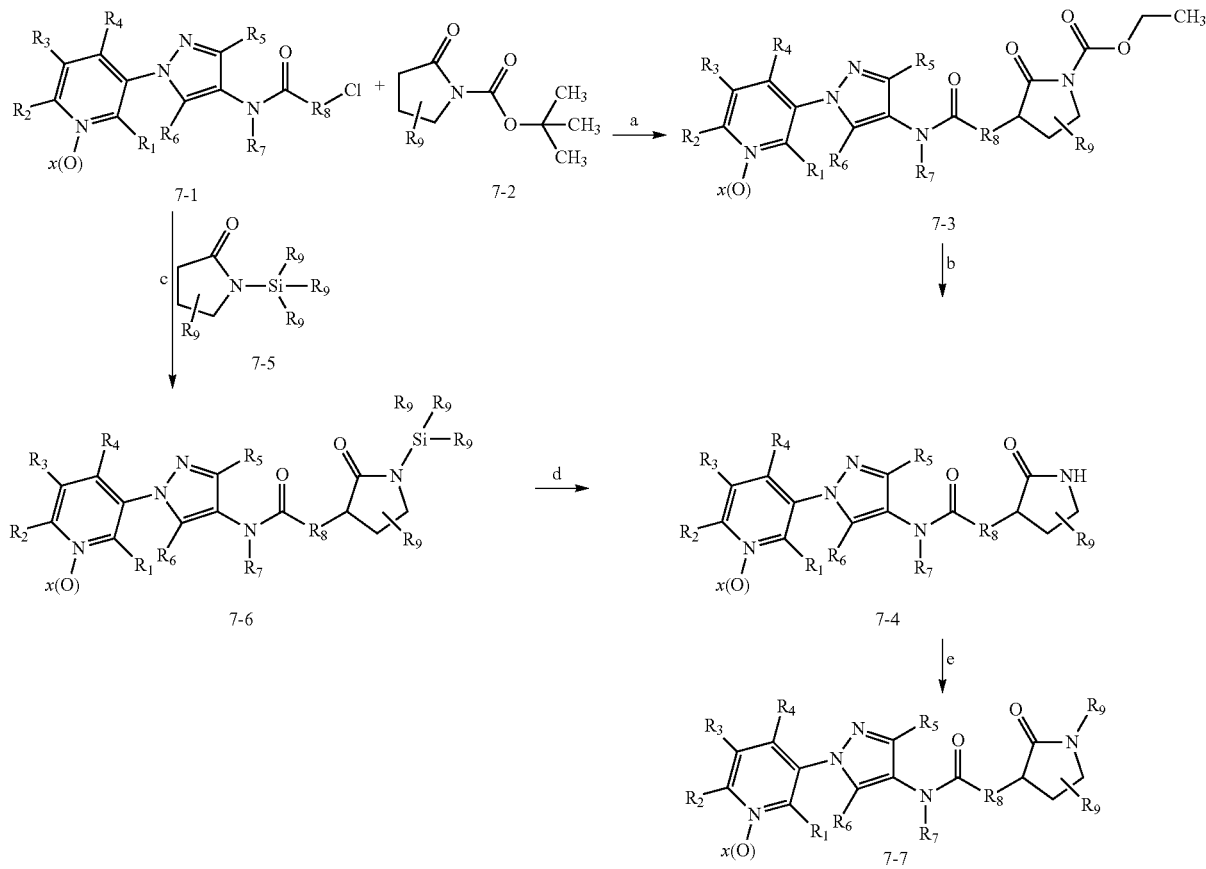

Scheme 7

In step a of Scheme 7, compounds of formula 7-1 may be treated with N-Boc protected compounds of formula 7-2, which may be pre-treated with a base, such as lithium bis(trimethylsilyl)amide (LiHMDS), in a polar aprotic solvent, such as tetrahydrofuran (THF), at a temperature from about −78° C. to about −60° C. to yield N-Boc protected bis-heterocyclic amide of formula 7-3. In step b, N-Boc protected bis-heterocyclic amide of formula 7-3 may then be treated with an acid, such as TFA, in a polar aprotic solvent, such as $CH_2Cl_2$, at a temperature from about 0° C. to about 30° C. to yield compounds 7-4.

Alternatively, as shown in step c of Scheme 7, compounds of formula 7-1 may be treated with N-silyl protected compounds of formula 7-5, which may be pre-treated with a base, such as n-butyllithium, in a polar aprotic solvent, such as THF, at a temperature from about −78° C. to about −60° C. to yield N-silyl protected bis-heterocyclic amide of formula 7-6. In step d, compounds of formula 7-6 may be treated with a fluoride source, such as tetrabutylammonium fluoride, in a polar aprotic solvent, such as THF, at a temperature from about 0° C. to about 30° C., to yield compounds 7-4. In step e, compounds of formula 7-4 may be treated with a base, such as sodium hydride, and an alkylating reagent, such as 2,2,2-trifluoroethyl trifluromethanesulfonate, in a polar aprotic solvent, such as THF, at a temperature from about −30° C. to about 40° C., to yield compounds 7-7.

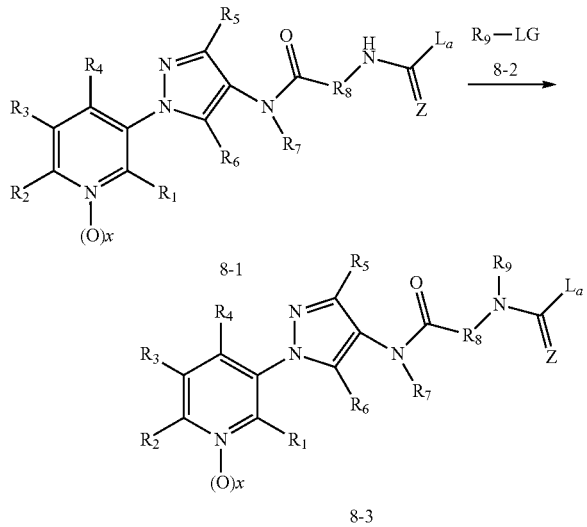

Scheme 8

In Scheme 8, compounds of formula 8-1 may be treated with a suitable base, such as NaH, and sequentially treated with an electrophile $R_9$-LG (8-2), such as an methyl iodide, in which LG is a leaving group, in an aprotic solvent, such as DMF, at a temperature from about 0° C. to about 30° C. to provide compounds of formula 8-3.

In one embodiment, compounds of formula 9-5 may be prepared as shown in Scheme 9.

Scheme 9

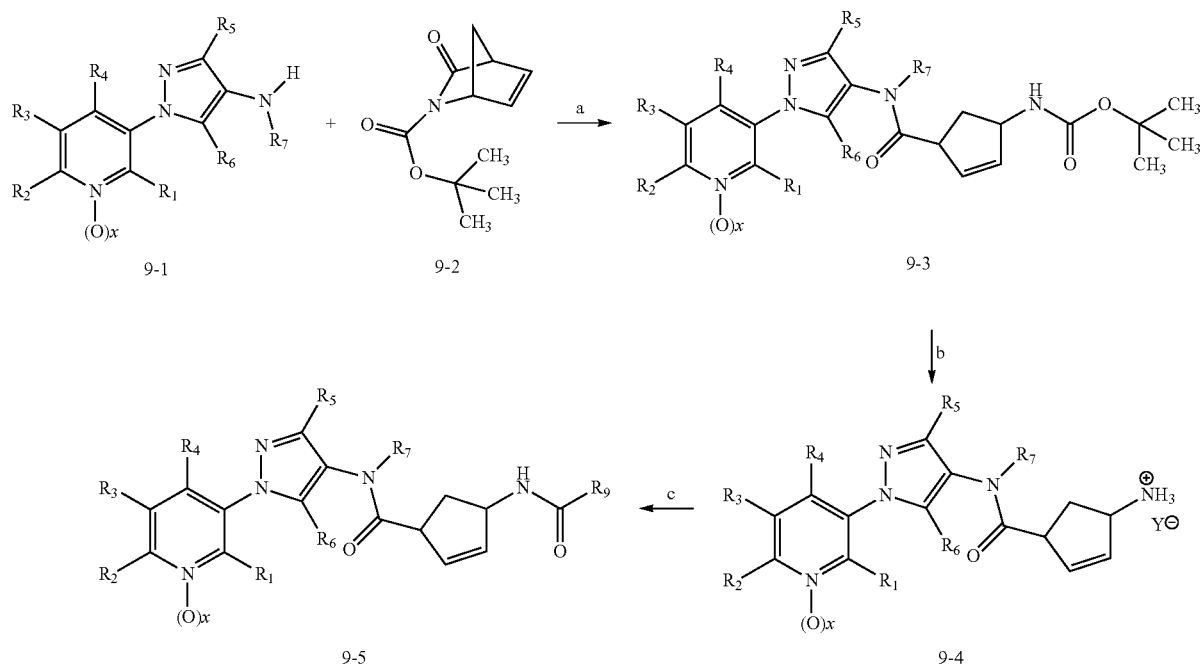

In step a of Scheme 9, 1-(pyridin-3-yl)-1H-pyrazol-4-amine of formula 9-1 may be deprotonated with a base, such as LiHMDS, and acylated with an N-Boc protected imide of formula 9-2 in a polar aprotic solvent, such as THF, at a temperature from about −78° C. to about 0° C. to yield an N-Boc protected bis-heterocyclic amide of formula 9-3.

In step b of Scheme 9, the N-Boc protected bis-heterocyclic amide (9-3) may be deprotected using an acid, such as TFA, in a polar aprotic solvent, such as $CH_2Cl_2$, at a temperature from about 0° C. to about 30° C. to yield bis-heterocyclic ammonium salt of formula 9-4, in which Y is a counter anion, such as trifluoroacetate.

In step c of Scheme 9, the bis-heterocyclic ammonium salt (9-4) may be acylated with an acid chloride, such as acetyl chloride, in a presence of a base, such as triethylamine, in a polar aprotic solvent, such as $CH_2Cl_2$, at a temperature from about 0° C. to about 60° C. to provide the products 9-5.

In one embodiment, the oxime of formula 10-6 may be prepared as shown in Scheme 10.

Scheme 10

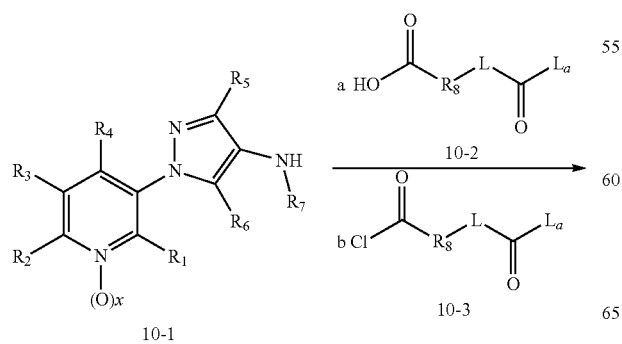

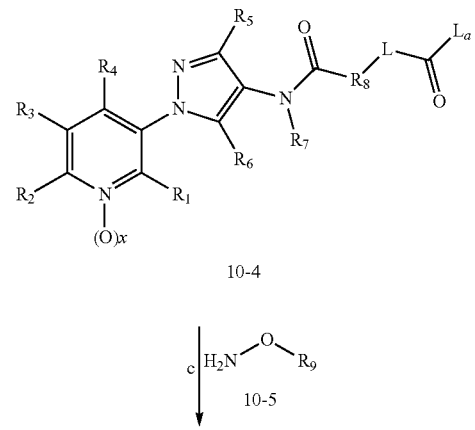

In step a of Scheme 10, 1-(pyridin-3-yl)-1H-pyrazol-4-amine of formula 10-1 may be treated with an acid of formula 10-2, in a presence of a coupling reagent, such as EDC, and a base, such as DMAP, in a polar aprotic solvent, such as $CH_2Cl_2$, at a temperature from about $-20°$ C. to about $70°$ C. to afford bis-heterocyclic ketone of formula 10-4. Alternatively, as shown in step b, bis-heterocyclic ketone (10-4) may be prepared by reacting 1-(pyridin-3-yl)-1H-pyrazol-4-amine of formula 10-1 with an acyl chloride of formula 10-3 in the presence of a base, such as DMAP, in a polar aprotic solvent, such as $CH_2Cl_2$. In step c, bis-heterocyclic ketone (10-4) may be reacted with a hydroxylamine of formula 10-5 or its hydrochloride salt, such as O-methylhydroxylamine hydrochloride or iso-propylhydroxylamine hydrochloride, in the presence of a base, such as DIPEA, triethylamine, or pyridine, in a protic solvent, such as ethanol (EtOH), at a temperature from about $25°$ C. to about $100°$ C. to afford the bis-heterocyclic amide oxime of formula 10-6.

In one embodiment, compounds of formula 11-8 may be prepared as shown in Scheme 11.

compounds of formula 11-3. In step b, the compounds of formula 11-3 may be treated with an alkyl amine of formula 11-4, such as methyl amine, in a protic solvent, such as ethanol, at a temperature from about $25°$ C. to about $150°$ C. to yield bis-heterocyclic amine of formula 11-5. In step c, bis-heterocyclic amine of formula 11-5 may be treated with an acyl chloride of formula 11-6, such as acetyl chloride or ethyl chloroformate, in the presence of a base, such as DMAP, DIPEA, triethylamine or pyridine, in an aprotic solvent, such as THF or $CH_2Cl_2$, at a temperature from about $0°$ C. to about $30°$ C. to yield bis-heterocyclic amide of formula 11-8. Alternatively, as shown in step d, bis-heterocyclic amine of formula 11-5 may be treated with a carboxylix acid of formula 11-7, in a presence of a coupling reagent, such as EDCI, and

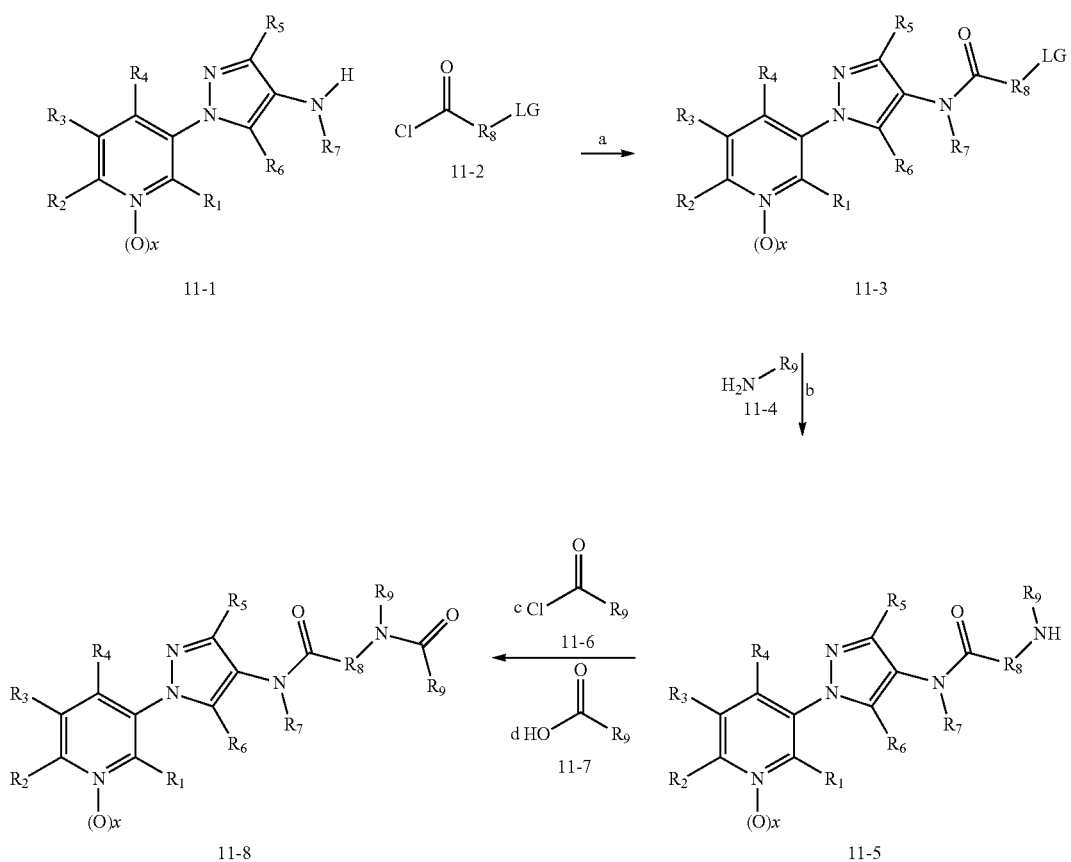

Scheme 11

In step a of Scheme 11, 1-(pyridin-3-yl)-1H-pyrazol-4-amine of formula 11-1 may be reacted with an acid chloride of formula 11-2, where LG is a leaving group such as Cl, in the presence of a proton scavenger, such as propylene oxide, DMAP or pyridine, and an aprotic solvent, such as DCE, at a temperature from about $-20°$ C. to about $200°$ C. to afford a base, such as DMAP, in a polar aprotic solvent, such as $CH_2Cl_2$, at a temperature from about $-20°$ C. to about $70°$ C. to provide compounds of formula 11-8.

In one embodiment, compounds of formula 12-6 may be prepared as shown in Scheme 12.

Scheme 12

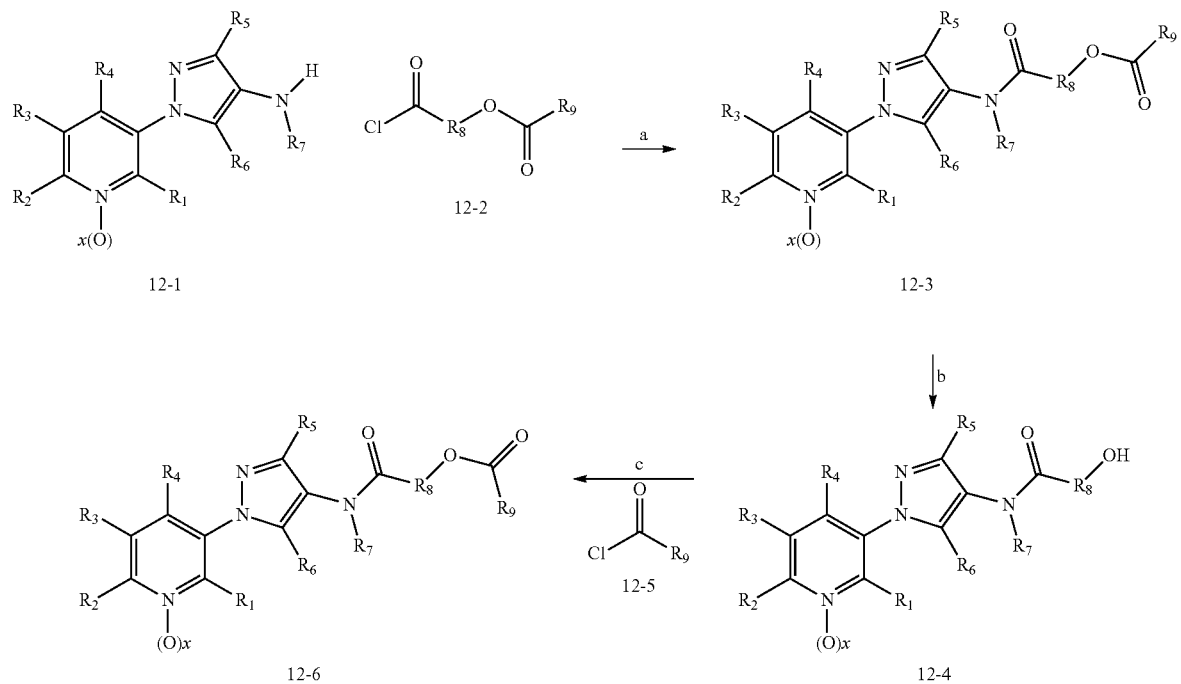

In step a of Scheme 12, 1-(pyridin-3-yl)-1H-pyrazol-4-amine of formula 12-1 may be reacted with an acid chloride of formula 12-2 in the presence of a base, such as DMAP, DIPEA, triethylamine or pyridine, in an aprotic solvent, such as THF or CH₂Cl₂, at a temperature from about 0° C. to about 30° C. to afford bis-heterocyclic compounds of formula 12-3. As shown in step b, treating the bis-heterocyclic compound of formula 12-3 with a base, such as aqueous 2M lithium hydroxide, in a polar solvent, such as methanol (MeOH), may afford the bis-heterocyclic compounds of formula 12-4. In step c, reacting the bis-heterocyclic compound of formula 12-4 with an acid chloride of formula 12-5 in a presence of a base, such as DMAP, DIPEA, triethylamine or pyridine, in an aprotic solvent, such as THF or CH₂Cl₂, at a temperature from about 0° C. to about 30° C. may yield compounds of formula 12-6.

In one embodiment, compounds of formula 13-4 may be prepared as shown in Scheme 13.

Scheme 13

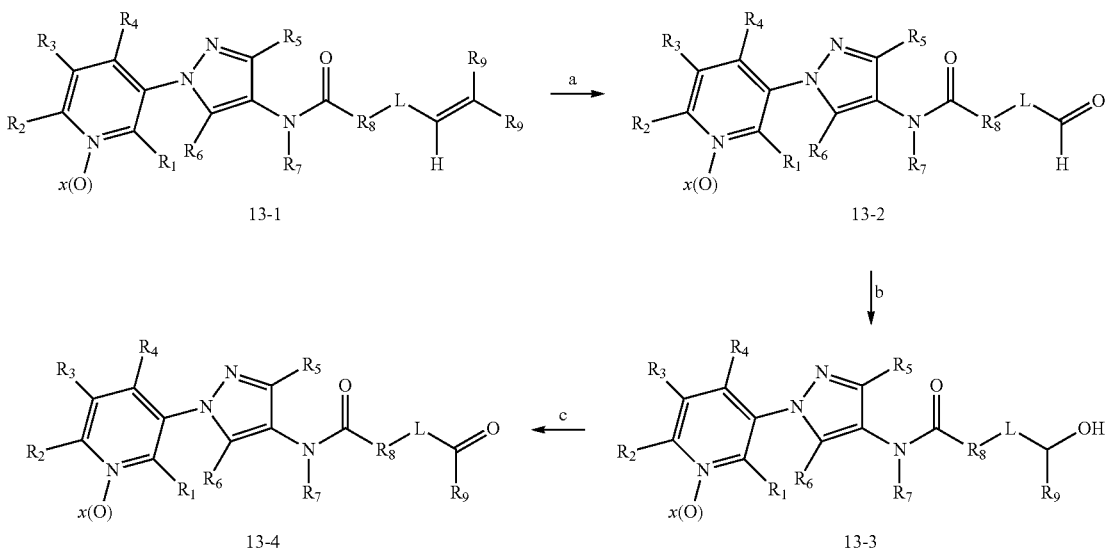

In step a of Scheme 13, compounds of formula 13-1 may be treated with an oxidant, such as ozone, in a polar solvent, such as $CH_2Cl_2$ and methanol, at a temperature from about −78° C. to about −40° C. to provide compounds of formula 13-2. In step b, compounds of formula 13-2 may be treated with a nucleophile, such as methylmagnesium bromide, in a polar aprotic solvent, such as THF, at a temperature from about −78° C. to about −40° C. to provide compounds of formula 13-3. In step c, compounds of formula 13-3 may be treated with an oxidant, such as Dess-Martin periodinane, in a polar aprotic solvent, such as $CH_2Cl_2$, at a temperature of from about −30° C. to about 30° C. to provide compounds of formula 13-4.

Pesticidally Acceptable Acid Addition Salts, Salt Derivatives, Solvates, Ester Derivatives, Polymorphs, Isotopes, Radionuclides and Stereoisomers In some embodiments, the compound of formula I may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, hydroxyethanesulfonic, and trifluoroacetic acids. Additionally, by way of a non-limiting example, an acid function can form salts including those derived from alkali or alkaline earth metals and those derived from ammonia and amines. Examples of preferred cations include sodium, potassium, and magnesium.

In some embodiments, the compound of formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

In further embodiments, the compound of formula I may be formulated into stable complexes with a solvent, such that the complex remains intact after the non-complexed solvent is removed. These complexes are often referred to as "solvates." However, it is particularly desirable to form stable hydrates with water as the solvent.

In some embodiments, the compound of formula I may be made into ester derivatives. These ester derivatives can then be applied in the same manner as the invention disclosed in this document is applied.

In some embodiments, the compound of formula I be made as various crystal polymorphs. Polymorphism is important in the development of agrochemicals since different crystal polymorphs or structures of the same molecule can have vastly different physical properties and biological performances.

In further embodiments, the compound of formula I may be made with different isotopes. Of particular importance are molecules having $^2H$ (also known as deuterium) in place of $^1H$.

In some embodiments, the compound of formula I may be made with different radionuclides. Of particular importance are molecules having $^{13}C$ or $^{14}C$.

In some embodiments, the of formula I may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Pesticidal Compositions

In one particular embodiment, a pesticidal composition comprises at least one compounds selected from a compound of formula I or any agriculturally acceptable salt thereof.

In some embodiments, a pesticidal composition comprises at least one compounds selected from a compound of formula I, or any agriculturally acceptable salt thereof, and a phytologically-acceptable inert carrier (e.g., solid carrier, or liquid carrier).

In one embodiment, the pesticidal composition may further comprise at least one additive selected from surfactant, a stabilizer, an emetic agent, a disintegrating agent, an antifoaming agent, a wetting agent, a dispersing agent, a binding agent, dyes, or fillers.

In some embodiments, the pesticidal compositions may be in the form of solid. Non-limiting examples of the solid forms may include power, dust or granular formulations.

In other embodiments, the pesticidal compositions may be in the form of liquid formulation. Examples of the liquid forms may include, but not limited to, dispersion, suspension, emulsion or solution in appropriate liquid carrier.

In further embodiments, the pesticidal compositions may be in the form of liquid dispersion, wherein the compound of formula I may be dispersed in water or other agriculturally suitable liquid carrier.

In yet further embodiments, the pesticidal compositions may be in the form of solution in an appropriate organic solvent. In one embodiment, the spray oils, which are widely used in agricultural chemistry, may be used as an organic solvent for the pesticidal compositions.

The pesticidal composition may be used in conjunction (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, and/or virucidal properties.

Furthermore, the pesticidal composition may be used in conjunction (such as, in a compositional mixture, or a simultaneous or sequential application) with one or more compounds that are antifeedants, bird repellents, chemosterilants, herbicide safeners, insect attractants, insect repellents, mammal repellents, mating disrupters, plant activators, plant growth regulators, and/or synergists.

Insecticides

Non-limiting examples of insecticides that may be used in combination with the compound of formula I may include 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, α/p/ω-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdépalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphosmethyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoximmethyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, Aeto-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, or zolaprofos.

Acaricides

Non-limiting examples of acaricides that may be used in combination with the compound of formula I may include acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorobenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfiram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfiram, sulfur, tetradifon, tetranactin, tetrasul, or thioquinox.

Nematicides

Non-limiting examples of nematicides that may be used in combination with the compound of formula I may include 1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, or thionazin.

Fungicides

Non-limiting examples of fungicides that may be used in combination with the compound of formula I may include (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S- methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, or zoxamide.

Herbicides

Non-limiting examples of herbicides that may be used in combination the compound of formula I may include 2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlornitrofen, chloropon, chlorotoluron, chloroxuron, chloroxynil, chlorprocarb, chlorpropham, chlorsulfuron, chlorthal, chlorthal-dimethyl, chlorthalmonomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butometyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, flurochloridone, fluroxypyr, fluroxypyr-butometyl, fluroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, or xylachlor.

Biopesticides

The compound of formula I may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g., *Metarhizium anisopliae*);
2. entomopathogenic nematodes (e.g., *Steinernema feltiae*); and
3. entomopathogenic viruses (e.g., *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

The compound of formula I may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2- benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-ethyl-2,2-dichloro-1-methylcyclopropanecarboxamide-2-(2,6-dichloro-α,α,α-trifluoro-p-tolyl)hydrazone.

The compound of formula I may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, or virucides.

Synergistic Mixtures and Synergists

The compound of formula I may be used in combination with at least one other insecticides to form a synergistic mixture where the mode of action of such compounds compared to the mode of action of the compound of formula I are the same, similar, or different. Examples of modes of action may include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, or ryanodine receptor (RyRs).

Additionally, the compound of formula I may be used in combination with at least one of fungicides, acaricides, herbicides or nematicides to form a synergistic mixture.

Furthermore, the compound of formula I may be used in combination with other active compounds, such as the compounds under the heading "OTHER ACTIVE COMPOUNDS," algicides, avicides, bactericides, molluscicides, rodenticides, virucides, herbicide safeners, adjuvants, and/or surfactants to form a synergistic mixture. Moreover, the following compounds are known as synergists and may be used in combination with the compound of formula I: piperonyl butoxide, piprotal, propyl isome, sesamex, sesamolin, sulfoxide, and tribufos.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when compound of formula I and/or any agriculturally acceptable salt thereof, are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore, preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g., plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pesticidal Activities

The disclosed pesticidal compositions may be used, for example, as nematicides, acaricides, pesticides, insecticides, miticides, and/or molluscicides.

In one particular embodiment, a method of controlling pests comprises applying a pesticidal composition comprising at least one compounds selected from a compound of formula I, or any agriculturally acceptable salt thereof, near a population of pests.

The compound of formula I are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a compound of formula I is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a compounds of formula I when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The compound of formula I may be used in mixtures, applied simultaneously or sequentially, alone or with other compounds to enhance plant vigor (e.g., to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The compound of formula I can be applied to the foliar and fruiting portions of plants to control pests. The molecules will either come in direct contact with the pest, or the pest will consume the pesticide when eating leaf, fruit mass, or extracting sap, that contains the pesticide. The compound of formula I can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a compounds of formula I.

The compound of formula I can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the compound of formula I may be desirable to control newly emerged larvae.

Systemic movement of pesticides in plants may be utilized to control pests on one portion of the plant by applying (for example, by spraying an area) the compounds of formula I to a different portion of the plant. For example, control of foliar-feeding insects can be achieved by drip irrigation or furrow application, by treating the soil with, for example, pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the compounds of formula I may further enhance the ability of a plant to better withstand stressful growing conditions. This results in a healthier, more vigorous plant, which can lead to higher yields at harvest time. Generally, about 1 gram of the compound of formula I to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the compound of formula I may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The compound of formula I may be used for controlling endoparasites and ectoparasites in the veterinary medicine sector or in the field of non-human animal keeping. The compound of formula I may be applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The compound of formula I may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The compound of formula I may also be used for controlling parasitic worms, especially of the intestine, in the animals listed above.

The compound of formula I may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The compounds of formula I may also be used on such new invasive species to control them in such new environment.

The compound of formula I may also be used in an area where plants, such as crops, are growing (e.g., pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g., increased biomass and/or increased content of valuable ingredients), improving the vigor of a plant (e.g., improved plant growth and/or greener leaves), improving the quality of a plant (e.g., improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A compound of formula I can be tested to determine its efficacy against pests. Furthermore, mode of action studies can be conducted to determine if said molecule has a different mode of action than other pesticides. Thereafter, such acquired data can be disseminated, such as by the interne, to third parties.

The disclosed pesticidal composition comprising compound of formula I may be used to control a wide variety of pests.

As a non-limiting example, in one or more embodiments, the method of the present disclosure may be used to control one or more members of *Lyriomiza sativae, Caliothrips phaseoli, Paratrioza cockerel, Spodoptera exigua, Myzus persicae, Nilaparvata lugens, Bemisia tabaci.*

In additional embodiments, the method of the present disclosure may be used to control one or more members of at least one of Phylum Arthropoda, Phylum Nematoda, Subphylum Chelicerata, Subphylum Myriapoda, Subphylum Hexapoda, Class Insecta, Class Arachnida, and Class Symphyla. In at least some embodiments, the method of the present disclosure may be used to control one or more members of at least one of Class Insecta and Class Arachnida.

In further embodiments, the method of the present disclosure may be used to control members of the Order Coleoptera (beetles) including, but not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turfgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomelids), *Cerotoma trifurcata* (bean leaf beetle), *Ceutorhynchus* spp. (weevils),

*Ceutorhynchus assimilis* (cabbage seedpod weevil), *Ceutorhynchus napi* (cabbage *curculio*), *Chaetocnema* spp. (chrysomelids), *Colaspis* spp. (soil beetles), *Conoderus scalaris*, *Conoderus stigmosus*, *Conotrachelus nenuphar* (plum *curculio*), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysomelids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana* (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In other embodiments, the method of the present disclosure may also be used to control members of the Order Dermaptera (earwigs).

In additional embodiments, the method of the present disclosure may be used to control members of the Order Dictyoptera (cockroaches) including, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In further embodiments, the method of the present disclosure may be used to control members of the Order Diptera (true flies) including, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In other embodiments, the method of the present disclosure may be used to control members of the Order Hemiptera (true bugs) including, but is not limited to, *Acrosternum hilare* (green stink bug), *Blissus leucopterus* (chinch bug), *Calocoris norvegicus* (potato mind), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (four-lined plant bug), *Psallus vaccinicola, Pseudacysta perseae, Scaptocoris castanea*, and *Triatoma* spp. (bloodsucking conenose bugs/kissing bugs).

In additional embodiments, the method of the present disclosure may be used to control members of the Order Homoptera (aphids, scales, whiteflies, leafhoppers) including, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus* spp., *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape *phylloxera*), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*. In at least some embodiments, the method of the present disclosure may be used to control *Myzus persicae*.

In other embodiments, the method of the present disclosure may be used to control members of the Order Hymenoptera (ants, wasps, and bees) including, but not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In certain embodiments, the method of the present disclosure may be used to control members of the Order Isoptera (termites) including, but not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes grassei*, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In additional embodiments, the method of the present disclosure may be used to control members of the Order Lepidoptera (moths and butterflies) including, but not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange *tortrix*), *Autographa gamma*, *Bonagota cranaodes*, *Borbo cinnara* (rice leaf folder), *Bucculatrix thurberiella* (cotton leafperforator), *Caloptilia* spp. (leaf miners), *Capua reticulana*, *Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella*, *Cossus cossus* (carpenter moth), *Crambus* spp. (Sod webworms), *Cydiafunebrana* (plum fruit moth), *Cydia molesta* (oriental fruit moth), *Cydia nignicana* (pea moth), *Cydia pomonella* (codling moth), *Darna diducta*, *Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum*, *Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema*, *Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella*, *Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maraca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia*, *Pandemis cerasana* (common currant *tortrix*), *Pandemis heparana* (brown apple *tortrix*), *Papilio demodocus*, *Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella*, *Phyllonorycter* spp. (leafminers), *Pieris rapae* (imported cabbageworm), *Plathypena scabra*, *Plodia interpunctella* (Indian meal moth), *Plutella xylostella* (diamondback moth), *Polychrosis viteana* (grape berry moth), *Prays endocarpa*, *Prays oleae* (olive moth), *Pseudaletia* spp. (noctuid moths), *Pseudaletia unipunctata* (armyworm), *Pseudoplusia includens* (soybean looper), *Rachiplusia nu*, *Scirpophaga incertulas*, *Sesamia* spp. (stemborers), *Sesamia inferens* (pink rice stem borer), *Sesamia nonagrioides*, *Setora nitens*, *Sitotroga cerealella* (Angoumois grain moth), *Sparganothis pilleriana*, *Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides*, *Thermisia gemmatalis*, *Tineola bisselliella* (webbing clothes moth), *Trichoplusia ni* (cabbage looper), *Tuta absoluta*, *Yponomeuta* spp., *Zeuzera coffeae* (red branch borer), and *Zeuzera pyrina* (leopard moth). In at least some embodiments, the method of the present disclosure may be used to control *Spodoptera exigua*.

The method of the present disclosure may be used to also control members of the Order Mallophaga (chewing lice) including, but not limited to, *Bovicola ovis* (sheep biting louse), *Menacanthus stramineus* (chicken body louse), and *Menopon gallinea* (common hen louse).

In additional embodiments, the method of the present disclosure may be used to control members of the Order Orthoptera (grasshoppers, locusts, and crickets) including, but not limited to, *Anabrus simplex* (Mormon cricket), *Gryllotalpi-* dae (mole crickets), *Locusta migratoria, Melanoplus* spp. (grasshoppers), *Microcentrum retinerve* (angularwinged katydid), *Pterophylla* spp. (kaydids), *chistocerca gregaria, Scudderia furcata* (forktailed bush katydid), and *Valanga nigricorni*.

In other embodiments, the method of the present disclosure may be used to control members of the Order Phthiraptera (sucking lice) including, but not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse).

In particular embodiments, the method of the present disclosure may be used to control members of the Order Siphonaptera (fleas) including, but not limited to, *Ctenocephalides canis* (dog flea), *Ctenocephalides felis* (cat flea), and *Pulex irritans* (human flea).

In additional embodiments, the method of the present disclosure may be used to control members of the Order Thysanoptera (*thrips*) including, but not limited to, *Frankliniella fusca* (tobacco *thrips*), *Frankliniella occidentalis* (western flower *thrips*), *Frankliniella shultzei, Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirtothrips dorsalis* (yellow tea *thrips*), *Taeniothrips rhopalantennalis*, and *Thrips* spp.

The method of the present disclosure may be used to also control members of the Order Thysanura (bristletails) including, but not limited to, *Lepisma* spp. (silverfish) and *Thermobia* spp. (firebrats).

In further embodiments, the method of the present disclosure may be used to control members of the Order Acari (mites and ticks) including, but not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (american dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus dims* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (twospotted spider mite), and *Varroa destructor* (honey bee mite).

In additional embodiments, the method of the present disclosure may be used to control members of the Order Nematoda (nematodes) including, but not limited to, *Aphelenchoides* spp. (foliar nematodes), *Belonolaimus* spp. (sting nematodes), *Criconemella* spp. (ring nematodes), *Dirofilaria immitis* (dog heartworm), *Ditylenchusspp.* (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In at least some embodiments, the method of the present disclosure may be used to control at least one insect in one or more of the Orders Lepidoptera, Coleoptera, Homoptera, Hemiptera, Thysanoptera, Isoptera, Orthoptera, Diptera, Hymenoptera, and Siphonaptera, and at least one mite in the Order Acari.

Insecticidal Testing

Example A: Bioassay for Green Peach Aphid (GPA) (*Myzus persicae*) (MYZUPE)

The green peach aphid (*Myzus persicae*) is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control} = 100*(X-Y)/X$$

where
X=No. of live aphids on solvent check plants and
Y=No. of live aphids on treated plants The results are indicated in the table entitled "Table 2. Biological Data for Green Peach Aphid (GPA) (MYZUPE) and Sweetpotato Whitefly-Crawler (WF) (BEMITA)" (see table section).

Example B: Insecticidal Test for Sweetpotato Whitefly-Crawler (WF) (*Bemisia tabaci*) (BEMITA) in Foliar Spray Assay The sweetpotato whitefly (*Bemisia tabaci*) has been reported as a serious pest of cultivated crops world-wide. It has an extremely wide host range attacking more than 500 species of plants from 63 plant families. Weeds often serve as alternate hosts of crop pests. Direct feeding damage is caused by the piercing and sucking sap from the foliage of plants. This feeding causes weakening and early wilting of the plant and reduces the plant growth rate and yield. Indirect damage results by the accumulation of honeydew produced by the whiteflies. Honeydew serves as a substrate for the growth of black sooty mold on leaves and fruit reducing photosynthesis and lessens the market value of the plant or yield. Damage is also caused when sweetpotato whitefly vectors plant viruses. The sweetpotato whitefly is considered the most common and important whitefly vector of plant viruses worldwide.

Cotton plants (*Gossypium hirsutum*) grown in 3-inch pots, with 1 small (4-5 cm) true leaves, were used as test substrate. The plants were infested with 200-400 whitefly eggs 4-5 days prior to chemical application. Four pots with individual plants were used for each treatment. Test compounds (2 mg) were dissolved in 1 mL of acetone solvent, forming stock solutions of 2000 ppm test compound. The stock solutions were diluted 10× with 0.025% Tween 20 in water (diluents) to obtain the solution at 200 ppm test compound. A hand-held aspirator-type sprayer was used for spraying a solution to both sides of cotton leaves until runoff. Reference plants (solvent check) were sprayed with the diluent only containing 10% by volume of acetone solvent. Treated plants were held in a holding room for 9 days at approximately 25° C. and ambient relative humidity (RH) prior to grading. Evaluation was conducted by counting the number of live 3-4 nymph stage per plant under a microscope. Percent control was measured by using Abbott's correction formula (W. S. Abbott, "A Method of Computing the Effectiveness of an Insecticide" J. Econ. Entomol. 18 (1925), pp. 265-267) as follows.

The results are indicated in the table entitled "Table 2. Biological Data for Green Peach Aphid (GPA) (MYZUPE) and Sweetpotato Whitefly-Crawler (WF) (BEMITA)" (see table section).

$$\text{Corrected \% Control} = 100 \times (X-Y)/X$$

where

X=No. of live nymphs on solvent check plants and

Y=No. of live nymphs on treated plants.

Table 2 shows the pesticidal activities of the pesticidal compounds against green peach aphid (GPA, MYZUPE) and sweetpotato whitefly-crawler (WF, BEMITA). The mortality efficiency of the pesticidal compounds against GPA and WF insects was determined after treatment. The mortality efficiency of the disclosed pesticidal compounds against GPA and WF insects was rated as shown in Table 1.

TABLE 1

Mortality Rating for Green Peach Aphid (GPA) and Whitefly (WF)

| % Control (or Mortality) | Rating |
|---|---|
| 80-100 | A |
| More than 0-Less than 80 | B |
| Not Tested | C |
| No activity noticed in this bioassay | D |

TABLE 2

Biological Data for Green Peach Aphid (MYZUPE) and Sweetpotato Whitefly-crawler (BEMITA)

| | Insect Species | |
|---|---|---|
| No. | GPA 200 ppm | WF 200 ppm |
| F1 | A | A |
| F2 | A | A |
| F3 | A | A |
| F4 | A | A |
| F5 | A | A |
| F6 | A | A |
| F7 | B | A |
| F8 | A | A |
| F9 | A | B |
| F10 | B | A |
| F11 | B | A |
| F12 | A | A |
| F13 | B | A |
| F14 | B | A |
| F15 | B | A |
| F16 | A | A |
| F17 | B | A |
| F18 | B | A |
| F19 | A | A |
| F20 | A | A |
| F21 | B | A |
| F22 | B | A |
| F23 | B | A |
| F24 | A | A |
| F25 | B | A |
| F26 | A | B |
| F27 | B | A |
| F28 | A | A |
| F29 | A | A |
| F30 | A | A |
| F31 | A | A |
| F32 | A | A |
| F33 | B | A |
| F34 | B | A |
| F35 | A | A |
| F36 | A | A |
| F37 | B | A |
| F38 | A | A |
| F39 | A | A |
| F40 | B | B |
| F41 | C | C |
| F42 | A | A |
| F43 | B | A |
| F44 | A | A |
| F45 | C | C |
| F46 | B | A |
| F47 | C | C |
| F48 | A | A |
| F49 | A | A |
| F50 | B | A |
| F51 | A | A |
| F52 | A | A |
| F53 | A | A |
| F54 | A | A |
| F55 | B | A |
| F56 | A | A |
| F57 | A | A |
| F58 | A | A |
| F59 | A | A |
| F60 | A | A |
| F61 | A | B |
| F62 | A | A |
| F63 | A | A |
| F64 | A | A |
| F65 | A | A |
| F66 | A | A |
| F67 | A | A |
| F68 | B | A |
| F69 | A | A |
| F70 | A | A |
| F71 | A | A |
| F72 | A | A |
| F73 | A | A |
| F74 | A | A |
| F75 | A | A |
| F76 | B | B |
| F77 | A | A |
| F78 | A | A |
| F79 | B | B |
| F80 | B | A |
| F81 | A | A |
| F82 | B | A |
| F83 | A | B |
| F84 | A | A |
| F85 | A | A |

TABLE 2-continued

Biological Data for Green Peach Aphid (MYZUPE) and Sweetpotato Whitefly-crawler (BEMITA)

| No. | GPA 200 ppm | WF 200 ppm |
|---|---|---|
| F86 | A | A |
| F87 | C | C |
| F88 | B | A |
| F89 | A | A |
| F90 | B | A |
| F91 | A | A |
| F92 | A | A |
| F93 | A | A |
| F94 | A | A |
| F95 | B | B |
| F96 | A | A |
| F97 | A | A |
| F98 | A | A |
| F99 | B | A |
| F100 | B | A |
| F101 | B | A |
| F102 | A | A |
| F103 | A | A |
| F104 | A | A |
| F105 | B | A |
| F106 | B | B |
| F107 | A | A |
| F108 | A | A |
| F109 | B | A |
| F110 | A | A |
| F111 | A | A |
| F112 | B | A |
| F113 | A | A |
| F114 | A | A |
| F115 | B | A |
| F116 | B | A |
| F117 | A | A |
| F118 | A | A |
| F119 | A | A |
| F120 | A | A |
| F121 | A | A |
| F122 | B | A |
| F123 | B | A |
| F124 | A | A |
| F125 | A | A |
| F126 | B | A |
| F127 | B | A |
| F128 | A | A |
| F129 | B | A |
| F130 | A | A |
| F131 | A | A |
| C1 | D | B |
| C2 | B | A |
| C3 | B | C |
| C4 | B | C |
| C5 | B | D |
| C10 | A | A |
| C11 | B | A |
| C12 | A | A |
| C13 | A | A |
| C14 | A | A |
| P1 | A | A |
| P16 | A | B |
| P20 | A | B |
| P21 | A | B |
| P23 | A | A |
| P24 | A | B |
| FA1 | B | A |
| FA2 | B | A |
| FA3 | A | A |
| FA4 | B | A |
| FA5 | A | B |
| FA6 | A | B |
| FA7 | A | D |
| FA8 | A | B |
| FA9 | A | D |
| FA10 | A | A |
| FA11 | A | A |
| FA12 | B | B |
| FA13 | C | C |
| FA14 | A | A |
| FA15 | A | A |
| FA16 | B | B |
| FA17 | B | B |
| FA18 | A | A |
| FA19 | B | A |
| FA20 | A | A |
| FA21 | B | C |
| FA22 | B | A |
| FA23 | B | C |
| FA24 | B | C |
| FA25 | B | C |
| FA26 | B | A |
| FA27 | B | B |
| FA28 | B | B |
| FA29 | B | A |
| FA30 | D | B |
| FA31 | D | B |
| FA32 | B | B |
| FA33 | A | A |
| FA34 | A | A |
| FA35 | B | A |
| FA36 | B | B |
| FA37 | B | A |
| FA38 | B | B |
| FA39 | B | B |
| FA40 | B | A |
| FA41 | A | B |
| FA42 | A | B |
| FA43 | A | A |
| FA44 | A | A |
| FA45 | A | B |
| FA46 | B | A |
| FA47 | C | C |
| FA48 | C | C |
| FA49 | B | A |
| FA50 | A | A |
| FA51 | C | C |
| FA52 | C | C |
| FA53 | C | C |
| FA54 | C | C |
| FA55 | C | C |
| FA56 | C | C |
| FA57 | A | B |
| FA58 | A | C |
| FA59 | A | A |
| FA60 | A | A |
| FA61 | A | A |
| FA62 | A | A |
| FA63 | A | A |
| FA64 | A | A |
| FA65 | A | A |
| FA66 | A | A |
| FA67 | C | C |
| FA68 | D | A |
| FA69 | B | A |
| FA70 | B | A |
| FA71 | B | B |
| FA72 | B | A |
| FA73 | A | B |
| FA74 | A | B |
| FA75 | B | A |
| FA76 | B | A |
| FA77 | B | A |
| CA1 | A | C |
| CA2 | B | A |
| CA3 | C | C |

The following examples serve to explain embodiments of the present invention in more detail. These examples should not be construed as being exhaustive or exclusive as to the scope of this invention.

EXAMPLES

These examples are for illustration purposes and are not to be construed as limiting the disclosure to only the embodiments disclosed in these examples.

Starting materials, reagents, and solvents that were obtained from commercial sources were used without further purification. Anhydrous solvents were purchased as SURE/SEAL™ from Aldrich and were used as received. Melting points were obtained on a Thomas Hoover Unimelt capillary melting point apparatus or an OptiMelt Automated Melting Point System from Stanford Research Systems and are uncorrected. Examples using "room temperature" were conducted in climate controlled laboratories with temperatures ranging from about 20° C. to about 24° C. Molecules are given their known names, named according to naming programs within ISIS Draw, ChemDraw or ACD Name Pro. If such programs are unable to name a molecule, the molecule is named using conventional naming rules. $^1$H NMR spectral data are in ppm (δ) and were recorded at 300, 400 or 600 MHz. $^{13}$C NMR spectral data are in ppm (δ) and were recorded at 75, 100 or 150 MHz. $^{19}$F NMR spectral data are in ppm (δ) and were recorded at 376 MHz, unless otherwise stated.

Example 1

Preparation of N-(3-chloro-1-(pyridin-3-yl)-1H-pyrazol-4-yl)-N-(cyclopropylmethyl)-2-(2-oxopyrrolidin-1-yl)acetamide Compound F98

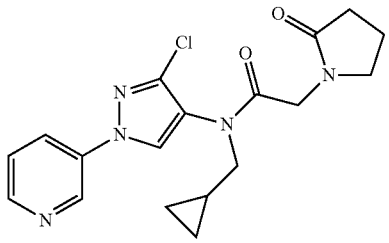 [SMILES: O=C1CCCN1CC(=O)N(CC1CC1)c1cn(-c2cccnc2)nc1Cl]

To a 7 mL vial was added 3-chloro-N-(cyclopropylmethyl)-1-(pyridin-3-yl)-1H-pyrazol-4-amine (0.124 g, 0.500 mmol) (prepared according to the U.S. Publication No. 2012/0110702), DMAP (0.183 g, 1.50 mmol), 2-(2-oxopyrrolidin-1-yl)acetic acid (0.143 g, 1.00 mmol), EDCI (0.240 g, 1.25 mmol) followed by CH$_2$Cl$_2$ (1 mL). The reaction mixture was stirred at a temperature of about 25° C. for 18 hours before it was purified by silica gel chromatography (0%-15% MeOH/CH$_2$Cl$_2$) to afford the title compound F98 as a light yellow oil (0.131 g, 70%).

The following molecules were made in accordance with the procedures disclosed in example 1:

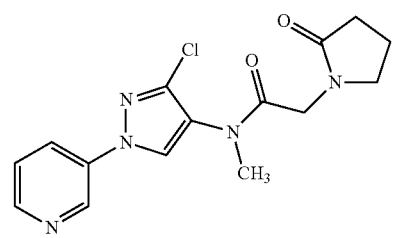

N-(3-Chloro-1-(pyridin-3-yl)-1H-pyrazol-4-yl)-N-methyl-2-(2-oxopyrrolidin-1-yl)acetamide (Compound F6) was isolated as an off-white solid (0.167 g, 100%).

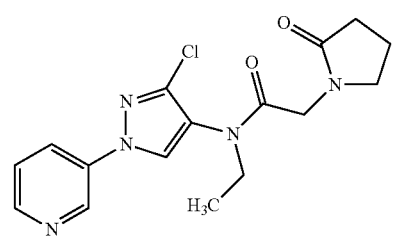

N-(3-Chloro-1-(pyridin-3-yl)-1H-pyrazol-4-yl)-N-ethyl-2-(2-oxopyrrolidin-1-yl)acetamide (Compound F124) was isolated as a light yellow oil (0.169 g, 97%).

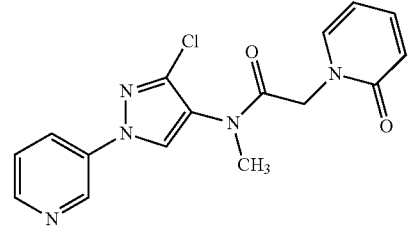

N-(3-Chloro-1-(pyridin-3-yl)-1H-pyrazol-4-yl)-N-methyl-2-(2-oxopyridin-1(2H)-yl)acetamide (Compound F3) was isolated as a white semi-solid (0.056 g, 33%).

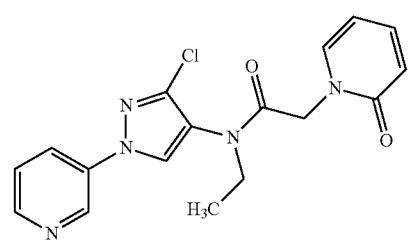

N-(3-Chloro-1-(pyridin-3-yl)-1H-pyrazol-4-yl)-N-ethyl-2-(2-oxopyridin-1(2H)-yl)acetamide (Compound F122) was isolated as a white semi-solid (0.054 g, 30%).

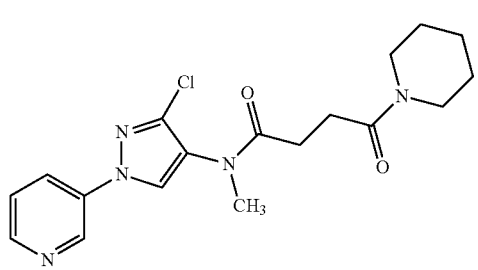
F33

N-(3-Chloro-1-(pyridin-3-yl)-1H-pyrazol-4-yl)-N-methyl-4-oxo-4-(piperidin-1-yl)butanamide (Compound F33) was isolated as a white solid (0.181 g, 95%).

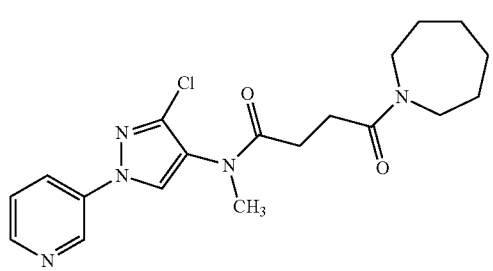
F27

4-(Azepan-1-yl)-N-(3-chloro-1-(pyridin-3-yl)-1H-pyrazol-4-yl)-N-methyl-4-oxobutanamide (Compound F27) was isolated as a white solid (0.188 g, 96%).

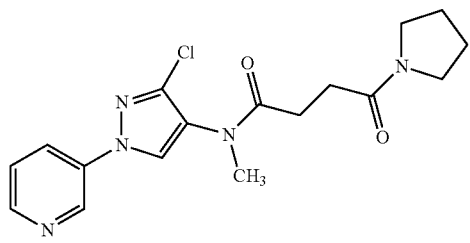
F37

N-(3-Chloro-1-(pyridin-3-yl)-1H-pyrazol-4-yl)-N-methyl-4-oxo-4-(pyrrolidin-1-yl)butanamide (Compound F37) was isolated as a white solid (0.180 g, 99%).

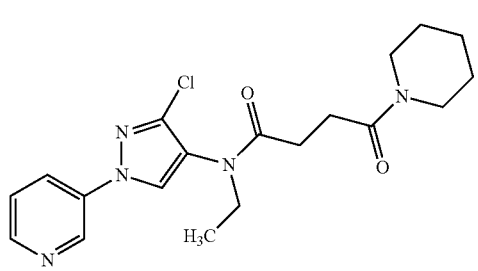
F21

N-(3-Chloro-1-(pyridin-3-yl)-1H-pyrazol-4-yl)-N-ethyl-4-oxo-4-(piperidin-1-yl)butanamide (Compound F21) was isolated as an off-white solid (0.192 g, 98%).

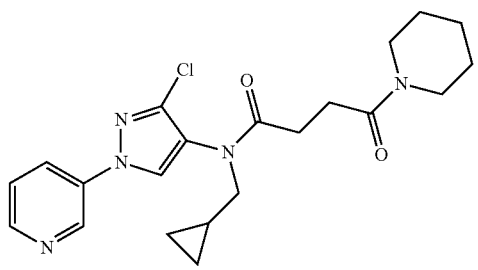
F82

N-(3-Chloro-1-(pyridin-3-yl)-1H-pyrazol-4-yl)-N-(cyclopropylmethyl)-4-oxo-4-(piperidin-1-yl)butanamide (Compound F82) was isolated as an off-white-solid (0.140 g, 67%).

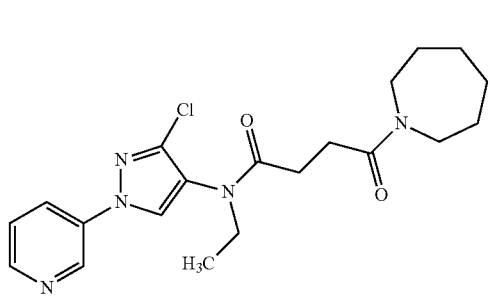
F100

4-(Azepan-1-yl)-N-(3-chloro-1-(pyridin-3-yl)-1H-pyrazol-4-yl)-N-ethyl-4-oxobutanamide (Compound F100) was isolated as an off-white solid (0.181 g, 90%).

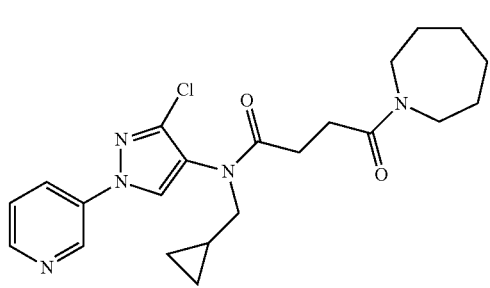
F18

4-(Azepan-1-yl)-N-(3-chloro-1-(pyridin-3-yl)-1H-pyrazol-4-yl)-N-(cyclopropylmethyl)-4-oxobutanamide (Compound F18) was isolated as an off-white solid (0.167 g, 78%).

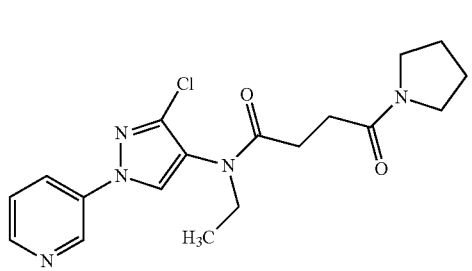
F106

N-(3-Chloro-1-(pyridin-3-yl)-1H-pyrazol-4-yl)-N-ethyl-4-oxo-4-(pyrrolidin-1-yl)butanamide (Compound F106) was isolated as a light yellow semi-solid (0.125 g, 67%).

N-(3-Chloro-1-(pyridin-3-yl)-1H-pyrazol-4-yl)-N-methyl-2-(2-oxoazepan-1-yl)acetamide (Compound F22) was isolated as an off-white solid (0.162 g, 90%).

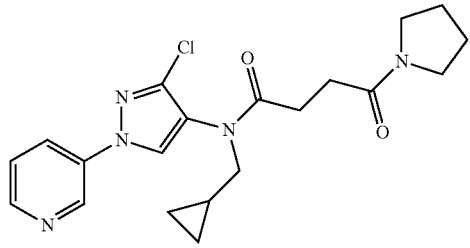

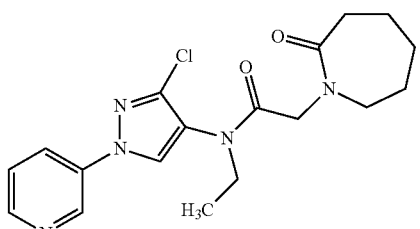

N-(3-Chloro-1-(pyridin-3-yl)-1H-pyrazol-4-yl)-N-(cyclopropylmethyl)-4-oxo-4-(pyrrolidin-1-yl)butanamide (Compound F95) was isolated as a light yellow solid (0.130 g, 65%).

N-(3-Chloro-1-(pyridin-3-yl)-1H-pyrazol-4-yl)-N-ethyl-2-(2-oxoazepan-1-yl)acetamide (Compound F123) was isolated as a light yellow semi-solid (0.152 g, 81%).

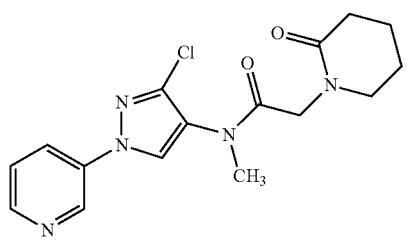

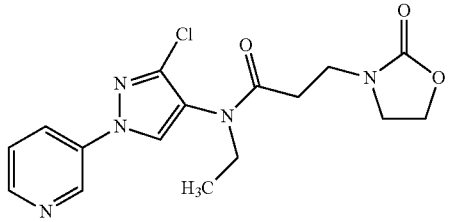

N-(3-Chloro-1-(pyridin-3-yl)-1H-pyrazol-4-yl)-N-methyl-2-(2-oxopiperidin-1-yl)acetamide (Compound F77) was isolated as an off-white solid (0.062 g, 36%).

N-(3-Chloro-1-(pyridin-3-yl)-1H-pyrazol-4-yl)-N-ethyl-3-(2-oxooxazolidin-3-yl)propanamide (Compound 69) was isolated as a colorless semi-solid (0.178 g, 98%).

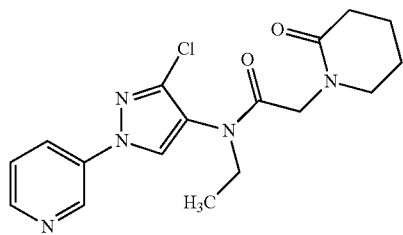

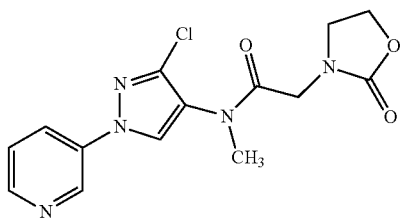

N-(3-Chloro-1-(pyridin-3-yl)-1H-pyrazol-4-yl)-N-ethyl-2-(2-oxopiperidin-1-yl)acetamide (Compound F47) was isolated as an off-white solid (0.045 g, 25%).

N-(3-Chloro-1-(pyridin-3-yl)-1H-pyrazol-4-yl)-N-methyl-2-(2-oxooxazolidin-3-yl)acetamide (Compound F111) was isolated as a white solid (0.150 g, 89%).

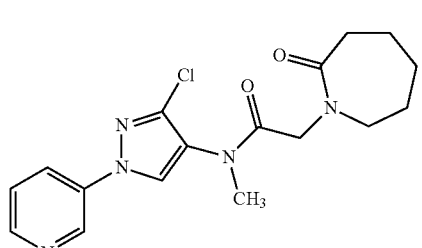

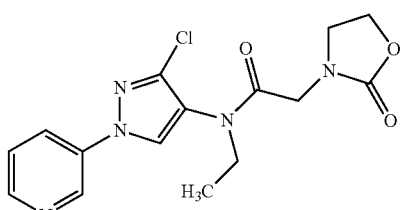

N-(3-Chloro-1-(pyridin-3-yl)-1H-pyrazol-4-yl)-N-ethyl-2-(2-oxooxazolidin-3-yl)acetamide (Compound F48) was isolated as a white solid (0.119 g, 68%).

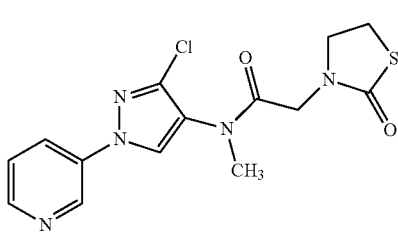
F7

N-(3-Chloro-1-(pyridin-3-yl)-1H-pyrazol-4-yl)-N-methyl-2-(2-oxothiazolidin-3-yl)acetamide (Compound F7) was isolated as a white solid (0.166 g, 94%).

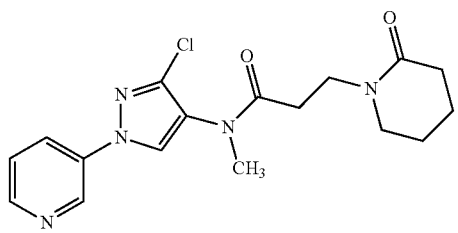
F49

N-(3-Chloro-1-(pyridin-3-yl)-1H-pyrazol-4-yl)-N-methyl-3-(2-oxopiperidin-1-yl)propanamide (Compound F49) was isolated as a colorless oil (0.193 g, 96%).

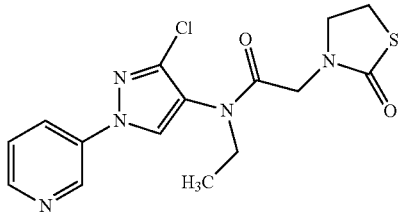
F10

N-(3-Chloro-1-(pyridin-3-yl)-1H-pyrazol-4-yl)-N-ethyl-2-(2-oxothiazolidin-3-yl)acetamide (Compound F10) was isolated as a white solid (0.146 g, 80%).

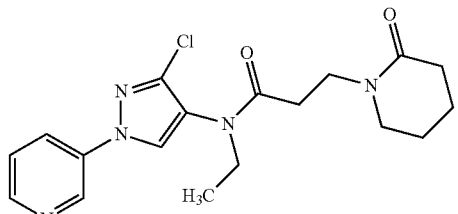
F8

N-(3-Chloro-1-(pyridin-3-yl)-1H-pyrazol-4-yl)-N-ethyl-3-(2-oxopiperidin-1-yl)propanamide (Compound F8) was isolated as a white solid (0.155 g, 82%).

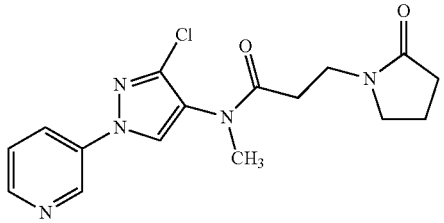
F107

N-(3-Chloro-1-(pyridin-3-yl)-1H-pyrazol-4-yl)-N-methyl-3-(2-oxopyrrolidin-1-yl)propanamide (Compound F107) was isolated as a colorless semi-solid (0.167 g, 96%).

N-(3-Chloro-1-(pyridin-3-yl)-1H-pyrazol-4-yl)-N-ethyl-3-(2-oxothiazolidin-3-yl)propanamide (Compound F88) was isolated as a colorless oil (0.091 g, 48%).

F39

N-(3-Chloro-1-(pyridin-3-yl)-1H-pyrazol-4-yl)-N-ethyl-3-(2-oxopyrrolidin-1-yl)propanamide (Compound F39) was isolated as a colorless oil (0.147 g, 81%).

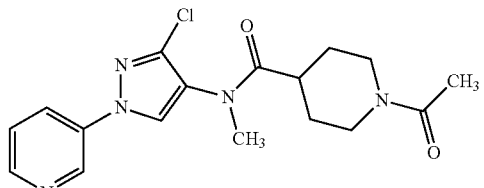
F29

1-Acetyl-N-(3-chloro-1-(pyridin-3-yl)-1H-pyrazol-4-yl)-N-methylpiperidine-4-carboxamide
(Compound F29) was isolated as a white semi-solid (0.206 g, 85%).

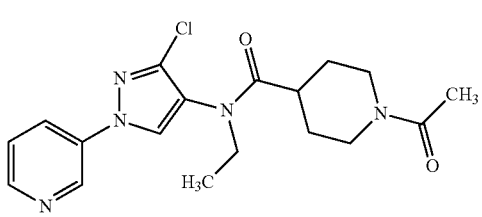

F61

1-Acetyl-N-(3-chloro-1-(pyridin-3-yl)-1H-pyrazol-4-yl)-N-ethylpiperidine-4-carboxamide (Compound F61) was isolated as a white semi-solid (0.217 g, 87%).

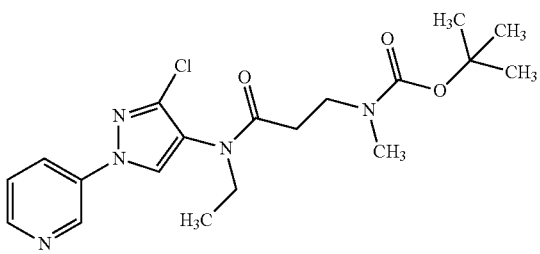

F52 tert-Butyl(3-((3-chloro-1-(pyridin-3-yl)-1H-pyrazol-4-yl)(ethyl)amino)-3-oxopropyl)(methyl)carbamate (Compound F52) was isolated as a colorless oil (0.192 g, 75%).

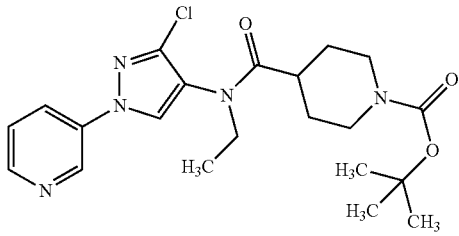

F110 tert-Butyl 4-((3-chloro-1-(pyridin-3-yl)-1H-pyrazol-4-yl)(ethyl carbamoyl) piperidine-1-carboxylate (Compound F110) was isolated as a white semi-solid (2 g, 77%).

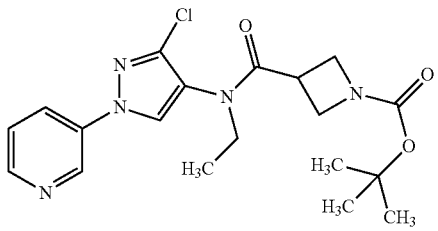

F26 tert-Butyl 3-((3-chloro-1-(pyridin-3-yl)-1H-pyrazol-4-yl)(ethyl) carbamoyl azetidine-1-carboxylate (Compound F26) was isolated as a white semi-solid (2 g, 82%).

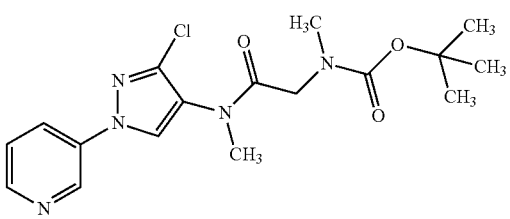

F90 tert-Butyl(2-((3-chloro-1-(pyridin-3-yl)-1H-pyrazol-4-yl)(methyl)amino)-2-oxoethyl)(methyl)carbamate (Compound F90) was isolated as a colorless oil (2 g, 73%).

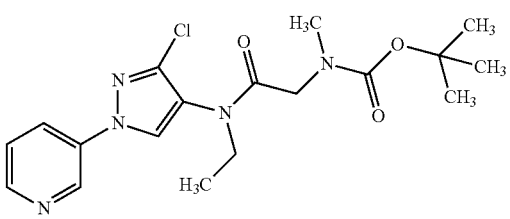

F4 tert-Butyl(2-((3-chloro-1-(pyridin-3-yl)-1H-pyrazol-4-yl)(ethyl)amino)-2-oxoethyl)(methyl)carbamate (Compound F4) was isolated as a colorless oil (0.616 g, 87%).

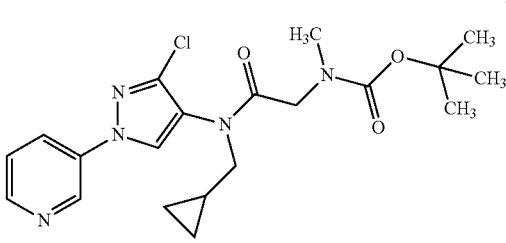

F76 tert-Butyl(2-((3-chloro-1-(pyridin-3-yl)-1H-pyrazol-4-yl)(cyclopropylmethyl)amino)-2-oxoethyl)(methyl)carbamate (Compound F76) was isolated as a white semi-solid (0.642 g, 95%).

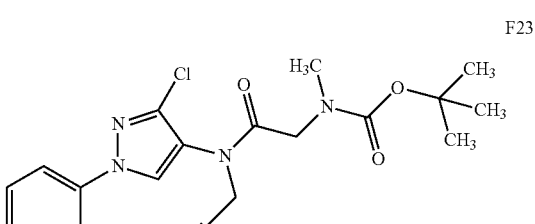

F23 tert-Butyl(2-((3-chloro-1-(pyridin-3-yl)-1H-pyrazol-4-yl)(prop-2-yn-1-yl)amino)-2-oxoethyl)(methyl)carbamate (Compound F23) was isolated as a white solid (0.513 g, 74%).

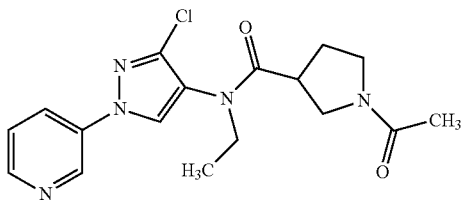
P20

1-Acetyl-N-(3-chloro-1-(pyridin-3-yl)-1H-pyrazol-4-yl)-N-ethylpyrrolidine-3-carboxamide (Compound P20) was isolated as a white solid (0.202 g, 88%).

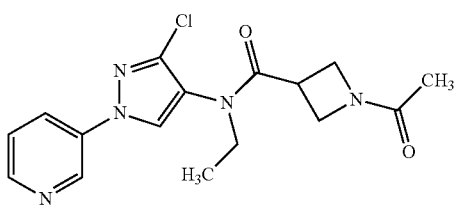
P23

1-Acetyl-N-(3-chloro-1-(pyridin-3-yl)-1H-pyrazol-4-yl)-N-ethylazetidine-3-carboxamide (Compound P23) was isolated as a white solid (0.162 g, 74%).

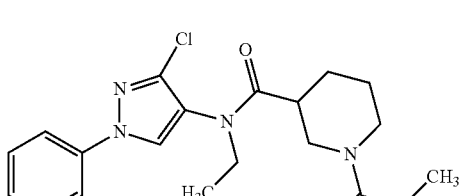
FA3

N-(3-Chloro-1-(pyridin-3-yl)-1H-pyrazol-4-yl)-N-ethyl-1-isobutyrylpiperidine-3-carboxamide (Compound FA3) was isolated as a white semi-solid (0.216 g, 80%).

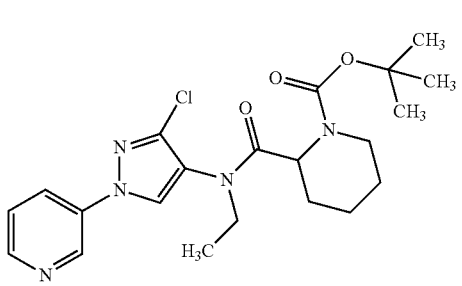
FA13 tert-Butyl 2-((3-chloro-1-(pyridin-3-yl)-1H-pyrazol-4-yl)(ethyl)carbamoyl) piperidine-1-carboxylate (Compound FA13) was isolated as a white semi-solid (0.123 g, 28%).

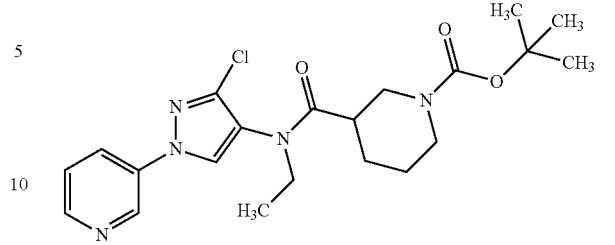
FA18 tert-Butyl 3-((3-chloro-1-(pyridin-3-yl)-1H-pyrazol-4-yl)(ethyl)carbamoyl) piperidine-1-carboxylate (Compound FA18) was isolated as a yellow semi-solid (1.08 g, 45%).

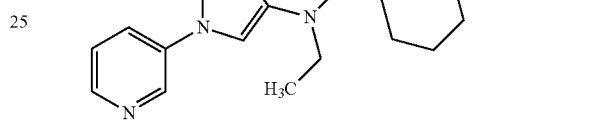
FA32

1-Acetyl-N-(3-chloro-1-(pyridin-3-yl)-1H-pyrazol-4-yl)-N-ethylpiperidine-2-carboxamide (Compound FA32) was isolated as a yellow oil (0.121 g, 61%).

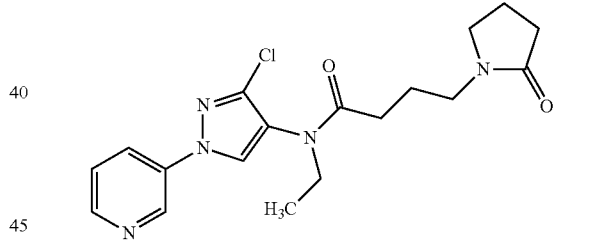
FA33

N-(3-Chloro-1-(pyridin-3-yl)-1H-pyrazol-4-yl)-N-ethyl-4-(2-oxopyrrolidin-1-yl)butanamide (Compound FA33) was isolated as a yellow oil (0.151 g, 72%).

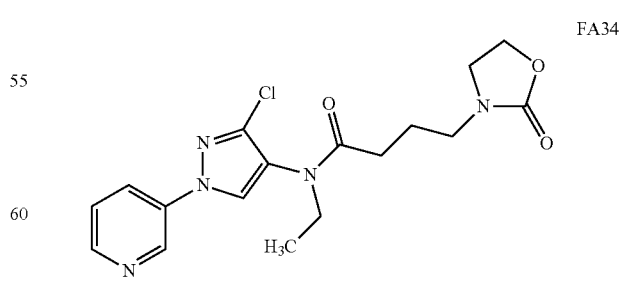
FA34

N-(3-Chloro-1-(pyridin-3-yl)-1H-pyrazol-4-yl)-N-ethyl-4-(2-oxooxazolidin-3-yl)butanamide (Compound FA34) was isolated as a yellow oil (0.148 g, 71%).

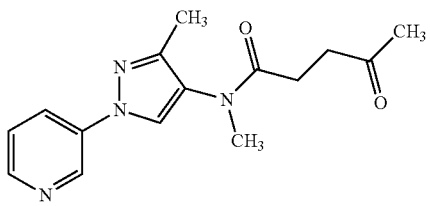

N-methyl-N-(3-methyl-1-(pyridin-3-yl)-1H-pyrazol-4-yl)-4-oxopentanamide (Compound FA69) was isolated as a colorless oil (0.114 g, 75%).

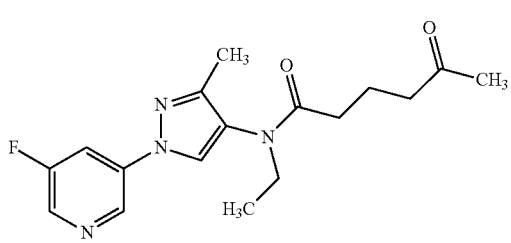

N-Ethyl-N-(1-(5-fluoropyridin-3-yl)-3-methyl-1H-pyrazol-4-yl)-5-oxohexanamide (Compound FA70) was isolated as a colorless oil (0.119 g, 79%).

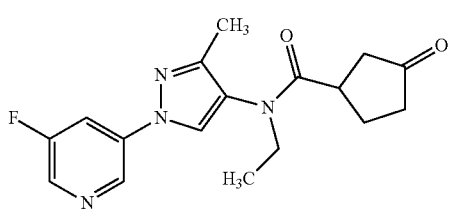

N-Ethyl-N-(1-(5-fluoropyridin-3-yl)-3-methyl-1H-pyrazol-4-yl)-3-oxocyclopentanecarboxamide (Compound FA71) was isolated as a tan solid (0.1 g, 62%).

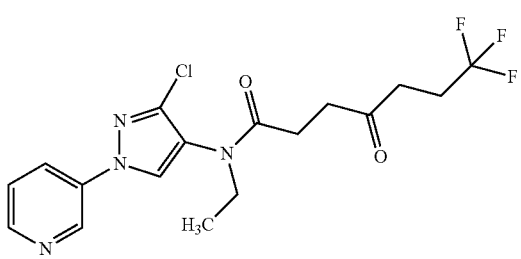

N-(3-Chloro-1-(pyridin-3-yl)-1H-pyrazol-4-yl)-N-ethyl-7,7,7-trifluoro-4-oxoheptanamide (Compound FA76) was isolated as a brown viscous oil (0.059 g, 50%).

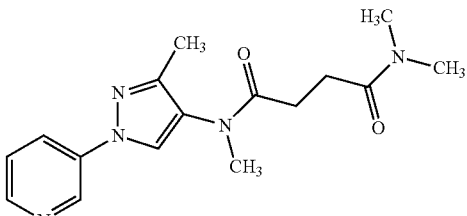

N-[3-Chloro-1-(3-pyridyl)pyrazol-4-yl]-N-ethyl-2-methyl-pent-4-enamide (Compound CA1) was isolated as a clear, colorless oil (0.502 g, 75%): $^1$H NMR (400 MHz, CDCl$_3$) δ 8.94 (dd, J=2.7, 0.8 Hz, 1H), 8.63 (dd, J=4.8, 1.5 Hz, 1H), 8.05 (ddd, J=8.3, 2.8, 1.5 Hz, 1H), 7.91 (s, 1H), 7.46 (ddd, J=8.4, 4.8, 0.8 Hz, 1H), 5.75-5.59 (m, 1H), 5.07-4.97 (m, 2H), 3.69 (d, J=47.8 Hz, 2H), 2.44 (ddt, J=28.2, 14.3, 7.2 Hz, 2H), 2.07 (tdd, J=7.5, 6.2, 5.0 Hz, 1H), 1.15 (t, J=7.2 Hz, 3H), 1.09 (d, J=6.6 Hz, 3H); ESIMS m/z 319 ([M+H]$^+$).

Example 2

Preparation of N1,N1,N4-trimethyl-N4-(3-methyl-1-(pyridin-3-yl)-1H-pyrazol-4-yl)succinamide Compound F62

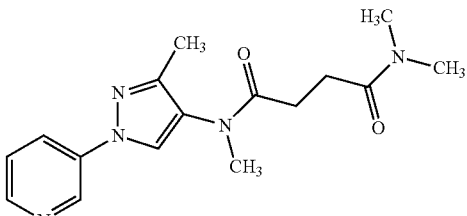

To an ice cold solution of 4-(dimethylamino)-4-oxobutanoic acid (0.174 g, 1.20 mmol) in CH$_2$Cl$_2$ (2 mL) was added DIPEA (0.208 mL, 1.120 mmol) followed by isobutyl chloroformate (0.138 mL, 1.06 mmol). The mixture was stirred for 10 minutes, and the resulting mixed anhydride was added to a solution of N,3-dimethyl-1-(pyridin-3-yl)-1H-pyrazol-4-amine (0.100 g, 0.531 mmol) in CH$_2$Cl$_2$ (0.66 mL). The reaction mixture was stirred at room temperature (about 22° C.) for one hour. The crude reaction mixture was concentrated and purified via reverse phase column chromatography (0%-100% acetonitrile (MeCN)/water) to give the desired product F62 as a white solid (0.155 g, 83%).

The following molecules were made in accordance with the procedures disclosed in example 2:

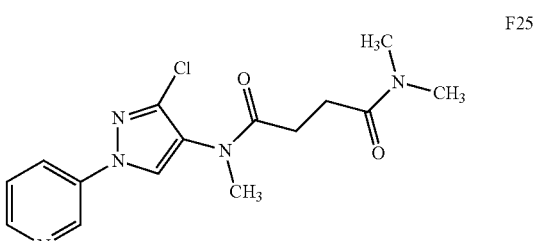

N1-(3-Chloro-1-(pyridin-3-yl)-1H-pyrazol-4-yl)-N1,N4,N4-trimethyl succinamide (Compound F25) was isolated as a white solid (0.122 g, 68%).

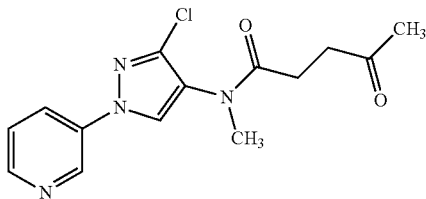

FA75

N-(3-Chloro-1-(pyridin-3-yl)-1H-pyrazol-4-yl)-N-methyl-4-oxopentanamide (FA75) was isolated as a brown solid (1.26 g, 58%).

Example 3

Preparation of 4-((3-chloro-1-(pyridin-3-yl)-1H-pyrazol-4-yl)(ethyl)amino)-4-oxobutanoic acid Compound C1

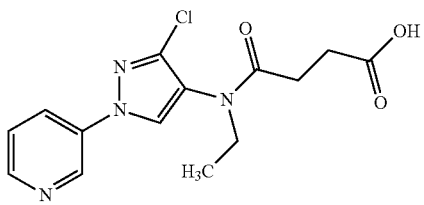 [SMILES: CCN(C(=O)CCC(=O)O)c1cn(-c2cccnc2)nc1Cl]

To a 100 mL round-bottomed flask with a stir bar was added 3-chloro-N-ethyl-1-(pyridin-3-yl)-1H-pyrazol-4-amine (0.500 g, 2.25 mmol), DMAP (0.0274 g, 0.225 mmol), triethylamine (0.469 mL, 3.37 mmol), and dihydrofuran-2,5-dione (0.449 g, 4.49 mmol) with DCE (22.5 mL). After heating at a temperature of about 60° C. under nitrogen ($N_2$) overnight, the reaction mixture was concentrated and purified by silica gel flash column chromatography eluting with 0%-15% MeOH/$CH_2Cl_2$ to afford the title compound C1 as an off-white solid (0.635 g, 86%): IR (thin film) 3097, 1661 $cm^{-1}$; $^1$H NMR (400 MHz, $CDCl_3$) δ 9.00 (s, 1H), 8.59 (d, J=4.8 Hz, 1H), 8.15 (ddd, J=8.4, 2.6, 1.4 Hz, 1H), 8.12 (s, 1H), 7.49 (dd, J=8.4, 4.8 Hz, 1H), 3.72 (q, J=7.2 Hz, 2H), 3.49 (s, 1H), 2.72 (d, J=10.6 Hz, 2H), 2.47 (t, J=6.4 Hz, 2H), 1.16 (t, J=7.2 Hz, 3H); ESIMS m/z 323 ([M+H]$^+$).

Example 4

Preparation of N1-(3-chloro-1-(pyridin-3-yl)-1H-pyrazol-4-yl)-N1-ethyl-N4-methyl-N4-(3,3,3-trifluoropropyl)succinamide Compound F108

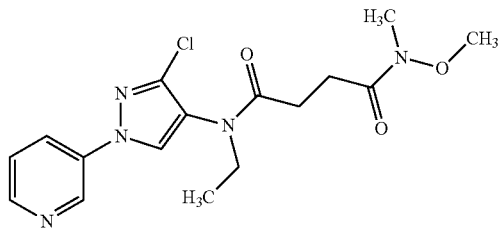

A solution of 4-((3-chloro-1-(pyridin-3-yl)-1H-pyrazol-4-yl)(ethyl)amino)-4-oxobutanoic acid (0.100 g, 0.310 mmol), DMAP (0.129 g, 1.05 mmol), and 3,3,3-trifluoro-N-methylpropan-1-amine (0.0394 g, 0.310 mmol) in dry $CH_2Cl_2$ (1.0 mL) was cooled to a temperature of about 0° C. under $N_2$. N,N'-Methanediylidenedicyclohexanamine (0.153 mg, 0.744 mmol) was added, and the reaction was slowly warmed up to room temperature under $N_2$, then stirred at room temperature overnight. The reaction mixture was filtered using additional $CH_2Cl_2$ (0.5 mL) to remove solids and concentrated under reduced pressure. The residue was purified by silica gel chromatography eluting with 0%-5% MeOH/$CH_2Cl_2$ to afford the title compound F108 as a clear viscous oil (0.078 g, 57%).

The following molecules were made in accordance with the procedures disclosed in example 4:

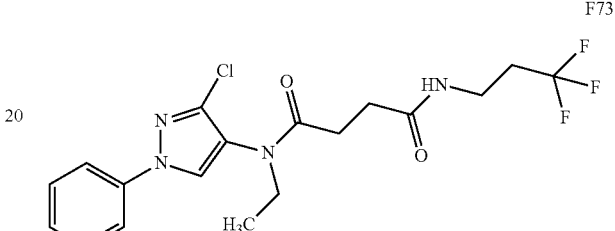

F73

N1-(3-Chloro-1-(pyridin-3-yl)-1H-pyrazol-4-yl)-N1-ethyl-N4-(3,3,3-trifluoropropyl)succinamide (Compound F73) was isolated as a clear foam (0.389 g, 76%).

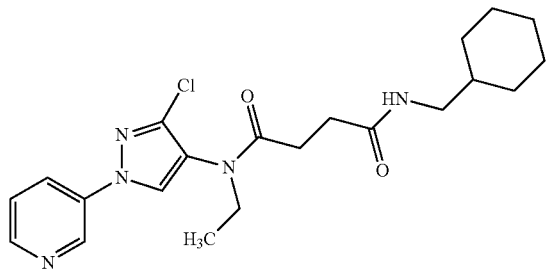

F78

N1-(3-Chloro-1-(pyridin-3-yl)-1H-pyrazol-4-yl)-N1-ethyl-N4-methoxy-N4-methylsuccinamide (Compound F78) was isolated as a white semi-solid (0.307 g, 65%).

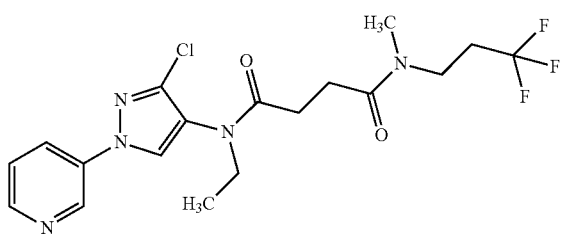 [SMILES: CCN(C(=O)CCC(=O)N(C)CCC(F)(F)F)c1cn(-c2cccnc2)nc1Cl]

F15

N1-(3-Chloro-1-(pyridin-3-yl)-1H-pyrazol-4-yl)-N4-(cyclohexylmethyl)-N1-ethylsuccinamide (Compound F15) was isolated as a light yellow solid (0.048 g, 52%).

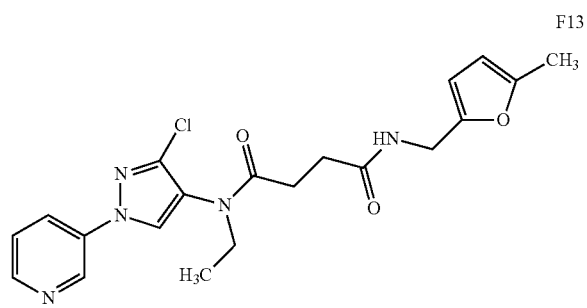 [SMILES: CCN(C(=O)CCC(=O)NCc1ccc(C)o1)c1cn(-c2cccnc2)nc1Cl]

F13

N1-(3-Chloro-1-(pyridin-3-yl)-1H-pyrazol-4-yl)-N1-ethyl-N4-((5-methylfuran-2-yl)methyl)succinamide (Compound F13) was isolated as a slightly yellow solid (0.072 g, 64%).

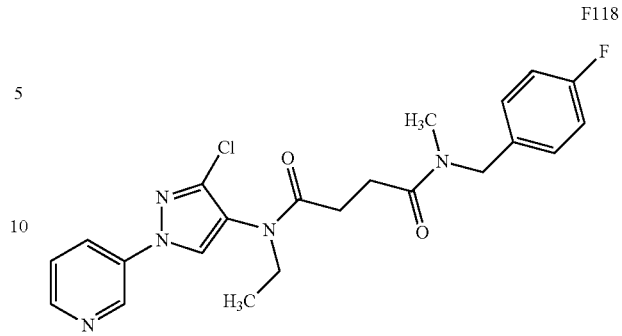

F118

N1-(3-Chloro-1-(pyridin-3-yl)-1H-pyrazol-4-yl)-N1-ethyl-N4-(4-fluorobenzyl)-N4-methylsuccinamide (Compound F118) was isolated as a cloudy white viscous semi-solid (0.041 g, 36%).

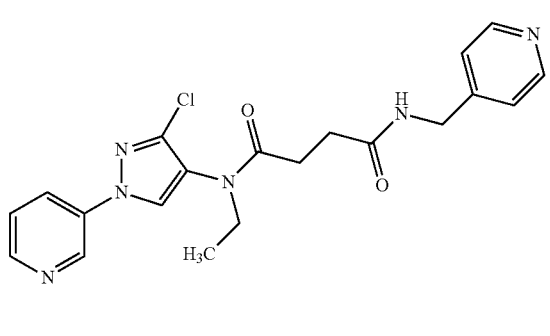

F115

N1-(3-Chloro-1-(pyridin-3-yl)-1H-pyrazol-4-yl)-N1-ethyl-N4-(pyridin-4-ylmethyl)succinamide (Compound F115) was isolated as a light yellow solid (0.076 g, 64%).

F30

N1-(3-Chloro-1-(pyridin-3-yl)-1H-pyrazol-4-yl)-N4-(cyclopropylmethyl)-N1-ethyl-N4-methylsuccinamide (Compound F30) was isolated as a light yellow clear viscous oil (0.069 g, 70%).

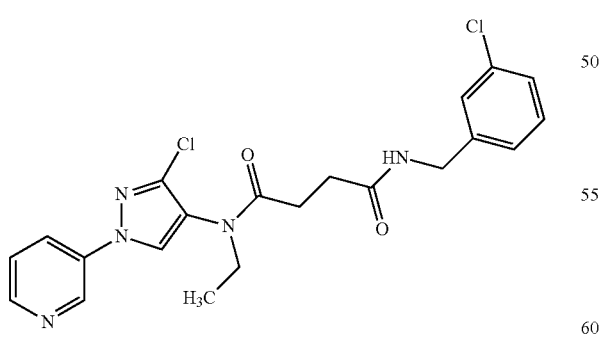

F68

N1-(3-Chloro-1-(pyridin-3-yl)-1H-pyrazol-4-yl)-N4-(3-chlorobenzyl)-N1-ethylsuccinamide (Compound F68) was isolated as a viscous slightly cloudy oil (0.083 g, 71%).

F70

N1-(3-Chloro-1-(pyridin-3-yl)-1H-pyrazol-4-yl)-N4-(cyclopropylmethyl)-N1-ethylsuccinamide (Compound F70) was isolated as a white semi-solid (0.037 g, 38%).

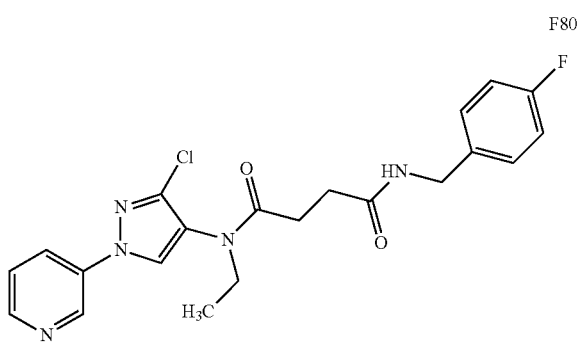 [SMILES: CCN(C(=O)CCC(=O)NCc1ccc(F)cc1)c1cn(-c2cccnc2)nc1Cl]

N1-(3-Chloro-1-(pyridin-3-yl)-1H-pyrazol-4-yl)-N1-ethyl-N4-(4-fluorobenzyl)succinamide (Compound F80) was isolated as a white solid (0.087 g, 79%).

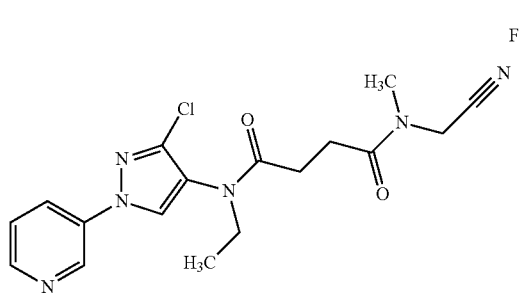

N1-(3-Chloro-1-(pyridin-3-yl)-1H-pyrazol-4-yl)-N4-(cyanomethyl)-N1-ethyl-N4-methylsuccinamide (Compound F55) was isolated as a brown viscous semi-solid (0.066 g, 67%).

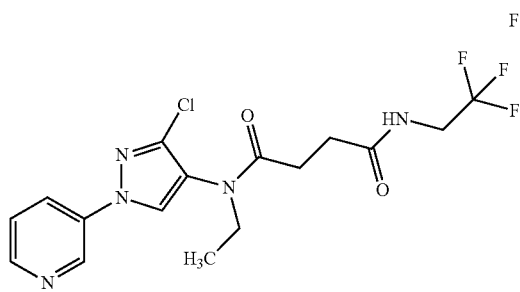

N1-(3-Chloro-1-(pyridin-3-yl)-1H-pyrazol-4-yl)-N1-ethyl-N4-(2,2,2-trifluoroethyl)succinamide (Compound F67) was isolated as a white solid (0.064 g, 61%).

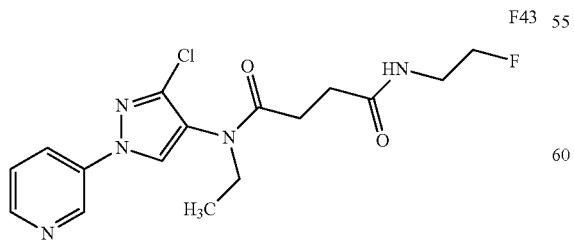

N1-(3-Chloro-1-(pyridin-3-yl)-1H-pyrazol-4-yl)-N1-ethyl-N4-(2-fluoroethyl) succinamide (Compound F43) was isolated as a clear semi-solid (0.070 g, 74%).

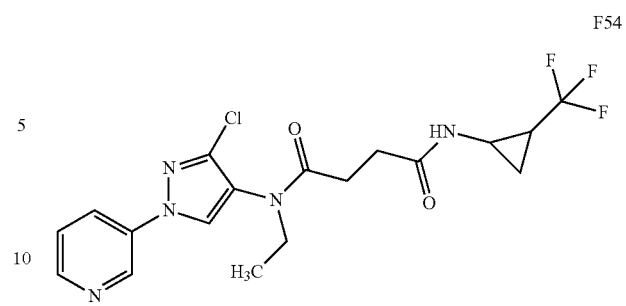

N1-(3-Chloro-1-(pyridin-3-yl)-1H-pyrazol-4-yl)-N1-ethyl-N4-(2-(trifluoromethyl)cyclopropyl)succinamide (Compound F54) was isolated as a white semi-solid (0.036 g, 31%).

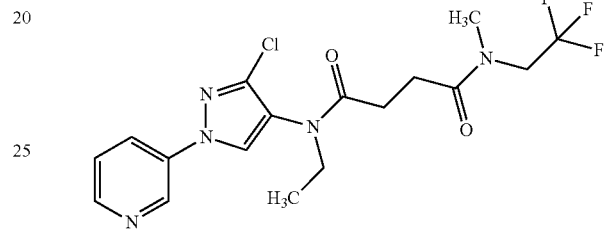

N1-(3-Chloro-1-(pyridin-3-yl)-1H-pyrazol-4-yl)-N1-ethyl-N4-methyl-N4-(2,2,2-trifluoroethyl)succinamide (Compound F85) was isolated as a light brown viscous semi-solid (0.086 g, 80%).

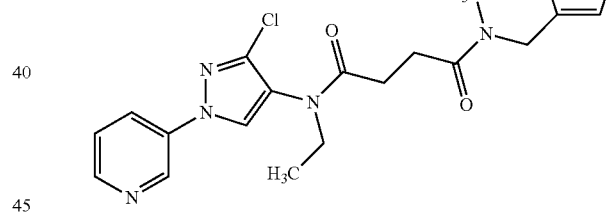

N1-(3-Chloro-1-(pyridin-3-yl)-1H-pyrazol-4-yl)-N1-ethyl-N4-(furan-2-ylmethyl)-N4-methylsuccinamide (Compound FA77) was isolated as an orange oil (0.074 g, 69%).

Example 5

Preparation of N-(2-((3-chloro-1-(pyridin-3-yl)-1H-pyrazol-4-yl)(ethyl)amino)-2-oxoethyl)-N-methylbenzamide Compound F83

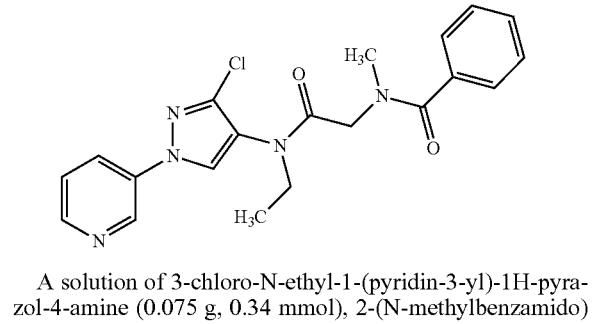

A solution of 3-chloro-N-ethyl-1-(pyridin-3-yl)-1H-pyrazol-4-amine (0.075 g, 0.34 mmol), 2-(N-methylbenzamido)

acetic acid (0.098 g, 0.51 mmol), and DMAP (0.062 g, 0.51 mmol) in dry diethyl ether (1.0 mL) and dry CH$_2$Cl$_2$ (1.1 mL) was cooled to a temperature of about 0° C. under N$_2$. DCC (0.17 g, 0.81 mmol) was added, and the reaction was slowly warmed up to room temperature under N$_2$, then stirred at room temperature overnight. The reaction mixture was filtered using additional CH$_2$Cl$_2$ (0.5 mL) to remove solids and concentrated under reduced pressure. The residue was purified by silica gel chromatography eluting with 0%-10% MeOH/CH$_2$Cl$_2$ to afford the title compound F83 as a white solid (0.12 g, 87%).

The following molecules were made in accordance with the procedures disclosed in example 5:

F19

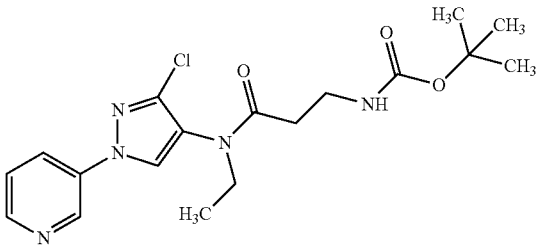

tert-Butyl(3-((3-chloro-1-(pyridin-3-yl)-1H-pyrazol-4-yl)(ethyl)amino)-3-oxopropyl)carbamate (Compound F19) was isolated as a white solid (1.506 g, 83%).

F2

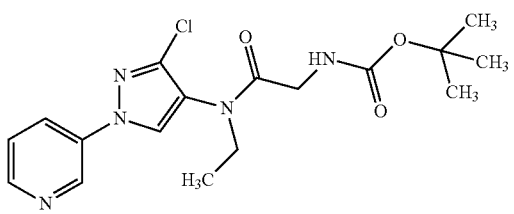

tert-Butyl(2-((3-chloro-1-(pyridin-3-yl)-1H-pyrazol-4-yl)(ethyl)amino)-2-oxoethyl)carbamate (Compound F2) was isolated as a pink solid (1.256 g, 71%).

Example 6

Preparation of 3-amino-N-(3-chloro-1-(pyridin-3-yl)-1H-pyrazol-4-yl)-N-ethylpropanamide Compound C2

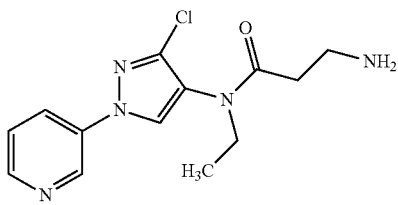 [SMILES: CCN(C(=O)CCN)c1cn(-c2cccnc2)nc1Cl]

To a solution of tert-butyl(3-((3-chloro-1-(pyridin-3-yl)-1H-pyrazol-4-yl) (ethyl)amino)-3-oxopropyl)carbamate (0.100 g, 0.254 mmol) in dry CH$_2$Cl$_2$ (0.254 mL, 0.254 mmol), TFA (0.254 mL, 0.254 mmol) was added at room temperature under N$_2$. The reaction was stirred at room temperature for about 2 hours. Saturated aqueous sodium bicarbonate (NaHCO$_3$) (about 5 mL) was carefully added until reaction mixture became basic. The reaction product was extracted with CH$_2$Cl$_2$ (3×5 mL), dried and concentrated. Crude product was generally used without purification in most cases. The product can be purified by reverse phase silica gel chromatography eluting with 10%-100% MeCN/water to afford the title compound C2 as a viscous light yellow oil (0.0160 g, 22%): IR (thin film) 3368, 3091, 1657 cm$^{-1}$; $^1$H NMR (400 MHz, CDCl$_3$) δ 8.95 (dd, J=2.8, 0.8 Hz, 1H), 8.62 (dd, J=4.7, 1.5 Hz, 1H), 8.04 (ddd, J=8.3, 2.7, 1.4 Hz, 1H), 7.98 (s, 1H), 7.46 (ddd, J=8.3, 4.7, 0.8 Hz, 1H), 3.71 (q, J=7.2 Hz, 2H), 2.97 (t, J=6.1 Hz, 2H), 2.32 (t, J=6.1 Hz, 2H), 1.72 (s, 2H), 1.16 (t, J=7.2 Hz, 3H); HRMS-FAB (m/z) ([M+H]$^+$) calc'd for C$_{13}$H$_{17}$Cl N$_5$O, 294.1116. found, 294.1117.

Example 7

Preparation of N-(3-((3-chloro-1-(pyridin-3-yl)-1H-pyrazol-4-yl)(ethyl)amino)-3-oxopropyl)-2,2-difluoro-1-methylcyclopropanecarboxamide Compound F113

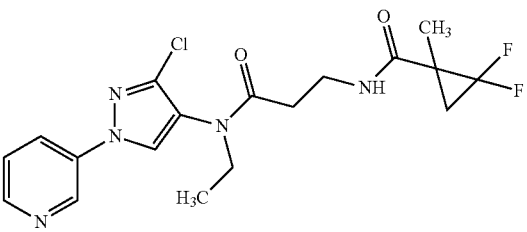 [SMILES: CCN(C(=O)CCNC(=O)C1(C)CC1(F)F)c1cn(-c2cccnc2)nc1Cl]

A solution of 3-amino-N-(3-chloro-1-(pyridin-3-yl)-1H-pyrazol-4-yl)-N-ethylpropanamide (0.074 mg, 0.25 mmol), DMAP (0.047 mg, 0.38 mmol), 2,2-difluoro-1-methylcyclopropanecarboxylic acid (0.052 mg, 0.38 mmol) in dry CH$_2$Cl$_2$ (1.69 mL) was cooled to a temperature of about 0° C. under N$_2$. DCC (0.13 g, 0.61 mmol) was added, and the reaction was slowly warmed up to room temperature under N$_2$, then stirred at room temperature overnight. The reaction mixture was filtered using additional CH$_2$Cl$_2$ (0.5 mL) to remove solids and concentrated under reduced pressure. The product was purified by silica gel chromatography eluting with 0%-10% MeOH/CH$_2$Cl$_2$ to afford the title compound F113 as a yellow viscous oil (0.029 g, 26% over 2 steps from compound C2).

The following molecules were made in accordance with the procedures disclosed in example 7:

F75

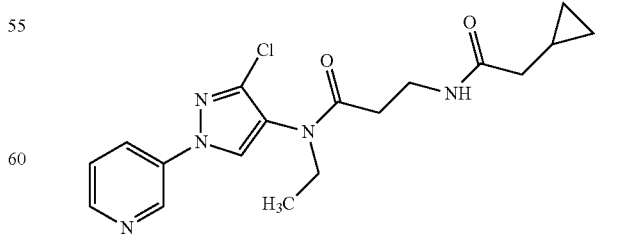

N-(3-Chloro-1-(pyridin-3-yl)-1H-pyrazol-4-yl)-3-(2-cyclopropylacetamido)-N-ethylpropanamide (Compound F75) was isolated as a white hard sticky foam (0.090 g, 84%).

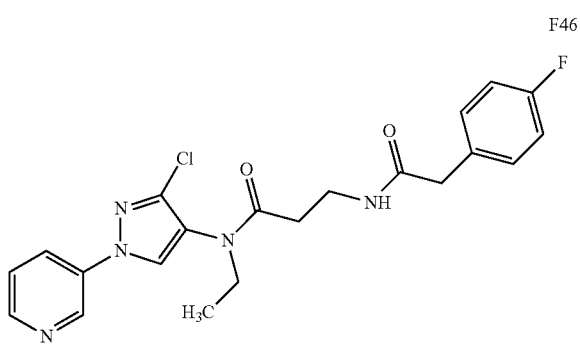 [SMILES: CCN(C(=O)CCNC(=O)Cc1ccc(F)cc1)c1cn(-c2cccnc2)nc1Cl]

N-(3-Chloro-1-(pyridin-3-yl)-1H-pyrazol-4-yl)-N-ethyl-3-(2-(4-fluorophenyl) acetamido) propanamide (Compound F46) was isolated as a white solid (0.066 g, 83%).

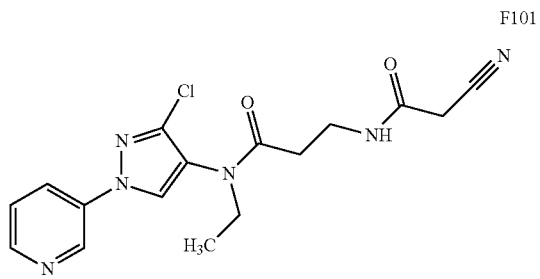 [SMILES: CCN(C(=O)CCNC(=O)CC#N)c1cn(-c2cccnc2)nc1Cl]

N-(3-Chloro-1-(pyridin-3-yl)-1H-pyrazol-4-yl)-3-(2-cyanoacetamido)-N-ethylpropanamide (Compound F101) was isolated as a light yellow solid (0.075 g, 83%).

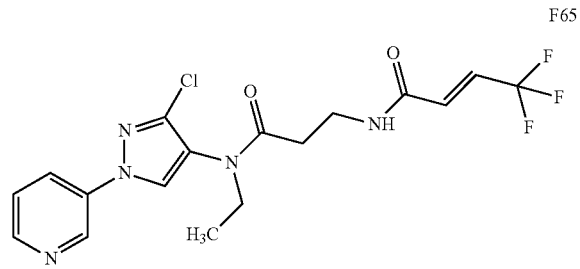 [SMILES: CCN(C(=O)CCNC(=O)/C=C/C(F)(F)F)c1cn(-c2cccnc2)nc1Cl]

(E)-N-(3-((3-Chloro-1-(pyridin-3-yl)-1H-pyrazol-4-yl)(ethyl)amino)-3-oxopropyl)-4,4,4-trifluorobut-2-enamide (Compound F65) was isolated as a brown solid (0.026 g, 24% over two steps from compound C2).

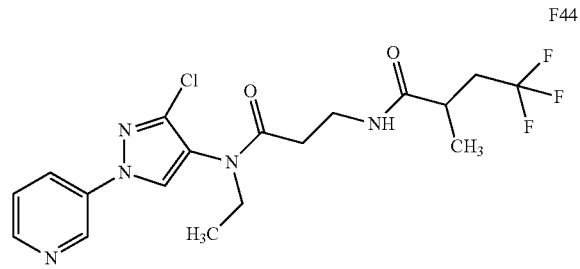 [SMILES: CCN(C(=O)CCNC(=O)C(C)CC(F)(F)F)c1cn(-c2cccnc2)nc1Cl]

N-(3-((3-Chloro-1-(pyridin-3-yl)-1H-pyrazol-4-yl)(ethyl)amino)-3-oxopropyl)-4,4,4-trifluoro-2-methylbutanamide (Compound F44) was isolated as an off-white foam (0.050 g, 37% over two steps from compound C2).

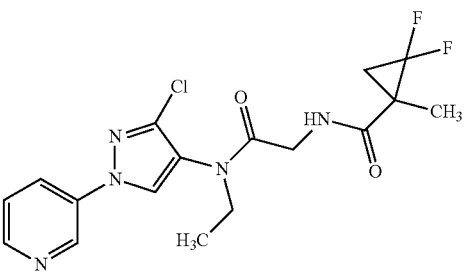

N-(2-((3-Chloro-1-(pyridin-3-yl)-1H-pyrazol-4-yl)(ethyl)amino)-2-oxoethyl)-2,2-difluoro-1-methylcyclopropanecarboxamide (Compound F1) was isolated as a white solid (0.055 g, 41% over two steps from compound C2).

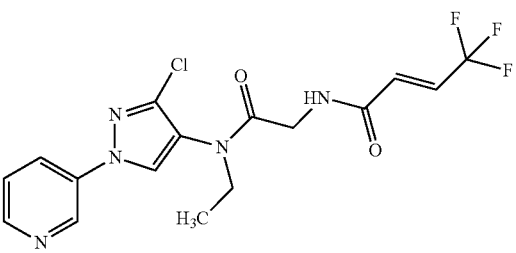

(E)-N-(2-((3-Chloro-1-(pyridin-3-yl)-1H-pyrazol-4-yl)(ethyl)amino)-2-oxoethyl)-4,4,4-trifluorobut-2-enamide (Compound F99) was isolated as an orange oil (0.061 g, 46% over two steps from compound C2).

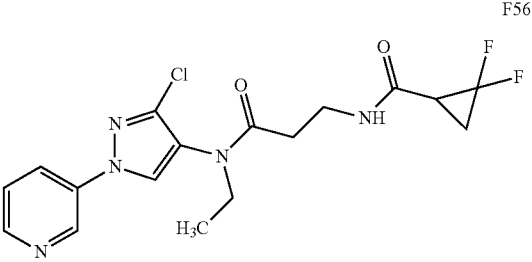 [SMILES: CCN(C(=O)CCNC(=O)C1CC1(F)F)c1cn(-c2cccnc2)nc1Cl]

N-(3-((3-Chloro-1-(pyridin-3-yl)-1H-pyrazol-4-yl)(ethyl)amino)-3-oxopropyl)-2,2-difluorocyclopropanecarboxamide (Compound F56) was isolated as a light brown solid (0.045 g, 35% over two steps from compound C2).

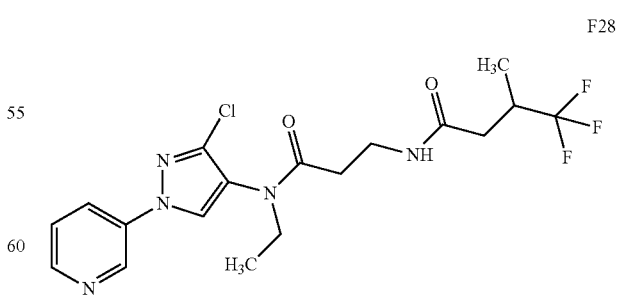

N-(3-((3-Chloro-1-(pyridin-3-yl)-1H-pyrazol-4-yl)(ethyl)amino)-3-oxopropyl)-4,4,4-trifluoro-3-methylbutanamide (Compound F28) was isolated as an off-white foam (0.044 g, 33% over two steps from compound C2).

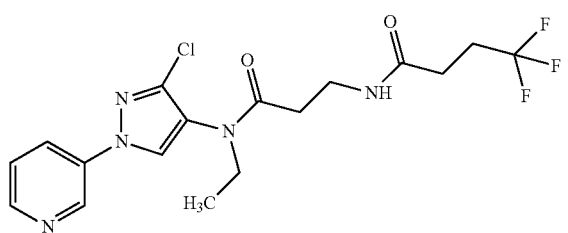

F12

N-(3-((3-Chloro-1-(pyridin-3-yl)-1H-pyrazol-4-yl)(ethyl)amino)-3-oxopropyl)-4,4,4-trifluorobutanamide (Compound F12) was isolated as an off-white semi-solid (0.044 g, 33% over two steps from compound C2).

F97

N-(2-((3-Chloro-1-(pyridin-3-yl)-1H-pyrazol-4-yl)(ethyl)amino)-2-oxoethyl)-4,4,4-trifluorobutanamide (Compound F97) was isolated as an off-white solid (0.080 g, 61% over two steps from compound C2).

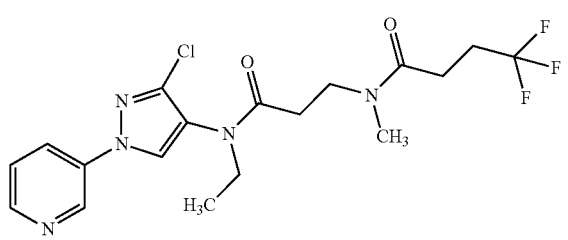

F94

N-(3-((3-Chloro-1-(pyridin-3-yl)-1H-pyrazol-4-yl)(ethyl)amino)-3-oxopropyl)-4,4,4-trifluoro-N-methylbutanamide (Compound F94) was isolated as a viscous clear oil (0.083 g, 81%).

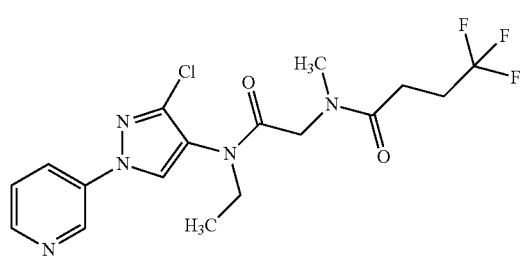

F5

N-(2-((3-Chloro-1-(pyridin-3-yl)-1H-pyrazol-4-yl)(ethyl)amino)-2-oxoethyl)-4,4,4-trifluoro-N-methylbutanamide (Compound F5) was isolated as a light yellow foam (0.076 g, 75%).

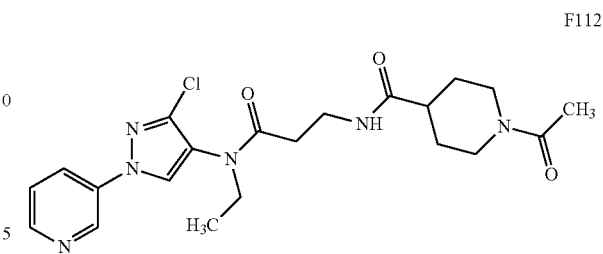

F112

1-Acetyl-N-(3-((3-chloro-1-(pyridin-3-yl)-1H-pyrazol-4-yl)(ethyl)amino)-3-oxopropyl)piperidine-4-carboxamide (Compound F112) was isolated as a white foam (35 mg, 19% over two steps from compound C11).

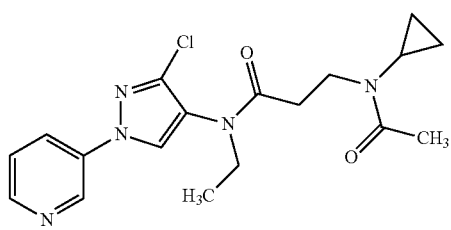

F9

N-(3-Chloro-1-(pyridin-3-yl)-1H-pyrazol-4-yl)-3-(N-cyclopropylacetamido)-N-ethylpropanamide (Compound F9) was isolated as a yellow oil (0.074 g, 59%).

P16

N-(3-Chloro-1-(pyridin-3-yl)-1H-pyrazol-4-yl)-N-ethyl-1-(3,3,3-trifluoropropanoyl)piperidine-4-carboxamide (Compound P16) was isolated as a white semi-solid (0.154 g, 81%).

P21

N-(3-Chloro-1-(pyridin-3-yl)-1H-pyrazol-4-yl)-N-ethyl-1-(3,3,3-trifluoropropanoyl)pyrrolidine-3-carboxamide (Compound P21) was isolated as a white semi-solid (0.13 g, 58%).

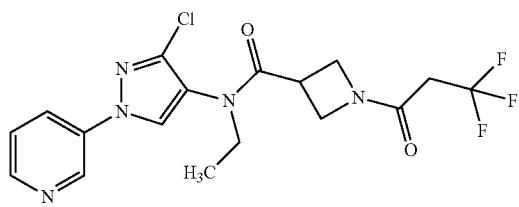

P24

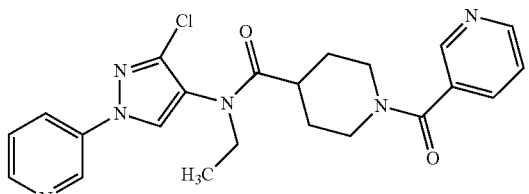

FA8

N-(3-Chloro-1-(pyridin-3-yl)-1H-pyrazol-4-yl)-N-ethyl-1-nicotinoylpiperidine-4-carboxamide (Compound FA8) was isolated as a white semi-solid (0.138 g, 60%).

N-(3-Chloro-1-(pyridin-3-yl)-1H-pyrazol-4-yl)-N-ethyl-1-(3,3,3-trifluoropropanoyl)azetidine-3-carboxamide (Compound P24) was isolated as a colorless oil (0.11 g, 50%).

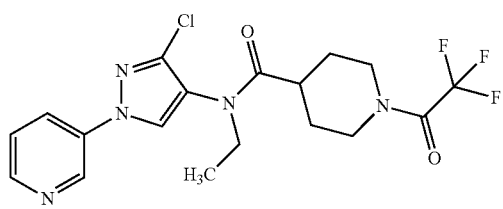

FA5

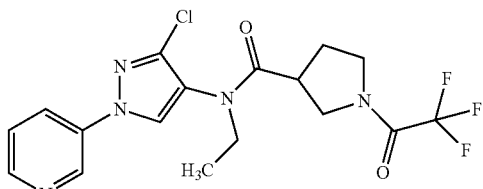

FA9

N-(3-Chloro-1-(pyridin-3-yl)-1H-pyrazol-4-yl)-N-ethyl-1-(2,2,2-trifluoroacetyl)pyrrolidine-3-carboxamide (Compound FA9) was isolated as a colorless oil (0.074 g, 34%).

N-(3-Chloro-1-(pyridin-3-yl)-1H-pyrazol-4-yl)-N-ethyl-1-(2,2,2-trifluoroacetyl)piperidine-4-carboxamide (Compound FA5) was isolated as a white solid (0.069 g, 31%).

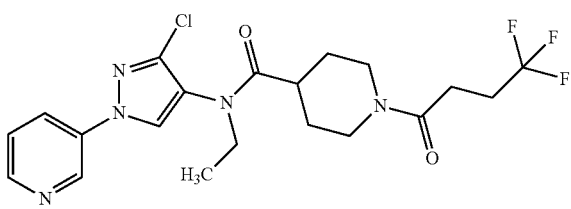

FA6

FA10

N-(3-Chloro-1-(pyridin-3-yl)-1H-pyrazol-4-yl)-N-ethyl-1-(4,4,4-trifluorobutanoyl)piperidine-4-carboxamide (Compound FA6) was isolated as a yellow solid (0.158 g, 66%).

N-(3-Chloro-1-(pyridin-3-yl)-1H-pyrazol-4-yl)-N-ethyl-1-(4,4,4-trifluorobutanoyl)pyrrolidine-3-carboxamide (Compound FA10) was isolated as a white semi-solid (0.138 g, 59%).

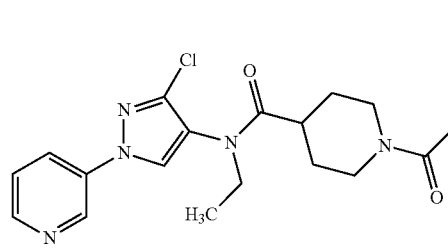

FA7

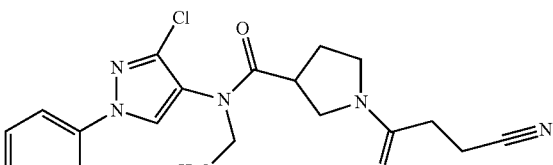

FA11

N-(3-Chloro-1-(pyridin-3-yl)-1H-pyrazol-4-yl)-1-(3-cyanopropanoyl)-N-ethylpiperidine-4-carboxamide (Compound FA7) was isolated as a yellow solid (0.199 g, 55%).

N-(3-Chloro-1-(pyridin-3-yl)-1H-pyrazol-4-yl)-1-(3-cyanopropanoyl)-N-ethylpyrrolidine-3-carboxamide (Compound FA11) was isolated as a yellow semi-solid (0.113 g, 51%).

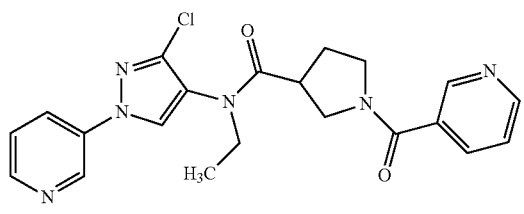

FA12

N-(3-Chloro-1-(pyridin-3-yl)-1H-pyrazol-4-yl)-N-ethyl-1-nicotinoylpyrrolidine-3-carboxamide (Compound FA12) was isolated as a colorless oil (0.14 g, 59%).

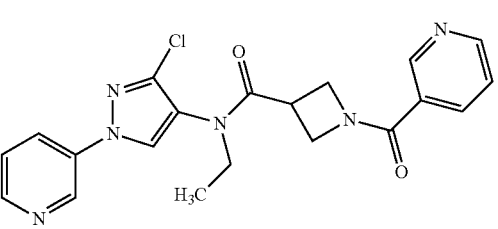

FA17

N-(3-Chloro-1-(pyridin-3-yl)-1H-pyrazol-4-yl)-N-ethyl-1-nicotinoyl azetidine-3-carboxamide (FA17) was isolated as a colorless oil (0.136 g, 63%).

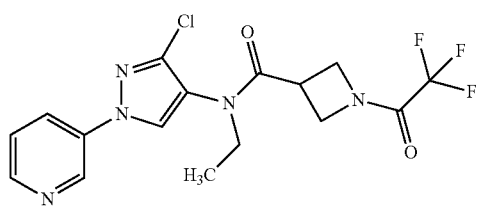

FA14

N-(3-Chloro-1-(pyridin-3-yl)-1H-pyrazol-4-yl)-N-ethyl-1-(2,2,2-trifluoroacetyl)azetidine-3-carboxamide (FA14) was isolated as a colorless oil (0.122 g, 58%).

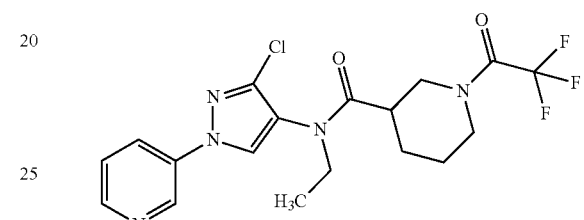

FA41

N-(3-Chloro-1-(pyridin-3-yl)-1H-pyrazol-4-yl)-N-ethyl-1-(2,2,2-trifluoroacetyl)piperidine-3-carboxamide (Compound FA41) was isolated as a white semi-solid (0.057 g, 25%).

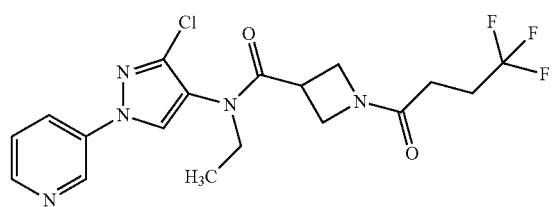

FA15

N-(3-Chloro-1-(pyridin-3-yl)-1H-pyrazol-4-yl)-N-ethyl-1-(4,4,4-trifluorobutanoyl)azetidine-3-carboxamide (FA15) was isolated as a colorless oil (0.135 g, 60%).

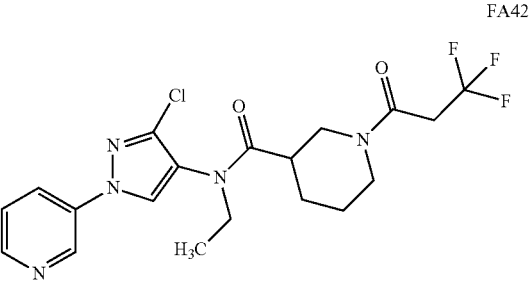 [SMILES: CCN(C(=O)C1CCCN(C(=O)CC(F)(F)F)C1)c1cn(-c2cccnc2)nc1Cl]

FA42

N-(3-Chloro-1-(pyridin-3-yl)-1H-pyrazol-4-yl)-N-ethyl-1-(3,3,3-trifluoropropanoyl)piperidine-3-carboxamide (Compound FA42) was isolated as a white semi-solid (0.13 g, 56%).

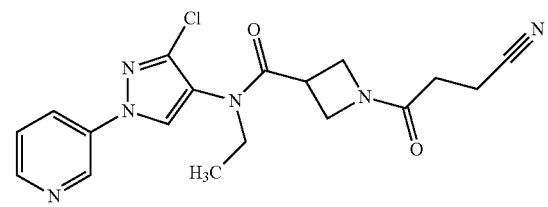

FA16

N-(3-Chloro-1-(pyridin-3-yl)-1H-pyrazol-4-yl)-1-(3-cyanopropanoyl)-N-ethylazetidine-3-carboxamide (FA16) was isolated as a white solid (0.097 g, 48%).

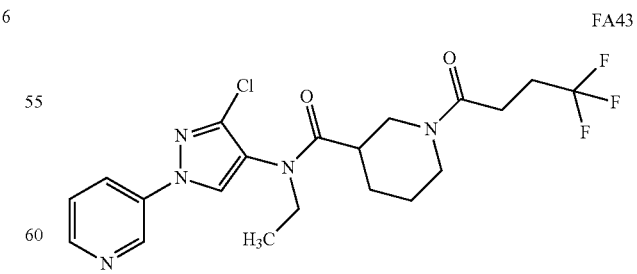

FA43

N-(3-Chloro-1-(pyridin-3-yl)-1H-pyrazol-4-yl)-N-ethyl-1-(4,4,4-trifluorobutanoyl)piperidine-3-carboxamide (Compound FA43) was isolated as a yellow semi-solid (0.178 g, 74%).

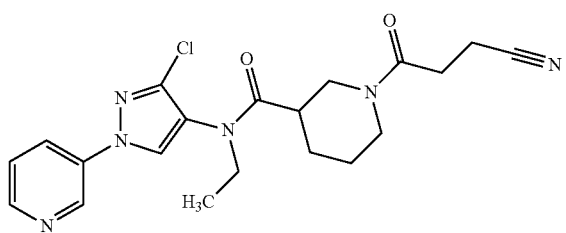

N-(3-chloro-1-(pyridin-3-yl)-1H-pyrazol-4-yl)-1-(3-cyanopropanoyl)-N-ethylpiperidine-3-carboxamide (Compound FA44) was isolated as a white semi-solid (0.148 g, 68%).

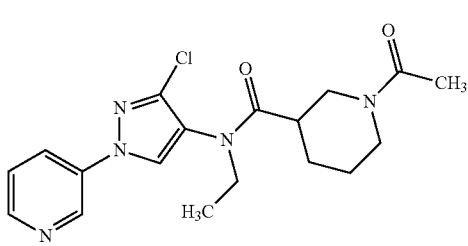

1-Acetyl-N-(3-chloro-1-(pyridin-3-yl)-1H-pyrazol-4-yl)-N-ethylpiperidine-3-carboxamide (Compound FA45) was isolated as a yellow solid (0.087 g, 44%).

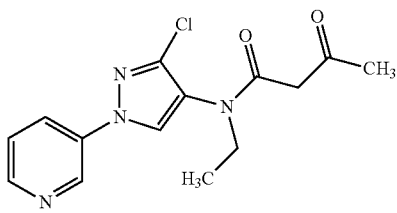

N-(3-chloro-1-(pyridin-3-yl)-1H-pyrazol-4-yl)-N-ethyl-3-oxobutanamide (Compound FA66) was isolated as a yellow oil (0.151 g, 44%).

Example 8

Preparation of N-(3-((3-chloro-1-(pyridin-3-yl)-1H-pyrazol-4-yl)(ethyl)amino)-3-oxopropyl)-3,3,3-trifluoro-N-methylpropanamide Compound F102

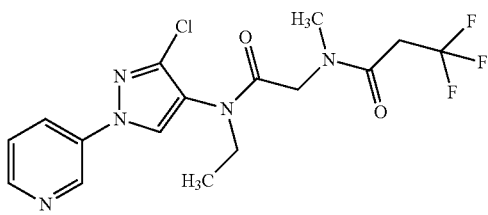 [SMILES: CCN(C(=O)CN(C)C(=O)CC(F)(F)F)c1cn(-c2cccnc2)nc1Cl]

A solution of N-(3-chloro-1-(pyridin-3-yl)-1H-pyrazol-4-yl)-N-ethyl-3-(methyl amino)propanamide (0.070 g, 0.23 mmol) in dry $CH_2Cl_2$ (0.76 mL) was cooled to a temperature of about 0° C. under $N_2$. To the solution, DMAP (0.014 g, 0.11 mmol), pyridine (0.028 mL, 0.34 mmol), and 3,3,3-trifluoropropanoyl chloride (0.026 mL, 0.25 mmol) were added sequentially. The reaction was slowly warmed up to room temperature under $N_2$, then stirred at room temperature overnight. The reaction was diluted with water (2 mL) and stirred for five minutes. Layers were separated, and the aqueous layer was extracted with $CH_2Cl_2$ (2×2 mL). The combined organic extracts were dried and concentrated under reduced pressure. The residue was purified by silica gel chromatography eluting with 0%-5% $MeOH/CH_2Cl_2$ to afford the title compound F102 as a white semi-solid (0.062 g, 63%).

The following molecules were made in accordance with the procedures disclosed in example 8:

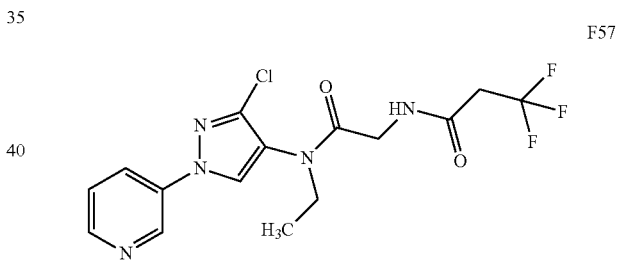

N-(3-((3-Chloro-1-(pyridin-3-yl)-1H-pyrazol-4-yl)(ethyl)amino)-3-oxopropyl)-3,3,3-trifluoropropanamide (Compound F63) was isolated as a white solid (0.039 g, 31% over 2 steps from compound C2).

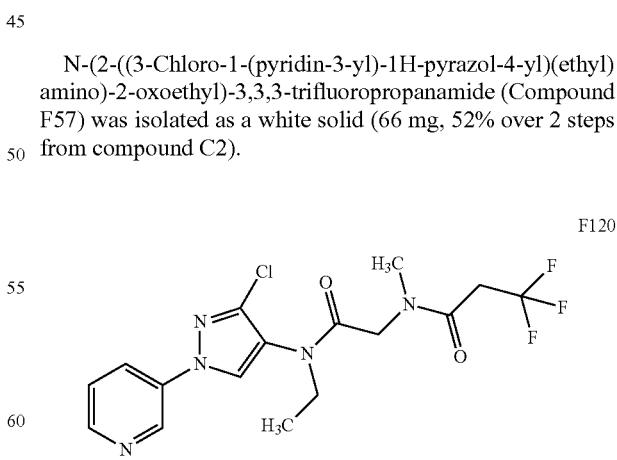

N-(2-((3-Chloro-1-(pyridin-3-yl)-1H-pyrazol-4-yl)(ethyl)amino)-2-oxoethyl)-3,3,3-trifluoropropanamide (Compound F57) was isolated as a white solid (66 mg, 52% over 2 steps from compound C2).

N-(2-((3-Chloro-1-(pyridin-3-yl)-1H-pyrazol-4-yl)(ethyl)amino)-2-oxoethyl)-3,3,3-trifluoro-N-methylpropanamide (Compound F120) was isolated as a white solid (0.057 g, 54%).

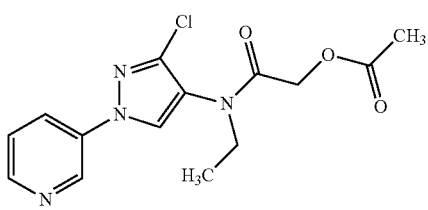

FA72

2-((3-Chloro-1-(pyridin-3-yl)-1H-pyrazol-4-yl)(ethyl)amino)-2-oxoethyl acetate (Compound FA72) was isolated as a white solid (0.068 g, 27%).

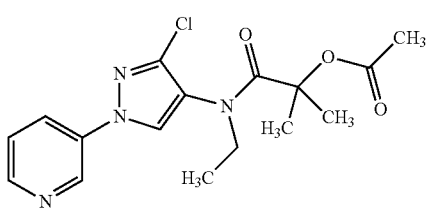

FA73

1-((3-Chloro-1-(pyridin-3-yl)-1H-pyrazol-4-yl)(ethyl)amino)-2-methyl-1-oxopropan-2-ylacetate (Compound FA73) was isolated as an off-white solid (0.173 g, 73%).

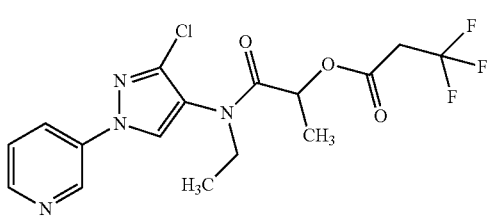

FA74

1-((3-Chloro-1-(pyridin-3-yl)-1H-pyrazol-4-yl)(ethyl)amino)-1-oxopropan-2-yl 3,3,3-trifluoropropanoate (Compound FA74) was isolated as a yellow oil (0.087 g, 63%).

Example 9

Preparation of tert-butyl 3-(3-((3-chloro-1-(pyridin-3-yl)-1H-pyrazol-4-yl)(ethyl)amino)-3-oxopropyl)-2-oxopyrrolidine-1-carboxylate Compound F128

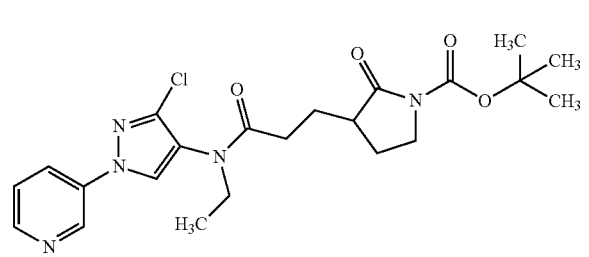 [SMILES: CCN(C(=O)CCC1CCN(C(=O)OC(C)(C)C)C1=O)c1cn(-c2cccnc2)nc1Cl]

A solution of tert-butyl 2-oxopyrrolidine-1-carboxylate (1.24 mL, 1.35 mmol) in dry THF (3.86 mL) was cooled to a temperature of about −78° C. under $N_2$ using acetone/dry ice bath. A 1M THF solution of LiHMDS (1.62 mL, 1.62 mmol) was added, and the reaction was stirred at a temperature of about −78° C. for 45 minutes. To the mixture, a solution of 3-chloro-N-(3-chloro-1-(pyridin-3-yl)-1H-pyrazol-4-yl)-N-ethylpropanamide (0.465 g, 1.49 mmol) in THF (3.86 mL) was added dropwise and stirred at a temperature of about −78° C. for 1 hour. The reaction was allowed to warm up to room temperature slowly and stirred overnight. The reaction mixture was quenched with saturated aqueous ammonium chloride ($NH_4Cl$, 5 mL), and the product was extracted with $CH_2Cl_2$ (3×5 mL), dried and concentrated. The residue was purified by silica gel chromatography by eluting with 20%-100% EtOAc/hexanes to afford the title compound F128 as a white foam (0.0770 g, 12%).

Example 10

Preparation of N-(3-chloro-1-(pyridin-3-yl)-1H-pyrazol-4-yl)-N-ethyl-3-(2-oxopyrrolidin-3-yl)propanamide Compound F131

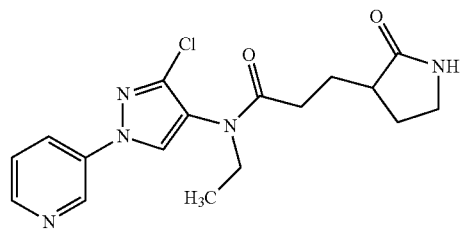 [SMILES: CCN(C(=O)CCC1CCNC1=O)c1cn(-c2cccnc2)nc1Cl]

To a solution of tert-butyl 3-(3-((3-chloro-1-(pyridin-3-yl)-1H-pyrazol-4-yl)(ethyl)amino)-3-oxopropyl)-2-oxopyrrolidine-1-carboxylate (0.076 g, 0.17 mmol) in dry $CH_2Cl_2$ (0.33 mL), TFA (0.33 mL) was added at room temperature under $N_2$. The reaction was stirred at room temperature for about 90 minutes. Saturated aqueous $NaHCO_3$ (about 10 mL) was carefully added until reaction mixture became basic. The product was extracted with $CH_2Cl_2$ (3×10 mL), dried and concentrated. The residue was purified by silica gel chromatography by eluting with 0%-15% MeOH/$CH_2Cl_2$ to afford the title compound F131 as a white foam (0.041 g, 66%).

Example 11

Preparation of tert-butyl(3-((3-chloro-1-(pyridin-3-yl)-1H-pyrazol-4-yl)(ethyl)amino)-3-oxopropyl)(methyl)carbamate Compound F52

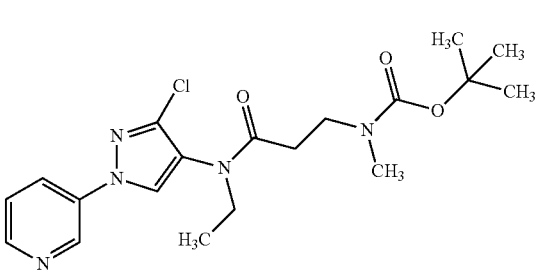 [SMILES: CCN(C(=O)CCN(C)C(=O)OC(C)(C)C)c1cn(-c2cccnc2)nc1Cl]

To a clean vial with a stir bar tert-butyl(3-((3-chloro-1-(pyridin-3-yl)-1H-pyrazol-4-yl)(ethyl)amino)-3-oxopropyl)carbamate (1.5 g, 3.8 mmol) was added and sealed with a septum cap. The headspace was purged with N₂, dry DMF (5.4 mL) was added via a syringe, and the reaction was cooled to a temperature of about 0° C. in an ice bath under N₂. NaH (60% dispersion in oil, 0.21 g, 5.3 mmol) was carefully added and stirred at a temperature of 0° C. for 30 minutes. Methyl iodide (0.29 mL, 4.6 mmol) was then added and stirred for 30 minutes at a temperature of 0° C. With the addition of methyl iodide, reaction became light yellow slurry. The reaction was warmed up to room temperature and stirred for 2 hours. As reaction warmed up, it turned to bright orange color. The reaction was quenched by the slow addition of water (100 mL). The suspension was vigorously stirred at room temperature for 2 hours. The water was filtered off, and remaining slurry was washed with hexanes. The slurry was then dissolved in methanol and passed through the filter. The resulting solution was concentrated, dried under high vacuum to afford brown, viscous oil (1.6 g, 78%).

Example 12

Preparation of 2-(1-(tert-butyldimethylsilyl)-2-oxoacetidin-3-yl)acetic acid

Compound C3

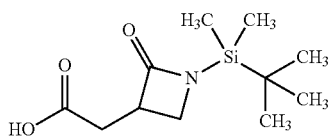

A stirred solution of 3-allyl-1-(tert-butyldimethylsilyl)azetidin-2-one (4.90 g, 22.2 mmol) in a mixture of carbon tetrachloride(CCl₄)/MeCN/water (50 mL/50 mL/100 mL) was charged with sodium periodate (18.9 g, 88.7 mmol) followed by ruthenium (III) chloride trihydrate (0.114 g, 0.440 mmol) at room temperature and stirred for 3 hours. The reaction mixture was diluted with water (100 mL) and extracted with CH₂Cl₂ (3×100 mL). The combined organic layers were dried over sodium sulfate (Na₂SO₄), filtered and concentrated under reduced pressure to afford the title compound C3 as a black semi solid (4.58 g, 85%): IR (KBr) 2956, 2929, 2351, 1732, 1681, 1361, 1215 cm⁻¹; ¹H NMR (400 MHz, CDCl₃) δ 3.62-3.59 (m, 1H), 3.46 (t, J=6.0 Hz, 1H), 3.05 (dd, J=6.4 Hz, 2.8 Hz, 1H), 2.88 (dd, J=17.2 Hz, 5.6 Hz, 1H), 2.67 (dd, J=17.2 Hz, 10.0 Hz, 1H), 0.96 (s, 9H), 0.25 (s, 3H), 0.23 (s, 3H); ESIMS m/z 244 ([M+H]⁺).

The following molecules were made in accordance with the procedures disclosed in example 12:

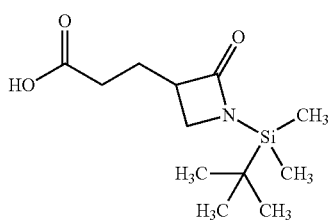

C4

3-(1-(tert-Butyldimethylsilyl)-2-oxoazetidin-3-yl)propanoic acid (Compound C4) was isolated as a black semi solid (5.07 g, 89%): IR (KBr) 2929, 2858, 2376, 1718, 1695, 1345, 1219 cm⁻¹; ¹H NMR (400 MHz, CDCl₃) δ 3.37-3.32 (m, 2H), 2.93-2.91 (m, 1H), 2.56-2.48 (m, 2H), 2.10-1.97 (m, 2H), 0.95 (s, 9H), 0.25 (s, 3H), 0.23 (s, 3H); ESIMS m/z 258 ([M+H]⁺).

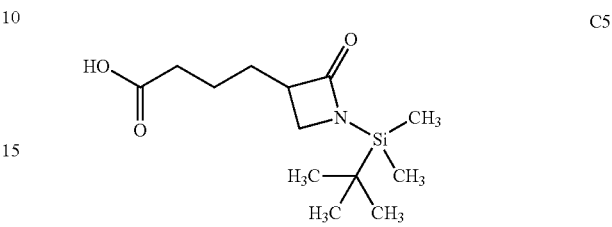

C5

4-(1-(tert-Butyldimethylsilyl)-2-oxoazetidin-3-yl)butanoic acid (Compound C5) was isolated as a black semi solid (5.17 g, 86%): IR (KBr): 2954, 2858, 2358, 1728, 1467, 1350, 1199 cm⁻¹; ¹H NMR (400 MHz, CDCl₃) δ 3.37-3.28 (m, 2H), 2.93 (dd, J=2.8 Hz, 6.0 Hz, 1H), 2.43 (t, J=6.8 Hz, 2H), 1.89-1.66 (m, 4H), 0.97 (s, 9H), 0.25 (s, 3H), 0.23 (s, 3H); ESIMS m/z 272 ([M+H]⁺).

Example 13

Preparation of N-(3-chloro-1-(pyridin-3-yl)-1H-pyrazol-4-yl)-N-ethyl-2-(2-oxoazetidin-3-yl)acetamide Compound F71

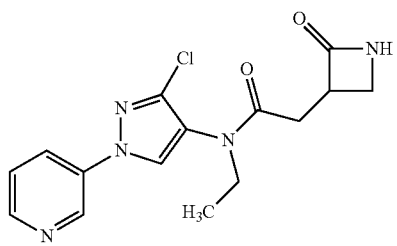 [SMILES: CCN(C(=O)CC1CNC1=O)c1cn(-c2cccnc2)nc1Cl]

A stirred solution of 2-(1-(tert-butyldimethylsilyl)-2-oxoacetidin-3-yl)acetic acid (4.10 g, 16.9 mmol) and 3-chloro-N-ethyl-1-(pyridin-3-yl)-1H-pyrazol-4-amine (2.48 g, 11.2 mmol) in EtOAc (50 mL) was charged with triethylamine (6.24 mL, 44.8 mmol) followed by n-propanephosphonic acid anhydride (T3P®) (50% in DMF, 22.5 mmol) at room temperature. The resultant reaction mixture was heated at reflux for 3 hours. The reaction mixture was diluted with water (50 mL) and extracted with EtOAc (3×100 mL). The combined organic layers were washed with brine solution (100 mL), dried over Na₂SO₄, filtered and concentrated under reduced pressure. The residue was purified by flash chromatography eluting with 1%-10% MeOH/CH₂Cl₂ to afford the title compound F71 as an off white solid (1.60 g, 43%).

The following molecules were made in accordance with the procedures disclosed in example 13:

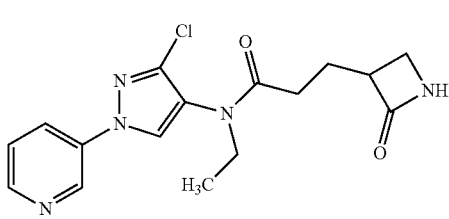

N-(3-Chloro-1-(pyridin-3-yl)-1H-pyrazol-4-yl)-N-ethyl-3-(2-oxoazetidin-3-yl)acetamide (Compound F50) was isolated as a light yellow gum (1.7 g, 45%).

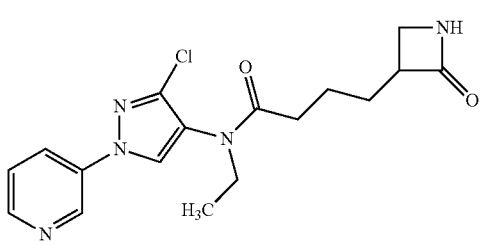

N-(3-Chloro-1-(pyridin-3-yl)-1H-pyrazol-4-yl)-N-ethyl-4-(2-oxoazetidin-3-yl)acetamide (Compound F58) was isolated as a light yellow gum (2.5 g, 63%).

Example 14

Preparation of N-(3-chloro-1-(pyridin-3-yl)-1H-pyrazol-4-yl)-N-ethyl-2-(1-methyl-2-oxoazetidin-3-yl)acetamide Compound F32

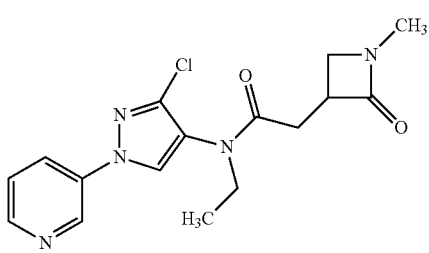 [SMILES: CCN(C(=O)CC1CN(C)C1=O)c1cn(-c2cccnc2)nc1Cl]

To a suspension of NaH (60% dispersion in oil, 0.029 g, 0.72 mmol) in DMF (2 mL) was added N-(3-chloro-1-(pyridin-3-yl)-1H-pyrazol-4-yl)-N-ethyl-2-(2- oxoazetidin-3-yl)acetamide (0.20 g, 0.60 mmol) in DMF (0.5 mL), dropwise, at a temperature of about −10° C. over one minute. The reaction mixture was charged with methyl iodide (0.093 g, 0.66 mmol) in DMF (0.5 mL), dropwise, and stirred for 5 minutes. The reaction mixture was quenched with ice water (10 mL) and extracted with EtOAc (3×15 mL). The organic layers were combined and washed with water (3×10 mL) and brine (10 mL), dried over $Na_2SO_4$, and concentrated under reduced pressure. The residue was purified by flash chromatography eluting with 1%-8% MeOH/$CH_2Cl_2$ to afford the title compound F32 as a gum (0.065 g, 31%).

The following molecules were made in accordance with the procedures disclosed in example 14:

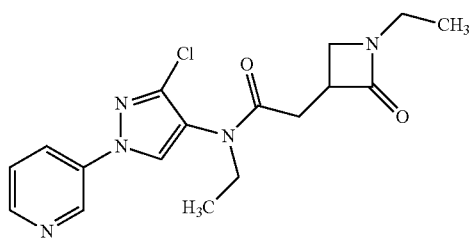

N-(3-Chloro-1-(pyridin-3-yl)-1H-pyrazol-4-yl)-N-ethyl-2-(1-ethyl-2-oxoazetidin-3-yl)acetamide (Compound F84) was isolated as a gum (0.033 g, 15%).

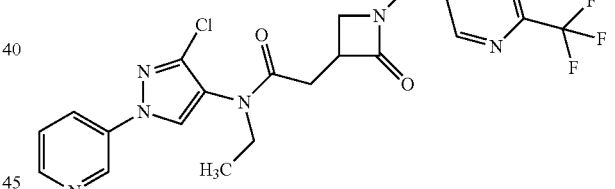

N-(3-Chloro-1-(pyridin-3-yl)-1H-pyrazol-4-yl)-N-ethyl-2-(2-oxo-1-(4-trifluoro methyl)benzyl)azetidin-3-yl)acetamide (Compound F14) was isolated as a gum (0.080 g, 27%).

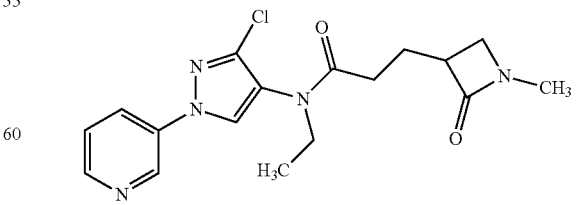

N-(3-Chloro-1-(pyridin-3-yl)-1H-pyrazol-4-yl)-N-ethyl-2-(2-oxo-1-(6-trifluoromethyl)pyridin-3-yl)methyl)azetidin-3-yl)acetamide) (Compound F117) was isolated as a gum (0.050 g, 17%).

N-(3-Chloro-1-(pyridin-3-yl)-1H-pyrazol-4-yl)-N-ethyl-3-(1-methyl-2-oxoazetidin-3-yl)propanamide (Compound F119) was isolated as a gum (0.054 g, 25%).

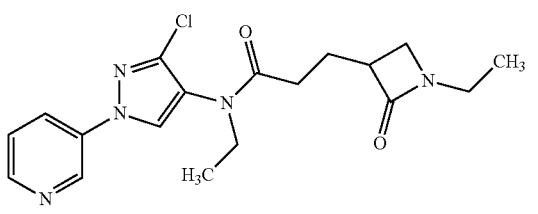

F103

N-(3-Chloro-1-(pyridin-3-yl)-1H-pyrazol-4-yl)-N-ethyl-3-(1-ethyl-2-oxoazetidin-3-yl)propanamide (Compound F103) was isolated as a gum (0.076 g, 34%).

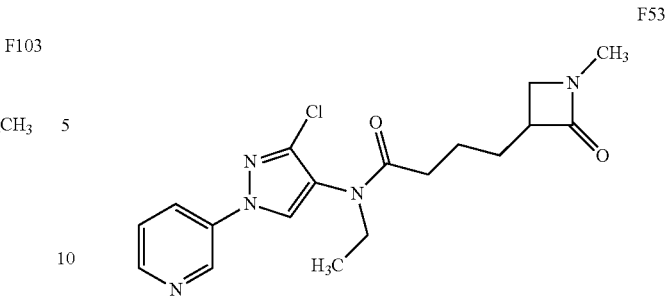

F53

N-(3-Chloro-1-(pyridin-3-yl)-1H-pyrazol-4-yl)-N-ethyl-4-(1-methyl-2-oxoazetidin-3-yl)butanamide (Compound F53) was isolated as a gum (0.112 g, 50%).

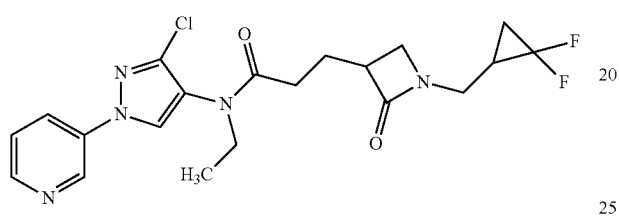

F74

N-(3-Chloro-1-(pyridin-3-yl)-1H-pyrazol-4-yl)-3-1(1-((2,2-difluoro cyclopropyl)methyl)-2-oxoazetidin-3-yl)-N-ethylpropanamide (Compound F74) was isolated as a gum (0.0098 g, 8%).

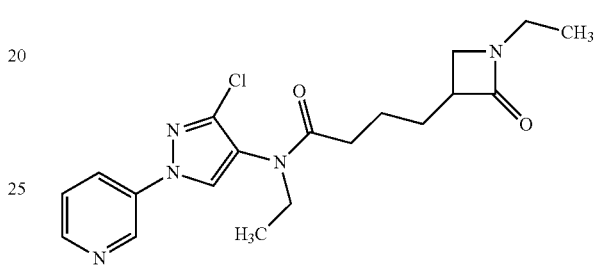

F81

N-(3-Chloro-1-(pyridin-3-yl)-1H-pyrazol-4-yl)-N-ethyl-4-(1-ethyl-2-oxoazetidin-3-yl)butanamide (Compound F81) was isolated as a gum (0.112 g, 48%).

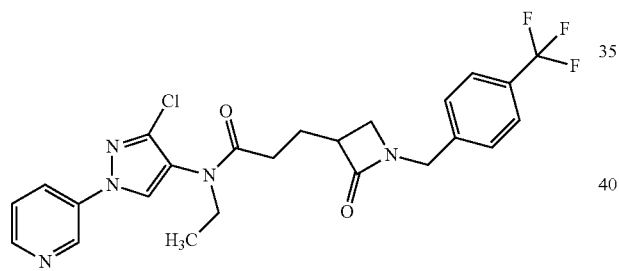

F129

N-(3-Chloro-1-(pyridin-3-yl)-1H-pyrazol-4-yl)-N-ethyl-3-(2-oxo-1-(4-trifluoro methyl)benzyl)azetidin-3-yl)propanamide (Compound F129) was isolated as a gum (0.166 g, 55%).

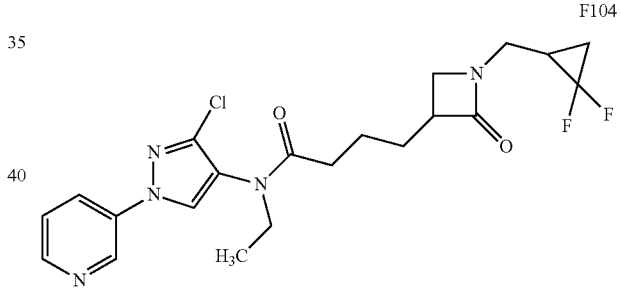

F104

N-(3-Chloro-1-(pyridin-3-yl)-1H-pyrazol-4-yl)-4-(1-(2,2-difluorocyclopropyl)methyl)-2-oxoazetidin-3-yl)-N-ethylbutanamide (Compound F104) was isolated as a gum (0.010 g, 8%).

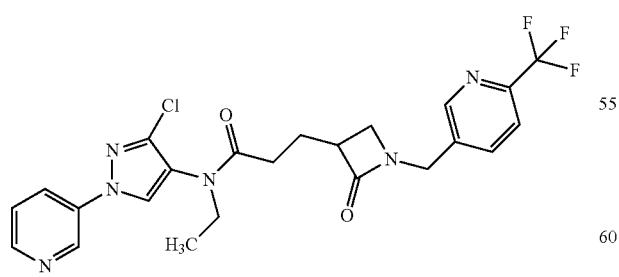

F91

N-(3-Chloro-1-(pyridin-3-yl)-1H-pyrazol-4-yl)-N-ethyl-3-(2-oxo-1-((6-(trifluoromethyl)pyridin-3-yl)methyl)azetidin-3-yl)propanamide (Compound F91) was isolated as a gum (0.057 g, 19%).

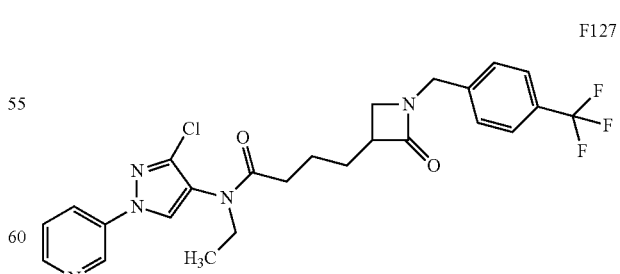

F127

N-(3-Chloro-1-(pyridin-3-yl)-1H-pyrazol-4-yl)-N-ethyl-4-(2-oxo-1-(4-(trifluoromethyl)benzyl) azetidin-3-yl)butanamide (Compound F127) was isolated as a gum (0.121 g, 39%).

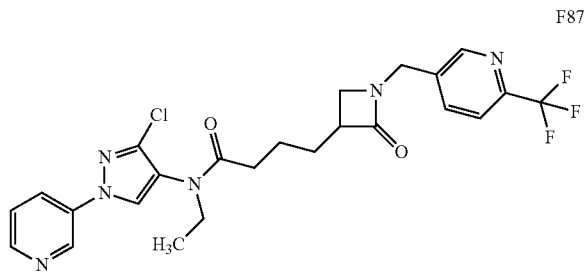 [SMILES: CCN(C(=O)CCCC1CN(Cc2ccc(C(F)(F)F)nc2)C1=O)c1cn(-c2cccnc2)nc1Cl]

N-(3-Chloro-1-(pyridin-3-yl)-1H-pyrazol-4-yl)-N-ethyl-4-(2-oxo-1-(((6-(trifluoromethyl)pyridin-3-yl)methyl)azetidin-3-yl)butanamide (Compound F87) was isolated as a gum (0.125 g, 40%).

Example 15

Preparation of tert-butyl((1R,4S)-4-((3-chloro-1-(pyridin-3-yl)-1H-pyrazol-4-yl)(methyl) carbamoyl)cyclopent-2-en-1-yl)carbamate Compound F109

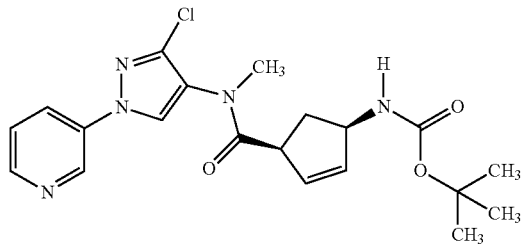 [SMILES: CN(C(=O)[C@@H]1C=C[C@H](NC(=O)OC(C)(C)C)C1)c1cn(-c2cccnc2)nc1Cl]

A solution of 3-chloro-N-methyl-1-(pyridin-3-yl)-1H-pyrazol-4-amine (0.20 g, 0.96 mmol) in THF (10 mL) was cooled to a temperature of about −78° C. LHMDS (1 M solution in hexanes, 1.0 mL, 1.00 mmol) was added, and the solution was stirred at a temperature of about −78° C. for 15 minutes. A solution of (1R,4S)-tert-butyl 3-oxo-2-azabicyclo[2.2.1]hept-5-ene-2- carboxylate (0.20 g, 0.96 mmol) dissolved in THF (3 mL) was added to the solution at a temperature of about −78° C. in one portion. After stirring for one hour at a temperature of about −78° C., the cooling bath was removed and the reaction warmed to a temperature of about 20° C. After stirring for an additional five minutes, acetic acid (AcOH, 0.1 mL) was added to the solution. The reaction mixture was concentrated and purified via silica gel chromatography eluting with EtOAc/hexanes to give the title compound F109 as a white solid (0.25 g, 59%).

The following molecules were made in accordance with the procedures disclosed in example 15:

F116

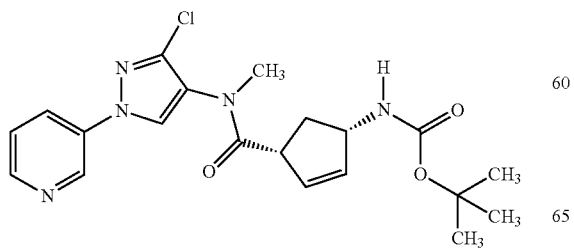

tert-Butyl((1S,4R)-4-((3-chloro-1-(pyridin-3-yl)-1H-pyrazol-4-yl)(methyl) carbamoyl)cyclopent-2-en-1-yl)carbamate (Compound F116) was isolated as a pink foam (3.46 g, 60%).

Example 16

Preparation (1S,4R)-4-amino-N-(3-chloro-1-(pyridin-3-yl)-1H-pyrazol-4-yl)-N-methylcyclopent-2-enecarboxamide 2,2,2-trifluoroacetate Compound C6

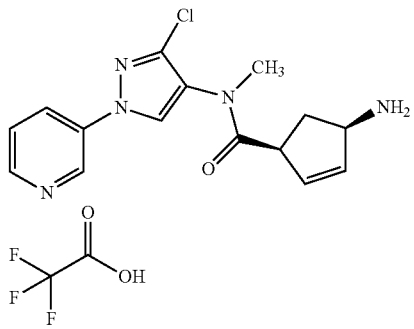

To a solution of tert-butyl((1R,4S)-4-((3-chloro-1-(pyridin-3-yl)-1H-pyrazol-4-yl)(methyl)carbamoyl)cyclopent-2-en-1-yl)carbamate (0.13 g, 0.31 mmol) in $CH_2Cl_2$ (4 mL) was added TFA (4 mL). The reaction was left to stand for 20 minutes with occasional swirling. The reaction mixture was concentrated in vacuo at a temperature of about 40° C. resulting in the isolation of the title compound C6 as a clear oil (0.13 g, 94%): $^1$H NMR (400 MHz, $CD_3OD$) δ 9.02 (dd, J=2.7, 0.7 Hz, 1H), 8.70 (s, 1H), 8.54 (dd, J=5.0, 1.4 Hz, 1H), 8.30 (ddd, J=8.4, 2.7, 1.4 Hz, 1H), 7.63 (ddd, J=8.4, 5.0, 0.7 Hz, 1H), 6.09 (ddd, J=5.6, 2.7, 1.0 Hz, 1H), 5.92 (dt, J=5.6, 2.1 Hz, 1H), 4.16 (d, J=7.7 Hz, 1H), 3.80-3.72 (m, 1H), 2.98 (s, 3H), 2.29 (dt, J=14.3, 7.9 Hz, 1H), 2.01 (dt, J=14.3, 2.5 Hz, 1H); $^{13}$C NMR (101 MHz, $CDCl_3$) δ 179.16, 164.09, 163.71, 163.33, 162.94, 145.04, 142.05, 141.15, 137.81, 136.71, 134.11, 134.06, 132.73, 131.26, 129.77, 123.78, 120.92, 118.06, 115.21, 59.80, 51.85, 40.50, 36.87; ESIMS m/z 318 ([M+H]$^+$).

Example 17

Preparation of (1S,4R)-N-(3-chloro-1-(pyridin-3-yl)-1H-pyrazol-4-yl)-N-methyl-4-(2,2,2-trifluoroacetamido)cyclopent-2-enecarboxamide (Compound F126) and (1S,4R)-4-acetamido-N-(3-chloro-1-(pyridin-3-yl)-1H-pyrazol-4-yl)-N-methyl-cyclopent-2-enecarboxamide (Compound F24)

-continued

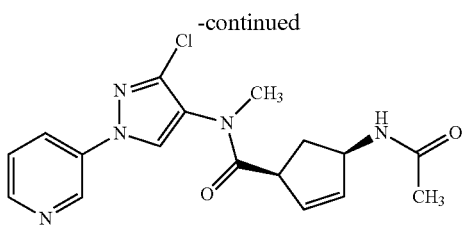

To a solution of (1S,4R)-4-amino-N-(3-chloro-1-(pyridin-3-yl)-1H-pyrazol-4-yl)-N-methylcyclopent-2-enecarboxamide 2,2,2-trifluoroacetate (0.906 mg, 2.10 mmol) dissolved in CH$_2$Cl$_2$ (25 mL) was added triethylamine (0.637 mg, 6.29 mmol) and acetyl chloride (1 M in CH$_2$Cl$_2$, 3.15 mL, 3.15 mmol). After stirring for 24 hours, the reaction was diluted with saturated aqueous NaHCO$_3$ (15 mL) and the phases were separated. The organic layer was dried with anhydrous Na$_2$SO$_4$, filtered and concentrated. The resulting residue was purified by silica gel chromatography eluting first with EtOAC/hexanes providing F126 as a white foam (0.417 g, 48%) followed by eluting with MeOH/CH$_2$Cl$_2$ to provide compound F24 as a white foam (0.364 g, 48%).

Example 18

Preparation (1R,4S)-4-amino-N-(3-chloro-1-(pyridin-3-yl)-1H-pyrazol-4-yl)-N-methylcyclopent-2-enecarboxamide dihydrochloride Compound C7

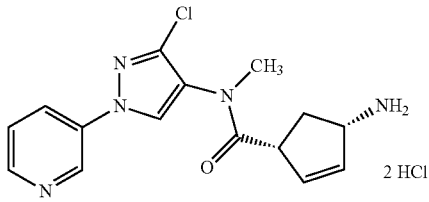 [SMILES: CN(C(=O)[C@H]1C=C[C@@H](N)C1)c1cn(-c2cccnc2)nc1Cl]

Solid tert-butyl((1S,4R)-4-((3-chloro-1-(pyridin-3-yl)-1H-pyrazol-4-yl)(methyl) carbamoyl)cyclopent-2-en-1-yl)carbamate (0.10 g, 0.25 mmol) was combined with hydrochloric acid (HCl, 4 M in 1,4-dioxane, 2.0 mL, 8.0 mmol) and MeOH (1 mL). After stirring for 3.5 hours, the reaction mixture was concentrated to afford the title compound C7 as a greenish yellow solid (0.095 g, 99%): $^1$H NMR (400 MHz, CD$_3$OD) δ 9.51 (d, J=2.3 Hz, 1H), 9.15-9.09 (m, 2H), 8.90 (d, J=5.5 Hz, 1H), 8.30 (dd, J=8.7, 5.6 Hz, 1H), 6.26-6.19 (m, 1H), 6.06 (dt, J=5.5, 1.7 Hz, 1H), 4.30 (d, J=7.4 Hz, 1H), 3.89 (d, J=7.5 Hz, 1H), 3.30 (s, 3H), 2.43 (dt, J=15.0, 7.7 Hz, 1H), 2.13 (dt, J=14.4, 2.5 Hz, 1H); $^{13}$C NMR (101 MHz, CD$_3$OD) δ 176.53, 142.82, 141.12, 139.99, 138.74, 136.06, 134.13, 131.51, 130.90, 129.52, 127.40, 68.16, 57.35, 37.99, 34.44; ESIMS m/z 318 ([M+H]$^+$).

Example 19

Preparation of (1R,4S)-4-acetamido-N-(3-chloro-1-(pyridin-3-yl)-1H-pyrazol-4-yl)-N-methyl-cyclopent-2-enecarboxamide Compound F86

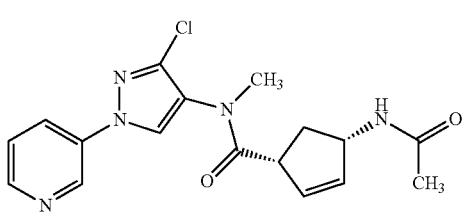 [SMILES: CC(=O)N[C@@H]1C=C[C@H](C(=O)N(C)c2cn(-c3cccnc3)nc2Cl)C1]

To a suspension of (1R,4S)-4-amino-N-(3-chloro-1-(pyridin-3-yl)-1H-pyrazol-4-yl)-N-methylcyclopent-2-enecarboxamide dihydrochloride (0.065 g, 0.17 mmol) in CH$_2$Cl$_2$ (2 mL) was added triethylamine (0.084 g, 0.83 mmol) followed by acetyl chloride (1 M in CH$_2$Cl$_2$, 0.25 mL, 0.25 mmol). After stirring for 24 hours, the reaction product was purified by direct application to silica gel chromatography eluting with MeOH/CH$_2$Cl$_2$ to provide the title compound F86 as yellow foam (0.040 g, 67%).

Example 20

Preparation of (R)-4-acetamido-N-(3-chloro-1-(pyridin-3-yl)-1H-pyrazol-4-yl)-N-methyl-cyclopent-1-enecarboxamide Compound F41

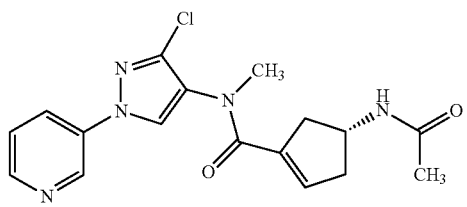 [SMILES: CC(=O)N[C@@H]1CC=C(C(=O)N(C)c2cn(-c3cccnc3)nc2Cl)C1]

To a solution of (1R,4S)-4-acetamido-N-(3-chloro-1-(pyridin-3-yl)-1H-pyrazol-4-yl)-N-methyl-cyclopent-2-enecarboxamide (0.230 g, 0.639 mmol) dissolved in dimethylsulfoxide (DMSO, 10 mL) was added 1,8-diazabicyclo[5.4.0]undec-7-ene (DBU, 4.00 mL, 26.7 mmol). After stirring for 4 hours at a temperature of 100° C., the reaction was cooled and diluted with saturated aqueous NH$_4$Cl (200 mL) and extracted with EtOAc. The organic layer was dried with anhydrous Na$_2$SO$_4$, filtered and concentrated. The resulting residue was purified by silica gel chromatography eluting with MeOH/CH$_2$Cl$_2$ to provide the title compound F41 as a yellow oil (0.120 g, 44%).

Example 21

Preparation of tert-butyl((1S,4R)-4-((3-chloro-1-(pyridin-3-yl)-1H-pyrazol-4-yl)(methyl)carbamoyl)cyclopentan-1-yl)carbamate Compound F45

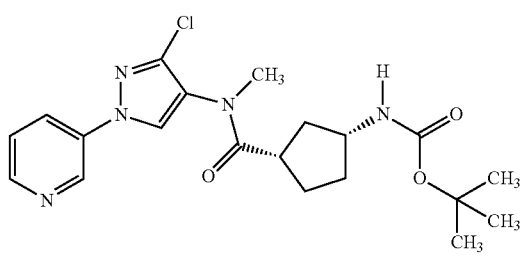 [SMILES: CN(C(=O)[C@H]1CC[C@@H](NC(=O)OC(C)(C)C)C1)c1cn(-c2cccnc2)nc1Cl]

To a solution of 3-chloro-N-methyl-1-(pyridin-3-yl)-1H-pyrazol-4-amine (0.109 g, 0.523 mmol) and (1S,3R)-3-((tert-butoxycarbonyl)amino)cyclopentanecarboxylic acid (0.120 g, 0.523 mmol) in DMF (2.09 mL) was added 0-(7-azabenzotriazol-1-yl)-N,N,N',N'-tetramethyl uronium hexafluorophosphate (HATU, 0.219 g, 0.576 mmol) to give a brown solution. To this solution was added 4-methylmorpholine (0.115 mL, 1.05 mmol). The reaction was stirred at room temperature overnight. The material was diluted with EtOAc and water. The organic layer was dried with MgSO4, filtered and concentrated to give orange oil, which was purified by silica gel chromatography eluting with EtOAc/hexanes provided the title compound F45 as an orange oil (0.100 g, 39%).

Example 22

Preparation of N-(3-chloro-1-(pyridin-3-yl)-1H-pyrazol-4-yl)-N-ethyl-4-oxopentanamide Compound C8

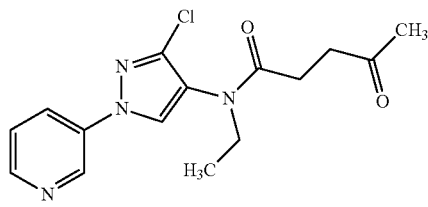 [SMILES: CCN(C(=O)CCC(C)=O)c1cn(-c2cccnc2)nc1Cl]

To a mixture of 3-chloro-N-ethyl-1-(pyridin-3-yl)-1H-pyrazol-4-amine (1.00 g, 4.49 mmol), 4-oxopentanoic acid (0.626 g, 5.39 mmol) and DMAP (0.658 g, 5.39 mmol) in diethyl ether (10 mL) was added N,N'-methanediylidenebis(propan-2-amine) (0.680 g, 5.39 mmol) at a temperature of about 0° C., and the mixture stirred for 30 minutes. The mixture was warmed to room temperature and stirred at room temperature for 1 hour. To the mixture was added another 1.2 eq of diisopropyl carbodiimide (0.820 g, 6.47 mmol) and stirred at room temperature for 16 hours. The mixture was quenched with saturated aqueous NH$_4$Cl and diluted with EtOAc. The organic phase was separated, and the aqueous phase extracted with EtOAc. The combined organic phase was washed with brine, dried over MgSO$_4$ and filtered. Removal of the volatiles under reduced pressure gave light brown gum, which was purified on silica gel eluting with MeOH/CH$_2$Cl$_2$ to give the title compound C8 as a colorless gum (1.41 g, 93%): $^1$H NMR (400 MHz, CDCl$_3$) δ 9.03 (dd, J=4.9, 2.6 Hz, 2H), 8.61 (m, 2H), 8.16 (d, J=3.2 Hz, 1H), 8.11 (dddd, J=8.4, 4.1, 2.6, 1.3 Hz, 2H), 7.50 (dt, J=8.5, 4.4 Hz, 2H), 3.66 (q, J=7.0 Hz, 2H), 2.76 (t, J=6.2 Hz, 2H), 2.37 (t, J=6.1 Hz, 3H), 1.12 (td, J=7.1, 1.3 Hz, 3H); ESIMS m/z 321 ([M+H]$^+$).

Example 23

Preparation of (E/Z)-N-(3-chloro-1-(pyridin-3-yl)-1H-pyrazol-4-yl)-N-ethyl-4-(methoxyimino)pentanamide Compound F92

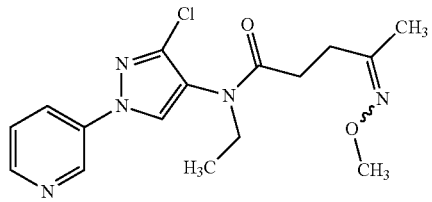 [SMILES: CCN(C(=O)CCC(C)=NOC)c1cn(-c2cccnc2)nc1Cl]

To a stirred solution of N-(3-chloro-1-(pyridin-3-yl)-1H-pyrazol-4-yl)-N-ethyl-4-oxopentanamide (0.142 g, 0.443 mmol) dissolved in a mixture of pyridine (0.44 mL) and ethanol (0.44 mL) was added O-methylhydroxylamine hydrochloride (0.129 mg, 1.50 mmol). The reaction mixture was heated at a temperature of 60° C. for 16 hours. The reaction mixture was cooled to room temperature, diluted with CH$_2$Cl$_2$ and then washed with water. The phases were separated, the combined organic layers were dried over MgSO$_4$, filtered, concentrated and purified by silica gel chromatography eluting with 0%-50% acetone/hexanes to afford the title compound F92 as a colorless oil (0.116 g, 75%).

The following molecules were made in accordance with the procedures disclosed in example 23:

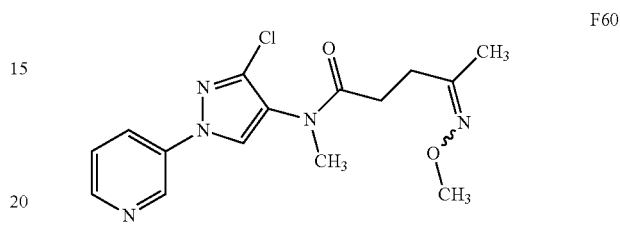

(E/Z)-N-(3-Chloro-1-(pyridin-3-yl)-1H-pyrazol-4-yl)-4-(methoxyimino)-N-methylpentanamide (Compound F60) was isolated as a colorless oil (0.188 g, 75%).

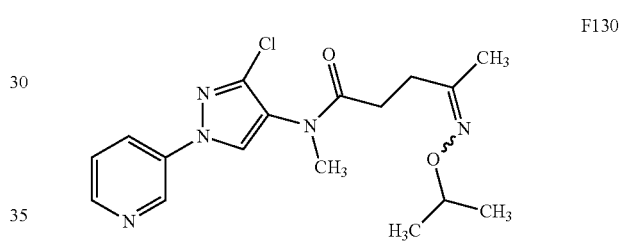

(E/Z)-N-(3-Chloro-1-(pyridin-3-yl)-1H-pyrazol-4-yl)-4-(isopropoxyimino)-N-methylpentanamide (Compound F130) was isolated as a colorless oil (0.135 g, 68%).

Example 24

Preparation of 3-chloro-N-(3-chloro-1-(pyridin-3-yl)-1H-pyrazol-4-yl)-N-ethylpropanamide Compound C9

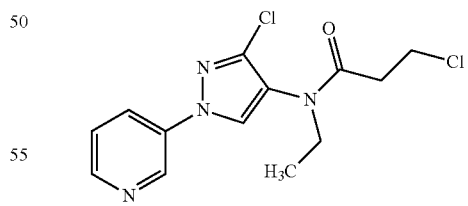

To a stirred solution of 3-chloro-N-ethyl-1-(pyridin-3-yl)-1H-pyrazol-4-amine dihydrochloride (1.00 g, 3.38 mmol) in CH$_2$Cl$_2$ (7 mL) was added propylene oxide (1.00 mL, 13.5 mmol) followed by 3-chloropropanoyl chloride (0.360 mL, 3.72 mmol). This was stirred at room temperature for 16 hours, and then the reaction mixture was then diluted with CH$_2$Cl$_2$ and washed with water. The phases were separated, the organic were dried, concentrated and purified by silica gel chromatography eluting with 0%-50% acetone/hexanes to afford a white solid (0.850 g, 80%): mp 85-86° C.; $^1$H NMR (400 MHz, CDCl$_3$) δ 8.96 (d, J=2.6 Hz, 1H), 8.64 (dd, J=4.7, 1.4 Hz, 1H), 8.05 (ddd, J=8.3, 2.7, 1.4 Hz, 1H), 7.98 (s, 1H), 7.47 (ddd, J=8.4, 4.8, 0.6 Hz, 1H), 3.80 (t, J=6.7 Hz, 2H), 3.74 (q, J=7.1 Hz, 2H), 2.64 (t, J=6.7 Hz, 2H), 1.18 (t, J=7.2 Hz, 3H); ESIMS m/z 313 ([M+H]$^+$).

The following molecules were made in accordance with the procedures disclosed in example 24:

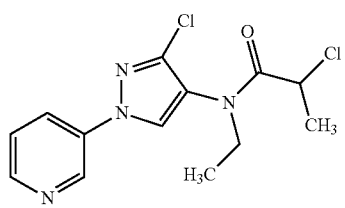

C10

2-Chloro-N-(3-chloro-1-(pyridin-3-yl)-1H-pyrazol-4-yl)-N-ethylpropanamide (Compound C10) was isolated as a white solid (1.25 g, 59%).

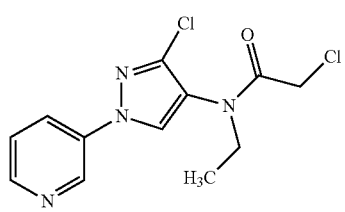

CA2

2-Chloro-N-[3-chloro-1-(3-pyridyl)pyrazol-4-yl]-N-ethyl-acetamide (Compound CA2) was isolated as an orange oil (0.579 g, 86%): $^1$H NMR (400 MHz, CDCl$_3$) δ 9.21 (s, 1H), 8.97 (d, J=2.6 Hz, 1H), 8.70-8.61 (m, 1H), 8.07 (s, 1H), 7.53-7.41 (m, 1H), 4.07-3.90 (m, 21H), 3.73 (s, 2H), 1.22-1.11 (m, 3H).

Example 25

Preparation of N-(3-chloro-1-(pyridin-3-yl)-1H-pyrazol-4-yl)-N-ethyl-3-(methylamino)propanamide Compound C11

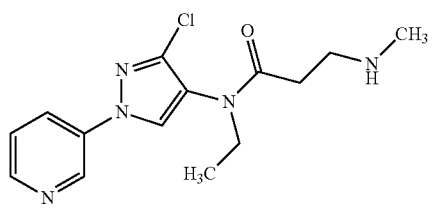 [SMILES: CCN(C(=O)CCNC)c1cn(-c2cccnc2)nc1Cl]

Monomethylamine (33% solution in EtOH, 11 mL, 90 mmol) and 3-chloro-N-(3-chloro-1-(pyridin-3-yl)-1H-pyrazol-4-yl)-N-ethylpropanamide (1.9 g, 6.0 mmol) was capped in a 10-20 mL vial and heated on a BIOTAGE INITIATOR® microwave reactor for 1 hour at a temperature of about 100° C. with external IR-sensor temperature monitoring from the side of the vessel. The reaction mixture was then concentrated and purified by silica gel chromatography eluting with 0%-10% MeOH/CH$_2$Cl$_2$ to afford a yellow oil (1.7 g, 93%): IR (KBr thin film) 3055, 2971, 2773, 1656 cm$^{-1}$; $^1$H NMR (400 MHz, Acetone-d$_6$) δ 9.12 (dd, J=6.7, 2.6 Hz, 1H), 8.90 (s, 1H), 8.58 (dd, J=4.7, 1.4 Hz, 1H), 8.25 (m, 1H), 7.56 (m, 1H), 3.67 (q, J=7.1 Hz, 2H), 3.01 (t, J=6.5 Hz, 2H), 2.66 (t, J=6.4 Hz, 2H), 2.50 (s, 3H), 1.12 (t, J=7.2 Hz, 3H); ESIMS m/z 308 ([M+H]$^+$).

Example 26

Preparation of N-(3-chloro-1-(pyridin-3-yl)-1H-pyrazol-4-yl)-N-ethyl-3-(N-methylacetamido) propanamide Compound F64

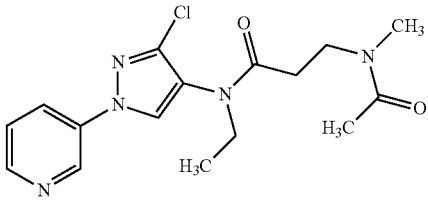 [SMILES: CCN(C(=O)CCN(C)C(C)=O)c1cn(-c2cccnc2)nc1Cl]

To a stirred solution of N-(3-chloro-1-(pyridin-3-yl)-1H-pyrazol-4-yl)-N-ethyl-3-(methylamino) propanamide dihydrochloride (0.060 g, 0.16 mmol) in CH$_2$Cl$_2$ (0.5 mL) was added DIPEA (0.081 g, 0.60 mmol) followed by acetyl chloride (0.019 mg, 0.24 mmol). The reaction mixture was stirred for 16 hours. The reaction mixture was then diluted with CH$_2$Cl$_2$ and washed with water. The organic phase was separated, dried, concentrated, and then purified by silica gel chromatography eluting with 0%-10% MeOH/CH$_2$Cl$_2$ to afford the title compound F64 as a colorless oil (0.025 g, 45%).

The following molecules were made in accordance with the procedures disclosed in example 26:

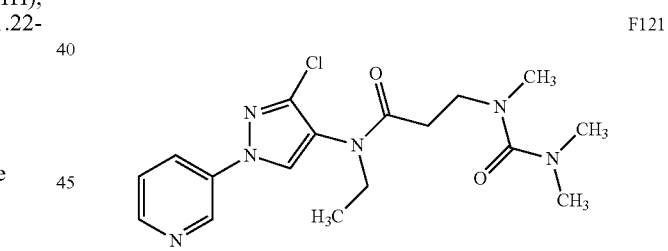

F121

N-(3-Chloro-1-(pyridin-3-yl)-1H-pyrazol-4-yl)-N-ethyl-3-(1,3,3-trimethylureido)propanamide (Compound F121) was isolated as a light yellow oil (0.071 g, 66%).

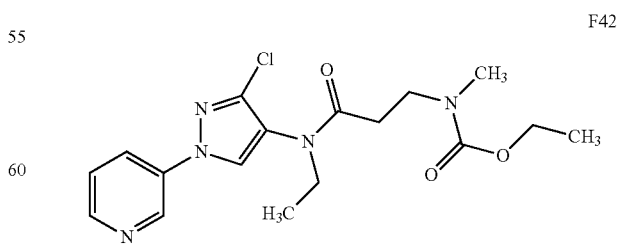

F42

Ethyl(3-((3-chloro-1-(pyridin-3-yl)-1H-pyrazol-4-yl)(ethyl)amino)-3-oxopropyl)(methyl)carbamate (Compound F42) was isolated as colorless oil (0.065 g, 71%).

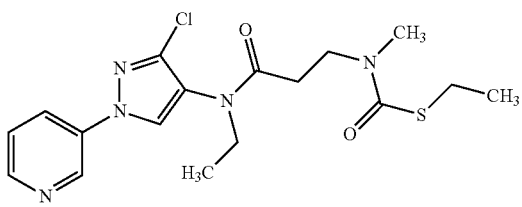

F40

S-Ethyl(3-((3-chloro-1-(pyridin-3-yl)-1H-pyrazol-4-yl)(ethyl)amino)-3-oxopropyl)(methyl) carbamothioate (Compound F40) was isolated as a colorless oil (0.065 g, 68%).

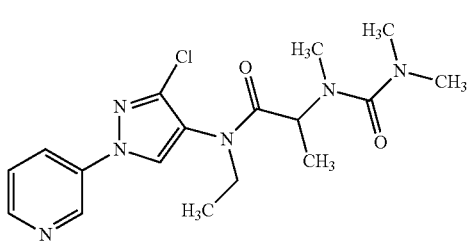

F114

N-(3-Chloro-1-(pyridin-3-yl)-1H-pyrazol-4-yl)-N-ethyl-2-(1,3,3-trimethylureido)propanamide (Compound F114) was isolated as an orange solid (0.147 g, 96%).

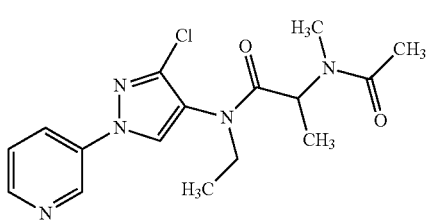

F96

N-(3-Chloro-1-(pyridin-3-yl)-1H-pyrazol-4-yl)-N-ethyl-2-(N-methylacetamido)propanamide (Compound F96) was isolated as an oil (0.096 g, 68%).

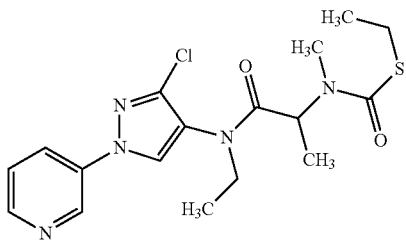

F79

S-Ethyl(1-((3-chloro-1-(pyridin-3-yl)-1H-pyrazol-4-yl)(ethyl)amino)-1-oxopropan-2-yl)(methyl) carbamothioate (Compound F79) was isolated as a yellow oil (0.060 g, 41%).

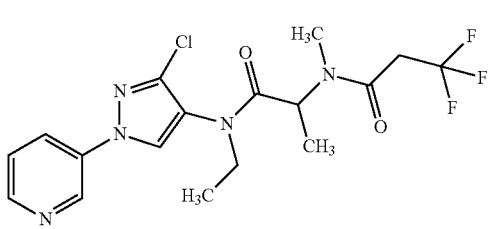

F66

N-(1-((3-Chloro-1-(pyridin-3-yl)-1H-pyrazol-4-yl)(ethyl)amino)-1-oxopropan-2-yl)-3,3,3-trifluoro-N-methylpropanamide (Compound F66) was isolated as a colorless oil (0.096 g, 57%).

Example 27

Preparation of 1-((3-chloro-1-(pyridin-3-yl)-1H-pyrazol-4-yl)(ethyl)amino)-1-oxopropan-2-yl acetate Compound C12

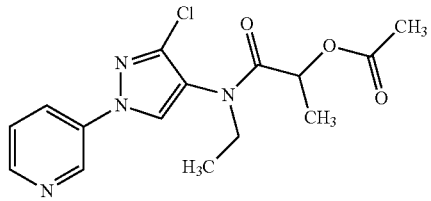 [SMILES: CCN(C(=O)C(C)OC(C)=O)c1cn(-c2cccnc2)nc1Cl]

To a stirred solution of 3-chloro-N-ethyl-1-(pyridin-3-yl)-1H-pyrazol-4-amine dihydrochloride (3.00 g, 10.2 mmol) in CH$_2$Cl$_2$ (20 mL) cooled in an ice bath were added triethylamine (5.7 mL, 40.6 mmol) followed by dropwise addition 1-chloro-1-oxopropan-2-yl acetate (1.3 mL, 10.2 mmol). The reaction mixture was stirred overnight warming to room temperature. The reaction mixture was then diluted with CH$_2$Cl$_2$ and washed with water. The phases were separated, and the organics were dried over MgSO$_4$, filtered and concentrated. The residue was purified by silica gel chromatography eluting with 0%-70% acetone/hexanes to afford the title compound C12 as a tan taffy-like solid (3.2 g, 93%): $^1$H NMR (400 MHz, CDCl$_3$) δ 8.99 (d, J=2.5 Hz, 1H), 8.62 (dd, J=4.8, 1.3 Hz, 1H), 8.18 (s, 1H), 8.04 (ddd, J=8.3, 2.7, 1.4 Hz, 1H), 7.46 (ddd, J=8.4, 4.8, 0.5 Hz, 1H), 5.01 (d, J=6.5 Hz, 1H), 3.54 (m, 2H), 2.09 (s, 3H), 1.39 (d, J=6.8 Hz, 3H), 1.17 (t, J=7.2 Hz, 3H); $^{13}$C NMR (101 MHz, CDCl$_3$) δ 171.01, 148.62, 140.57, 140.24, 135.63, 127.56, 126.33, 124.06, 122.58, 67.49, 43.74, 20.61, 16.80, 12.57 (one carbon signal not located); ESIMS m/z 336.4 ([M+H]$^+$), 335.0 ([M−H]$^−$).

Example 28

Preparation of N-(3-chloro-1-(pyridin-3-yl)-1H-pyrazol-4-yl)-N-ethyl-2-hydroxypropanamide Compound C13

To a stirred solution of 1-((3-chloro-1-(pyridin-3-yl)-1H-pyrazol-4-yl)(ethyl)amino)-1-oxopropan-2-yl acetate (2.4 g, 7.1 mmol) in MeOH (9 mL) and THF (9 mL) was added lithium hydroxide (LiOH, 2 M, 7.0 mL, 14 mmol). The reaction mixture was stirred for two hours at room temperature, and then the reaction mixture pH was made neutral by the addition of aq. 2M HCl. After the mixture was then extracted with EtOAc, the organics phases were combined, dried over MgSO$_4$, filtered and concentrated in vacuo to afford the title compound C13 as a white solid (1.9 g, 88%): mp 137-138° C.; $^1$H NMR (400 MHz, DMSO) δ 9.08 (d, J=2.5 Hz, 1H), 8.98 (s, 1H), 8.58 (dd, J=4.7, 1.1 Hz, 1H), 8.23 (ddd, J=8.4, 2.6, 1.3 Hz, 1H), 7.59 (dd, J=8.3, 4.7 Hz, 1H), 4.97 (d, J=7.6 Hz, 1H), 4.08 (m, 1H), 3.57 (d, J=50.6 Hz, 2H), 1.10 (d, J=6.5 Hz, 3H), 1.07 (t, J=7.1 Hz, 3H); ESIMS m/z 295.6 ([M+H]$^+$).

Example 29

Preparation of 1-((3-chloro-1-(pyridin-3-yl)-1H-pyrazol-4-yl)(ethyl)amino)-1-oxopropan-2-yl dimethylcarbamate Compound F93

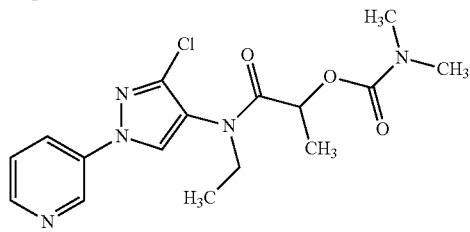 [SMILES: CCN(C(=O)C(C)OC(=O)N(C)C)c1cn(-c2cccnc2)nc1Cl]

To a stirred solution of N-(3-chloro-1-(pyridin-3-yl)-1H-pyrazol-4-yl)-N-ethyl-2-hydroxypropanamide (0.10 g, 0.34 mmol) in CH$_2$Cl$_2$ (1.1 mL) was added dimethylcarbamic chloride (0.073 g, 0.68 mmol). The reaction mixture was stirred at room temperature for 16 hours, and then diluted with CH$_2$Cl$_2$, washed with water. The phases were separated, dried and concentrated. The residue was purified by basic alumina gel chromatography eluting with 0%-70% acetone/hexanes to afford the title compound F93 as a light yellow oil (0.11 g, 87%).

The following molecules were made in accordance with the procedures disclosed in example 29:

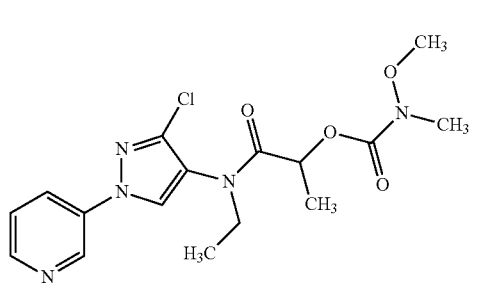

1-((3-Chloro-1-(pyridin-3-yl)-1H-pyrazol-4-yl) (ethyl)amino)-1-oxopropan-2-yl methoxy(methyl)carbamate (Compound F16) was isolated as a colorless oil (0.127 g, 82%).

Example 30

Preparation of tert-butyl 3-((3-chloro-1-(pyridin-3-yl)-1H-pyrazol-4-yl)(ethyl)carbamoyl)pyrrolidine-1-carboxylate Compound F11

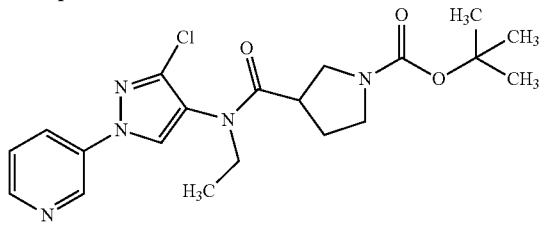

To a stirred solution of 3-chloro-N-ethyl-1-(pyridin-3-yl)-1H-pyrazol-4-amine dihydrochloride (0.20 g, 0.68 mmol) in CH$_2$Cl$_2$ (1.4 mL) were added DIPEA (0.35 g, 2.7 mmol) followed by 1-(tert-butoxycarbonyl)pyrrolidine-3-carboxylic acid (0.22 g, 1.0 mmol) and EDCI (0.20 g, 1.0 mmol). The reaction mixture was stirred at room temperature for 16 hours, then concentrated. The residue was purified by silica gel chromatography eluting with 0%-50% acetone/hexanes to afford a colorless oil (0.14 g, 49%).

Example 31

Preparation of N-(3-chloro-1-(pyridin-3-yl)-1H-pyrazol-4-yl)-N-methyl-3-(2-oxooxazolidin-3-yl)propanamide Compound F31

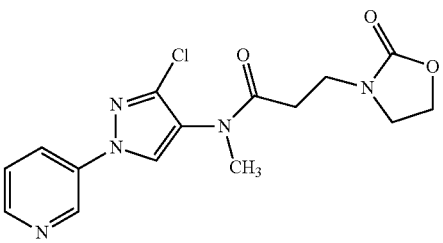 [SMILES: CN(C(=O)CCN1CCOC1=O)c1cn(-c2cccnc2)nc1Cl]

To a solution of oxazolidin-2-one (0.038 g, 0.44 mmol) in DMF (3 mL) was added NaH (60% dispersion in oil, 0.011 g, 0.44 mmol). The mixture was stirred at a temperature of about 0° C. for 10 minutes, and 3-chloro-N-(3-chloro-1-(pyridin-3-yl)-1H- pyrazol-4-yl)-N-methyl propanamide (0.12 g, 0.40 mmol) was added. The resulting brown-yellow mixture was stirred at room temperature for two hours and diluted with saturated aqueous NH$_4$Cl. The mixture was diluted with EtOAc and saturated aqueous NaCl solution. The organic phase was separated, and the aqueous phase extracted with EtOAc (2×50 mL). The combined EtOAc extracts was dried over MgSO$_4$, filtered, and concentrated under reduced pressure to give light brown gum. The gum was purified on silica gel eluting with MeOH/CH$_2$Cl$_2$ to give the title compound F31 as a colorless oil (0.13 g, 94%).

The following molecules were made in accordance with the procedures disclosed in example 31:

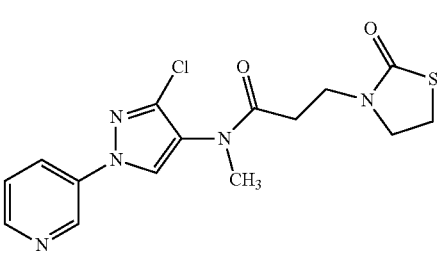

N-(3-Chloro-1-(pyridin-3-yl)-1H-pyrazol-4-yl)-N-methyl-3-(2-oxothiazolidin-3-yl)propanamide (Compound F38) was isolated as a light brown gum (0.029 g, 19%).

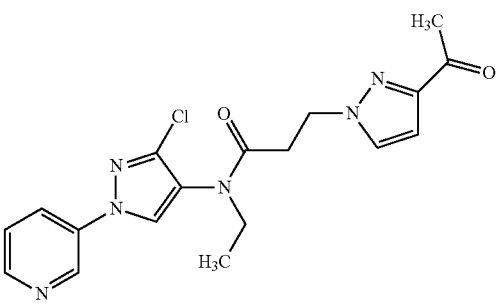

3-(3-Acetyl-1H-pyrazol-1-yl)-N-(3-chloro-1-(pyridin-3-yl)-1H-pyrazol-4-yl)-N-ethylpropanamide (Compound FA68) was isolated as a light brown oil (0.221 g, 59% yield).

Example 32

Preparation of N-(3-((3-chloro-1-(pyridin-3-yl)-1H-pyrazol-4-yl)(ethyl)amino)-3-oxopropyl)-N-(2,2-difluoroethyl)-2,2-difluorocyclopropanecarboxamide Compound F34

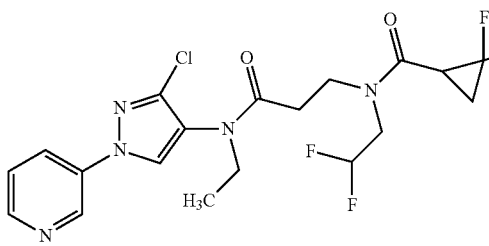

To a solution of N-(3-chloro-1-(pyridin-3-yl)-1H-pyrazol-4-yl)-3-((2,2-difluoroethyl)amino)-N-ethylpropanamide (0.10 g, 0.28 mmol) in CH$_2$Cl$_2$ (2 mL) were added 2,2-difluoro cyclopropanecarboxylic acid (0.041 g, 0.34 mmol), DMAP (0.034 g, 0.28 mmol) and N-(3-chloro-1-(pyridin-3-yl)-1H-pyrazol-4-yl)-3-((2,2-difluoroethyl)amino)-N-ethylpropanamide (0.10 g, 0.28 mmol), and the mixture stirred at room temperature for 2 hours. The mixture was diluted with CH$_2$Cl$_2$ and washed with saturated aqueous NH$_4$Cl and brine, dried over MgSO$_4$, and concentrated under reduced pressure to give pink oil. The residue oil was purified on silica gel eluting with MeOH/CH$_2$Cl$_2$ to give the title compound F34 as a colorless oil (0.079 g, 58%).

The following molecules were made in accordance with the procedures disclosed in example 32:

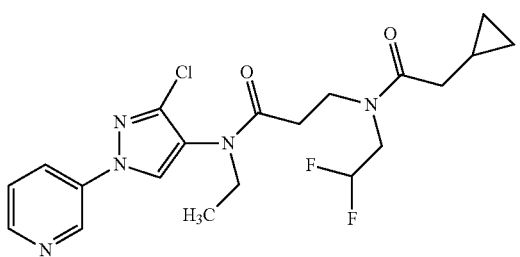

N-(3-Chloro-1-(pyridin-3-yl)-1H-pyrazol-4-yl)-3-(2-cyclopropyl-N-(2,2-difluoroethyl)acetamido)-N-ethylpropanamide (Compound F125) was isolated as a colorless oil (0.092 g, 75%).

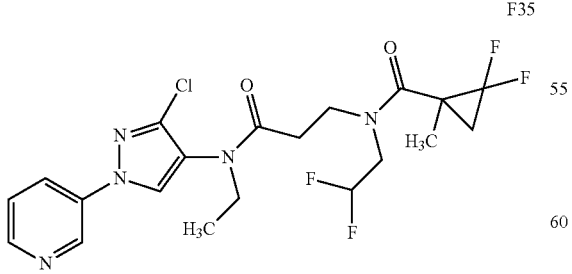

N-(3-((3-Chloro-1-(pyridin-3-yl)-1H-pyrazol-4-yl)(ethyl)amino)-3-oxopropyl)-N-(2,2-difluoroethyl)-2,2-difluoro-1-methylcyclopropane carboxamide (Compound F35) was isolated as a light brown oil (0.068 g, 51% yield).

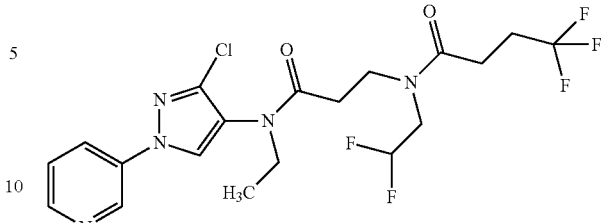

N-(3-((3-Chloro-1-(pyridin-3-yl)-1H-pyrazol-4-yl)(ethyl)amino)-3-oxopropyl)-N-(2,2-difluoroethyl)-4,4,4-trifluorobutanamide (Compound F89) was isolated as a colorless oil (0.079 g, 56%).

Example 33

Preparation of N-(3-((3-chloro-1-(pyridin-3-yl)-1H-pyrazol-4-yl)(ethyl)amino)-3-oxopropyl)-N-(2,2-difluoroethyl)-1H-imidazole-1-carboxamide Compound F17

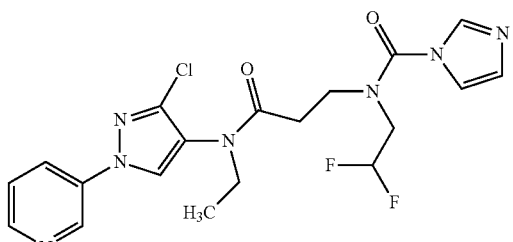

To a solution of N-(3-chloro-1-(pyridin-3-yl)-1H-pyrazol-4-yl)-3-((2,2-difluoroethyl)amino)-N-ethylpropanamide (0.10 g, 0.28 mmol) in DMF (1 mL) was added carbonyl dimidazole (0.045 g, 0.28 mmol), and the mixture stirred at room temperature for 3 hours. To the mixture was added (2,2-difluorocyclopropyl)methanol (0.030 g, 0.28 mmol) and stirred at room temperature for 12 hours. The mixture was diluted with CH$_2$Cl$_2$ and washed with saturated aqueous NH$_4$Cl and brine, dried over MgSO$_4$, and concentrated under reduced pressure to give brown oil. The residue oil was purified on silica gel eluting with MeOH/CH$_2$Cl$_2$ to give the title compound F17 as a colorless gum (0.069 g, 55%).

Example 34

Preparation of (E)-N-(3-chloro-1-(pyridin-3-yl)-1H-pyrazol-4-yl)-N-ethyl-4-(hydroxyimino)pentanamide Compound F105

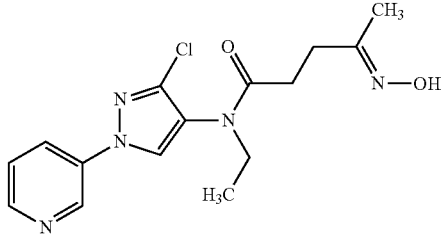 [SMILES: CCN(C(=O)CC/C(C)=N/O)c1cn(-c2cccnc2)nc1Cl]

To a solution of N-(3-chloro-1-(pyridin-3-yl)-1H-pyrazol-4-yl)-N-ethyl-4-oxo pentanamide (0.10 g, 0.31 mmol) in THF (3.0 mL) was added a solution of sodium acetate (0.064 g, 0.78 mmol) and hydroxylamine.HCl salt (0.033 g, 0.47 mmol) in water (0.5 mL), and the mixture stirred for one hour. The mixture was diluted with EtOAc and water. The organic phase was separated, and the aqueous extracted with EtOAc. The combined organic phase was washed with brine, dried over MgSO₄, and filtered. Removal of the volatiles under reduced pressure gave colorless gum, which was purified on silica gel eluting with MeOH/CH₂Cl₂ to give the title compound F105 as a colorless gum (0.088 g, 80%).

The following molecules were made in accordance with the procedures disclosed in example 34:

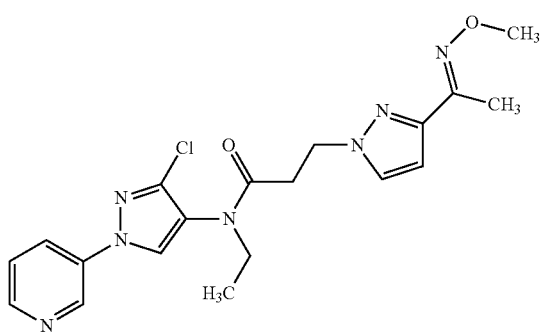
FA1

(E/Z)-N-(3-Chloro-1-(pyridin-3-yl)-1H-pyrazol-4-yl)-N-ethyl-3-(3-(1-(methoxyimino)ethyl)-1H-pyrazol-1-yl)propanamide (Compound FA1) was isolated as a light yellow oil (0.043 g, 80%).

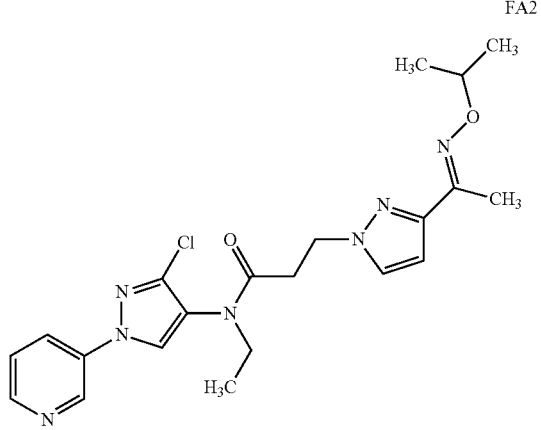 [SMILES: CCN(C(=O)CCn1ccc(/C(C)=N/OC(C)C)n1)c1cn(-c2cccnc2)nc1Cl]
FA2

(E/Z)-N-(3-Chloro-1-(pyridin-3-yl)-1H-pyrazol-4-yl)-N-ethyl-3-(3-(1-(isopropoxyimino)ethyl)-1H-pyrazol-1-yl)propanamide (Compound FA2) was isolated as a colorless gum (0.048 g, 84%).

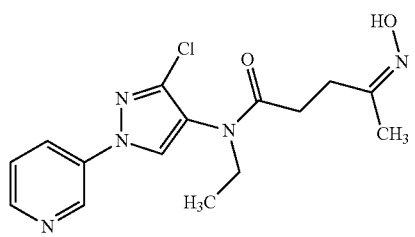
FA46

(Z)-N-(3-Chloro-1-(pyridin-3-yl)-1H-pyrazol-4-yl)-N-ethyl-4-(hydroxyimino)pentanamide (Compound FA46) was isolated as a colorless oil (0.158 g, 62%).

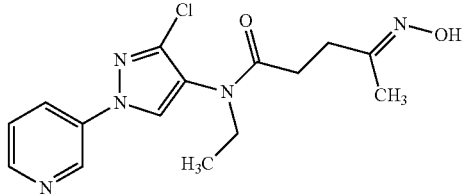
FA47

(E)-N-(3-Chloro-1-(pyridin-3-yl)-1H-pyrazol-4-yl)-N-ethyl-4-(hydroxyimino)pentanamide (Compound FA47) was isolated as a colorless oil (0.065 g, 26%).

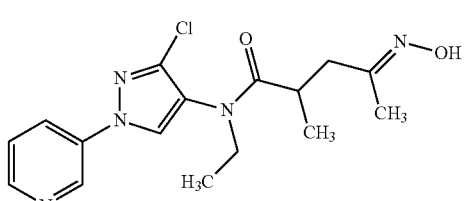
FA52

(E)-N-(3-Chloro-1-(pyridin-3-yl)-1H-pyrazol-4-yl)-N-ethyl-4-(hydroxyimino)-2-methylpentanamide (Compound FA52) was isolated as a colorless oil (0.015 g, 16%).

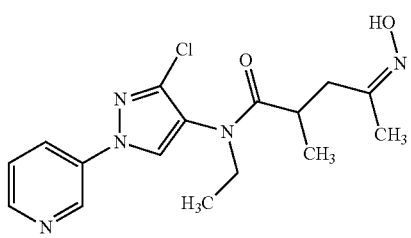
FA53

(Z)-N-(3-Chloro-1-(pyridin-3-yl)-1H-pyrazol-4-yl)-N-ethyl-4-(hydroxyimino)-2-methylpentanamide (Compound FA53) was isolated as a colorless oil (0.051 g, 54%).

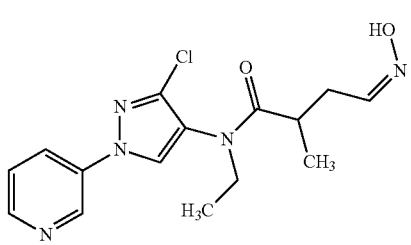
FA54

(Z)-N-(3-Chloro-1-(pyridin-3-yl)-1H-pyrazol-4-yl)-N-ethyl-4-(hydroxyimino)-2-methylbutanamide (Compound FA54) was isolated as a colorless oil (0.098 g, 17%).

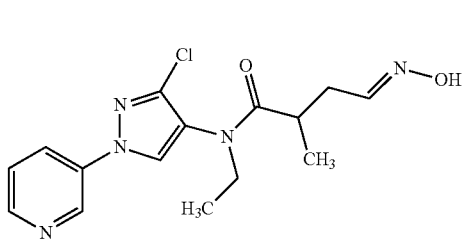
FA55

(E)-N-(3-Chloro-1-(pyridin-3-yl)-1H-pyrazol-4-yl)-N-ethyl-4-(hydroxyimino)-2-methylbutanamide (Compound FA55) was isolated as a colorless oil (0.148 g, 26%).

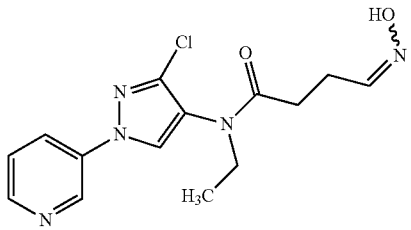

FA56

(E/Z)-N-(3-Chloro-1-(pyridin-3-yl)-1H-pyrazol-4-yl)-N-ethyl-4-(hydroxyimino)butanamide (Compound FA56) was isolated as a colorless oil (0.204 g, 68%).

Example 35

Preparation of (E/Z)-N-(3-chloro-1-(pyridin-3-yl)-1H-pyrazol-4-yl)-4-((2,2-difluorocyclopropyl) methoxy)imino)-N-ethylpentanamide Compound F72

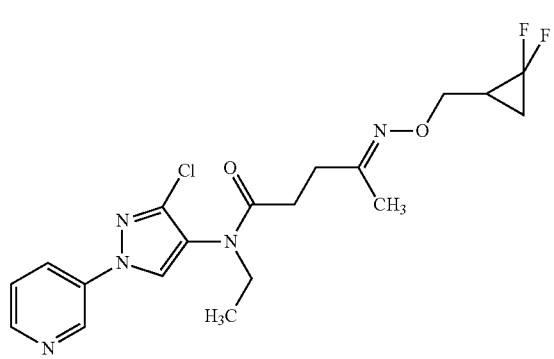 [SMILES: CCN(C(=O)CC/C(C)=N/OCC1CC1(F)F)c1cn(-c2cccnc2)nc1Cl]

To a solution of (E/Z)-N-(3-chloro-1-(pyridin-3-yl)-1H-pyrazol-4-yl)-N-ethyl-4-(hydroxyimino)pentanamide (0.10 g, 0.30 mmol) in dry THF (1 mL) at a temperature of about 0° C. under $N_2$ was added NaH (60% dispersion in oil, 0.013 g, 0.31 mmol) followed by 2-(bromomethyl)-1,1-difluorocyclopropane (0.056 g, 0.33 mmol). The mixture was stirred for one hour and warmed to room temperature. After stirring for additional one hour, the mixture was quenched with saturated aqueous $NH_4Cl$ and diluted with EtOAc. The organic phase was separated, and the aqueous phase extracted with EtOAc. The combined organic phase was washed with brine, dried over $MgSO_4$, and filtered. Removal of the volatiles under reduced pressure gave colorless gum, which was purified on silica gel eluting with $MeOH/CH_2Cl_2$ to give the title compound F72 as a brown oil (0.062 g, 46%).

The following molecules were made in accordance with the procedures disclosed in example 35:

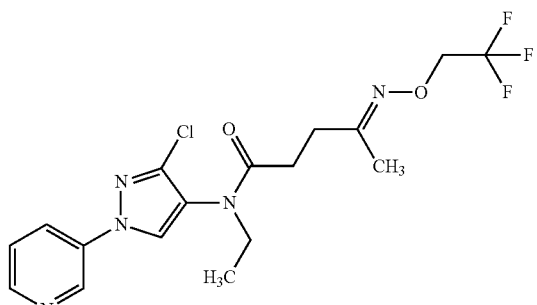

F51

(E/Z)-N-(3-Chloro-1-(pyridin-3-yl)-1H-pyrazol-4-yl)-N-ethyl-4-((2,2,2-trifluoroethoxy)imino)pentanamide (Compound F51) was isolated as a colorless oil (0.071 g, 54%).

F20

(E/Z)-N-(3-Chloro-1-(pyridin-3-yl)-1H-pyrazol-4-yl)-4-((2-(2,2-difluoro cyclopropyl)ethoxy)imino)-N-ethylpentanamide (Compound F20) was isolated as a colorless oil (0.059 g, 43%).

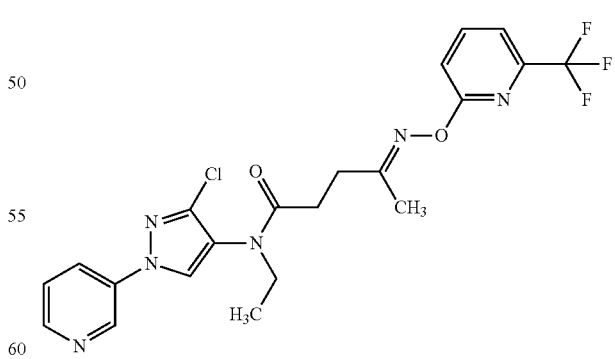

F59

(E/Z)-N-(3-Chloro-1-(pyridin-3-yl)-1H-pyrazol-4-yl)-N-ethyl-4-((6-(trifluoromethyl)pyridin-2-yl)oxy)imino)pentanamide (Compound F59) was isolated as a colorless oil (0.095 g, 75%).

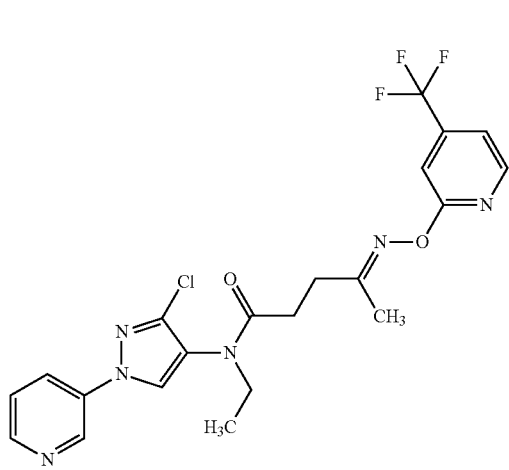

F36

(E/Z)-N-(3-Chloro-1-(pyridin-3-yl)-1H-pyrazol-4-yl)-N-ethyl-4-((4-(trifluoromethyl)pyridin-2-yl)oxy)imino)pentanamide (Compound F36) was isolated as a colorless oil (0.095 g, 82%).

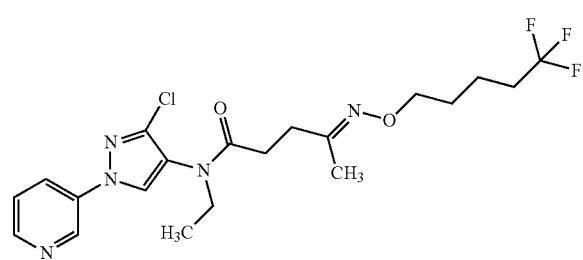

FA4

(E/Z)-N-(3-Chloro-1-(pyridin-3-yl)-1H-pyrazol-4-yl)-N-ethyl-4-((5,5,5-trifluoropentyl)oxy)imino)pentanamide (Compound FA4) was isolated as a colorless gum (0.071 g, 52%).

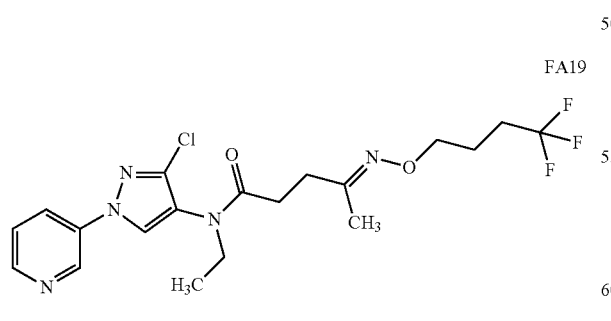

FA19

(E/Z)-N-(3-Chloro-1-(pyridin-3-yl)-1H-pyrazol-4-yl)-N-ethyl-4-(4,4,4-trifluorobutoxyl)imino)pentanamide (Compound FA19) was isolated as a light yellow gum (0.098 g, 74%).

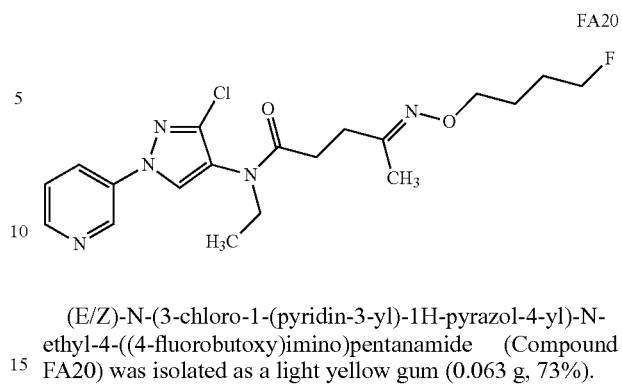

FA20

(E/Z)-N-(3-chloro-1-(pyridin-3-yl)-1H-pyrazol-4-yl)-N-ethyl-4-((4-fluorobutoxy)imino)pentanamide (Compound FA20) was isolated as a light yellow gum (0.063 g, 73%).

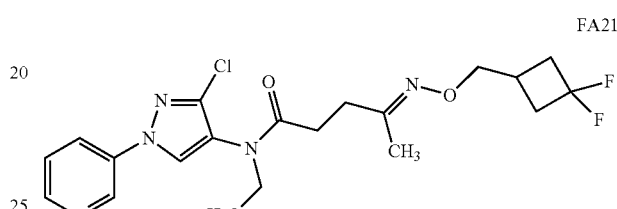

FA21

(E/Z)-N-(3-Chloro-1-(pyridin-3-yl)-1H-pyrazol-4-yl)-4-((3,3-difluorocyclobutyl)methoxy)imino)-N-ethylpentanamide (Compound FA21) was isolated as colorless gum (0.045 g, 34%).

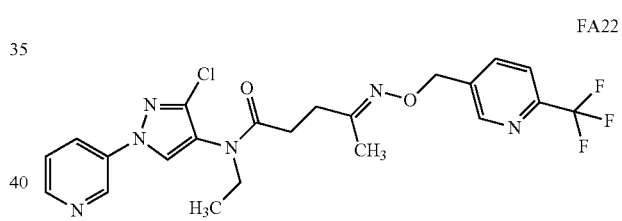

FA22

(E/Z)-N-(3-Chloro-1-(pyridin-3-yl)-1H-pyrazol-4-yl)-N-ethyl-4-((6-(trifluoromethyl)pyridin-3-yl)methoxy)imino)pentanamide (Compound FA22) was isolated as a light brown gum (0.135 g, 87%).

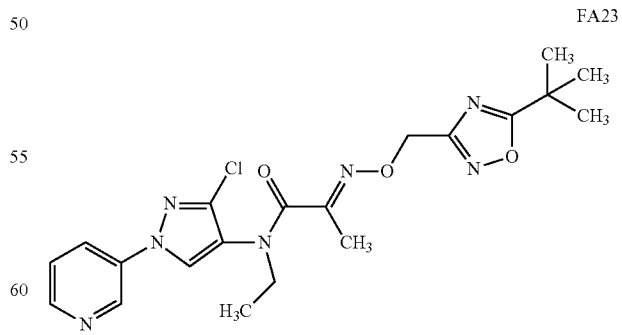

FA23

(E/Z)-4-(((5-(tert-Butyl)-1,2,4-oxadiazol-3-yl)methoxy)imino)-N-(3-chloro-1-(pyridin-3-yl)-1H-pyrazol-4-yl)-N-ethylpentanamide (Compound FA23) was isolated as a light brown gum (0.124 g, 83%).

FA24

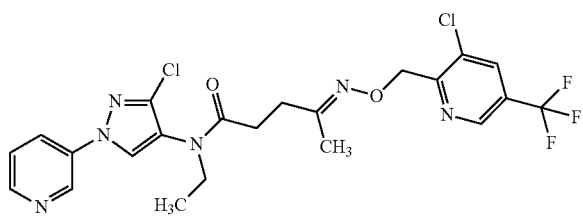

(E/Z)-N-(3-Chloro-1-(pyridin-3-yl)-1H-pyrazol-4-yl)-4-(((3-chloro-5-(trifluoromethyl)pyridin-2-yl)methoxy)imino)-N-ethylpentanamide (Compound FA24) was isolated a light brown gum (0.102 g, 61%).

FA25

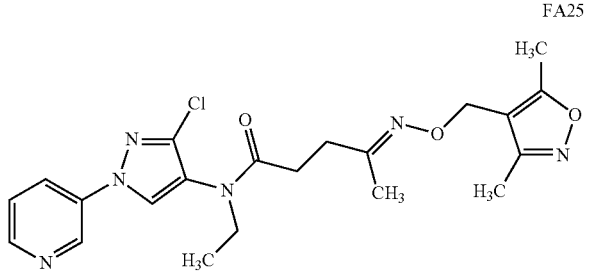 [SMILES: CCN(C(=O)CC/C(C)=N/OCc1c(C)noc1C)c1cn(-c2cccnc2)nc1Cl]

(E/Z)-N-(3-Chloro-1-(pyridin-3-yl)-1H-pyrazol-4-yl)-4-(((3,5-dimethylisoxazol-4-yl)methoxy)imino)-N-ethylpentanamide (Compound FA25) was isolated as a light brown gum (0.099 g, 71%).

FA26

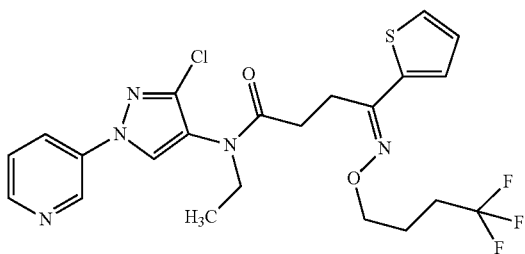

(E)-N-(3-Chloro-1-(pyridin-3-yl)-1H-pyrazol-4-yl)-N-ethyl-4-(thiophen-2-yl)-4-((4,4,4-trifluorobutoxy)imino)butanamide (Compound FA26) was isolated as light yellow gum (0.051 g, 38%).

FA27

(Z)-N-(3-Chloro-1-(pyridin-3-yl)-1H-pyrazol-4-yl)-N-ethyl-4-(thiophen-2-yl)-4-((4,4,4-trifluorobutoxy)imino)butanamide (Compound FA27) was isolated as a light yellow gum (0.018 g, 13%).

FA28

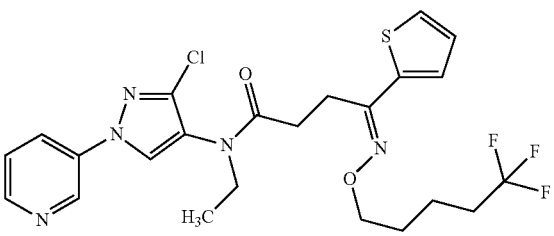

(E)-N-(3-Chloro-1-(pyridin-3-yl)-1H-pyrazol-4-yl)-N-ethyl-4-(thiophen-2-yl)-4-((5,5,5-trifluoropentyl)oxy)imino)butanamide (Compound FA28) was isolated as a light brown gum (0.055 g, 40%).

FA29

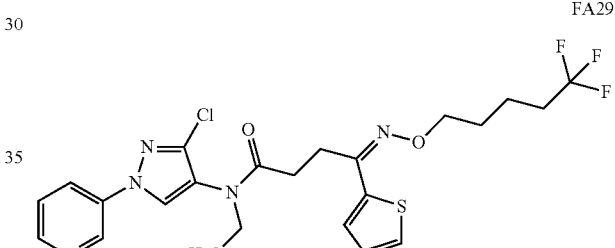

(Z)-N-(3-Chloro-1-(pyridin-3-yl)-1H-pyrazol-4-yl)-N-ethyl-4-(thiophen-2-yl)-4-(((5,5,5-trifluoropentyl)oxy)imino)butanamide (Compound FA29) was isolated as a light brown gum (0.021 g, 14%).

FA30

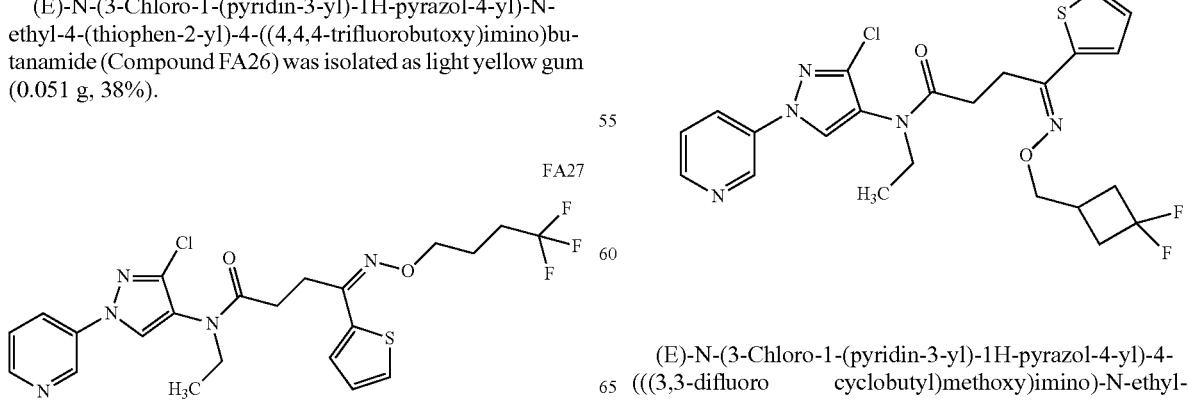

(E)-N-(3-Chloro-1-(pyridin-3-yl)-1H-pyrazol-4-yl)-4-(((3,3-difluoro cyclobutyl)methoxy)imino)-N-ethyl-4-(thiophen-2-yl)butanamide (Compound FA30) was isolated as a light brown gum (0.053 g, 42%).

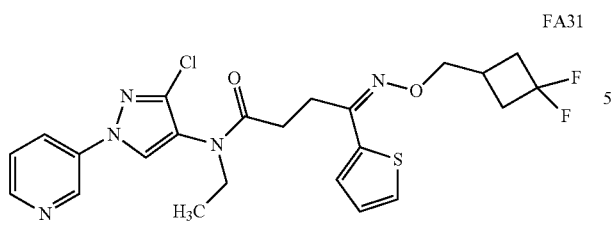

FA31

(Z)-N-(3-Chloro-1-(pyridin-3-yl)-1H-pyrazol-4-yl)-4-((3,3-difluoro cyclobutyl)methoxy)imino)-N-ethyl-4-(thiophen-2-yl)butanamide (Compound FA31) was isolated as a light brown gum (0.022 g, 17%).

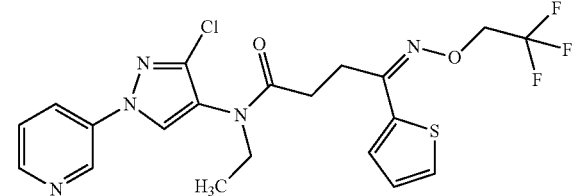

FA35

(E/Z)-N-(3-Chloro-1-(pyridin-3-yl)-1H-pyrazol-4-yl)-N-ethyl-4-(thiophen-2-yl)-4-(2,2,2-trifluoroethoxyl)imino)butanamide (Compound FA35) was isolated as a light brown gum (0.088 g, 69%).

FA36

(E)-N-(3-Chloro-1-(pyridin-3-yl)-1H-pyrazol-4-yl)-N-ethyl-4-(thiophen-2-yl)-4-((6-(trifluoromethyl) pyridin-3-yl)methoxy)imino)butanamide (Compound FA36) was isolated as a light brown gum (0.058 g, 39%).

FA37

(Z)-N-(3-Chloro-1-(pyridin-3-yl)-1H-pyrazol-4-yl)-N-ethyl-4-(thiophen-2-yl)-4-(((6-(trifluoromethyl) pyridin-3-yl)methoxy)imino)butanamide (Compound FA37) was isolated as light brown gum (0.030 g, 20%).

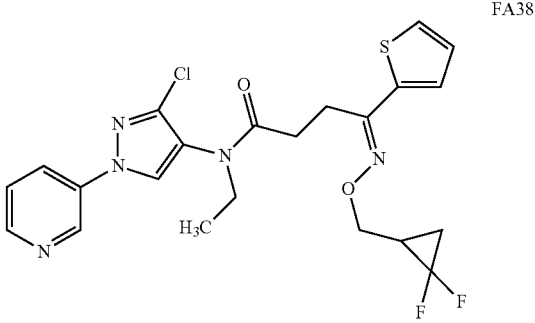 [SMILES: CCN(C(=O)CC/C(=N\OCC1CC1(F)F)c1cccs1)c1cn(-c2cccnc2)nc1Cl]

FA38

(E)-N-(3-Chloro-1-(pyridin-3-yl)-1H-pyrazol-4-yl)-4-(((2,2-difluorocyclopropyl)methoxy)imino)-N-ethyl-4-(thiophen-2-yl)butanamide (Compound FA38) was isolated as a light brown gum (0.040 g, 31%).

FA39

(Z)-N-(3-Chloro-1-(pyridin-3-yl)-1H-pyrazol-4-yl)-4-((2,2-difluorocyclopropyl)methoxy)imino)-N-ethyl-4-(thiophen-2-yl)butanamide (Compound FA39) was isolated as a light brown gum (0.018 g, 14%).

FA40

(E/Z)-N-(3-Chloro-1-(pyridin-3-yl)-1H-pyrazol-4-yl)-N-ethyl-4-((4-(trifluoromethoxy)benzyl)oxy)imino)pentanamide (Compound FA40) was isolated as a light brown gum (0.044 g, 27%).

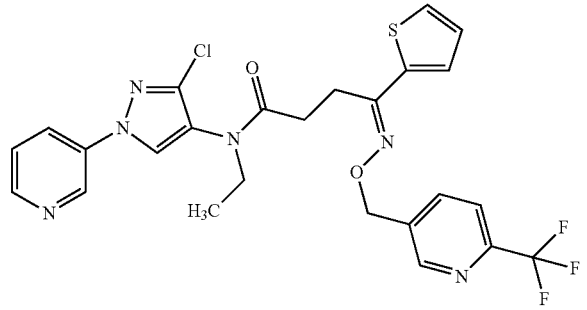

FA49

(Z)-N-(3-Chloro-1-(pyridin-3-yl)-1H-pyrazol-4-yl)-4-((2-(2,2-difluoro cyclopropyl)ethoxy)imino)-N-ethylpentanamide (Compound FA49) was isolated as a colorless oil (0.55 g, 56%).

(Z)-N-(3-Chloro-1-(pyridin-3-yl)-1H-pyrazol-4-yl)-4-((2-(2,2-difluorocyclopropyl) ethoxy)imino)-N-ethyl-2-methylbutanamide (Compound FA59) was isolated as a colorless oil (0.096 g, 47%).

FA50

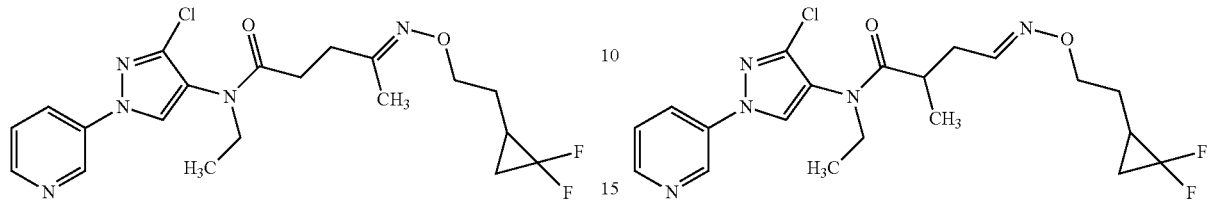

FA60

(E)-N-(3-Chloro-1-(pyridin-3-yl)-1H-pyrazol-4-yl)-4-((2-(2,2-difluoro cyclopropyl)ethoxy)imino)-N-ethylpentanamide (Compound FA50) was isolated as a colorless oil (0.57 g, 67%).

(E)-N-(3-Chloro-1-(pyridin-3-yl)-1H-pyrazol-4-yl)-4-((2-(2,2-difluorocyclopropyl)ethoxy)imino)-N-ethyl-2-methylbutanamide (Compound FA60) was isolated as a colorless oil (0.059 g, 47%).

FA57

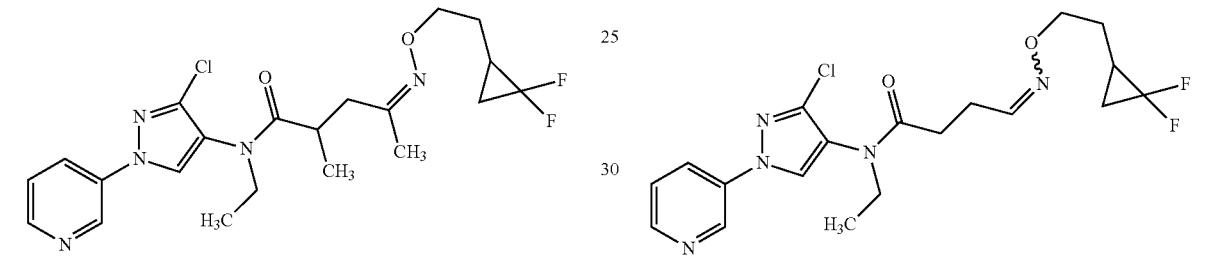

FA61

(Z)-N-(3-Chloro-1-(pyridin-3-yl)-1H-pyrazol-4-yl)-4-((2-(2,2-difluoro cyclopropyl)ethoxy)imino)-N-ethyl-2-methylpentanamide (Compound FA57) was isolated as a colorless oil (0.026 g, 41%).

(E/Z)-N-(3-Chloro-1-(pyridin-3-yl)-1H-pyrazol-4-yl)-4-((2-(2,2-difluorocyclopropyl)ethoxy)imino)-N-ethylbutanamide (Compound FA61) was isolated as a colorless oil (0.208 g, 79%).

Example 36

Preparation of N-(3-chloro-1-(pyridin-3-yl)-1H-pyrazol-4-yl)-3-((2,2-difluoroethyl))amino)-N-ethylpropanamide

FA58

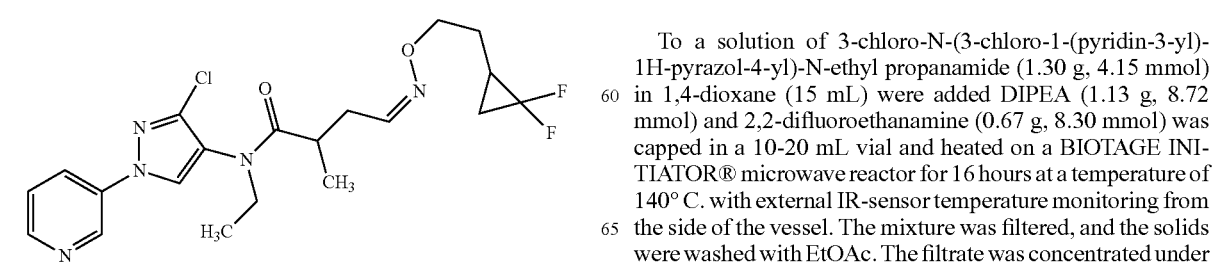

Compound C14

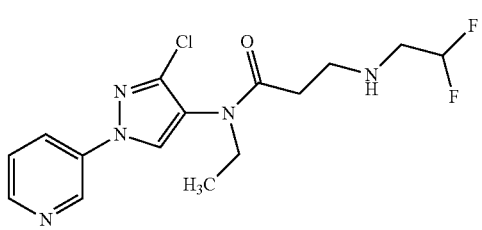 [SMILES: CCN(C(=O)CCNCC(F)F)c1cn(-c2cccnc2)nc1Cl]

(E)-N-(3-Chloro-1-(pyridin-3-yl)-1H-pyrazol-4-yl)-4-((2-(2,2-difluoro cyclopropyl)ethoxy)imino)-N-ethyl-2-methylpentanamide (Compound FA58) was isolated as a colorless oil (0.011 g, 57%).

FA59

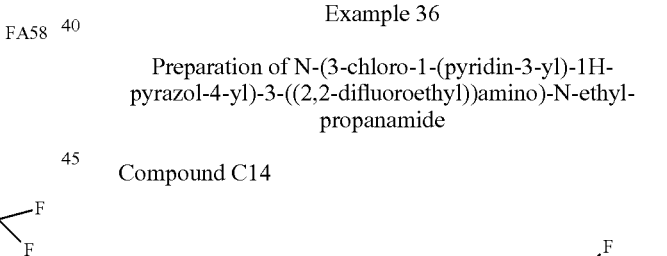

To a solution of 3-chloro-N-(3-chloro-1-(pyridin-3-yl)-1H-pyrazol-4-yl)-N-ethyl propanamide (1.30 g, 4.15 mmol) in 1,4-dioxane (15 mL) were added DIPEA (1.13 g, 8.72 mmol) and 2,2-difluoroethanamine (0.67 g, 8.30 mmol) was capped in a 10-20 mL vial and heated on a BIOTAGE INITIATOR® microwave reactor for 16 hours at a temperature of 140° C. with external IR-sensor temperature monitoring from the side of the vessel. The mixture was filtered, and the solids were washed with EtOAc. The filtrate was concentrated under reduced pressure to give brown gum, which was purified on silica gel eluting MeOH/CH$_2$Cl$_2$ to give the title compound C14 as a brown gum (1.22 g, 73.9%).

Example PE1

Preparation of N-(3-chloro-1-(pyridin-3-yl)-1H-pyrazol-4-yl)-N -ethyl-2-(2-oxo-3-(3,3,3-trifluoropropyl) pyrrolidin-1-yl)acetamide Compound P3

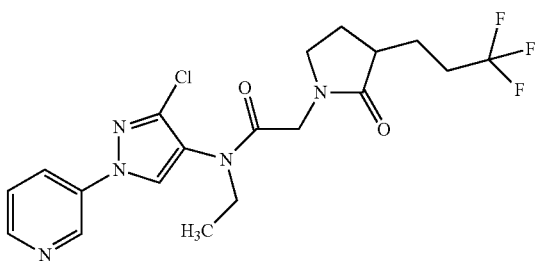 [SMILES: CCN(C(=O)CN1CCC(CCC(F)(F)F)C1=O)c1cn(-c2cccnc2)nc1Cl]

To 3-(3,3,3-trifluoropropyl)pyrrolidin-2-one in an appropriate reaction vessel may be added NaH (from about 1.0 eq to about 2.0 equivalent) in a solvent, such as THF (at a concentration between about 0.01 M to about 1 M) followed by 2-chloro-N-(3-chloro-1-(pyridin-3-yl)-1H-pyrazol-4-yl)-N-ethylacetamide (from about 0.5 eq to about 1.5 eq). The reaction may be stirred at a temperature from about 0° C. to about 25° C. until determined to be complete. After completion of the reaction, the product may be obtained using standard organic chemistry techniques for workup and purification.

The following compounds in Table 5 may be prepared according to the procedures disclosed in example PE1: P1, P2, P3, P4, P5, P6, P7.

Example PE2

Preparation of N-(3-chloro-1-(pyridin-3-yl)-1H-pyrazol-4-yl)-N-ethyl-2-(2-oxo-1-(3,3,3-trifluoropropyl) pyrrolidin-3-yl)acetamide Compound P6

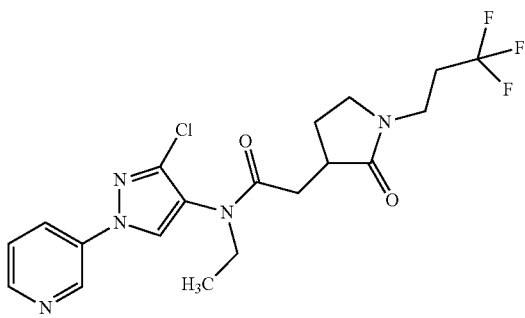 [SMILES: CCN(C(=O)CC1CCN(CCC(F)(F)F)C1=O)c1cn(-c2cccnc2)nc1Cl]

To N-(3-chloro-1-(pyridin-3-yl)-1H-pyrazol-4-yl)-N-ethyl-2-(2-oxopyrrolidin-3-yl)acetamide in an appropriate reaction vessel may be added NaH (from about 1.0 eq to about 2.0 equivalent) in a solvent, such as THF (at a concentration between about 0.01 M to about 1 M) followed by 2-chloro-N-(3-chloro-1-(pyridin-3-yl)-1H-pyrazol-4-yl)-N-ethylacetamide (from about 1.0 eq to about 2.0 eq). The reaction may be stirred at a temperature from about 0° C. to about 25° C. until determined to be complete. After completion of the reaction, the product may be obtained using standard organic chemistry techniques for workup and purification.

The following compounds in Table 5 may be prepared according to the procedures disclosed in example PE2: P8, P9, P10, P11, P12, P13, P14, P15, P18, P19.

Example PE3

Preparation of N-(3-chloro-1-(pyridin-3-yl)-1H-pyrazol-4-yl)-N -ethyl-1-(3,3,3-trifluoropropanoyl) piperidine-4-carboxamide Compound P16

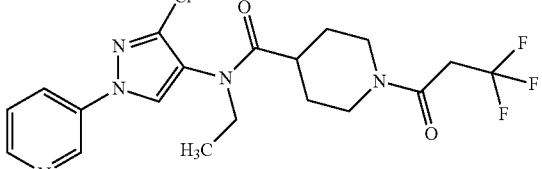

In an appropriate reaction vessel, to N-(3-chloro-1-(pyridin-3-yl)-1H -pyrazol-4-yl)-N-ethylpiperidine-4-carboxamide may be added 3,3,3-trifluoropropanoic acid (about 1.0 to about 2.0 eq), DMAP (about 2.0 to about 3.0 eq), and EDCI (about 1.5 to about 3.0 eq) in a solvent, such as CH$_2$Cl$_2$ (at a concentration between about 0.01 M to about 1 M). The reaction may be stirred at a temperature from about 0° C. to about 50° C. until determined to be completed. After completion of the reaction, the product may be obtained using standard organic chemistry techniques for workup and purification.

The following compounds in Table 5 may be prepared according to the procedures disclosed in example PE3: P16, P17, P20, P21, P22, P23, P24, P25, P28, P29, P30, P31, P32, P33.

Example PE4

Preparation of (E/Z)-N-(3-chloro-1-(pyridin-3-yl)-1H-pyrazol-4-yl)-N-ethyl-7,7,7-trifluoro-3-(methoxyimino)heptanamide Compound P26

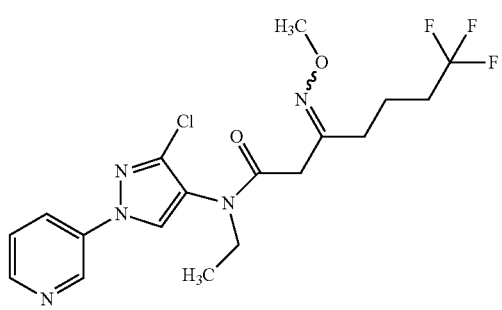 [SMILES: CCN(C(=O)CC(CCCC(F)(F)F)=NOC)c1cn(-c2cccnc2)nc1Cl]

In an appropriate reaction vessel, to N-(3-chloro-1-(pyridin-3-yl)-1H -pyrazol-4-yl)-N-ethyl-7,7,7-trifluoro-3-oxoheptanamide may be added a solvent system, such as pyridine and ethanol (at a concentration between about 0.01 M to about 1 M) and O-methyl hydroxylamine.hydrochloride (about 2.0 to about 3.0 eq). The reaction may be stirred at a temperature from about 25° C. to about 80° C. until determined to be completed. Following completion of the reaction, the product may be obtained using standard organic chemistry techniques for workup and purification.

The following compounds in Table 5 may be prepared according to the procedures disclosed in example PE4: P26, P27.

Example PE5

Preparation of (1S,3R)-N-(3-chloro-1-(pyridin-3-yl)-1H-pyrazol-4-yl)-N-ethyl-3-(N-methylacetamido) cyclopentanecarboxamide Compound P36

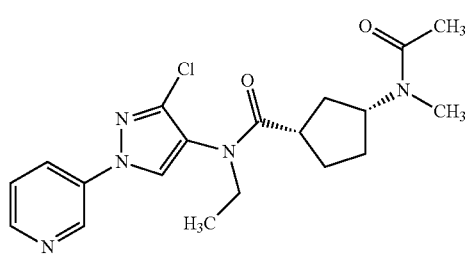 [SMILES: CCN(C(=O)[C@H]1CC[C@@H](N(C)C(C)=O)C1)c1cn(-c2cccnc2)nc1Cl]

In an appropriate reaction vessel, to (1S,3R)-N-(3-chloro-1-(pyridine -3-yl)-1H-pyrazol-4-yl)-N-ethyl-3-(methylamino)cyclopentanecarboxamide may be added acetyl chloride (about 1.0 to about 2.0 eq) and DMAP (about 2.0 to about 3.0 eq) in a solvent, such as $CH_2Cl_2$ (at a concentration between about 0.01 M to about 1 M). The reaction may be stirred at a temperature from about 0° C. to about 50° C. until determined to be completed. Following completion of the reaction, the product may be obtained using standard organic chemistry techniques for workup and purification.

The following compounds in Table 5 may be prepared according to the procedures disclosed in example PE5: P34, P35, P36, P37.

Example PE6

Preparation of N-(3-chloro-1-(pyridin-3-yl)-1H-pyrazol-4-yl)-N-ethyl-1-(3,3,3-trifluoropropanoyl) piperidine-4-carboxamide Compound P39

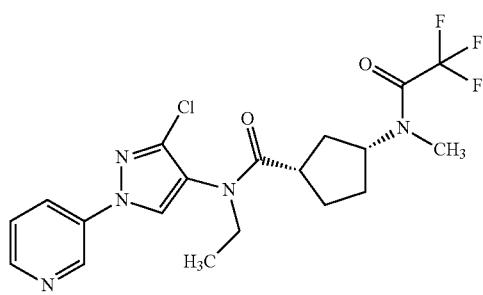 [SMILES: CCN(C(=O)[C@H]1CC[C@@H](N(C)C(=O)C(F)(F)F)C1)c1cn(-c2cccnc2)nc1Cl]

In an appropriate reaction vessel, to (1S,3R)-N-(3-chloro-1-(pyridine -3-yl)-1H-pyrazol-4-yl)-N-ethyl-3-(methylamino)cyclopentanecarboxamide may be added trifluoroacetic anhydride (about 1.0 to about 2.0 eq) and N-methylmorpholine (about 2.0 to about 3.0 eq) in a solvent, such as $CH_2Cl_2$ (at a concentration between about 0.01 M to about 1 M). The reaction may be stirred at a temperature from about 0° C. to about 50° C. until determined to be completed. Following completion of the reaction, the product may be obtained using standard organic chemistry techniques for workup and purification.

The following compounds in Table 5 may be prepared according to the procedures disclosed in example PE6: P38, P39.

Example 37

Preparation of N-[3-chloro-1-(3-pyridyl)pyrazol-4-yl]-N-ethyl-3-[2-oxo-1-(2,2,2-trifluoroethyl)pyrrolidin-3-yl]propanamide Compound P1

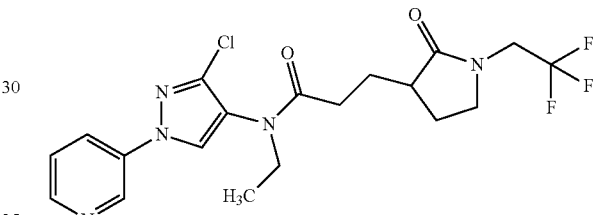

N-(3-Chloro-1-(pyridin-3-yl)-1H-pyrazol-4-yl)-N-ethyl-3-(2-oxopyrrolidin-3-yl)propanamide (0.037 g, 0.10 mmol) was added to a vial with stir bar, followed sodium hydride (60% in mineral oil, 0.010 g, 0.26 mmol). The vial was placed under $N_2$ and chilled to 0° C. THF (1 mL) was then added and the reaction was allowed to stir for 30 minutes 2,2,2-Trifluoroethyl trifluoromethanesulfonate (0.037 mL, 0.26 mmol) was added neat, dropwise. The reaction stirred overnight. The reaction was adsorbed onto CELITE®. Purification by flash column chromatography using $MeOH/CH_2Cl_2$ as eluent provided the title compound as a colorless oil (0.011 g, 24%).

The following molecules were made in accordance with the procedures disclosed in example 37:

FA62

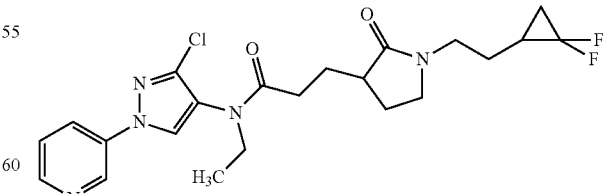

N-(3-Chloro-1-(pyridin-3-yl)-1H-pyrazol-4-yl)-3-(1-(2-(2,2-difluorocyclopropyl)ethyl)-2-oxopyrrolidin-3-yl)-N-ethylpropanamide (Compound FA62) was isolated as a colorless oil (0.026 g, 40%).

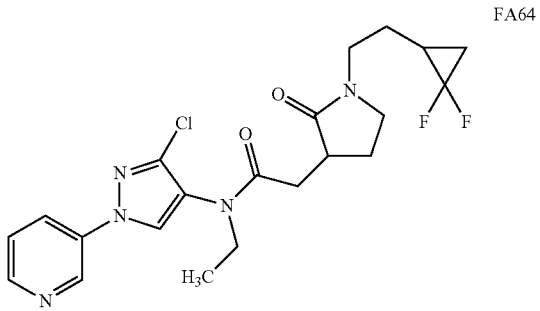 [SMILES: CCN(C(=O)CC1CCN(CCC2CC2(F)F)C1=O)c1cn(-c2cccnc2)nc1Cl]

N-(3-Chloro-1-(pyridin-3-yl)-1H-pyrazol-4-yl)-2-(1-(2-(2,2-difluorocyclopropyl)ethyl)-2-oxopyrrolidin-3-yl)-N-ethylacetamide (Compound FA64) was isolated as a colorless oil (0.027 g, 35%).

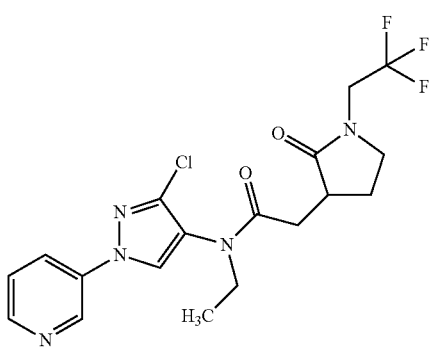

N-(3-Chloro-1-(pyridin-3-yl)-1H-pyrazol-4-yl)-N-ethyl-2-(2-oxo-1-(2,2,2-trifluoroethyl)pyrrolidin-3-yl)acetamide (Compound FA65) was isolated as a colorless oil (0.047 g, 63%).

Example 38

Preparation of N-[3-chloro-1-(3-pyridyl)pyrazol-4-yl]-N-ethyl-2-methyl-4-oxo-butanamide Compound FA48

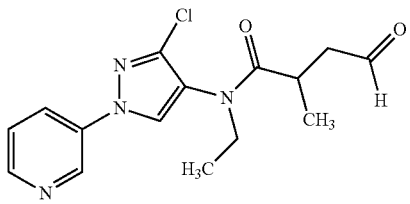 [SMILES: CCN(C(=O)C(C)CC=O)c1cn(-c2cccnc2)nc1Cl]

To N-(3-Chloro-1-(pyridin-3-yl)-1H-pyrazol-4-yl)-N-ethyl-2-methylpent-4-enamide (0.450 g, 1.41 mmol) in a flask with a stir bar dissolved in CH$_2$Cl$_2$ (13 mL) and MeOH (1.3 mL) was added Sudan III indicator solution (0.01 M, 0.060 mL). The flask was attached to an ozone generator and a flow of oxygen was initiated, with stirring. The reaction was cooled to −78° C., and the ozone production was bubbled through the solution for approxmately 6 minutes before the pink color was absent and the yellow solution started to turn green/blue. The ozone generation was arrested, and pure oxygen was bubbled through the reaction for approximately 5 minutes as the dark colors faded and the yellow color became prominent. While still at −78° C., triphenylphosphine (0.555 g, 2.12 mmol) was added as a solid, and the cooling bath was removed. A nitrogen gas inlet was attached to the flask, and the reaction was allowed to warm slowly to room temperature. The product was then concentrated and loaded onto CELITE®. Purification by flash column chromatography using 0-40% acetone/hexanes provided the title compound as a clear yellow oil that crystallized upon standing (0.390 g, 73%).

Example 39

Preparation of N-[3-chloro-1-(3-pyridyl)pyrazol-4-yl]-N-ethyl-2-methyl-4-oxo-pentanamide Compound FA51

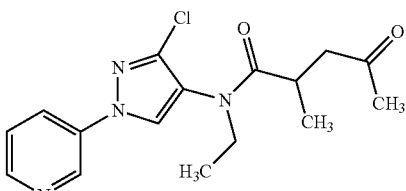

N-(3-chloro-1-(pyridin-3-yl)-1H-pyrazol-4-yl)-N-ethyl-2-methyl-4-oxobutanamide (0.390 g, 1.22 mmol) was dissolved in THF (12 mL) at −78° C. To this stirring solution was added dropwise methylmagnesium bromide (0.446 mL, 1.34 mmol). The reaction mixture was stirred at −78° C. for 30 minutes and was warmed to 0° C., at which point the reaction was quenched with a saturated aqueous NH$_4$Cl solution. The reaction product was extracted with diethyl ether, and the combined organics were washed with brine, then dried over Na$_2$SO$_4$ and concentrated under vacuum to provide a yellow oil. The oil was loaded onto CELITE® and purified by flash column chromatography using 0-50% acetone/hexanes as eluent. The secondary alcohol recovered as an impure oil was used immediately. The residual oil was taken up in CH$_2$Cl$_2$ (10 mL) and buffered with NaHCO$_3$ (0.153 g, 1.82 mmol). The resulting mixture was cooled to 0° C. and Dess-Martin periodinane (0.516 g, 1.22 mmol) was added in a single portion. The reaction mixture was stirred at 0° C. for 1 hour, then was warmed to room temperature. The reaction was quenched by slow addition of a saturated aqueous sodium bisulfite solution, and extracted with CH$_2$Cl$_2$. The organic layer was washed with brine, dried over Na$_2$SO$_4$ and concentrated to an oil that was loaded directly onto CELITE®. Purification by flash column chromatography using 0-40% acetone/hexanes as eluent provided the title compound as a clear, colorless oil. (0.0900 g, 20% over two steps).

Example 40

Preparation of N-[3-chloro-1-(3-pyridyl)pyrazol-4-yl]-N-ethyl-2-(2-oxopyrrolidin-3-yl)acetamide Compound FA63

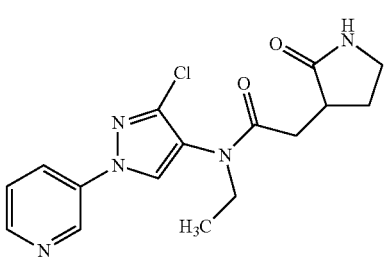 [SMILES: CCN(C(=O)CC1CCNC1=O)c1cn(-c2cccnc2)nc1Cl]

DIPEA (0.629 mL, 4.41 mmol) was dissolved in THF (20 mL) and cooled to about −78° C. n-Butylithium (1.77 mL, 4.41 mmol) was then added, and the reaction mixture was warmed to about 0° C. for 10 minutes, then re-cooled to about −78° C. Then, 1-(tert-butyldimethylsilyl)pyrrolidin-2-one (0.800 g, 4.01 mmol) was added, and the reaction mixture was warmed to 23° C. and stirred for 1 hour. The reaction was then re-chilled to −78° C., and 2-chloro-N-(3-chloro-1-(pyridin-3-yl)-1H-pyrazol-4-yl)-N-ethylacetamide (0.600 g, 2.01 mmol) was then added dropwise as a solution in THF (3 mL). The reaction mixture was stirred cold for 30 minutes, then was allowed to slowly warm to room temperature. After 1 hour, the reaction was quenched with a NH$_4$Cl solution and extracted with diethyl ether. The organics were washed with brine, dried over Na$_2$SO$_4$, and concentrated. The resulting oil was purified by flash column chromatography using 0-40% acetone/hexanes as eluent provided the intermediate 2-(1-(tert-butyldimethylsilyl)-2-oxopyrrolidin-3-yl)-N-(3-chloro-1-(pyridin-3-yl)-1H-pyrazol-4-yl)-N-ethylacetamide (0.604 g, 1.31 mmol). $^1$H NMR analysis indicated a mixture of molecules present favoring the desired product of about 5:1 over main byproduct. The mixture carried through to the deprotection step without further purification. 2-(1-(tert-Butyldimethylsilyl)-2-oxopyrrolidin-3-yl)-N-(3-chloro-1-(pyridin-3-yl)-1H-pyrazol-4-yl)-N-ethylacetamide (0.604 g, 1.31 mmol) was dissolved in THF (13 mL) and added was tetrabutylammonium fluoride (TBAF, 1.96 mL, 1.96 mmol). The reaction mixture was stirred for 30 minutes. The reaction product was concentrated onto CELITE® and purified by flash column chromatography using 40-100% acetone/hexanes as eluent providing the title compound (0.204 g, 30% over 2 steps).

Example 41

Preparation of 3-(but-3-en-1-yl)pyrrolidin-2-one

Compound CA3

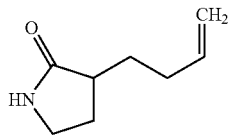

DIPEA (0.393 mL, 2.76 mmol) was dissolved in THF (25 mL) and chilled to −78° C. n-Butyllithium (1.10 mL, 2.76 mmol) was then added, and the reaction was warmed to 0° C. and re-chilled to −78° C. 1-(tert-Butyldimethylsilyl)pyrrolidin-2-one (0.500 g, 2.51 mmol) was then added as a solution in THF (1 mL), and the reaction mixture was warmed to room temperature for 1 hour. The reaction was then re-cooled to −78° C., and 4-bromobut-1-ene (0.305 mL, 3.01 mmol) was added dropwise in THF (1 mL). The reaction mixture was slowly warmed to room temperature overnight. The reaction was concentrated to an oil and loaded onto CELITE®. Purification by flash column chromatography using 0-30% acetone/hexanes provided the title compound (0.218 g, 62%): $^1$H NMR (400 MHz, CDCl$_3$) δ 6.15 (s, 1H), 5.82 (ddt, J=17.0, 10.2, 6.6 Hz, 1H), 5.09-4.87 (m, 2H), 3.42-3.24 (m, 2H), 2.44-2.25 (m, 2H), 2.24-2.05 (m, 2H), 1.99 (dddd, J=13.6, 9.4, 6.9, 4.1 Hz, 1H), 1.78 (dq, J=12.1, 8.4 Hz, 1H), 1.45 (dtd, J=13.7, 9.1, 5.5 Hz, 1H); $^{13}$C NMR (101 MHz, CDCl$_3$) δ 180.44, 137.92, 115.13, 40.29, 40.16, 31.45, 30.05, 27.60; ESIMS m/z 138 ([M−H]$^-$).

Example 42

Preparation of 3-(3-but-3-enyl-2-oxo-pyrrolidin-1-yl)-N-[3-chloro-1-(3-pyridyl)pyrazol-4-yl]-N-ethyl-propanamide Compound FA67

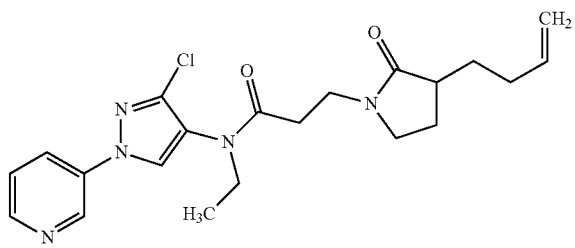 [SMILES: C=CCCC1CCN(CCC(=O)N(CC)c2cn(-c3cccnc3)nc2Cl)C1=O]

To 3-chloro-N-(3-chloro-1-(pyridin-3-yl)-1H-pyrazol-4-yl)-N-ethylpropan amide (0.500 g, 1.60 mmol) in acetone (8 mL) was added sodium iodide (0.359 g, 2.40 mmol). The reaction was heated to reflux for 24 hours. The reaction product was filtered and concentrated to provide N-(3-chloro-1-(pyridin-3-yl)-1H-pyrazol-4-yl)-N-ethyl-3-iodopropanamide (0.363 g, 0.898 mmol), which was used immediately without further purification. To 3-(but-3-en-1-yl)pyrrolidin-2-one (0.125 g, 0.898 mmol) dissolved in DMF (4.49 ml) was added sodium hydride (60% in mineral oil, 0.0360 g, 0.898 mmol). The reaction stirred for 45 minutes. Then, N-(3-Chloro-1-(pyridin-3-yl)-1H-pyrazol-4-yl)-N-ethyl-3-iodopropanamide (0.363 g, 0.898 mmol) was added as a solution in DMF (2 mL). The reaction mixture was allowed to stir at room temperature overnight. The reaction product was poured into water, extracted with diethyl ether, and washed with brine. The organics were dried and concentrated to give an oil that was purified by flash column chromatography using 0-60% acetone/hexanes as eluent providing the title compound as a clear, colorless oil. (0.257 g, 69%).

Table 3, Table 4, and Table 5 show non-limiting examples of the compounds of formula I.

Compounds F1, F5, F9, F12, F28, F44, F46, F56, F65, F65, F75, F94, F97, F99, F101, F112, F113, P16, P21, P24, FA5, FA6, FA7, FA8, FA9, FA10, FA11, FA12, FA14, FA15, FA16, FA17, FA41, FA42, FA43, FA44, FA45, and FA66 were prepared according to example 7.

Compounds F2, F19, and F83 were prepared according of example 5.

Compounds F3, F4, F6, F7, F8, F10, F18, F21, F22, F23, F26, F27, F29, F33, F37, F39, F47, F48, F49, F52, F61, F69, F76, F77, F82, F88, F90, F95, F98, F100, F106, F107, F110, F111, F122, F123, F124, P20, P23, FA3, FA13, FA18, FA32, FA33, FA34, FA69, FA70, FA71, and FA76 were prepared according to example 1.

Compound F11 was prepared according to example 30.

Compounds F13, F15, F30, F43, F54, F55, F67, F68, F70, F73, F78, F80, F85, F108, F115, F118, and FA77 were prepared according of example 4.

Compounds F14, F32, F53, F74, F81, F84, F87, F91, F103, F104, F117, F119, F127, and F129 were prepared according of example 14.

Compounds F16 and F93 were prepared according of example 29.

Compound F17 was prepared according to example 33.

Compounds F20, F36, F51, F59, F72, FA4, FA19, FA20, FA21, FA22, FA23, FA24, FA25, FA26, FA27, FA28, FA29, FA30, FA31, FA35, FA36, FA37, FA38, FA39, FA40, FA49, FA50, FA57, FA58, FA59, FA60, and FA61 were prepared according of example 35.

Compounds F24 and F126 were prepared according of example 17.

Compounds F25, F62, and FA75 were prepared according of example 2.

Compounds F31, F38, and FA68 were prepared according of example 31.

Compounds F34, F35, F89, and F125 were prepared according of example 32.

Compounds F40, F42, F64, F66, F79, F96, F114, and F121 were prepared according of example 26.

Compound F41 was prepared according to example 20.

Compound F45 was prepared according to example 21.

Compounds F50, F58, and F71 were prepared according of example 13.

Compound F52 was prepared according to example 11.

Compounds F57, F63, F102, F120, FA72, FA73, and FA74 were prepared according of example 8.

Compounds F60, F92, and F130 were prepared according of example 23.

Compound F86 was prepared according to example 19.

Compounds F105, FA1, FA2, FA46, FA47, FA52, FA53, FA54, FA55, and FA56 were prepared according to example 34.

Compounds F109 and F116 were prepared according of example 15.

Compound F128 was prepared according to example 9.

Compound F131 was prepared according to example 10.

Compounds P1, FA62, FA64, and FA65 were prepared according to example 37.

Compound FA48 was prepared according to example 38.

Compound FA51 was prepared according to example 39.

Compound FA40 was prepared according to example 40.

Compound FA67 was prepared according to example 42.

While the present disclosure may be susceptible to various modifications and alternative forms, specific embodiments have been described by way of example in detail herein. However, it should be understood that the present disclosure is not intended to be limited to the particular forms disclosed. Rather, the present disclosure is to cover all modifications, equivalents, and alternatives falling within the scope of the present disclosure as defined by the following appended claims and their legal equivalents.

TABLE 3

| No. | Formula | Appearance, Melting Point | Mass (m/z) | $^1$H NMR | $^{13}$C NMR, $^{19}$F NMR, IR |
|---|---|---|---|---|---|
| F1 | | White Solid | HRMS-ESI [M + H]$^+$ calcd for C$_{17}$H$_{19}$ClF$_2$N$_5$O$_2$, 398.1190; found, 398.1209 | (400 MHz, CDCl$_3$) δ 9.00-8.91 (m, 1H), 8.65 (dd, J = 4.8, 1.4 Hz, 1H), 8.05 (ddd, J = 8.3, 2.7, 1.5 Hz, 1H), 7.99 (s, 1H), 7.48 (ddd, J = 8.4, 4.8, 0.8 Hz, 1H), 6.76 (s, 1H), 3.87 (d, J = 4.1 Hz, 2H), 3.75 (q, J = 7.2 Hz, 2H), 2.15 (ddd, J = 13.4, 7.9, 6.1 Hz, 1H), 1.51 (t, J = 2.3 Hz, 3H), 1.27 (ddd, J = 11.7, 7.8, 4.9 Hz, 1H), 1.20 (t, J = 12 Hz, 3H) | $^{19}$F NMR (376 MHz, CDCl$_3$) δ −135.58 (d, J = 153.5 Hz), −136.56 (d, J = 153.5 Hz) IR (thin film) 3336, 3093, 1656 cm$^{-1}$ |
| F2 | | Pink Solid | HRMS-ESI [M + H]$^+$ calcd for C$_{17}$H$_{23}$ClN$_5$O$_3$, 380.1484; found, 380.1494 | (400 MHz, CDCl$_3$) δ 8.93 (dd, J = 2.7, 0.7 Hz, 1H), 8.64 (dd, J = 4.7, 1.4 Hz, 1H), 8.03 (ddd, J = 8.3, 2.8, 1.5 Hz, 1H), 7.98 (s, 1H), 7.46 (ddd, J = 8.3, 4.8, 0.8 Hz, 1H), 5.37 (br s, 1H), 3.81-3.67 (multiple peaks, 4H), 1.42 (s, 9H), 1.17 (t, J = 7.2 Hz, 3H) | IR (thin film) 3341, 3094, 1675 cm$^{-1}$ |
| F3 | | White Semi-Solid | ESIMS 344.1 ([M + H]$^+$) | (400 MHz, CDCl$_3$) δ 9.07 (s, 1H), 8.64 (d, J = 4.8 Hz, 1H), 8.43 (s, 1H), 8.12 (ddd, J = 8.3, 2.6, 1.3 Hz, 1H), 7.51 (dd, J = 8.3, 4.8 Hz, 1H), 7.38 (ddd, J = 9.0, 6.6, 2.1 Hz, 1H), 7.31 (ddd, J = 6.7, 2.1, 0.7 Hz, 1H), 6.54 (dt, J = 9.0, 0.9 Hz, 1H), 6.23 (td, J = 6.7, 1.3 Hz, 1H), 4.54 (s, 2H), 3.29 (s, 3H) | IR (thin film) 1658 cm$^{-1}$ |
| F4 | | Yellow Solid | HRMS-ESI [M + H]$^+$ calcd for C$_{18}$H$_{25}$ClN$_5$O$_3$, 394.1640; found, 394.1646 | $^1$H NMR (400 MHz, CDCl$_3$) δ 8.95 (d, J = 2.8 Hz, 1H), 8.63 (t, J = 5.4 Hz, 1H), 8.11-7.87 (multiple peaks, 2H), 7.45 (dd, J = 8.4, 4.8 Hz, 1H), 3.81 (d, J = 27.7 Hz, 2H), 3.71 (q, J = 7.1 Hz, 2H), 2.91 (d, J = 9.9 Hz, 3H), 1.44 (s, 9H), 1.26-1.01 (m, 3H) | IR (thin film) 3528, 3092, 1687 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F5 | (structure) | Light Yellow Foam | HRMS-ESI [M + H]⁺ calcd for $C_{17}H_{20}ClF_3N_5O_2$, 418.1252; found, 418.126 | (400 MHz, CDCl₃) δ 8.97 (d, J = 2.7 Hz, 1H), 8.69-8.59 (m, 1H), 8.10 (s, 1H), 8.06-7.98 (m, 1H), 7.52-7.42 (m, 1H), 3.96 (br s, 2H), 3.73 (dq, J = 14.4, 7.2 Hz, 2H), 3.11 (s, 2.6H, major), 2.96 (s, 0.4H, minor), 2.68-2.57 (m, 2H), 2.56-2.36 (m, 2H), 1.18 (dt, J = 12.7, 7.2 Hz, 3H) | ¹⁹F NMR (376 MHz, CDCl₃) δ −66.58 (minor rotamer), −66.65 (major rotamer) IR (thin film) 3515, 3093, 1679, 1652 cm⁻¹ |
| F6 | (structure) | White Solid, 102-104° C. | ESIMS 344.7 ([M + H]⁺) | (400 MHz, CDCl₃) δ 8.97 (d, J = 2.7 Hz, 1H), 8.63 (dd, J = 4.7, 1.4 Hz, 1H), 8.13 (s, 1H), 8.02 (ddd, J = 8.3, 2.7, 1.4 Hz, 1H), 7.45 (dd, J = 8.4, 4.7 Hz, 1H), 3.94 (s, 2H), 3.54 (t, J = 7.1 Hz, 2H), 3.25 (s, 3H), 2.38 (t, J = 8.1 Hz, 2H), 2.13-2.04 (m, 2H) | IR (thin film) 1666 cm⁻¹ |
| F7 | (structure) | White Solid, 154-156° C. | ESIMS 352.0 ([M + H]⁺) | (400 MHz, CDCl₃) δ 8.97 (d, J = 2.6 Hz, 1H), 8.63 (dd, J = 4.8, 1.3 Hz, 1H), 8.11 (s, 1H), 8.01 (ddd, J = 8.3, 2.7, 1.4 Hz, 1H), 7.46 (dd, J = 8.3, 4.8 Hz, 1H), 3.96 (s, 2H), 3.81 (t, J = 7.3 Hz, 2H), 3.32 (t, J = 7.3 Hz, 2H), 3.25 (s, 3H) | IR (thin film) 1686, 1650 cm⁻¹ |
| F8 | (structure) | White Solid, 114-117° C. | ESIMS 376.2 ([M + H]⁺) | (400 MHz, CDCl₃) δ 9.00 (d, J = 2.6 Hz, 1H), 8.61 (dd, J = 4.7, 1.4 Hz, 1H), 8.12 (s, 1H), 8.06 (ddd, J = 8.3, 2.7, 1.5 Hz, 1H), 7.45 (ddd, J = 8.4, 4.8, 0.5 Hz, 1H), 3.68 (q, J = 7.0 Hz, 2H), 3.59 (t, J = 7.1 Hz, 2H), 3.36 (t, J = 5.5 Hz, 2H), 2.46 (t, J = 7.1 Hz, 2H), 2.31 (t, J = 6.2 Hz, 2H), 1.84-1.68 (m, 4H), 1.14 (t, J = 7.2 Hz, 3H) | |

TABLE 3-continued

| No. | Formula | Appearance, Melting Point | Mass (m/z) | ¹H NMR | ¹³C NMR, ¹⁹F NMR, IR |
|---|---|---|---|---|---|
| F9 | (cyclopropyl-N-acetyl propanamide linked to 3-chloro-1-(pyridin-3-yl)-1H-pyrazol-4-yl with N-ethyl) | Yellow Oil | ESIMS 376 ([M + H]⁺) | (400 MHz, CDCl₃) δ 9.02 (dd, J = 2.7, 0.8 Hz, 1H), 8.61 (dd, J = 4.8, 1.5 Hz, 1H), 8.17 (s, 1H), 8.07 (ddd, J = 8.4, 2.7, 1.5 Hz, 1H), 7.45 (ddd, J = 8.4, 4.8, 0.8 Hz, 1H), 3.67 (q, J = 7.1 Hz, 2H), 3.64-3.55 (m, 2H), 2.73 (tt, J = 7.0, 4.0 Hz, 1H), 2.50-2.36 (m, 2H), 2.15 (s, 3H), 1.14 (t, J = 7.2 Hz, 3H), 0.96-0.84 (m, 2H), 0.79-0.68 (m, 2H) | ¹³C NMR (101 MHz, CDCl₃) δ 173.8, 171.3, 148.4, 140.6, 140.2, 135.7, 127.1, 126.3, 124.0, 123.8, 43.8, 43.2, 32.7, 30.8, 22.7, 13.0, 9.3 (2C) |
| F10 | (thiazolidinone-methyl carbonyl linked to 3-chloro-1-(pyridin-3-yl)-1H-pyrazol-4-yl with N-ethyl) | White Solid 131-132° C. | ESIMS 366.1 ([M + H]⁺) | (400 MHz, CDCl₃) δ 8.98 (d, J = 2.6 Hz, 1H), 8.64 (dd, J = 4.7, 1.3 Hz, 1H), 8.08 (s, 1H), 8.03 (ddd, J = 8.3, 2.7, 1.4 Hz, 1H), 7.55-7.39 (m, 1H), 3.92 (s, 2H), 3.80 (s, 2H), 3.71 (q, J = 7.1 Hz, 2H), 3.32 (t, J = 7.3 Hz, 2H), 1.17 (t, J = 7.2 Hz, 3H) | IR (thin film) 1658 cm⁻¹ |
| F11 | (tert-butoxycarbonyl pyrrolidine-3-carbonyl linked to 3-chloro-1-(pyridin-3-yl)-1H-pyrazol-4-yl with N-ethyl) | Colorless Solid 51-53° C. | ESIMS 421 ([M + H]⁺); 419 ([M − H]⁻) | (400 MHz, CDCl₃) δ 8.97 (s, 1H), 8.64 (dd, J = 4.7, 1.3 Hz, 1H), 8.06 (s, 1H), 7.98 (dd, J = 8.3, 2.7, 1.4 Hz, 1H), 7.47 (dd, J = 8.2, 4.8 Hz, 1H), 3.55 (m, 5H), 3.22 (m, 1H), 2.95 (d, J = 8.5 Hz, 1H), 2.18 (m, 1H), 1.94 (s, 1H), 1.43 (s, 9H), 1.16 (t, J = 7.1 Hz, 3H) | |
| F12 | (4,4,4-trifluorobutanamide linked to 3-chloro-1-(pyridin-3-yl)-1H-pyrazol-4-yl with N-ethyl) | Off-White Semi-Solid | HRMS-ESI [M + H]⁺ calcd for C₁₇H₂₀ClF₃N₅O₂, 418.1252; found, 418.1260 | (400 MHz, CDCl₃) δ 8.94 (d, J = 2.6 Hz, 1H), 8.64 (dd, J = 4.8, 1.4 Hz, 1H), 8.04 (ddd, J = 8.3, 2.7, 1.4 Hz, 1H), 7.93 (s, 1H), 7.47 (ddd, J = 8.3, 4.8, 0.8 Hz, 1H), 6.41 (t, J = 5.8 Hz, 1H), 3.71 (q, J = 7.2 Hz, 2H), 3.51 (q, J = 6.0 Hz, 2H), 2.55-2.37 (multiple peaks, 4H), 2.37-2.31 (m, 2H), 1.17 (t, J = 7.2 Hz, 3H) | ¹⁹F NMR (376 MHz, CDCl₃) δ −66.70 IR (thin film) 3317, 3087, 1656 m⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F13 | | Slightly Yellow Solid | HRMS-ESI [M + H]$^+$ calcd for C$_{20}$H$_{23}$ClN$_5$O$_3$, 416.1484; found, 416.1476 | (400 MHz, CDCl$_3$) δ 8.98-8.93 (m, 1H), 8.62 (dd, J = 4.7, 1.4 Hz, 1H), 8.06-7.97 (multiple peaks, 2H), 7.45 (ddd, J = 8.4, 4.8, 0.8 Hz, 1H), 6.09 (d, J = 3.1 Hz, 1H), 6.07-5.97 (m, 1H), 5.88 (dt, J = 3.1, 1.1 Hz, 1H), 4.35 (d, J = 5.4 Hz, 2H), 3.70 (q, J = 7.1 Hz, 2H), 2.51 (br s, 4H), 2.33-2.17 (m, 3H), 1.14 (t, J = 7.2 Hz, 3H) | IR (thin film) 3302, 3087, 1655 cm$^{-1}$ |
| F14 | | Light Brown Gum | ESIMS 492 ([M + H]$^+$) | (400 MHz, CDCl$_3$) δ 8.89 (d, J = 2.4 Hz, 1H), 8.57 (dd, J = 4.4 Hz, 1H), 7.80 7.97 (m, 1H), 7.92 (s, 1H), 7.52 (d, J = 8.0 Hz, 2H), 7.40 (dd, J = 8.4 Hz, 4.8 Hz, 1H), 7.27 (d, J = 8.4 Hz, 2H), 4.38-4.29 (m, 2H), 3.61 (q, J = 6.8 Hz, 2H), 3.51-3.49 (m, 1H), 3.40 (t, J = 5.6 Hz, 1H), 2.96-2.95 (m, 1H), 2.65 (dd, J = 17.2 Hz, 4.4 Hz, 1H), 2.36-2.28 (m, 1H), 1.07 (t, J = 7.2 Hz, 3H) | IR (KBr): 3089, 2926, 2308, 1745, 1666, 1440, 1325, 1120 cm$^{-1}$ |
| F15 | | Light Yellow Solid | HRMS-ESI [M + H]$^+$ calcd for C$_{20}$H$_{23}$ClN$_5$O$_3$, 416.1484; found, 416.1476 | (400 MHz, CDCl$_3$) δ 8.98-8.93 (m, 1H), 8.62 (dd, J = 4.7, 1.4 Hz, 1H), 8.06-7.97 (multiple peaks, 2H), 7.45 (ddd, J = 8.4, 4.8, 0.8 Hz, 1H), 6.09 (d, J = 3.1 Hz, 1H), 6.07-5.97 (m, 1H), 5.88 (dt, J = 3.1, 1.1 Hz, 1H), 4.35 (d, J = 5.4 Hz, 2H), 3.70 (q, J = 7.1 Hz, 2H), 2.51 (br s, 4H), 2.33-2.17 (m, 3H), 1.14 (t, J = 7.2 Hz, 3H) | $^{13}$C NMR (101 MHz, CDCl$_3$) δ 172.41, 172.02, 148.61, 140.81, 140.13, 135.66, 126.63, 126.31, 124.05, 123.82, 45.78, 43.97, 37.93, 31.50, 30.79, 29.66, 26.39, 25.83, 13.08 IR (thin film) 3315, 3087, 1653 cm$^{-1}$ |
| F16 | | Colorless Oil | ESIMS 382 ([M + H]$^+$) | (400 MHz, CDCl$_3$) δ 8.99 (d, J = 2.6 Hz, 1H), 8.61 (dd, J = 4.7, 1.4 Hz, 1H), 8.24 (s, 1H), 8.02 (ddd, J = 8.3, 2.7, 1.4 Hz, 1H), 7.43 (ddd, J = 8.3, 4.8, 0.5 Hz, 1H), 5.02 (q, J = 6.7 Hz, 1H), 3.98 (s, 1H), 3.72 (s, 3H), 3.39 (s, 1H), 3.16 (s, 3H), 1.40 (d, J = 6.8 Hz, 3H), 1.16 (t, J = 7.2 Hz, 3H) | IR (thin film) 2977, 2936, 1676 m$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F17 | (structure) | Colorless Gum | | (400 MHz, CDCl₃) δ 8.95 (dd, J = 2.7, 0.7 Hz, 1H), 8.64 (dd, J = 4.7, 1.4 Hz, 1H), 8.04 (ddd, J = 8.3, 2.7, 1.4 Hz, 1H), 7.93 (s, 1H), 7.88 (t, J = 1.1 Hz, 1H), 7.47 (ddd, J = 8.3, 4.7, 0.7 Hz, 1H), 7.24 (t, J = 1.5 Hz, 1H), 7.11 (dd, J = 1.6, 0.9 Hz, 1H), 6.28-5.73 (m, 1H), 3.92-3.79 (m, 4H), 3.70 (q, J = 7.2 Hz, 2H), 2.50 (t, J = 6.4 Hz, 2H), 1.16 (t, J = 7.2 Hz, 3H) | ¹⁹F NMR (376 MHz, CDCl₃) δ -121.88 IR (thin film) 1638 cm⁻¹ |
| F18 | (structure) | Off-White Solid 131-133° C. | ESIMS 430.2 ([M + H]⁺) | (400 MHz, CDCl₃) δ 8.97 (d, J = 2.5 Hz, 1H), 8.61 (dd, J = 4.7, 1.4 Hz, 1H), 8.13 (s, 1H), 8.04 (ddd, J = 8.3, 2.7, 1.5 Hz, 1H), 7.44 (ddd, J = 8.3, 4.8, 0.5 Hz, 1H), 3.54 (d, J = 6.8 Hz, 2H), 3.48 (dd, J = 12.3, 6.9 Hz, 4H), 2.60 (d, J = 58.7 Hz, 4H), 1.79-1.67 (m, 4H), 1.55 (dd, J = 6.4, 3.8 Hz, 4H), 1.04-0.85 (m, 1H), 0.57-0.40 (m, 2H), 0.24-0.09 (m, 2H) | IR (thin film) 1638 cm⁻¹ |
| F19 | (structure) | White Solid | HRMS-ESI [M + Na]⁺ calcd for C₁₈H₂₄ClN₅NaO₃, 416.1460; found, 416.1459 | (400 MHz, CDCl₃) δ 8.95 (s, 1H), 8.63 (d, J = 4.6 Hz, 1H), 8.05 (ddd, J = 8.3, 2.7, 1.5 Hz, 1H), 7.95 (s, 1H), 7.51-7.42 (m, 1H), 5.22 (s, 1H), 3.71 (q, J = 7.2 Hz, 2H), 3.38 (q, J = 6.0 Hz, 2H), 2.33 (t, J = 5.8 Hz, 2H), 1.41 (s, 9H), 1.16 (t, J = 7.2 Hz, 3H) | IR (thin film) 3346, 3093, 1697, 1661 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F20 | | Colorless Oil | ESIMS 440.2 ([M + H]⁺) | (400 MHz, CDCl₃) δ 8.95 (dt, J = 2.2, 1.0 Hz, 1H), 8.62 (dd, J = 4.8, 1.5 Hz, 1H), 8.04 (ddd, J = 8.3, 2.8, 1.5 Hz, 1H), 7.93 (S, 1H), 7.45 (ddd, J = 8.3, 4.7, 0.7 Hz, 1H), 4.03 (t, J = 6.3 Hz, 2H), 3.70 (q, J = 7.1 Hz, 2H), 2.51 (dd, J = 8.5, 6.9 Hz, 2H), 2.41-2.31 (m, 2H), 1.81 (s, 3H), 1.80 (m, 1H), 1.71 (ddd, J = 17.0, 8.7, 5.3 Hz, 1H), 1.52 (m, 1H), 1.44-1.28 (m, 1H), 1.21-1.08 (m, 3H), 0.89 (dtd, J = 12.8, 7.5, 3.5 Hz, 1H) | IR (thin film) 3092, 2968, 2932, 1662 cm⁻¹ |
| F21 | | Off-White Solid 108-110° C. | ESIMS 390.2 ([M + H]⁺) | (400 MHz, CDCl₃) δ 8.97 (d, J = 2.6 Hz, 1H), 8.61 (dd, J = 4.7, 1.4 Hz, 1H), 8.12 (s, 1H), 8.03 (ddd, J = 8.3, 2.7, 1.4 Hz, 1H), 7.44 (ddd, J = 8.3, 4.8, 0.6 Hz, 1H), 3.71 (q, J = 7.2 Hz, 2H), 3.57-3.46 (m, 2H), 3.46-3.39 (m, 2H), 2.65 (d, J = 6.1 Hz, 2H), 2.48 (d, J = 6.0 Hz, 2H), 1.65-1.50 (m, 6H), 1.15 (t, J = 7.2 Hz, 3H) | IR (thin film) 1624 cm⁻¹ |
| F22 | | Off-White Solid 145-148° C. | ESIMS 362.1 ([M + H]⁺) | (400 MHz, CDCl₃) δ 8.97 (d, J = 2.5 Hz, 1H), 8.62 (dd, J = 4.7, 1.3 Hz, 1H), 8.17 (s, 1H), 8.01 (ddd, J = 8.3, 2.7, 1.4 Hz, 1H), 7.44 (dd, J = 8.3, 4.8 Hz, 1H), 4.02 (s, 2H), 3.46 (s, 2H), 3.24 (s, 3H), 2.57-2.45 (m, 2H), 1.78-1.64 (m, 6H) | IR (thin film) 1678, 1628 cm⁻¹ |

TABLE 3-continued

| No. | Formula | Appearance, Melting Point | Mass (m/z) | 1H NMR | 13C NMR, 19F NMR, IR |
|---|---|---|---|---|---|
| F23 | | White Solid | ESIMS 304 ([M − BOC]+) | (400 MHz, CDCl3) δ 8.96 (bs, 1H), 8.63 (dd, J = 4.9 Hz, 1H), 8.21-7.86 (m, 2H), 7.46 (dd, J = 8.3, 4.8 Hz, 1H), 4.65-4.30 (m, 2H), 4.02-3.70 (bs, 2H), 3.06-2.79 (m, 3H), 2.25 (bs, 1H), 1.44 (s, 9H) | IR (thin film) 1696 cm−1 |
| F24 | | White Foam | ESIMS 360 ([M + H]+) | (400 MHz, CDCl3) δ 8.97 (d, J = 2.6 Hz, 1H), 8.63 (dd, J = 4.8, 1.4 Hz, 1H), 8.12 (s, 1H), 8.07 (ddd, J = 8.3, 2.7, 1.5 Hz, 1H), 7.48 (dd, J = 8.3, 4.8 Hz, 1H), 6.74 (d, J = 9.0 Hz, 1H), 5.91 (dt, J = 5.5, 2.2 Hz, 1H), 5.73 (dddd, J = 5.5, 2.5, 1.1 Hz, 1H), 5.05 (dddd, J = 9.6, 7.0, 3.4, 1.7 Hz, 1H), 3.57 (dq, J = 8.3, 2.3 Hz, 1H), 3.26 (s, 3H), 2.25 (dt, J = 13.8, 8.3 Hz, 1H), 1.99 (s, 3H), 1.87 (dt, J = 13.8, 2.3 Hz, 1H) | 13C NMR (101 MHz, CDCl3) δ 175.49, 169.10, 148.61, 139.94, 135.58, 134.80, 134.75, 131.43, 126.34, 126.32, 125.50, 124.13, 54.05, 47.37, 37.49, 35.19, 23.46 |
| F25 | | White Solid 123-126° C. | | (400 MHz, CDCl3) δ 8.96 (d, J = 2.4 Hz, 1H), 8.61 (dd, J = 4.7, 1.4 Hz, 1H), 8.19 (s, 1H), 8.02 (ddd, J = 8.3, 2.7, 1.5 Hz, 1H), 7.44 (ddd, J = 8.3, 4.8, 0.6 Hz, 1H), 3.24 (s, 3H), 3.04 (s, 3H), 2.93 (s, 3H), 2.67 (t, J = 6.3 Hz, 2H), 2.51 (t, J = 6.3 Hz, 2H) | 13C NMR (101 MHz, CDCl3) δ 173.2, 171.8, 148.5, 140.1, 135.7, 126.5, 126.3, 125.8, 124.0, 37.1, 36.9, 35.5, 28.5, 28.4 IR (thin film) 3431, 1629, 1585 cm−1 |
| F26 | | White Semi-Solid | ESIMS 306.1 ([M + H]+) | (400 MHz, CDCl3) δ 8.94 (dd, J = 2.8, 0.8 Hz, 1H), 8.64 (dd, J = 4.7, 1.4 Hz, 1H), 8.03 (ddd, J = 8.4, 2.7, 1.4 Hz, 1H), 7.90 (s, 1H), 7.47 (ddd, J = 8.3, 4.8, 0.8 Hz, 1H), 4.24-4.09 (m, 2H), 3.86-3.65 (m, 4H), 3.32 (tt, J = 8.8, 6.4 Hz, 1H), 1.41 (s, 9H), 1.17 (t, J = 7.2 Hz, 3H) | IR (thin film) 1670 cm−1 |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F27 | 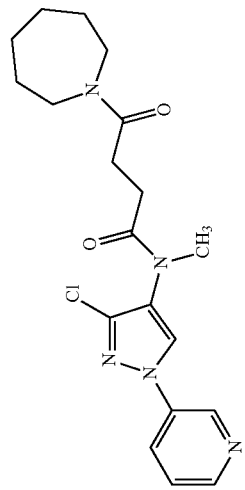 | White Solid 99-101° C. | ESIMS 390.2 ([M + H]$^+$) | (400 MHz, CDCl$_3$) δ 8.96 (d, J = 2.6 Hz, 1H), 8.60 (dd, J = 4.7, 1.4 Hz, 1H), 8.18 (s, 1H), 8.02 (ddd, J = 8.3, 2.7, 1.5 Hz, 1H), 7.44 (ddd, J = 8.4, 4.8, 0.5 Hz, 1H), 3.51-3.45 (m, 4H), 3.24 (s, 3H), 2.68 (t, J = 6.4 Hz, 2H), 2.53 (t, J = 6.4 Hz, 2H), 1.75 (dd, J = 11.3, 5.7 Hz, 2H), 1.68 (dd, J = 11.4, 5.6 Hz, 2H), 1.60-1.52 (m, 4H) | IR (thin film) 1658 cm$^{-1}$ |
| F28 | 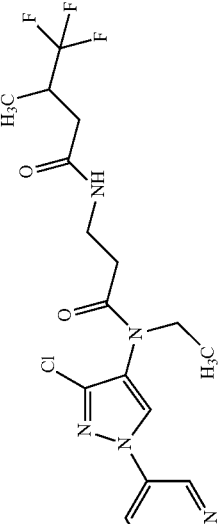 | Off-White Foam | HRMS-ESI [M + H]$^+$ calcd for C$_{18}$H$_{22}$ClF$_3$N$_5$O$_2$, 432.1409; found, 432.1420 | (400 MHz, CDCl$_3$) δ 8.94 (d, J = 2.7 Hz, 1H), 8.64 (dd, J = 4.8, 1.4 Hz, 1H), 8.05 (ddd, J = 8.3, 2.7, 1.4 Hz, 1H), 7.93 (s, 1H), 7.47 (ddd, J = 8.4, 4.8, 0.8 Hz, 1H), 6.41 (t, J = 6.0 Hz, 1H), 3.81-3.61 (m, 2H), 3.60-3.40 (m, 2H), 2.83 (tddd, J = 9.0, 7.0, 4.5, 2.1 Hz, 1H), 2.51 (dd, J = 14.8, 4.8 Hz, 1H), 2.41-2.27 (m, 2H), 2.08 (dd, J = 14.8, 9.1 Hz, 1H), 1.17 (t, J = 7.2 Hz, 3H), 1.14 (d, J = 6.9 Hz, 3H) | $^{19}$F NMR (376 MHz, CDCl$_3$) δ −73.55 IR (thin film) 3323, 3088, 1655 cm$^{-1}$ |
| F29 | 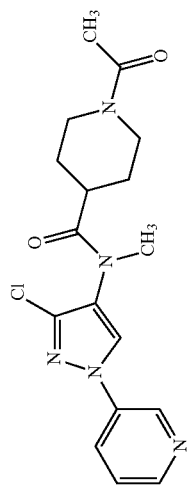 | White Semi-Solid | ESIMS 362.2 ([M + H]$^+$) | (400 MHz, CDCl$_3$) δ 9.01-8.92 (m, 1H), 8.64 (dd, J = 4.8, 1.5 Hz, 1H), 8.06 (ddd, J = 8.4, 2.7, 1.4 Hz, 1H), 8.01 (s, 1H), 7.53-7.40 (m, 1H), 4.55 (d, J = 13.3 Hz, 1H), 3.82 (d, J = 13.5 Hz, 1H), 3.23 (s, 3H), 3.02-2.85 (m, 1H), 2.63-2.38 (m, 2H), 2.07 (s, 3H), 1.94-1.64 (m, 4H) | IR (thin film) 1630 cm$^{-1}$ |
| F30 | 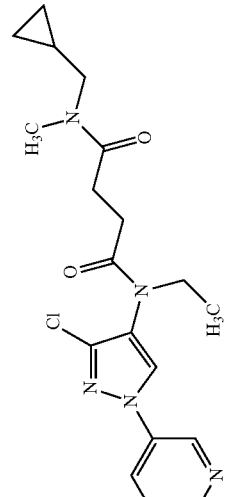 | Light Yellow Clear Viscous Oil | HRMS-ESI [M + H]$^+$ calcd for C$_{19}$H$_{25}$ClN$_5$O$_2$, 390.1691; found, 390.1695. | (400 MHz, CDCl$_3$) δ 8.98 (s, 1H), 8.61 (s, 1H), 8.12 (d, J = 0.6 Hz, 1H), 8.09-7.98 (m, 1H), 7.45 (dd, J = 8.4, 4.7 Hz, 1H), 3.71 (q, J = 7.1 Hz, 2H), 3.23 (t, J = 7.2 Hz, 2H), 3.02 (d, J = 43.3 Hz, 3H), 2.67 (br s, 2H), 2.49 (br s, 2H), 1.15 (td, J = 7.2, 0.8 Hz, 3H), 1.03-0.85 (m, 1H), 0.62-0.53 (m, 1H), 0.51-0.44 (m, 1H), 0.22 (ddt, J = 11.9, 6.1, 4.7 Hz, 2H) | IR (thin film) 3081, 1642 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F31 | | Colorless Oil | ESIMS 350 ([M + H]⁺) | (400 MHz, CDCl₃) δ 8.97 (d, J = 2.7 Hz, 1H), 8.62 (dd, J = 4.8, 1.5 Hz, 1H), 8.08 (s, 1H), 8.03 (ddd, J = 8.3, 2.7, 1.5 Hz, 1H), 7.45 (dd, J = 8.5, 4.7 Hz, 1H), 4.35-4.25 (m, 2H), 3.75-3.63 (m, 2H), 3.53 (t, J = 6.5 Hz, 2H), 3.24 (s, 3H), 2.53 (t, J = 6.5 Hz, 2H) | IR (thin film) 3095, 2921, 1734, 1659 cm⁻¹ |
| F32 | | Light Green Gum | ESIMS 348 ([M + H]⁺) | (400 MHz, CDCl₃) δ 8.95 (d, J = 2.4 Hz, 1H), 8.63 (d, J = 4.0 Hz, 1H), 8.05-8.02 (m, 1H), 7.98 (s, 1H), 7.46 (dd, J = 8.4, 4.8 Hz, 1H), 3.67 (q, J = 7.2 Hz, 2H), 3.53-3.52 (m, 2H), 3.06 (d, J = 3.6 Hz, 1H), 2.80 (s, 3H), 2.72 (dd, J = 16.8 Hz, 3.6 Hz, 1H), 2.42-2.35 (m, 1H), 1.16 (t, J = 7.2 Hz, 3H) | IR (KBr): 3439, 2924, 1743, 1666, 1440, 1261 cm⁻¹ |
| F33 | | White Solid 129-131° C. | ESIMS 376.2 ([M + H]⁺) | (400 MHz, CDCl₃) δ 8.96 (d, J = 2.5 Hz, 1H), 8.60 (dd, J = 4.7, 1.4 Hz, 1H), 8.18 (s, 1H), 8.02 (ddd, J = 8.3, 2.7, 1.4 Hz, 1H), 7.44 (ddd, J = 8.3, 4.7, 0.5 Hz, 1H), 3.53-3.41 (m, 4H), 3.24 (s, 3H), 2.67 (t, J = 6.4 Hz, 2H), 2.51 (t, J = 6.4 Hz, 2H), 1.64-1.50 (m, 6H) | IR (thin film) 1630 cm⁻¹ |
| F34 | | Colorless Oil | ESIMS 462.2 ([M + H]⁺) | (400 MHz, CDCl₃) δ 9.08-8.83 (m, 1H), 8.63 (ddd, J = 7.0, 4.8, 1.5 Hz, 1H), 8.03 (ddd, J = 8.4, 2.7, 1.4 Hz, 1H), 7.92 (d, J = 9.3 Hz, 1H), 7.52-7.38 (m, 1H), 6.16-5.70 (m, 1H), 4.02 (m, 1H), 3.82-3.47 (m, 5H), 2.89 (m, 1H), 2.67-2.50 (m, 1H), 2.45 (d, J = 5.7 Hz, 1H), 2.24-2.09 (m, 1H), 1.78-1.60 (m, 1H), 1.21-1.09 (m, 3H) | IR (thin film) 3098, 2977, 1650 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F35 | | Light Brown Oil | ESIMS 476.3 ([M + H]⁺) | (400 MHz, CDCl₃) δ 8.95 (d, J = 2.7 Hz, 1H), 8.63 (dt, J = 4.7, 2.4 Hz, 1H), 8.17- 8.02 (m, 1H), 8.02-7.90 (m, 1H), 7.46 (ddd, J = 8.1, 4.8, 2.8 Hz, 1H), 6.34-5.66 (m, 1H), 4.02-3.28 (m, 6H), 2.48 (t, J = 7.6 Hz, 1H), 1.85 (ddd, J = 13.6, 8.3, 4.5 Hz, 1H), 1.44 (dt, J = 5.2, 2.3 Hz, 3H), 1.35-0.98 (m, 5H) | IR (thin film) 3096, 2977, 1650 cm⁻¹ |
| F36 | | Colorless Oil | ESIMS 481.3 ([M + H]⁺) | (400 MHz, CDCl₃) δ 8.94 (dd, J = 5.6, 2.6 Hz, 1H), 8.61 (dd, J = 4.7, 1.4 Hz, 1H), 8.38 (d, J = 5.1 Hz, 1H), 8.05 (s, 1H), 8.03-7.97 (m, 1H), 7.49-7.39 (m, 1H), 7.36 (d, J = 1.4 Hz, 1H), 7.18 (dt, J = 5.1, 1.0 Hz, 1H), 3.74 (q, J = 7.2 Hz, 2H), 2.82 (t, J = 7.4 Hz, 0.6H), 2.73 (t, J = 6.7 Hz, 1.4H), 2.53 (t, J = 6.7 Hz, 2H), 2.19-2.03 (m, 3H), 1.21-1.04 (m, 3H) | IR (thin film) 3089, 2974, 1665 cm⁻¹ |
| F37 | | White Solid 116-118° C. | ESIMS 362.1 ([M + H]⁺) | (400 MHz, CDCl₃) δ 8.96 (d, J = 2.5 Hz, 1H), 8.60 (dd, J = 4.7, 1.4 Hz, 1H), 8.20 (s, 1H), 8.02 (ddd, J = 8.4, 2.7, 1.4 Hz, 1H), 7.44 (ddd, J = 8.3, 4.8, 0.4 Hz, 1H), 3.49-3.43 (m, 4H), 3.24 (s, 3H), 2.66-2.58 (m, 2H), 2.52 (t, J = 6.2 Hz, 2H), 1.95 (dd, J = 13.2, 6.7 Hz, 2H), 1.85 (dd, J = 13.5, 6.5 Hz, 2H) | IR (thin film) 1648, 1622 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F38 | | Colorless Gum | ESIMS 366.7 ([M + H]⁺) | (400 MHz, CDCl₃) δ 8.97 (d, J = 2.8 Hz, 1H), 8.63 (dd, J = 4.8, 1.5 Hz, 1H), 8.10 (s, 1H), 8.03 (ddd, J = 8.4, 2.8, 1.5 Hz, 1H), 7.45 (dd, J = 8.5, 4.7 Hz, 1H), 4.57-4.43 (m, 2H), 3.98 (dd, J = 9.5, 8.0 Hz, 2H), 3.86 (t, J = 6.3 Hz, 2H), 3.24 (s, 3H), 2.72 (t, J = 6.3 Hz, 2H) | IR (thin film) 3094, 2933, 1659 cm⁻¹ |
| F39 | | Colorless Oil | ESIMS 362.1 ([M + H]⁺) | (400 MHz, CDCl₃) δ 8.99 (d, J = 2.5 Hz, 1H), 8.62 (dd, J = 4.7, 1.4 Hz, 1H), 8.11 (s, 1H), 8.05 (ddd, J = 8.4, 2.7, 1.5 Hz, 1H), 7.45 (ddd, J = 8.4, 4.8, 0.5 Hz, 1H), 3.68 (dd, J = 14.2, 7.2 Hz, 2H), 3.53 (t, J = 6.9 Hz, 2H), 3.46 (t, J = 7.1 Hz, 2H), 2.43 (t, J = 6.9 Hz, 2H), 2.33 (t, J = 8.1 Hz, 2H), 2.06-1.96 (m, 2H), 1.15 (t, J = 7.2 Hz, 3H) | IR (thin film) 1658 cm⁻¹ |
| F40 | | Light Yellow Oil | ESIMS 397 ([M + H]⁺) | (400 MHz, CDCl₃) δ 8.99 (d, J = 2.5 Hz, 1H), 8.62 (d, J = 4.7 Hz, 1H), 8.07 (m, 2H), 7.46 (dd, J = 8.2, 4.8 Hz, 1H), 3.68 (m, 4H), 3.00 (s, 3H), 2.79 (s, 2H), 2.44 (s, 2H), 1.21 (m, 6H) | IR (thin film) 3387, 3089, 2973, 2931 cm⁻¹ |
| F41 | | Yellow Oil | | (400 MHz, CDCl₃) δ 8.94 (d, J = 2.6 Hz, 1H), 8.61 (dd, J = 4.8, 1.5 Hz, 1H), 8.03 (ddd, J = 8.3, 2.7, 1.5 Hz, 1H), 8.00 (s, 1H), 7.46 (dd, J = 8.3, 4.8 Hz, 1H), 5.80 (d, J = 6.5 Hz, 1H), 4.46 (qt, J = 7.6, 3.8 Hz, 1H), 3.30 (s, 3H), 2.83-2.69 (m, 2H), 2.44-2.31 (m, 1H), 2.28-2.18 (m, 1H), 1.88 (s, 3H) | ¹³C NMR (101 MHz, CDCl₃) δ 169.59, 167.84, 148.61, 140.02, 139.88, 136.66, 135.60, 126.20, 125.37, 124.14, 53.44, 48.71, 41.08, 40.65, 23.30 (two aromatic carbon not located) IR (thin film) 3287, 3080, 2920, 2849, 1646, 1584, 1545 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F42 | (structure) | Colorless Oil | ESIMS 381 ([M + H]⁺) | (400 MHz, CDCl₃) δ 9.00 (d, J = 2.6 Hz, 1H), 8.62 (d, J = 4.3 Hz, 1H), 8.06 (m, 2H), 7.46 (s, 1H), 4.02 (m, 2H), 3.70 (q, J = 6.9 Hz, 2H), 3.54 (t, J = 7.0 Hz, 2H), 2.89 (s, 3H), 2.41 (m, 2H), 1.19 (m, 6H) | IR (thin film) 2978, 1660, 1584 cm⁻¹ |
| F43 | (structure) | Clear Semi-Solid | HRMS-ESI [M + H]⁺ calcd for C₁₆H₂₀ClFN₅O₂, 368.1284; found, 368.1304 | (400 MHz, CDCl₃) δ 8.96 (d, J = 2.7 Hz, 1H), 8.62 (dd, J = 4.8, 1.5 Hz, 1H), 8.07-8.00 (m, 2H), 7.46 (dd, J = 8.3, 4.8 Hz, 1H), 6.23 (br s, 1H), 4.54 (t, J = 4.8 Hz, 1H), 4.42 (t, J = 4.8 Hz, 1H), 3.70 (q, J = 7.2 Hz, 2H), 3.63-3.56 (m, 1H), 3.52 (q, J = 5.1 Hz, 1H), 2.52 (q, J = 5.4 Hz, 4H), 1.15 (t, J = 7.2 Hz, 3H) | IR (thin film) 3316, 3087, 1652 cm⁻¹ |
| F44 | (structure) | Off-White Foam | HRMS-ESI ([M + H]⁺ calcd for C18H22ClF3N5O2, 432.1409; found, 432.1422 | (400 MHz, CDCl₃) δ 8.94 (d, J = 2.6 Hz, 1H), 8.63 (dd, J = 4.7, 1.4 Hz, 1H), 8.03 (ddd, J = 8.3, 2.7, 1.4 Hz, 1H), 7.91 (s, 1H), 7.46 (ddd, J = 8.3, 4.8, 0.8 Hz, 1H), 6.44 (t, J = 5.9 Hz, 1H), 3.70 (ddt, J = 31.2, 13.6, 6.9 Hz, 2H), 3.62-3.37 (m, 2H), 2.66 (dqd, J = 14.8, 10.9, 8.6 Hz, 1H), 2.55-2.44 (m, 1H), 2.44-2.25 (m, 2H), 2.18-2.00 (m, 1H), 1.26-1.20 (m, 3H), 1.17 (t, J = 7.2 Hz, 3H) | ¹⁹F NMR (376 MHz, CDCl₃) δ −64.77 IR (thin film) 3320, 3088, 1655 cm⁻¹ |
| F45 | (structure) | Orange Oil | ESIMS 420 (M + H)+ | (400 MHz, CDCl₃) δ 8.95 (dd, J = 2.7, 0.8 Hz, 1H), 8.63 (dd, J = 4.8, 1.4 Hz, 1H), 8.05 (ddd, J = 8.4, 2.8, 1.5 Hz, 1H), 7.99 (s, 1H), 7.47 (ddd, J = 8.3, 4.8, 0.8 Hz, 1H), 5.60 (d, J = 8.0 Hz, 1H), 4.03 (s, 1H), 3.24 (s, 3H), 2.86 (t, J = 4.8 Hz, 1H), 2.03-1.84 (m, 2H), 1.80-1.64 (m, 4H), 1.44 (s, 9H) | ¹³C NMR (101 MHz, CDCl₃) δ 178.09, 155.42, 148.68, 140.44, 139.97, 135.62, 126.31, 125.98, 125.74, 124.13, 78.89, 52.36, 39.73, 37.35, 36.86, 34.02, 29.04, 28.48 |

TABLE 3-continued

| No. | Formula | Appearance, Melting Point | Mass (m/z) | ¹H NMR | ¹³C NMR, ¹⁹F NMR, IR |
|---|---|---|---|---|---|
| F46 | (4-fluorophenylacetamide-propyl chain on N-ethyl, 3-chloro-1-(pyridin-3-yl)pyrazol-4-yl) | White Solid | HRMS-ESI [M + H]⁺ calcd for $C_{21}H_{22}ClFN_5O_2$, 430.1441; found, 430.1445 | (400 MHz, CDCl₃) δ 9.03-8.86 (m, 1H), 8.63 (dd, J = 4.8, 1.4 Hz, 1H), 8.02 (ddd, J = 8.3, 2.7, 1.4 Hz, 1H), 7.86 (s, 1H), 7.46 (ddd, J = 8.4, 4.7, 0.7 Hz, 1H), 7.26-7.19 (m, 2H), 7.09-6.97 (m, 2H), 6.33-6.22 (m, 1H), 3.66 (q, J = 7.2 Hz, 2H), 3.55-3.39 (multiple peaks, 4H), 2.31 (t, J = 5.7 Hz, 2H), 1.14 (t, J = 7.2 Hz, 3H) | ¹⁹F NMR (376 MHz, CDCl₃) δ −115.49 IR (thin film) 3302, 3071, 1651 cm⁻¹ |
| F47 | (2-oxopiperidin-1-yl-acetamide, N-ethyl, 3-chloro-1-(pyridin-3-yl)pyrazol-4-yl) | Off-White Solid 109-112° C. | ESIMS 362.1 ([M + H]⁺) | (400 MHz, CDCl₃) δ 8.99 (d, J = 2.6 Hz, 1H), 8.62 (dd, J = 4.8, 1.4 Hz, 1H), 8.15 (s, 1H), 8.02 (ddd, J = 8.3, 2.7, 1.4 Hz, 1H), 7.45 (dd, J = 8.4, 4.7 Hz, 1H), 3.92 (s, 2H), 3.73-3.66 (m, 2H), 3.47-3.33 (m, 2H), 2.47-2.26 (m, 2H), 1.88-1.82 (m, 4H), 1.17 (t, J = 7.2 Hz, 3H) | IR (thin film) 1672, 1627 cm⁻¹ |
| F48 | (2-oxooxazolidin-3-yl-acetamide, N-ethyl, 3-chloro-1-(pyridin-3-yl)pyrazol-4-yl) | White Solid 126-129° C. | ESIMS 350.1 ([M + H]⁺) | (400 MHz, CDCl₃) δ 8.98 (d, J = 2.6 Hz, 1H), 8.64 (dd, J = 4.7, 1.3 Hz, 1H), 8.09 (s, 1H), 8.03 (ddd, J = 8.4, 2.7, 1.4 Hz, 1H), 7.46 (ddd, J = 8.3, 4.8, 0.5 Hz, 1H), 4.39 (t, J = 8.0 Hz, 2H), 3.87 (s, 2H), 3.81-3.60 (m, 4H), 1.17 (t, J = 7.2 Hz, 3H) | IR (thin film) 1736, 1669 cm⁻¹ |
| F49 | (2-oxopiperidin-1-yl-propanamide, N-methyl, 3-chloro-1-(pyridin-3-yl)pyrazol-4-yl) | Colorless Oil | ESIMS 362.1 ([M + H]⁺) | (400 MHz, CDCl₃) δ 9.00 (d, J = 2.5 Hz, 1H), 8.61 (dd, J = 4.7, 1.3 Hz, 1H), 8.15 (s, 1H), 8.06 (ddd, J = 8.4, 2.7, 1.5 Hz, 1H), 7.44 (ddd, J = 8.3, 4.8, 0.6 Hz, 1H), 3.60 (t, J = 7.1 Hz, 2H), 3.37 (t, J = 5.6 Hz, 2H), 3.22 (s, 3H), 2.50 (t, J = 7.1 Hz, 2H), 2.32 (dd, J = 12.2, 5.8 Hz, 2H), 1.80-1.76 (m, 4H) | IR (thin film) 1661, 1619 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F50 | [structure] | Light Yellow Gum | ESIMS 348 ([M + H]$^+$) | (400 MHz, CDCl$_3$) δ 9.01 (d, J = 2.4 Hz, 1H), 8.64 (d, J = 4.0 Hz, 1H), 8.09-8.06 (m, 2H), 7.47 (dd, J = 8.4 Hz, 4.8 Hz, 1H), 5.59 (s, 1H), 3.76-3.66 (m, 2H), 3.45 (t, J = 5.6 Hz, 1H), 3.28-3.26 (m, 1H), 3.00 (dd, J = 5.6, 2.5 Hz, 1H), 2.45-2.33 (m, 2H), 2.19-2.09 (m, 1H), 2.06-1.97 (m, 1H), 1.18 (t, J = 7.2 Hz, 3H) | IR (KBr): 3435, 2974, 2829, 1743, 1658, 1487, 1357, 1180 cm$^{-1}$ |
| F51 | [structure] | Colorless Oil | ESIMS 418.2 ([M + H]$^+$) | (400 MHz, CDCl$_3$) δ 9.00-8.90 (m, 1H), 8.62 (dd, J = 4.7, 1.4 Hz, 1H), 8.03 (ddd, J = 8.3, 2.8, 1.6 Hz, 1H), 7.91 (d, J = 4.9 Hz, 1H), 7.45 (ddd, J = 8.3, 4.7, 0.8 Hz, 1H), 4.38-4.24 (m, 2H), 3.70 (q, J = 7.2 Hz, 2H), 2.53 (t, J = 7.0 Hz, 2H), 2.38 (t, J = 7.4 Hz, 2H), 1.86 (s, 3H), 1.15 (dd, J = 7.8, 6.7 Hz, 3H) | IR (thin film) 3092, 2974, 2932, 1663 cm$^{-1}$ |
| F52 | [structure] | Brown Viscous Oil | HRMS-ESI [M + H]$^+$ calcd for C$_{19}$H$_{27}$ClN$_5$O$_3$, 408.1797; found, 408.1802 | (400 MHz, CDCl$_3$) δ 8.99 (d, J = 2.6 Hz, 1H), 8.62 (dt, J = 4.7, 1.5 Hz, 1H), 8.15-8.01 (multiple peaks, 2H), 7.51-7.36 (m, 1H), 3.70 (q, J = 7.0 Hz, 2H), 3.50 (t, J = 7.0 Hz, 2H), 2.84 (br s, 3H), 2.39 (br s, 2H), 1.37 (br s, 9H), 1.15 (t, J = 7.2 Hz, 3H) | IR (thin film) 3512, 3092, 1667 cm$^{-1}$ |
| F53 | [structure] | Light Yellow Gum | ESIMS 376 ([M + H]$^+$) | (400 MHz, CDCl$_3$) δ 9.02 (d, J = 2.4 Hz, 1H), 8.64 (d, J = 4.0 Hz, 1H), 8.11-8.08 (m, 1H), 8.03 (s, 1H), 7.48 (dd, J = 8.4 Hz, 4.8 Hz, 1H), 3.74-3.67 (m, 2H), 3.34 (t, J = 5.2 Hz, 1H), 3.14-3.12 (m, 1H), 2.95 (dd, J = 5.6 Hz, 2.4 Hz, 1H), 2.80 (s, 3H), 2.22 (t, J = 6.0 Hz, 2H), 1.76-1.71 (m, 4H), 1.17 (t, J = 7.2 Hz, 3H) | IR (KBr): 3091, 2929, 1739, 1666, 1487, 1440, 1257, 1089 cm$^{-1}$ |

| No. | Formula | Appearance, Melting Point | Mass (m/z) | ¹H NMR | ¹³C NMR, ¹⁹F NMR, IR |
|---|---|---|---|---|---|
| F54 | | White Semi Solid | HRMS-ESI [M + H]+ calcd for C₁₈H₂₀ClF₃N₅O₂, 430.1252; found, 430.1266 | (400 MHz, CDCl₃) δ 9.03-8.94 (m, 1H), 8.62 (dd, J = 4.8, 1.5 Hz, 1H), 8.07-7.97 (multiple peaks, 2H), 7.45 (ddd, J = 8.4, 4.7, 0.8 Hz, 1H), 6.17 (br s, 1H), 3.80-3.60 (m, 2H), 3.03 (ddd, J = 8.0, 4.8, 3.2 Hz, 1H), 2.56-2.38 (m, 3H), 1.68 (dtd, J = 9.8, 6.5, 3.3 Hz, 1H), 1.30-1.19 (m, 2H), 1.15 (t, J = 7.2 Hz, 3H), 1.04 (dt, J = 10.9, 5.8 Hz, 1H) | ¹⁹F NMR (376 MHz, CDCl₃) δ −66.34 IR (thin film) 3294, 3091, 1653 cm⁻¹ |
| F55 | | Brown Viscous Semi-Solid | HRMS-ESI [M + H]+ calcd for C₁₇H₂₀ClN₆O₂, 375.1331; found, 375.1336 | (400 MHz, CDCl₃) δ 9.03-8.94 (m, 1H), 8.62 (dd, J = 4.7, 1.4 Hz, 1H), 8.09 (s, 1H), 8.04 (ddd, J = 8.3, 2.7, 1.5 Hz, 1H), 7.45 (ddd, J = 8.3, 4.8, 0.8 Hz, 1H), 4.33 (s, 2H), 3.70 (q, J = 7.2 Hz, 2H), 3.18 (s, 3H), 2.77-2.61 (m, 2H), 2.58-2.42 (m, 2H), 1.16 (t, J = 7.2 Hz, 3H) | IR (thin film) 3503, 3094, 2247, 1653 cm⁻¹ |
| F56 | | Light Brown Solid | HRMS-ESI [M + H]+ calcd for C₁₇H₁₉ClF₂N₅O₂, 398.1190; found, 398.1208 | (400 MHz, CDCl₃) δ 8.94 (dd, J = 2.7, 0.7 Hz, 1H), 8.63 (dd, J = 4.8, 1.5 Hz, 1H), 8.03 (ddd, J = 8.4, 2.7, 1.5 Hz, 1H), 7.94 (s, 1H), 7.46 (ddd, J = 8.3, 4.8, 0.8 Hz, 1H), 6.66-6.50 (m, 1H), 3.73 (dh, J = 13.8, 7.0 Hz, 2H), 3.63-3.44 (m, 2H), 2.38 (qdd, J = 17.0, 6.9, 4.3 Hz, 2H), 2.24 (ddd, J = 13.0, 10.8, 7.7 Hz, 1H), 2.08 (dtd, J = 12.5, 7.7, 6.2 Hz, 1H), 1.18 (t, J = 7.2 Hz, 3H) | ¹⁹F NMR (376 MHz, CDCl₃) δ −125.72 (d, J = 153.9 Hz), −141.43 (d, J = 153.9 Hz) IR (thin film) 3317, 3090, 1656 cm⁻¹ |
| F57 | | White Solid | HRMS-ESI [M + H]+ calcd for C₁₅H₁₆ClF₃N₅O₂, 390.0939; found, 390.0950 | (400 MHz, CDCl₃) δ 9.00-8.90 (m, 1H), 8.65 (dd, J = 4.8, 1.5 Hz, 1H), 8.05 (ddd, J = 8.4, 2.7, 1.5 Hz, 1H), 7.99 (s, 1H), 7.48 (ddd, J = 8.3, 4.8, 0.8 Hz, 1H), 6.75 (s, 1H), 3.98-3.84 (m, 2H), 3.75 (q, J = 7.2 Hz, 2H), 3.12 (q, J = 10.5 Hz, 2H), 1.20 (t, J = 12 Hz, 3H) | ¹⁹F NMR (376 MHz, CDCl₃) δ −63.03 IR (thin film) 3326, 3093, 1656 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F58 | | Light Yellow Gum | ESIMS 362 ([M + H]$^+$) | (400 MHz, DMSO-d$_6$) δ 9.08 (d, J = 2.8 Hz, 1H), 8.93 (s, 1H), 8.59 (dd, J = 4.4 Hz, 1.2 Hz, 1H), 8.22 (ddd, J = 8.0 Hz, 2.4 Hz, 1.2 Hz, 1H), 7.63 (bs, 1H), 7.59 (dd, J = 12.8 Hz, 4.8 Hz, 1H), 3.57 (q, J = 14.0 Hz, 6.8 Hz, 2H), 3.18 (t, J = 5.6 Hz, 1H), 3.02-3.01 (m, 1H), 2.77 (dd, J = 5.2 Hz, 2.4 Hz, 1H), 2.11 (t, J = 6.4 Hz, 2H), 1.56-1.53 (m, 4H), 1.06 (t, J = 6.8 Hz, 3H) | IR (KBr): 3277, 3093, 2933, 1747, 1658, 1585, 1440, 1250 cm$^{-1}$ |
| F59 | | Colorless Oil | ESIMS 481.3 ([M + H]$^+$) | $^1$H NMR (400 MHz, CDCl$_3$) δ 9.03-8.97 (m, 0.3H), 8.95-8.90 (m, 0.7H), 8.61 (ddd, J = 5.8, 4.8, 1.4 Hz, 1H), 8.06-7.95 (m, 2H), 7.70-7.80 (m, 1H), 7.44 (ddd, J = 8.3, 4.8, 0.7 Hz, 1H), 7.34 (m, 2H), 3.74 (q, J = 7.2 Hz, 1.4H), 3.60 (d, J = 7.4 Hz, 0.6H), 2.71 (t, J = 7.0 Hz, 2H), 2.51 (t, J = 7.0 Hz, 2H), 2.12 (s, 2.1H), 2.10 (s, 0.9H), 1.15 (m, 3H) | IR (thin film) 3090, 2981, 1656 cm$^{-1}$ |
| F60 | | Colorless Oil | ESIMS 336 ([M + H]$^+$) | (400 MHz, CDCl$_3$) δ 8.95 (d, J = 2.2 Hz, 1H), 8.62 (dd, J = 4.7, 1.2 Hz, 1H), 8.05 (ddd, J = 8.3, 2.6, 1.4 Hz, 1H), 8.00 (d, J = 11.0 Hz, 1H), 7.46 (dd, J = 8.1, 4.6 Hz, 1H), 3.78 (s, 3H), 3.24 (d, J = 2.8 Hz, 3H), 2.55 (ddd, J = 14.0, 8.1, 6.5 Hz, 2H), 2.40, (m, 2H), 1.80 (d, J = 2.4 Hz, 3H). Mixture of E and Z isomer in 3:1 ratio, major isomer report | |

| No. | Formula | Appearance, Melting Point | Mass (m/z) | $^1$H NMR | $^{13}$C NMR, $^{19}$F NMR, IR |
|---|---|---|---|---|---|
| F61 | 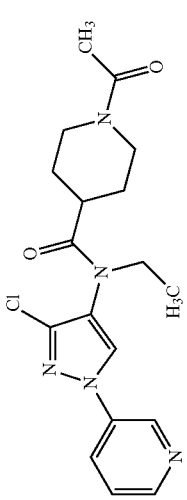 | White Semi-Solid | ESIMS 376.2 ([M + H]$^+$) | (400 MHz, CDCl$_3$) δ 8.97 (d, J = 2.7 Hz, 1H), 8.64 (dd, J = 4.8, 1.5 Hz, 1H), 8.07 (ddd, J = 8.3, 2.7, 1.5 Hz, 1H), 7.98 (s, 1H), 7.48 (ddd, J = 8.2, 4.8, 0.8 Hz, 1H), 4.54 (d, J = 13.3 Hz, 1H), 3.81 (d, J = 13.6 Hz, 1H), 3.69 (s, 2H), 3.01-2.86 (m, 1H), 2.46 (td, J = 11.1, 5.4 Hz, 2H), 2.07 (s, 3H), 1.85-1.64 (m, 4H), 1.15 (t, J = 7.1 Hz, 3H) | IR (thin film) 1631 cm$^{-1}$ |
| F62 | 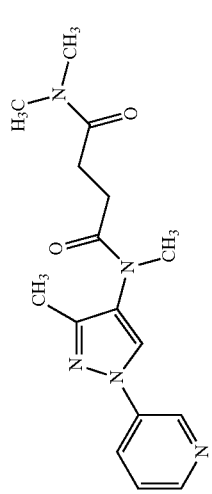 | White Solid 98-102° C. | ESIMS 316 ([M + H]$^+$) | (400 MHz, CDCl$_3$) δ 8.95 (d, J = 2.5 Hz, 1H), 8.55 (dd, J = 4.7, 1.3 Hz, 1H), 8.03-8.01 (m, 1.5H), 8.01-7.98 (m, 0.5H), 7.40 (ddd, J = 8.3, 4.8, 0.6 Hz, 1H), 3.22 (s, 3H), 3.04 (s, 3H), 2.93 (s, 3H), 2.64 (t, J = 6.4 Hz, 2H), 2.47 (t, J = 6.4 Hz, 2H), 2.31 (s, 3H) | $^{13}$C NMR (101 MHz, CDCl$_3$) δ 173.3, 171.7, 148.2, 147.6, 140.2, 136.2, 127.4, 126.1, 124.9, 123.9, 37.2, 37.1, 35.5, 28.7, 28.4, 11.1. |
| F63 | 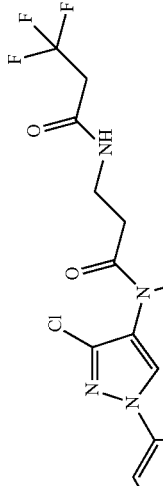 | White Solid | HRMS-ESI [M + H]$^+$ calcd for C$_{16}$H$_{18}$ClF$_3$N$_5$O$_2$, 404.1096; found, 404.1117 | (400 MHz, CDCl$_3$) δ 8.98-8.93 (m, 1H), 8.63 (dd, J = 4.8, 1.5 Hz, 1H), 8.04 (ddd, J = 8.3, 2.8, 1.5 Hz, 1H), 7.93 (s, 1H), 7.46 (ddd, J = 8.4, 4.8, 0.8 Hz, 1H), 6.68 (br s, 1H), 3.71 (q, J = 7.2 Hz, 2H), 3.55 (q, J = 5.9 Hz, 2H), 3.03 (q, J = 10.6 Hz, 2H), 2.45-2.32 (m, 2H), 1.17 (t, J = 7.2 Hz, 3H) | $^{19}$F NMR (376 MHz, CDCl$_3$) δ −63.08 IR (thin film) 3320, 3092, 1663 cm$^{-1}$ |
| F64 | 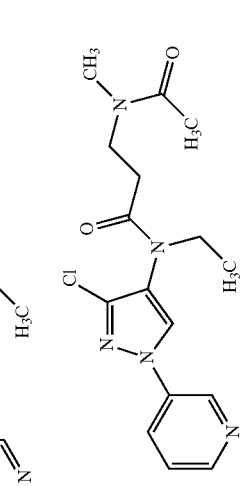 | Colorless Oil | ESIMS 350 ([M + H]$^+$) | (400 MHz, CDCl$_3$) δ 8.98 (m, 1H), 8.60 (ddd, J = 8.9, 4.7, 1.3 Hz, 1H), 8.09 (m, 1H), 8.04 (ddd, J = 8.4, 2.7, 1.4 Hz, 1H), 7.44 (ddd, J = 9.7, 8.5, 4.7 Hz, 1H), 3.65 (ddt, J = 36.1, 21.7, 7.1 Hz, 4H), 2.91 (d, J = 96.1 Hz, 3H), 2.40 (dt, J = 9.7, 7.0 Hz, 2H), 2.02 (d, J = 15.3 Hz, 3H), 1.14 (dt, J = 9.2, 7.2 Hz, 3H) | $^{13}$C NMR (101 MHz, CDCl$_3$) δ 171.32, 170.76 (d, J = 7.1 Hz), 148.80 (s), 148.57 (s), 140.58 (s), 140.19 (d, J = 16.2 Hz), 135.69 (s), 126.94 (s), 126.33 (t, J = 9.9 Hz), 124.09 (d, J = 12.2 Hz), 123.73 (s), 47.09 (s), 44.53 (s), 44.01 (d, J = 46.2 Hz), 37.04 (s), 32.82 (m), 21.91 (s), 21.17 (s), 13.05 (d, J = 3.3 Hz) |

| No. | Formula | Appearance, Melting Point | Mass (m/z) | $^1$H NMR | $^{13}$C NMR, $^{19}$F NMR, IR |
|---|---|---|---|---|---|
| F65 | | Brown Solid | HRMS-ESI [M + H]$^+$ calcd for C$_{17}$H$_{18}$ClF$_3$N$_5$O$_2$, 416.1096; found, 416.1105 | (400 MHz, CDCl$_3$) δ 8.94 (d, J = 2.7 Hz, 1H), 8.64 (dd, J = 4.7, 1.4 Hz, 1H), 8.04 (ddd, J = 8.3, 2.7, 1.4 Hz, 1H), 7.95 (s, 1H), 7.47 (dd, J = 8.4, 4.8 Hz, 1H), 6.80–6.67 (multiple peaks, 2H), 6.46 (dt, J = 15.4, 2.0 Hz, 1H), 3.71 (q, J = 12 Hz, 2H), 3.61 (q, J = 5.9 Hz, 2H), 2.50–2.33 (m, 2H), 1.17 (t, J = 12 Hz, 3H) | $^{19}$F NMR (376 MHz, CDCl$_3$) δ −65.02 IR (thin film) 3310, 3082, 1651 cm$^{-1}$ |
| F66 | | Colorless Oil | ESIMS 418 ([M + H]$^+$) | (400 MHz, CDCl$_3$) δ 8.97 (d, J = 2.4 Hz, 1H), 8.61 (dd, J = 4.8, 1.4 Hz, 1H), 8.06 (s, 1H), 8.01 (ddd, J = 8.3, 2.7, 1.5 Hz, 1H), 7.43 (ddd, J = 8.3, 4.8, 0.6 Hz, 1H), 5.31 (s, 1H), 3.69 (s, 2H), 3.16 (m, 2H), 3.03 (s, 3H), 1.27 (d, J = 7.1 Hz, 3H), 1.15 (t, J = 7.2 Hz, 3H) | IR (thin film) 3096, 2979, 2939, 1657 cm$^{-1}$ |
| F67 | | White Solid | HRMS-ESI [M + H]$^+$ calcd for C$_{16}$H$_{18}$ClF$_3$N$_5$O$_2$, 404.1096; found, 404.1099 | (400 MHz, CDCl$_3$) δ 8.96 (dd, J = 2.7, 0.7 Hz, 1H), 8.63 (dd, J = 4.8, 1.5 Hz, 1H), 8.08–7.95 (m, 2H), 7.46 (ddd, J = 8.3, 4.7, 0.7 Hz, 1H), 6.56–6.37 (m, 1H), 3.90 (qd, J = 9.1, 6.5 Hz, 2H), 3.70 (q, J = 7.2 Hz, 2H), 2.63–2.43 (m, 4H), 1.16 (t, J = 7.2 Hz, 3H) | $^{19}$F NMR (376 MHz, CDCl$_3$) δ −72.57 IR (thin film) 3309, 3090, 1656 cm$^{-1}$ |
| F68 | | Viscous Slightly Cloudy Oil | HRMS-ESI [M + H]$^+$ calcd for C21H22Cl2N5O2, 446.1145; found, 446.1148 | (400 MHz, CDCl$_3$) δ 8.62 (dd, J = 4.8, 1.5 Hz, 1H), 8.06–7.99 (multiple peaks, 2H), 7.45 (dd, J = 8.4, 4.8, 0.8 Hz, 1H), 7.35–7.12 (multiple peaks, 4H), 6.39–6.26 (m, 1H), 4.41 (d, J = 6.0 Hz, 2H), 3.70 (q, J = 7.1 Hz, 2H), 2.54 (br s, 4H), 1.14 (t, J = 7.2 Hz, 3H) | IR (thin film) 3308, 3086, 1653 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F69 | | Colorless Semi-Solid | ESIMS 364.1 ([M + H]⁺) | (400 MHz, CDCl₃) δ 8.98 (d, J = 2.6 Hz, 1H), 8.62 (dd, J = 4.7, 1.3 Hz, 1H), 8.07-8.01 (m, 2H), 7.46 (ddd, J = 8.4, 4.8, 0.5 Hz, 1H), 4.35-4.26 (m, 2H), 3.73-3.64 (m, 4H), 3.52 (t, J = 6.5 Hz, 2H), 2.49 (t, J = 6.5 Hz, 2H), 1.16 (t, J = 7.2 Hz, 3H) | IR (thin film) 1735, 1657 cm⁻¹ |
| F70 | | White Semi-Solid | ESIMS 364.1 ([M + H]⁺) | (400 MHz, CDCl₃) δ 8.98 (d, J = 2.6 Hz, 1H), 8.62 (dd, J = 4.7, 1.3 Hz, 1H), 8.07-8.01 (m, 2H), 7.46 (ddd, J = 8.4, 4.8, 0.5 Hz, 1H), 4.35-4.26 (m, 2H), 3.73-3.64 (m, 4H), 3.52 (t, J = 6.5 Hz, 2H), 2.49 (t, J = 6.5 Hz, 2H), 1.16 (t, J = 7.2 Hz, 3H) | IR (thin film) 3321, 3082, 1652 cm⁻¹ |
| F71 | | Off White Solid 157° C. | ESIMS 334 ([M + H]⁺) | (300 MHz, CDCl₃) δ 8.95 (d, J = 2.4 Hz, 1H), 8.63 (dd, J = 4.5 Hz, 1H), 8.05 (ddd, J = 8.4 Hz, 2.7 Hz, 1.2 Hz, 1H), 7.99 (s, 1H), 7.47 (dd, J = 8.4 Hz, 4.8 Hz, 1H), 5.65 (s, 1H), 3.74-3.60 (m, 4H), 3.15 (d, J = 3.3 Hz, 1H), 2.72 (dd, J = 17.1 Hz, 3.9 Hz, 1H), 2.49-2.40 (m, 1H), 1.16 (t, J = 7.2 Hz, 3H) | |
| F72 | | Brown Oil | ESIMS 426.3 ([M + H]⁺) | (400 MHz, CDCl₃) δ 8.96 (dd, J = 7.5, 2.7 Hz, 1H), 8.62 (dd, J = 4.8, 1.4 Hz, 1H), 8.11-7.98 (m, 1H), 7.94 (d, J = 3.9 Hz, 1H), 7.45 (dd, J = 8.3, 4.8 Hz, 1H), 4.07-3.98 (m, 2H), 3.70 (q, J = 7.1 Hz, 2H), 2.50 (d, J = 7.3 Hz, 2H), 2.39 (dd, J = 8.1, 6.3 Hz, 2H), 1.94-1.84 (m, 1H), 1.82 (s, 3H), 1.41 (tdd, J = 11.8, 7.8, 4.3 Hz, 1H), 1.19-1.10 (m, 3H), 1.09 (dt, J = 7.7, 4.3 Hz, 1H) | IR (thin film) 3093, 2973, 2932, 1661 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F73 | | Clear Foam | HRMS-ESI [M + H]⁺ calcd for C₁₇H₂₀ClF₃N₅O₂, 418.1252; found, 418.1257 | (400 MHz, CDCl₃) δ 8.96 (d, J = 2.6 Hz, 1H), 8.63 (dd, J = 4.8, 1.5 Hz, 1H), 8.08-7.99 (m, 2H), 7.46 (ddd, J = 8.3, 4.8, 0.7 Hz, 1H), 6.25 (s, 1H), 3.70 (q, J = 7.2 Hz, 2H), 3.49 (q, J = 6.4 Hz, 2H), 2.49 (s, 4H), 2.34 (qt, J = 10.8, 6.6 Hz, 2H), 1.15 (t, J = 7.2 Hz, 3H) | ¹⁹F NMR (376 MHz, CDCl₃) δ −65.13 IR (thin film) 3319, 1656 cm⁻¹ |
| F74 | | Light Yellow Gum | ESIMS 438 ([M + H]⁺) | (400 MHz, CDCl₃) δ 8.98 (d, J = 2.4 Hz, 1H), 8.61 (dd, J = 4.8 Hz, 1.2 Hz, 1H), 8.05 (ddd, J = 8.4 Hz, 2.8 Hz, 1.2 Hz, 1H), 8.02 (s, 1H), 7.44 (dd, J = 8.4 Hz, 4.8 Hz, 1H), 3.75-3.59 (m, 3H), 3.45-3.35 (m, 1H), 3.20-3.17 (m, 1H), 2.98-2.89 (m, 2H), 2.40-2.31 (m, 2H), 2.10-2.06 (m, 1H), 2.01-1.92 (m, 1H), 1.72-1.64 (m, 1H), 1.51-1.46 (m, 1H), 1.15 (t, J = 7.2 Hz, 3H), 1.11-1.05 (m, 1H) | IR (KBr): 3093, 2924, 2852, 1743, 1668, 1442, 1120 cm⁻¹ |
| F75 | | White Hard Sticky Foam | HRMS-ESI [M + H]⁺ calcd for C₁₈H₂₃ClN₅O₂, 376.1535; found, 376.1534 | (400 MHz, CDCl₃) δ 8.95 (d, J = 2.7 Hz, 1H), 8.63 (dd, J = 4.7, 1.4 Hz, 1H), 8.04 (ddd, J = 8.3, 2.8, 1.5 Hz, 1H), 7.96 (s, 1H), 7.46 (dd, J = 8.4, 4.7 Hz, 1H), 6.72 (t, J = 5.6 Hz, 1H), 3.71 (q, J = 7.2 Hz, 2H), 3.53 (q, J = 5.9 Hz, 2H), 2.37 (t, J = 5.7 Hz, 2H), 2.12 (d, J = 7.1 Hz, 2H), 1.17 (t, J = 7.2 Hz, 3H), 1.02-0.85 (m, 1H), 0.66-0.53 (m, 2H), 0.23-0.12 (m, 2H) | IR (thin film) 3310, 3080, 1654 cm⁻¹ |
| F76 | | White Semi Solid | ESIMS 320 ([M − BOC]⁺) | ¹H NMR (400 MHz, CDCl₃) δ 8.95 (bs, 1H), 8.63 (dd, J = 5.1 Hz, 1H), 8.17-7.88 (m, 2H), 7.54-7.36 (m, 1H), 3.99-3.41 (m, 4H), 2.97-2.82 (m, 3H), 1.44 (s, 9H), 1.12-0.83 (m, 1H), 0.59-0.39 (m, 2H), 0.28-0.08 (m, 2H) | IR (thin film) 1675 cm⁻¹ |

| No. | Formula | Appearance, Melting Point | Mass (m/z) | $^1$H NMR | $^{13}$C NMR, $^{19}$F NMR, IR |
|---|---|---|---|---|---|
| F77 | | Off-White Solid 133-136° C. | ESIMS 348.1 ([M + H]$^+$) | (400 MHz, CDCl$_3$) δ 8.98 (d, J = 2.6 Hz, 1H), 8.62 (dd, J = 4.7, 1.3 Hz, 1H), 8.19 (s, 1H), 8.01 (ddd, J = 8.4, 2.7, 1.4 Hz, 1H), 7.50-7.38 (m, 1H), 3.97 (s, 2H), 3.41 (d, J = 5.5 Hz, 2H), 3.25 (s, 3H), 2.38 (dd, J = 13.1, 6.8 Hz, 2H), 1.85 (dd, J = 6.5, 3.3 Hz, 4H) | IR (thin film) 1678, 1626 cm$^{-1}$ |
| F78 | | White Semi-Solid | HRMS-ESI [M + H]$^+$ calcd for C$_{16}$H$_{21}$ClN$_5$O$_3$, 366.1327; found, 366.1335 | (400 MHz, CDCl$_3$) δ 8.97 (dd, J = 2.7, 0.7 Hz, 1H), 8.61 (dd, J = 4.7, 1.4 Hz, 1H), 8.08 (s, 1H), 8.03 (ddd, J = 8.3, 2.7, 1.5 Hz, 1H), 7.45 (ddd, J = 8.4, 4.8, 0.8 Hz, 1H), 3.74 (s, 3H), 3.70 (q, J = 7.2 Hz, 2H), 3.17 (s, 3H), 2.78 (s, 2H), 2.46 (t, J = 6.6 Hz, 2H), 1.16 (t, J = 7.2 Hz, 3H) | IR (thin film) 1661 cm$^{-1}$ |
| F79 | | Yellow Oil | ESIMS 396 ([M + H]$^+$) | (400 MHz, CDCl$_3$) δ 8.98 (d, J = 2.3 Hz, 1H), 8.61 (d, J = 3.9 Hz, 1H), 8.05 (d, J = 7.8 Hz, 1H), 7.96 (s, 1H), 7.44 (dd, J = 8.3, 4.7 Hz, 1H), 5.20 (s, 1H), 3.70 (q, 2H), 2.91 (s, 3H), 2.63 (ddd, J = 20.3, 13.1, 6.8 Hz, 2H), 1.27 (d, J = 6.9 Hz, 3H), 1.16 (t, J = 7.1 Hz, 3H), 1.10 (t, J = 7.4 Hz, 3H) | IR (KBr thin film) 3096, 2974, 2932, 1640 cm$^{-1}$ |
| F80 | | White Solid | HRMS-ESI [M + H]$^+$ calcd for C$_{21}$H$_{22}$ClFN$_5$O$_2$, 430.1441; found, 430.1446 | (400 MHz, CDCl$_3$) δ 9.01-8.93 (m, 1H), 8.62 (dd, J = 4.7, 1.5 Hz, 1H), 8.03 (dd, J = 8.3, 2.7, 1.4 Hz, 1H), 8.00 (s, 1H), 7.45 (ddd, J = 8.4, 4.8, 0.8 Hz, 1H), 7.25 (dd, J = 8.1, 5.0 Hz, 2H), 7.06-6.97 (m, 2H), 6.21-6.14 (m, 1H), 4.43-4.34 (m, 2H), 3.70 (q, J = 7.1 Hz, 2H), 2.52 (s, 4H), 1.15 (t, J = 7.2 Hz, 3H) | $^{19}$F NMR (376 MHz, CDCl$_3$) δ −115.23 IR (thin film) 3309, 3085, 1654 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F81 | (structure) | Light Yellow Gum | ESIMS 390 ([M + H]⁺) | (400 MHz, CDCl₃) δ 9.02 (d, J = 2.4 Hz, 1H), 8.64 (d, J = 4.0 Hz, 1H), 8.11-8.08 (m, 1H), 8.04 (s, 1H), 7.48 (dd, J = 8.4 Hz, 4.8 Hz, 1H), 3.71 (q, J = 7.2 Hz, 2H), 3.33 (t, J = 5.2 Hz, 1H), 3.22 (q, J = 7.2 Hz, 2H), 3.09-3.06 (m, 1H), 2.94 (dd, J = 5.6 Hz, 2.4 Hz, 1H) 2.22 (t, J = 6.4 Hz, 2H), 1.75-1.72 (m, 4H), 1.17 (t, J = 7.2 Hz, 3H), 1.14 (t, J = 7.2 Hz, 3H) | IR (KBr): 3089, 2931, 1732, 1666, 1585, 1440, 1259 cm⁻¹ |
| F82 | (structure) | Off-White Solid 135° C. | ESIMS 416.2 ([M + H]⁺) | ¹H NMR (400 MHz, CDCl₃) δ 8.96 (d, J = 2.5 Hz, 1H), 8.61 (dd, J = 4.7, 1.3 Hz, 1H), 8.12 (s, 1H), 8.04 (ddd, J = 8.3, 2.7, 1.4 Hz, 1H), 7.44 (ddd, J = 8.4, 4.8, 0.5 Hz, 1H), 3.63-3.48 (m, 4H), 3.48-3.34 (m, 2H), 2.58 (d, J = 63.8 Hz, 4H), 1.57 (ddd, J = 22.6, 10.8, 5.1 Hz, 6H), 1.05-0.80 (m, 1H), 0.53-0.40 (m, 2H), 0.17 (q, J = 4.7 Hz, 2H) | IR (thin film) 1630 cm⁻¹ |
| F83 | (structure) | White Solid | HRMS-ESI [M + H]⁺ calcd for C₂₀H₂₁ClN₅O₂, 398.1378; found, 398.1379 | (400 MHz, CDCl₃) δ 9.00 (d, J = 2.7 Hz, 0.75H, major), 8.80 (s, 0.25H, minor), 8.63 (dd, J = 4.8, 1.5 Hz, 1H), 8.17 (s, 0.75H, major), 8.03 (dt, J = 8.1, 2.3 Hz, 0.75H, major), 7.95 (d, J = 8.6 Hz, 0.25H, minor), 7.54-7.33 (multiple peaks, 6H), 7.50 (s, 0.25H, minor), 4.10 (br s, 1.5H), 3.88-3.71 (m, 2H), 3.68 (br s, 0.5H, minor), 3.15 (s, 0.75H, minor), 3.08 (s, 2.25H, major), 1.20 (t, J = 7.2 Hz, 2.25H, major), 1.14 (t, J = 7.2 Hz, 0.75H, minor) | IR (thin film) 3087, 1680, 1631 cm⁻¹ |
| F84 | (structure) | Light Green Gum | ESIMS 362 ([M + H]⁺) | (400 MHz, CDCl₃) δ 8.95 (s, 1H), 8.63 (d, J = 4.0 Hz, 1H), 8.05-8.02 (m, 1H), 7.99 (s, 1H), 7.46 (dd, J = 4.8 Hz, 8.4 Hz, 1H), 3.69 (q, J = 7.2 Hz, 2H), 3.54-3.47 (m, 2H), 3.21 (q, J = 7.2 Hz, 2H), 3.06 (dd, J = 5.6 Hz, 1.6 Hz, 1H), 2.72 (dd, J = 16.8 Hz, 4.0 Hz, 1H), 2.40-2.34 (m, 1H), 1.17-1.12 (m, 6H) | IR (KBr): 3437, 2929, 2852, 1735, 1666, 1440, 1255 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F85 | | Light Brown Viscous Semi-Solid | HRMS-ESI [M + H]⁺ calcd for C₁₇H₂₀ClF₃N₅O₂, 394.1640; found, 394.1646 | (400 MHz, CDCl₃) δ 9.01-8.93 (m, 1H), 8.62 (dd, J = 4.8, 1.4 Hz, 1H), 8.09 (d, J = 5.0 Hz, 1H), 8.07-8.00 (m, 1H), 7.45 (ddt, J = 8.3, 4.8, 0.9 Hz, 1H), 4.11-3.91 (m, 2H), 3.70 (q, J = 7.1 Hz, 2H), 3.17 (s, 2.3H), 3.03 (s, 0.7H), 2.70 (br d, J = 16.9 Hz, 2H), 2.51 (s, 2H), 1.15 (t, J = 7.2 Hz, 3H) | ¹⁹F NMR (376 MHz, CDCl₃) δ −70.02 (major rotamer), −70.45 (minor rotamer) IR (thin film) 3093, 1660 cm⁻¹ |
| F86 | | Orange Oil | ESIMS 361 ([M + H]⁺) | (400 MHz, CDCl₃) δ 8.97 (d, J = 2.6 Hz, 1H), 8.63 (dd, J = 4.8, 1.4 Hz, 1H), 8.12 (s, 1H), 8.07 (ddd, J = 8.3, 2.7, 1.5 Hz, 1H), 7.48 (dd, J = 8.3, 4.8 Hz, 1H), 6.74 (d, J = 9.0 Hz, 1H), 5.91 (dt, J = 5.5, 2.2 Hz, 1H), 5.73 (dddd, J = 5.5, 2.5, 1.1 Hz, 1H), 5.05 (dddd, J = 9.6, 7.0, 3.4, 1.7 Hz, 1H), 3.57 (dq, J = 8.3, 2.3 Hz, 1H), 3.26 (s, 3H), 2.25 (dt, J = 13.8, 8.3 Hz, 1H), 1.99 (s, 3H), 1.87 (dt, J = 13.8, 2.3 Hz, 1H) | IR (thin film) 3287, 3066, 2937, 1650, 1584, 1534 cm⁻¹ |
| F87 | | Light Brown Gum | ESIMS 521 ([M + H]⁺) | (400 MHz, CDCl₃) δ 8.98 (d, J = 2.4 Hz, 1H), 8.62 (d, J = 3.6 Hz, 1H), 8.60 (s, 1H), 8.06 (ddd, J = 8.4 Hz, 2.4 Hz, 1.6 Hz, 1H), 7.99 (s, 1H), 7.77-7.75 (m, 1H), 7.68 (d, J = 8.0 Hz, 1H), 7.46 (dd, J = 8.4 Hz, 4.8 Hz, 1H), 4.44 (s, 2H), 3.69 (q, J = 14.4 Hz, 7.2 Hz, 2H), 3.31 (t, J = 5.2 Hz, 2H), 2.92 (dd, J = 5.2 Hz, 2.0 Hz, 1H), 2.19 (t, J = 6.8 Hz, 2H), 1.73-1.65 (m, 4H), 1.15 (t, J = 7.2 Hz, 3H) | IR (KBr): 3093, 2935, 1743, 1664, 1558, 1440, 1156 cm⁻¹ |
| F88 | | Colorless Oil | ESIMS 380.1 ([M + H]⁺) | (400 MHz, CDCl₃) δ 8.99 (d, J = 2.5 Hz, 1H), 8.62 (dd, J = 4.7, 1.4 Hz, 1H), 8.13-7.97 (m, 2H), 7.46 (ddd, J = 8.3, 4.8, 0.6 Hz, 1H), 3.76 (t, J = 7.3 Hz, 2H), 3.70 (dd, J = 14.0, 7.0 Hz, 2H), 3.57 (t, J = 6.5 Hz, 2H), 3.25 (t, J = 7.3 Hz, 2H), 2.47 (t, J = 6.5 Hz, 2H), 1.16 (t, J = 7.2 Hz, 3H) | IR (thin film) 1653 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F89 | | Light Brown Oil | ESIMS 482.2 ([M + H]$^+$) | (400 MHz, CDCl$_3$) δ 8.96 (t, J = 2.4 Hz, 1H), 8.70-8.53 (m, 1H), 8.04 (ddd, J = 8.3, 2.7, 1.5 Hz, 1H), 7.96 (d, J = 9.9 Hz, 1H), 7.50-7.40 (m, 1H), 6.13-5.72 (m, 1H), 3.87 (td, J = 14.5, 3.6 Hz, 1H), 3.81-3.63 (m, 4H), 3.63-3.49 (m, 1H), 2.75-2.67 (m, 1H), 2.62-2.33 (m, 5H), 1.17 (t, J = 6.9 Hz, 3H) | IR (thin film) 3094, 2976, 1650 cm$^{-1}$ |
| F90 | | Yellow Semi-Solid | | (400 MHz, CDCl$_3$) δ 8.95 (d, J = 2.5 Hz, 1H), 8.62 (d, J = 4.8 Hz, 1H), 8.14-7.84 (m, 2H), 7.59-7.35 (m, 1H), 3.94-3.72 (d, J = 25.9 Hz, 2H), 3.31-3.15 (m, 3H), 2.99-2.81 (m, 3H), 1.53-1.31 (s, 9H) | |
| F91 | | Light Yellow Gum | ESIMS 507 ([M + H]$^+$) | (400 MHz, CDCl$_3$) δ 8.98 (s, 1H), 8.62 (d, J = 3.6 Hz, 1H), 8.59 (s, 1H), 8.07-8.04 (m, 2H), 7.76-7.67 (m, 2H), 7.44 (dd, J = 8.4 Hz, 4.8 Hz, 1H), 4.49-4.36 (m, 2H), 3.74-3.64 (m, 2H), 3.34-3.25 (m, 2H), 2.91 (dd, J = 5.2 Hz, 2.0 Hz, 1H), 2.38-2.35 (m, 2H), 2.11-1.98 (m, 2H), 1.15 (t, J = 7.2 Hz, 3H) | IR (KBr) 3446, 2924, 1743, 1664, 1585, 1440, 1336, 1136 cm$^{-1}$ |
| F92 | | Colorless Oil | ESIMS 350 ([M + H]$^+$) | (400 MHz, CDCl$_3$) δ 8.96 (d, J = 2.3 Hz, 1H), 8.62 (m, 1H), 8.06 (ddt, J = 8.3, 2.7, 1.4 Hz, 1H), 7.98 (d, J = 11.0 Hz, 1H), 7.47 (ddd, J = 8.3, 4.8, 0.5 Hz, 1H), 3.78 (s, 2H), 3.71 (m, 3H), 2.51 (d, J = 7.6 Hz, 2H), 2.38 (d, J = 7.7 Hz, 2H), 1.80 (s, 3H), 1.16 (t, J = 7.2 Hz, 3H). Mixture of E and Z isomer in 3:1 ratio, major isomer reported | $^{13}$C NMR (101 MHz, CDCl$_3$) δ 172.14 (s), 156.21 (s), 148.61 (s), 141.00 (s), 139.98 (s), 135.69 (s), 126.30 (s), 124.16 (d, J = 7.6 Hz), 61.15 (d, J = 7.9 Hz), 43.83 (s), 31.20 (s), 30.11 (d, J = 13.4 Hz), 25.40 (s), 20.39 (s), 14.65 (s), 13.13 (s) |

TABLE 3-continued

| No. | Formula | Appearance, Melting Point | Mass (m/z) | ¹H NMR | ¹³C NMR, ¹⁹F NMR, IR |
|---|---|---|---|---|---|
| F93 | (structure) | Light Yellow Oil | ESIMS 367 ([M + H]⁺) | ¹H NMR (400 MHz, CDCl₃) δ 9.00 (d, J = 2.5 Hz, 1H), 8.61 (dd, J = 4.7, 1.2 Hz, 1H), 8.25 (s, 1H), 8.03 (ddd, J = 8.3, 2.6, 1.4 Hz, 1H), 7.44 (dd, J = 8.3, 4.8 Hz, 1H), 4.98 (q, J = 6.7 Hz, 1H), 3.70 (m, 2H), 2.96 (s, 3H), 2.88 (s, 3H), 1.36 (d, J = 6.8 Hz, 3H), 1.17 (t, J = 7.2 Hz, 3H) | |
| F94 | (structure) | Viscous Clear Oil | HRMS-ESI [M + H]⁺ calcd for C₁₈H₂₂ClF₃N₅O₂, 432.1409; found, 432.1417 | (400 MHz, CDCl₃) δ 9.03-8.95 (m, 1H), 8.63 (ddd, J = 7.2, 4.7, 1.5 Hz, 1H), 8.10-7.90 (multiple peaks, 2H), 7.46 (tdd, J = 8.3, 4.8, 0.7 Hz, 1H), 3.77-3.54 (multiple peaks, 4H), 3.06 (s, 2.2H, major), 2.84 (s, 0.8H, minor), 2.66-2.32 (multiple peaks, 6H), 1.16 (dt, J = 8.7, 7.2 Hz, 3H) | ¹⁹F NMR (376 MHz, CDCl₃) δ -66.52 (minor rotamer), -66.60 (major rotamer) IR (thin film) 3500, 3092, 1648 cm⁻¹ |
| F95 | (structure) | White Semi-Solid | ESIMS 402.0 ([M + H]⁺) | (400 MHz, CDCl₃) δ 8.97 (d, J = 2.5 Hz, 1H), 8.61 (dd, J = 4.7, 1.4 Hz, 1H), 8.14 (s, 1H), 8.04 (ddd, J = 8.3, 2.7, 1.5 Hz, 1H), 7.50-7.38 (m, 1H), 3.62-3.36 (m, 6H), 2.65-2.42 (m, 4H), 1.95 (p, J = 6.8 Hz, 2H), 1.84 (p, J = 6.6 Hz, 2H), 1.02-0.90 (m, 1H), 0.53-0.42 (m, 2H), 0.24-0.10 (m, 2H) | IR (thin film) 1625 cm⁻¹ |
| F96 | (structure) | Yellow Oil | | (400 MHz, CDCl₃) δ 8.99 (d, J = 2.5 Hz, 1H), 8.60 (dd, J = 4.8, 1.4 Hz, 1H), 8.10 (s, 1H), 8.02 (ddd, J = 8.3, 2.7, 1.5 Hz, 1H), 7.43 (ddd, J = 8.3, 4.8, 0.6 Hz, 1H), 3.70 (s, 2H), 3.01 (s, 3H), 1.99 (s, 3H), 1.76 (s, 1H), 1.25 (d, J = 7.1 Hz, 3H), 1.15 (t, J = 7.2 Hz, 3H) | IR (KBr thin film) 3093, 2978, 2934, 1632 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F97 | | Off-White Solid | HRMS-ESI [M + H]⁺ calcd for C₁₆H₁₈ClF₃N₅O₂, 404.1096; found, 404.1108 | (400 MHz, CDCl₃) δ 8.97-8.90 (m, 1H), 8.65 (dd, J = 4.8, 1.4 Hz, 1H), 8.05 (ddd, J = 8.4, 2.7, 1.5 Hz, 1H), 7.99 (s, 1H), 7.48 (ddd, J = 8.4, 4.8, 0.8 Hz, 1H), 6.46 (br s, 1H), 3.85 (d, J = 4.2 Hz, 2H), 3.74 (q, J = 7.2 Hz, 2H), 2.59-2.36 (multiple peaks, 4H), 1.19 (t, J = 7.2 Hz, 3H) | ¹⁹F NMR (376 MHz, CDCl₃) δ −66.83 IR (thin film) 3332, 3088, 1653 cm⁻¹ |
| F98 | | White Semi-Solid | ESIMS 374 ([M + H]⁺) | (400 MHz, CDCl₃) δ 8.98 (d, J = 2.5 Hz, 1H), 8.70-8.57 (m, 1H), 8.12 (s, 1H), 8.03 (ddd, J = 8.3, 2.7, 1.4 Hz, 1H), 7.46 (dd, J = 8.3, 4.8 Hz, 1H), 4.10-3.68 (m, 2H), 3.65-3.37 (m, 4H), 2.40 (t, J = 8.1 Hz, 2H), 2.18-1.95 (m, 2H), 1.04-0.92 (m, 1H), 0.58-0.42 (m, 2H), 0.26-0.11 (m, 2H) | IR (thin film) 1666 cm⁻¹ |
| F99 | | Orange Solid | HRMS-ESI [M + H]⁺ calcd for C₁₆H₁₆ClF₃N₅O₂, 402.0939; found, 402.0953 | (400 MHz, CDCl₃) δ 8.95 (dd, J = 2.7, 0.7 Hz, 1H), 8.66 (dd, J = 4.8, 1.4 Hz, 1H), 8.06 (ddd, J = 8.3, 2.7, 1.5 Hz, 1H), 8.01 (s, 1H), 7.48 (ddd, J = 8.3, 4.8, 0.8 Hz, 1H), 6.82-6.68 (multiple peaks, 2H), 6.56 (dq, J = 15.4, 1.9 Hz, 1H), 3.94 (d, J = 4.3 Hz, 2H), 3.76 (q, J = 7.2 Hz, 2H), 1.20 (t, J = 7.2 Hz, 3H) | ¹⁹F NMR (376 MHz, CDCl₃) δ −65.10 IR (thin film) 3317, 3086, 1648 cm⁻¹ |
| F100 | | Off-White Solid 104-106° C. | ESIMS 404.2 ([M + H]⁺) | (400 MHz, CDCl₃) δ 8.97 (d, J = 2.6 Hz, 1H), 8.61 (dd, J = 4.7, 1.4 Hz, 1H), 8.13 (s, 1H), 8.03 (ddd, J = 8.4, 2.7, 1.4 Hz, 1H), 7.44 (ddd, J = 8.3, 4.8, 0.6 Hz, 1H), 3.71 (q, J = 7.2 Hz, 2H), 3.53-3.43 (m, 4H), 2.66 (d, J = 5.7 Hz, 2H), 2.50 (d, J = 5.8 Hz, 2H), 1.74-1.63 (m, 4H), 1.62-1.49 (m, 4H), 1.15 (t, J = 7.2 Hz, 3H) | IR (thin film) 1625 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F101 | (structure) | Light Yellow Solid | HRMS-ESI [M + H]$^+$ calcd for C$_{16}$H$_{18}$ClN$_6$O$_2$, 361.1174; found, 361.1178 | (400 MHz, CDCl$_3$) δ 8.95 (d, J = 2.7 Hz, 1H), 8.64 (dd, J = 4.8, 1.5 Hz, 1H), 8.04 (ddd, J = 8.3, 2.7, 1.4 Hz, 1H), 7.97 (s, 1H), 7.47 (dd, J = 8.4, 4.8 Hz, 1H), 6.93 (br s, 1H), 3.72 (q, J = 7.3 Hz, 2H), 3.56 (q, J = 5.8 Hz, 2H), 3.33 (s, 2H), 2.39 (t, J = 5.7 Hz, 2H), 1.18 (t, J = 7.2 Hz, 3H) | IR (thin film) 3313, 3093, 2254, 1660 cm$^{-1}$ |
| F102 | (structure) | White Semi-Solid | HRMS-ESI [M + H]$^+$ calcd for C$_{16}$H$_{18}$ClN$_6$O$_2$, 361.1174; found, 361.1178 | (400 MHz, CDCl$_3$) δ 8.95 (d, J = 2.7 Hz, 1H), 8.64 (dd, J = 4.8, 1.5 Hz, 1H), 8.04 (ddd, J = 8.3, 2.7, 1.4 Hz, 1H), 7.97 (s, 1H), 7.47 dtd, J = 8.4, 4.8 Hz, 1H), 6.93 (br s, 1H), 3.72 (q, J = 7.3 Hz, 2H), 3.56 (q, J = 5.8 Hz, 2H), 3.33 (s, 2H), 2.39 (t, J = 5.7 Hz, 2H), 1.18 (t, J = 7.2 Hz, 3H) | IR (thin film) 3525, 3094, 1656 cm$^{-1}$ |
| F103 | (structure) | Light Green Gum | ESIMS 376 ([M + H]$^+$) | (400 MHz, CDCl$_3$) δ 8.98 (d, J = 2.4 Hz, 1H), 8.61 (d, J = 4.4 Hz, 1H), 8.06-8.04 (m, 2H), 7.45 (dd, J = 8.4 Hz, 4.8 Hz, 1H), 3.78-3.63 (m, 2H), 3.32 (t, J = 5.2 Hz, 1H), 3.24-3.10 (m, 3H), 2.90 (dd, J = 5.2 Hz, 2.0 Hz, 1H), 2.42-2.30 (m, 2H), 2.13-2.04 (m, 1H), 1.98-1.89 (m, 1H), 1.15 (t, J = 7.2 Hz, 3H), 1.09 (t, J = 7.2 Hz, 3H) | IR (KBr): 3089, 2972, 2358, 1735, 1649, 1440, 1355, 1246 cm$^{-1}$ |
| F104 | (structure) | Light Yellow Gum | ESIMS 452 ([M + H]$^+$) | (400 MHz, CDCl$_3$) δ 8.99 (d, J = 7.6 Hz, 1H), 8.63 (bs, 1H), 8.07 (d, J = 8.4 Hz, 1H), 7.99 (d, J = 1.2 Hz, 1H), 7.46 (bs, 1H), 3.72-3.60 (m, 3H), 3.59-3.33 (m, 1H), 3.13-3.12, (m, 1H), 3.04-2.94 (m, 2H), 2.20 (t, J = 6.8 Hz, 2H), 1.73-1.63 (m, 4H), 1.52-1.50 (m, 2H), 1.15 (t, J = 7.2 Hz, 3H), 1.11-1.07 (m, 1H) | IR (KBr): 3441, 2924, 2852, 1741, 1664, 1440, 1390 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| F105 | (pyrazole with Cl, N-pyridinyl, amide with N-ethyl and chain to C(CH₃)=N-OH) | Colorless Gum | ESIMS 336.2 ([M + H]⁺) | (400 MHz, CDCl₃) δ 8.95 (d, J = 2.6 Hz, 1H), 8.61 (dt, J = 4.9, 1.3 Hz, 1H), 8.05 (ddt, J = 8.3, 2.8, 1.4 Hz, 1H), 7.98-7.96 (s, 1H), 7.45 (ddd, J = 8.3, 4.8, 0.8 Hz, 1H), 3.76-3.65 (m, 2H), 2.62 (dd, J = 8.2, 7.1 Hz, 1H), 2.53 (dd, J = 8.2, 6.3 Hz, 1H), 2.37 (dd, J = 8.2, 6.5 Hz, 2H), 1.84 (s, 3H), 1.18-1.11 (m, 3H). One proton not located | |
| F106 | (pyrazole with Cl, N-pyridinyl, amide with N-ethyl and chain to pyrrolidinyl amide) | White Semi-Solid | ESIMS 376.2 ([M + H]⁺) | (400 MHz, CDCl₃) δ 8.98 (d, J = 2.6 Hz, 1H), 8.61 (dd, J = 4.7, 1.4 Hz, 1H), 8.14 (s, 1H), 8.03 (ddd, J = 8.3, 2.7, 1.5 Hz, 1H), 7.44 (ddd, J = 8.4, 4.8, 0.6 Hz, 1H), 3.71 (q, J = 7.1 Hz, 2H), 3.51-3.38 (m, 4H), 2.58 (dd, J = 32.2, 26.5 Hz, 4H), 2.01-1.90 (m, 2H), 1.90-1.79 (m, 2H), 1.15 (t, J = 7.2 Hz, 3H) | IR (thin film) 1625 cm⁻¹ |
| F107 | (pyrazole with Cl, N-pyridinyl, amide with N-methyl and chain to 2-oxopyrrolidinyl) | Colorless Semi-Solid | ESIMS 348.1 ([M + H]⁺) | (400 MHz, CDCl₃) δ 8.98 (d, J = 2.5 Hz, 1H), 8.62 (dd, J = 4.7, 1.4 Hz, 1H), 8.13 (s, 1H), 8.05 (ddd, J = 8.3, 2.7, 1.5 Hz, 1H), 7.45 (ddd, J = 8.3, 4.8, 0.5 Hz, 1H), 3.54 (t, J = 6.9 Hz, 2H), 3.46 (t, J = 7.1 Hz, 2H), 3.23 (s, 3H), 2.47 (t, J = 6.9 Hz, 2H), 2.33 (t, J = 8.1 Hz, 2H), 2.07-1.91 (m, 2H) | IR (thin film) 1656 cm⁻¹ |
| F108 | (pyrazole with Cl, N-pyridinyl, amide with N-ethyl and chain to N-methyl-N-(3,3,3-trifluoropropyl)amide) | Clear Viscous Oil | HRMS-ESI [M + H]⁺ calcd for C₁₈H₂₂ClF₃N₅O₂, 432.1409; found, 432.1411 | (400 MHz, CDCl₃) δ 8.97 (dd, J = 2.7, 0.6 Hz, 1H), 8.61 (dd, J = 4.8, 1.4 Hz, 1H), 8.10 (d, J = 1.8 Hz, 1H), 8.03 (ddd, J = 8.4, 2.7, 1.4 Hz, 1H), 7.45 (ddd, J = 8.3, 4.8, 0.8 Hz, 1H), 3.70 (q, J = 7.1 Hz, 1.53H), 3.66-3.59 (m, 0.47H), 3.59-3.52 (m, 2H), 3.07 (s, 2.3H), 2.93 (s, 0.7H), 2.64 (s, 2H), 2.56-2.44 (m, 2H), 2.35 (qt, J = 10.8, 7.2 Hz, 2H), 1.17-1.10 (m, 3H) | ¹⁹F NMR (376 MHz, CDCl₃) δ -65.34 (major rotamer), -65.39 (minor rotamer) IR (thin film) 3368, 1641 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F109 | 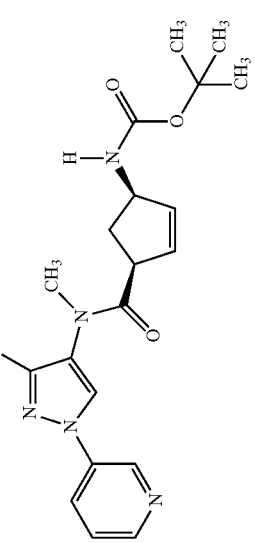 | White Solid | ESIMS 418 ([M + H]⁺) 416 ([M − H]⁻) | (400 MHz, CDCl₃) δ 9.01-8.93 (d, J = 2.8 Hz, 1H), 8.66-8.60 (m, 1H), 8.11-8.02 (m, 2H), 7.52-7.42 (m, 1H), 5.93-5.85 (m, 1H), 5.72-5.66 (m, 1H), 5.53-5.44 (d, J = 9.5 Hz, 1H), 4.80-4.67 (m, 1H), 3.58-3.47 (m, 1H), 3.30-3.21 (s, 3H), 2.35-2.22 (m, 1H), 1.90-1.80 (m, 1H), 1.51-1.34 (s, 9H) | ¹³C NMR (101 MHz, CDCl₃) δ 175.26, 155.23, 148.70, 140.31, 140.00, 135.61, 135.18, 130.99, 126.34, 125.92, 125.78, 124.12, 79.04, 55.69, 47.33, 37.49, 35.55, 28.45 |
| F110 | 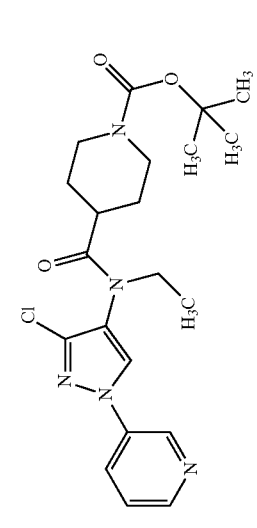 | White Semi-Solid | ESIMS 334.2 ([M + H − OtBu]⁺) | (400 MHz, CDCl₃) δ 8.97 (d, J = 2.7 Hz, 1H), 8.63 (dd, J = 4.7, 1.5 Hz, 1H), 8.07 (ddd, J = 8.3, 2.7, 1.4 Hz, 1H), 7.97 (s, 1H), 7.47 (ddd, J = 8.4, 4.7, 0.8 Hz, 1H), 4.18-3.95 (m, 2H), 3.77-3.59 (m, 2H), 2.66-2.47 (m, 2H), 2.37 (ddt, J = 11.3, 8.1, 3.9 Hz, 1H), 1.80-1.66 (m, 2H), 1.64-1.54 (m, 2H), 1.44 (s, 9H), 1.15 (t, J = 7.1 Hz, 3H) | IR (thin film) 1664 cm⁻¹ |
| F111 | 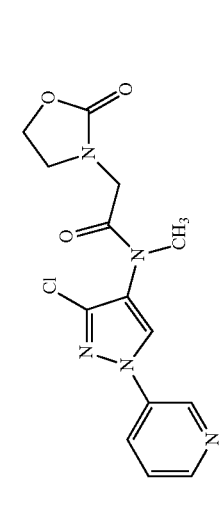 | White Solid 167-169° C. | ESIMS 336.1 ([M + H]⁺) | (400 MHz, CDCl₃) δ 8.98 (d, J = 2.5 Hz, 1H), 8.63 (dd, J = 4.7, 1.4 Hz, 1H), 8.14 (s, 1H), 8.03 (ddd, J = 8.3, 2.7, 1.4 Hz, 1H), 7.50-7.38 (m, 1H), 4.43-4.34 (m, 2H), 3.91 (s, 2H), 3.77 (t, J = 8.0 Hz, 2H), 3.26 (s, 3H) | IR (thin film) 1749, 1667 cm⁻¹ |
| F112 | 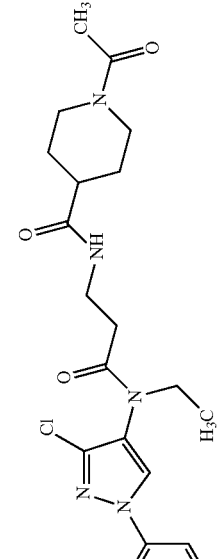 | White Foam | HRMS-ESI [M + H]⁺ calcd for C₂₁H₂₈ClN₄O₃, 447.1906; found, 447.1902 | (400 MHz, CDCl₃) δ 8.95 (d, J = 2.7 Hz, 1H), 8.64 (dd, J = 4.8, 1.5 Hz, 1H), 8.04 (ddd, J = 8.3, 2.7, 1.4 Hz, 1H), 7.96 (s, 1H), 7.50-7.43 (m, 1H), 6.49 (t, J = 5.6 Hz, 1H), 4.59 (d, J = 13.6 Hz, 1H), 3.85 (d, J = 13.7 Hz, 1H), 3.70 (q, J = 7.2 Hz, 2H), 3.55-3.43 (m, 2H), 3.08 (td, J = 13.6, 12.8, 2.9 Hz, 1H), 2.70-2.56 (m, 1H), 2.38-2.23 (multiple peaks, 3H), 2.09 (s, 3H), 1.86 (t, J = 13.4 Hz, 2H), 1.75-1.63 (m, 2H), 1.17 (t, J = 7.2 Hz, 3H) | IR (thin film) 3310, 3083, 1626, 1441 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| F113 | | Yellow Viscous Oil | HRMS-ESI [M + H]$^+$ calcd for C$_{18}$H$_{21}$ClF$_2$N$_5$O$_2$, 412.1346; found, 412.1368 | (400 MHz, CDCl$_3$) δ 8.94 (dd, J = 2.7, 0.8 Hz, 1H), 8.63 (dd, J = 4.7, 1.4 Hz, 1H), 8.03 (dd, J = 8.3, 2.7, 1.4 Hz, 1H), 7.93 (s, 1H), 7.46 (ddd, J = 8.3, 4.8, 0.8 Hz, 1H), 6.75-6.63 (m, 1H), 3.85-3.63 (m, 2H), 3.63-3.46 (m, 2H), 2.37 (qdd, J = 16.9, 6.7, 4.5 Hz, 2H), 2.14 (ddd, J = 13.5, 7.9, 6.0 Hz, 1H), 1.46 (t, J = 2.3 Hz, 3H), 1.28-1.21 (m, 1H), 1.17 (t, J = 7.2 Hz, 3H) | $^{19}$F NMR (376 MHz, CDCl$_3$) δ -135.79 (d, J = 153.1 Hz), -136.68 (d, J = 153.4 Hz) IR (thin film) 3335, 3091, 1658 cm$^{-1}$ |
| F114 | | Orange Solid 130-131° C. | ESIMS 379 ([M + H]$^+$) | (400 MHz, CDCl$_3$) δ 9.01 (d, J = 2.5 Hz, 1H), 8.59 (dd, J = 4.8, 1.4 Hz, 1H), 8.25 (s, 1H), 8.03 (ddd, J = 8.3, 2.7, 1.4 Hz, 1H), 7.42 (ddd, J = 8.3, 4.8, 0.6 Hz, 1H), 4.45 (dd, J = 14.4, 7.3 Hz, 1H), 3.92 (m, 1H), 3.47 (dt, J = 11.7, 5.9 Hz, 1H), 2.98 (s, 3H), 2.72 (s, 6H), 1.30 (d, J = 7.2 Hz, 3H), 1.16 (t, J = 7.2 Hz, 3H) | IR (thin film) 3311, 3079, 1656 cm$^{-1}$ |
| F115 | | Light Yellow Solid | HRMS-ESI [M + H]$^+$ calcd for C$_{20}$H$_{22}$ClN$_6$O$_2$, 413.1487; found, 413.1475 | (400 MHz, CDCl$_3$) δ 8.96 (dd, J = 2.7, 0.7 Hz, 1H), 8.62 (dd, J = 4.8, 1.5 Hz, 1H), 8.58-8.53 (m, 2H), 8.03 (ddd, J = 8.4, 2.7, 1.5 Hz, 1H), 8.00 (s, 1H), 7.45 (ddd, J = 8.4, 4.8, 0.8 Hz, 1H), 7.23-7.16 (m, 2H), 6.45-6.36 (m, 1H), 4.45 (d, J = 6.1 Hz, 2H), 3.71 (q, J = 7.2 Hz, 2H), 2.63-2.49 (multiple peaks, 4H), 1.16 (t, J = 7.2 Hz, 3H) | IR (thin film) 3311, 3079, 1656 cm$^{-1}$ |
| F116 | | White Foam | ESIMS 418 ([M + H]$^+$) 416 ([M – H]$^-$) | (400 MHz, CDCl$_3$) δ 8.97 (d, J = 2.7 Hz, 1H), 8.63 (dd, J = 4.4, 1.8 Hz, 1H), 8.11-8.03 (m, 2H), 7.47 (dd, J = 8.4, 4.7 Hz, 1H), 5.90 (dt, J = 4.4, 2.3 Hz, 1H), 5.73-5.65 (m, 1H), 5.48 (d, J = 9.1 Hz, 1H), 4.74 (t, J = 9.2 Hz, 1H), 3.53 (dt, J = 7.9, 2.5 Hz, 1H), 3.25 (d, J = 1.7 Hz, 3H), 2.28 (dt, J = 13.5, 8.4 Hz, 1H), 1.86 (dd, J = 13.6, 2.7 Hz, 1H), 1.44 (d, J = 1.7 Hz, 9H) | $^{13}$C NMR (101 MHz, CDCl$_3$) δ 175.24, 155.22, 148.62, 140.22, 139.97, 135.58, 135.13, 131.01, 126.29, 126.09, 125.69, 124.09, 78.99, 55.67, 47.31, 37.45, 35.54, 28.43 |

TABLE 3-continued

| No. | Formula | Appearance, Melting Point | Mass (m/z) | ¹H NMR | ¹³C NMR, ¹⁹F NMR, IR |
|---|---|---|---|---|---|
| F117 | | Light Yellow Gum | ESIMS 493 ([M + H]⁺) | (400 MHz, CDCl₃) δ 8.96 (d, J = 2.8 Hz, 1H), 8.64 (d, J = 3.6 Hz, 1H), 8.61 (s, 1H), 8.05 (ddd, J = 8.4 Hz, 2.8 Hz, 1.2 Hz, 1H), 7.99 (s, 1H), 7.80 (d, J = 6.8 Hz, 1H), 7.68 (d, J = 8.4 Hz, 1H), 7.47 (dd, J = 8.4 Hz, 4.8 Hz, 1H), 4.51-4.41 (m, 2H), 3.73-3.63 (m, 2H), 3.61-3.56 (m, 1H), 3.50 (t, J = 5.6 Hz, 1H), 3.10 (dd, J = 5.6 Hz, 2.0 Hz, 1H), 2.72 (dd, J = 16.8 Hz, 4.0 Hz, 1H), 2.41 (dd, J = 16.8 Hz, 10.0 Hz, 1H), 1.14 (t, J = 12 Hz, 3H) | IR (KBr): 3095, 2924, 1747, 1666, 1585, 1442, 1336, 1136 cm⁻¹ |
| F118 | | Cloudy White Viscous Semi-Solid | HRMS-ESI [M + H]⁺ calcd for C₂₂H₂₄ClFN₅O₂, 444.1597; found, 444.1602 | (400 MHz, CDCl₃) δ 8.97 (d, J = 2.7 Hz, 1H), 8.62 (dd, J = 4.8, 1.4 Hz, 1H), 8.11 (d, J = 1.8 Hz, 1H), 8.07-8.00 (m, 1H), 7.48-7.42 (m, 1H), 7.18 (ddd, J = 8.3, 5.2, 2.5 Hz, 2H), 7.09-6.94 (m, 2H), 4.54 (d, J = 5.3 Hz, 2H), 3.72 (q, J = 7.3 Hz, 2H), 2.96 (s, 2H, major), 2.90 (s, 1H, minor), 2.79-2.63 (m, 2H), 2.60-2.42 (m, 2H), 1.16 (td, J = 7.2, 3.5 Hz, 3H) | ¹⁹F NMR (376 MHz, CDCl₃) δ −114.88 (minor rotamer), −115.46 (major rotamer) IR (thin film) 3082, 1646 cm⁻¹ |
| F119 | | Light Green Gum | ESIMS 362 ([M + H]⁺) | (400 MHz, CDCl₃) δ 8.99 (d, J = 2.4 Hz, 1H), 8.61 (d, J = 3.6 Hz, 1H), 8.07-8.05 (m, 2H), 7.45 (dd, J = 8.4 Hz, 4.8 Hz, 1H), 3.76-3.62 (m, 2H), 3.33 (t, J = 5.2 Hz, 1H), 3.17-3.15 (m, 1H), 2.91 (dd, J = 5.2 Hz, 2.0 Hz, 1H), 2.77 (s, 3H), 2.42-2.30 (m, 2H), 2.13-2.04 (m, 1H), 1.99-1.90 (m, 1H), 1.15 (t, J = 7.2 Hz, 3H) | IR (KBr): 3473, 3089, 2926, 1732, 1716, 1427, 1247, 1114 cm⁻¹ |
| F120 | | White Solid | HRMS-ESI [M + H]⁺ calcd for C₁₆H₁₈ClF₃N₅O₂, 404.1096; found, 404.1096 | (400 MHz, CDCl₃) δ 8.98 (d, J = 2.8 Hz, 1H), 8.63 (d, J = 5.1 Hz, 1H), 8.09 (s, 1H), 8.02-7.96 (m, 1H), 7.46 (dd, J = 8.4, 4.8 Hz, 1H), 3.99 (br s, 2H), 3.71 (q, J = 7.4 Hz, 2H), 3.27 (q, J = 9.9 Hz, 2H), 3.15 (br s, 2.6H, major), 2.97 (s, 0.4H, minor), 1.17 (t, J = 7.2 Hz, 3H) | ¹⁹F NMR (376 MHz, CDCl₃) δ −62.48 (minor rotamer), −62.62 (major rotamer) IR (thin film) 3533, 3095, 1663 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F121 | (pyridinyl-pyrazole-Cl with N-ethyl amide linked to propyl-N(CH₃)-C(O)-N(CH₃)₂) | Light Yellow Oil | ESIMS 379 ([M + H]⁺) | (400 MHz, CDCl₃) δ 9.02 (d, J = 2.4 Hz, 1H), 8.62 (dd, J = 4.7, 1.4 Hz, 1H), 8.11 (s, 1H), 8.09 (ddd, J = 8.3, 2.7, 1.5 Hz, 1H), 7.45 (ddd, J = 8.3, 4.8, 0.7 Hz, 1H), 3.69 (d, J = 7.1 Hz, 2H), 3.47 (m, 2H), 2.79 (s, 3H), 2.76 (s, 6H), 2.42 (t, J = 7.1 Hz, 2H), 1.14 (t, J = 7.2 Hz, 3H) | ¹³C NMR (101 MHz, CDCl₃) δ 171.62, 165.01, 148.55, 140.59, 140.30, 135.73, 127.08, 126.37, 124.03, 123.80, 46.62, 43.72, 38.65, 37.20, 32.23, 13.07 |
| F122 | (pyridinyl-pyrazole-Cl with N-ethyl amide-CH₂-(2-pyridone)) | White Semi-Solid | ESIMS 376.1 ([M + H]⁺) | (400 MHz, CDCl₃) δ 9.04 (s, 1H), 8.64 (d, J = 4.8 Hz, 1H), 8.32 (s, 1H), 8.07 (ddd, J = 8.3, 2.7, 1.4 Hz, 1H), 7.47 (dd, J = 8.3, 4.7 Hz, 1H), 7.37 (ddd, J = 8.9, 6.6, 2.1 Hz, 1H), 7.29 (ddd, J = 6.7, 1.9, 0.6 Hz, 1H), 6.53 (dt, J = 9.2, 1.0 Hz, 1H), 6.22 (td, J = 6.7, 1.3 Hz, 1H), 4.65 (br s, 2H), 3.75 (q, J = 7.1 Hz, 2H), 1.19 (t, J = 7.2 Hz, 3H) | IR (thin film) 1657 cm⁻¹ |
| F123 | (pyridinyl-pyrazole-Cl with N-ethyl amide-CH₂-(caprolactam)) | White Semi-Solid | ESIMS 376.1 ([M + H]⁺) | (400 MHz, CDCl₃) δ 8.99 (d, J = 2.5 Hz, 1H), 8.62 (dd, J = 4.7, 1.3 Hz, 1H), 8.13 (s, 1H), 8.02 (ddd, J = 8.4, 2.7, 1.4 Hz, 1H), 7.45 (dd, J = 8.3, 4.8, 0.5 Hz, 1H), 4.19-3.77 (m, 2H), 3.70 (dd, J = 14.1, 7.0 Hz, 2H), 3.45 (s, 2H), 2.61-2.49 (m, 2H), 1.74 (s, 6H), 1.16 (t, J = 7.2 Hz, 3H) | IR (thin film) 1677, 1629 cm⁻¹ |
| F124 | (pyridinyl-pyrazole-Cl with N-ethyl amide-CH₂-(2-pyrrolidinone)) | Light Yellow Oil | ESIMS 348.9 ([M + H]⁺) | (400 MHz, CDCl₃) δ 8.98 (d, J = 2.6 Hz, 1H), 8.63 (dd, J = 4.8, 1.4 Hz, 1H), 8.09 (s, 1H), 8.03 (ddd, J = 8.3, 2.7, 1.5 Hz, 1H), 7.46 (dd, J = 8.3, 4.8 Hz, 1H), 3.90 (s, 2H), 3.70 (q, J = 7.1 Hz, 2H), 3.54 (t, J = 6.9 Hz, 2H), 2.39 (t, J = 8.2 Hz, 2H), 2.14-2.04 (m, 2H), 1.16 (t, J = 7.2 Hz, 3H) | IR (thin film) 1664 cm⁻¹ |

| No. | Formula | Appearance, Melting Point | Mass (m/z) | ¹H NMR | ¹³C NMR, ¹⁹F NMR, IR |
|---|---|---|---|---|---|
| F125 | | Light Brown Gum | ESIMS 440.3 ([M + H]⁺) | (400 MHz, CDCl₃) δ 8.98 (td, J = 6.3, 2.7 Hz, 1H), 8.63 (dd, J = 7.6, 4.8 Hz, 1H), 8.12-8.02 (m, 1H), 7.95 (s, 1H), 7.47 (td, J = 8.3, 4.5 Hz, 1H), 6.00-5.83 (m, 1H), 3.88-3.58 (m, 5H), 3.54 (d, J = 4.6 Hz, 1H), 2.40 (t, J = 7.1 Hz, 1H), 2.33 (d, J = 6.7 Hz, 1H), 2.27 (dd, J = 6.9, 3.3 Hz, 2H), 1.35-0.95 (m, 3H), 1.15-0.95 (m, 1H), 0.63-0.47 (m, 2H), 0.16 (dq, J = 24.0, 5.1 Hz, 2H) | IR (thin film) 3081, 2976, 1718, 1649 cm⁻¹ |
| F126 | | White Foam | ESIMS 412 ([M + H]⁺) | (400 MHz, CDCl₃) δ 9.01 (d, J = 2.6 Hz, 1H), 8.63 (dd, J = 4.7, 1.4 Hz, 1H), 8.46 (d, J = 8.9 Hz, 1H), 8.29 (s, 1H), 8.10 (ddd, J = 8.3, 2.7, 1.5 Hz, 1H), 7.49 (dd, J = 8.4, 4.7 Hz, 1H), 5.94 (dt, J = 5.6, 2.1 Hz, 1H), 5.88 (d, J = 5.6, 2.6 Hz, 1H), 5.07-4.99 (m, 1H), 3.68 (dq, J = 8.0, 1.9 Hz, 1H), 3.28 (s, 3H), 2.28 (dt, J = 13.8, 8.0 Hz, 1H), 2.03-1.98 (m, 1H) | ¹⁹F NMR (376 MHz, CDCl₃) δ −76.11 |
| F127 | | Light Yellow Gum | ESIMS 520 ([M + H]⁺) | (400 MHz, CDCl₃) δ 9.01 (d, J = 2.4 Hz, 1H), 8.64 (dd, J = 3.6 Hz, 1H), 8.09 (dd, J = 8.0 Hz, 1.2 Hz, 1H), 8.02 (s, 1H), 7.62 (d, J = 8.0 Hz, 2H), 7.48 (dd, J = 8.4 Hz, 4.8 Hz, 1H), 7.35 (d, J = 8.4 Hz, 2H), 4.41 (s, 2H), 3.71 (q, J = 7.2 Hz, 2H), 3.28 (t, J = 5.2 Hz, 1H), 3.19-3.18 (m, 1H), 2.90 (dd, J = 5.2 Hz, 2.0 Hz, 1H), 2.22 (t, J = 6.8 Hz, 2H), 1.77-1.73 (m, 4H), 1.17 (t, J = 7.2 Hz, 3H) | IR (KBr): 3091, 2927, 2308, 1743, 1666, 1440, 1325 cm⁻¹ |
| F128 | | White Foam | HRMS-ESI [M + Na]⁺ calcd for C₂₂H₂₈ClN₅NaO₄, 484.1722; found, 484.1744 | (400 MHz, CDCl₃) δ 8.98 (dd, J = 2.7, 0.8 Hz, 1H), 8.62 (dd, J = 4.8, 1.4 Hz, 1H), 8.06 (ddd, J = 8.4, 2.7, 1.5 Hz, 1H), 8.02 (s, 1H), 7.45 (ddd, J = 8.3, 4.8, 0.8 Hz, 1H), 3.83-3.60 (m, 3H), 3.54 (ddd, J = 10.9, 9.0, 7.3 Hz, 1H), 2.54 (p, J = 7.7 Hz, 1H), 2.38 (tq, J = 16.0, 7.7, 6.7 Hz, 2H), 2.17 (dddd, J = 11.9, 8.4, 7.3, 3.2 Hz, 1H), 1.99 (dq, J = 14.2, 7.3 Hz, 1H), 1.86 (tt, J = 14.2, 7.0 Hz, 2H), 1.67 (s, 1H), 1.50 (s, 9H), 1.15 (t, J = 7.2 Hz, 3H) | IR (thin film) 3512, 3096, 1776, 1714, 1665 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| F129 | | Light Brown Gum | ESIMS 506 ([M + H]⁺) | (300 MHz, CDCl₃) δ 8.98 (d, J = 2.4 Hz, 1H), 8.62 (d, J = 3.9 Hz, 1H), 8.07-8.00 (M, 2H), 7.60 (d, J = 7.8 Hz, 2H), 7.45 (dd, J = 8.4 Hz, 4.8 Hz, 1H), 7.32 (d, J = 7.8 Hz, 2H), 4.45-4.30 (m, 2H), 3.78-3.62 (m, 2H), 3.30-3.21 (m, 2H), 2.86 (dd, J = 1.8 Hz, 5.4 Hz, 1H), 2.40-2.35 (m, 2H), 2.14-1.91 (m, 2H), 1.15 (t, J = 7.2 Hz, 3H) | IR (KBr): 1737, 1658, 1643, 1585, 1487, 1327, 1142 cm⁻¹ |
| F130 | | Yellow Oil | ESIMS 364 ([M + H]⁺) | (400 MHz, CDCl₃) δ 8.93 (d, J = 2.4 Hz, 1H), 8.62 (m, 1H), 8.04 (ddd, J = 8.3, 2.7, 1.4 Hz, 1H), 7.98 (s, 1H), 7.46 (dd, J = 8.3, 4.7 Hz, 1H), 4.21 (dt, J = 12.4, 6.2 Hz, 1H), 3.24 (s, 3H), 2.52 (t, J = 6.8 Hz, 2H), 2.42 (t, J = 6.8 Hz, 2H), 1.79 (s, 3H), 1.17 (d, J = 6.2 Hz, 6H). Mixture of E and Z isomer in 9:1 ratio major isomer reported | |
| F131 | | Yellow Viscous Oil | HRMS-ESI [M + H]⁺ calcd for C₁₇H₂₁ClN₅O₂, 362.1378; found, 362.1408 | (400 MHz, CDCl₃) δ 9.05-8.95 (m, 1H), 8.61 (dd, J = 4.8, 1.4 Hz, 1H), 8.09-7.98 (multiple peaks, 2H), 7.44 (ddd, J = 8.3, 4.8, 0.8 Hz, 1H), 5.41 (s, 1H), 3.70 (ddt, J = 18.7, 13.6, 6.8 Hz, 2H), 3.36-3.19 (m, 2H), 2.49-2.21 (m, 4H), 1.99 (dq, J = 14.1, 6.9 Hz, 1H), 1.90-1.71 (m, 2H), 1.15 (t, J = 7.2 Hz, 3H) | IR (thin film) 3284, 1659 cm⁻¹ |
| P1 | | Colorless Oil | ESIMS 444 ([M + H]⁺) | (400 MHz, CDCl₃) δ 8.98 (dd, J = 2.7, 0.8 Hz, 1H), 8.62 (dd, J = 4.8, 1.5 Hz, 1H), 8.05 (ddd, J = 8.4, 2.7, 1.5 Hz, 1H), 8.02 (s, 1H), 7.45 (ddd, J = 8.4, 4.8, 0.8 Hz, 1H), 3.82 (q, J = 9.1 Hz, 2H), 3.70 (dq, J = 9.8, 6.8 Hz, 2H), 3.47-3.34 (m, 2H), 2.54-2.40 (m, 1H), 2.40-2.32 (m, 2H), 2.32-2.21 (m, 1H), 1.98 (dq, J = 14.3, 7.1 Hz, 1H), 1.86 (dq, J = 14.4, 7.4 Hz, 1H), 1.73 (dq, J = 12.8, 8.4 Hz, 1H), 1.15 (t, J = 7.1 Hz, 3H) | ¹³C NMR (101 MHz, CDCl₃) δ 177.22, 172.5, 148.5, 140.8, 140.2, 135.7, 126.6, 126.4, 124.0, 124.0, 46.2, 44.3, 44.0, 43.8, 39.8, 31.0, 26.6, 25.4, 13.1 |

TABLE 3-continued

| No. | Formula | Appearance, Melting Point | Mass (m/z) | ¹H NMR | ¹³C NMR, ¹⁹F NMR, IR |
|---|---|---|---|---|---|
| P16 | (structure: 3-chloro-1-(pyridin-3-yl)pyrazol-4-yl with N-ethyl amide of 1-(3,3,3-trifluoropropanoyl)piperidine-4-carboxamide) | White semi-solid | ESIMS 444 ([M + H]⁺) | (400 MHz, CDCl₃) δ 8.97 (d, J = 2.7 Hz, 1H), 8.64 (dd, J = 4.7, 1.5 Hz, 1H), 8.07 (ddd, J = 8.3, 2.7, 1.4 Hz, 1H), 7.98 (s, 1H), 7.48 (ddd, J = 8.3, 4.8, 0.8 Hz, 1H), 4.53 (d, J = 13.2 Hz, 1H), 3.79 (d, J = 14.0 Hz, 1H), 3.70 (s, 2H), 3.22 (qd, J = 10.1, 2.1 Hz, 2H), 3.03 (t, J = 12.8 Hz, 1H), 2.67-2.42 (m, 2H), 1.90-1.66 (m, 3H), 1.15 (t, J = 7.1 Hz, 3H) One aliphatic proton not located. | IR (thin film) 1648 cm⁻¹ |
| P20 | (structure: 3-chloro-1-(pyridin-3-yl)pyrazol-4-yl with N-ethyl amide of 1-acetylpyrrolidine-3-carboxamide) | White solid 43-46° C. | ESIMS 362 ([M + H]⁺) | (600 MHz, CDCl₃) δ 9.02-8.93 (m, 1H), 8.64 (ddd, J = 6.1, 4.7, 1.4 Hz, 1H), 8.09-8.02 (m, 1H), 8.01 (d, J = 2.5 Hz, 1H), 7.47 (dddd, J = 10.1, 8.3, 4.7, 0.8 Hz, 1H), 3.72 (ddd, J = 15.2, 10.1, 4.8 Hz, 2H), 3.69-3.58 (m, 3H), 3.56-3.46 (m, 2H), 3.38 (dt, J = 9.9, 7.7 Hz, 1H), 2.96 (p, J = 7.6 Hz, 1H), 2.01 (s, 3H), 1.16 (t, J = 12 Hz, 3H) Compound exists as 60:40 mixture of rotamers, only signals of major rotamer reported. | IR (thin film) 1626 cm⁻¹ |
| P21 | (structure: 3-chloro-1-(pyridin-3-yl)pyrazol-4-yl with N-ethyl amide of 1-(3,3,3-trifluoropropanoyl)pyrrolidine-3-carboxamide) | White semi-solid | ESIMS 430 ([M + H]⁺) | (400 MHz, CDCl₃) δ 9.01-8.94 (m, 1H), 8.65 (ddd, J = 4.6, 2.9, 1.4 Hz, 1H), 8.12-7.98 (m, 2H), 7.53-7.43 (m, 1H), 3.87-3.53 (m, 5H), 3.44 (dt, J = 9.6, 7.6 Hz, 1H), 3.13 (qd, J = 10.2, 7.0 Hz, 2H), 3.00 (p, J = 7.4 Hz, 1H), 2.45-2.32 (m, 1H), 2.16-2.03 (m, 1H), 1.35-1.07 (m, 3H) Compound exists as a mixture of 6:4 mixture of rotamers, only the signals of major rotamer is reported. | IR (thin film) 1653 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| P23 | | White solid 42-45° C. | ESIMS 348 ([M + H]$^+$) | (600 MHz, CDCl$_3$) δ 8.98-8.90 (m, 1H), 8.65 (dd, J = 4.8, 1.4 Hz, 1H), 8.03 (ddd, J = 8.4, 2.6, 1.4 Hz, 1H), 7.91 (s, 1H), 7.47 (ddd, J = 8.3, 4.8, 0.8 Hz, 1H), 4.47 (t, J = 7.1 Hz, 1H), 4.05 (t, J = 8.2 Hz, 2H), 3.86 (t, J = 9.3 Hz, 1H), 3.74 (s, 2H), 3.38 (tt, J = 8.9, 6.2 Hz, 1H), 1.84 (s, 3H), 1.18 (t, J = 7.2 Hz, 3H) | IR (thin film) 1644 cm$^{-1}$ |
| P24 | | Colorless oil | ESIMS 416 ([M + H]$^+$) | (400 MHz, CDCl$_3$) δ 8.99-8.91 (m, 1H), 8.65 (dd, J = 4.8, 1.4 Hz, 1H), 8.03 (ddd, J = 8.3, 2.7, 1.4 Hz, 1H), 7.94 (s, 1H), 7.48 (ddd, J = 8.4, 4.8, 0.8 Hz, 1H), 4.55 (dd, J = 8.2, 6.1 Hz, 1H), 4.13 (q, J = 6.8, 5.0 Hz, 2H), 3.93 (t, J = 9.6 Hz, 1H), 3.84-3.67 (m, 2H), 3.43 (tt, J = 8.9, 6.2 Hz, 1H), 2.94 (qd, J = 10.4, 1.6 Hz, 2H), 1.18 (t, J = 7.2 Hz, 3H) | IR (thin film) 1664 cm$^{-1}$ |
| FA1 | | Light yellow oil | ESIMS 416 ([M + H]$^+$) | (400 MHz, DMSO-d$_6$) δ 9.05 (dd, J = 2.7, 0.8 Hz, 1H), 8.82 (s, 1H), 8.59 (dd, J = 4.8, 1.4 Hz, 1H), 8.20 (ddd, J = 8.4, 2.8, 1.4 Hz, 1H), 7.67 (d, J = 2.4 Hz, 1H), 7.59 (ddd, J = 8.4, 4.8, 0.8 Hz, 1H), 6.39 (d, J = 2.3 Hz, 1H), 4.32 (t, J = 6.8 Hz, 2H), 3.84 (s, 3H), 3.57 (m, 2H), 2.66 (t, J = 6.5 Hz, 2H), 2.05 (s, 3H), 1.05 (t, J = 7.1 Hz, 3H) | IR (thin film) 3014, 2973, 2932, 1661, 1440 cm$^{-1}$ |
| FA2 | | Colorless gum | ESIMS 444 ([M + H]$^+$) | (400 MHz, DMSO-d$_6$) δ 9.05 (dd, J = 2.7, 0.8 Hz, 1H), 8.83 (d, J = 1.1 Hz, 1H), 8.59 (dd, J = 4.7, 1.4 Hz, 1H), 8.20 (ddd, J = 8.4, 2.8, 1.4 Hz, 1H), 7.66 (d, J = 2.3 Hz, 1H), 7.59 (ddd, J = 8.3, 4.7, 0.8 Hz, 1H), 6.39 (d, J = 2.3 Hz, 1H), 4.31 (m, 3H), 3.57 (d, J = 7.3 Hz, 2H), 2.66 (t, J = 6.7 Hz, 2H), 2.04 (s, 3H), 1.21 (d, J = 6.2 Hz, 6H), 1.05 (t, J = 7.1 Hz, 3H) | IR (thin film) 3040, 741, 440 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA3 | | White semi-solid | ESIMS 404 ([M + H]⁺) | (400 MHz, CDCl₃) δ 9.13 (d, J = 2.6 Hz, 1H), 8.62 (dd, J = 4.8, 1.5 Hz, 1H), 8.28-8.18 (m, 2H), 7.49-7.39 (m, 1H), 4.70-4.61 (m, 1H), 4.06 (dd, J = 13.8, 7.1 Hz, 1H), 3.83 (d, J = 13.5 Hz, 1H), 3.70 (d, J = 37.1 Hz, 1H), 3.37 (dq, J = 14.2, 7.2 Hz, 1H), 3.12-2.97 (m, 1H), 2.77-2.62 (m, 2H), 2.40-2.32 (m, 1H), 1.87 (d, J = 4.1 Hz, 1H), 1.42-1.22 (m, 2H), 1.13 (t, J = 7.2 Hz, 3H), 1.09 (d, J = 6.7 Hz, 3H), 0.99 (d, J = 6.7 Hz, 3H) Two rotational isomers, only signals of major isomer reported. | IR (thin film) 1647 cm⁻¹ |
| FA4 | | Colorless gum | ESIMS 460 ([M + H]⁺) | (400 MHz, CDCl₃) δ 8.95 (s, 1H), 8.63 (d, J = 4.6 Hz, 1H), 8.05 (ddd, J = 8.3, 2.7, 1.4 Hz, 1H), 7.94 (s, 0.8H), 7.93 (s, 0.2H), 7.46 (dd, J = 8.3, 4.7 Hz, 1H), 3.98 (t, J = 5.9 Hz, 1.6H), 3.91 (t, J = 6.2 Hz, 0.4H), 3.71 (q, J = 7.2 Hz, 2H), 2.58 (dd, J = 8.4, 7.0 Hz, 0.4H), 2.51 (dd, J = 8.3, 6.3 Hz, 1.6H), 2.41-2.30 (m, 2H), 2.16-1.99 (m, 2H), 1.85 (s, 0.6H), 1.80 (s, 2.4H), 1.72-1.62 (m, 4H), 1.16 (td, J = 7.2, 1.9 Hz, 3H) | IR (thin film) 3092, 2935, 2874, 1663 cm⁻¹ |
| FA5 | | White solid 62-66° C. | ESIMS 430 ([M + H]⁺) | (600 MHz, CDCl₃) δ 8.97 (d, J = 2.7 Hz, 1H), 8.65 (dd, J = 4.8, 1.4 Hz, 1H), 8.07 (ddd, J = 8.4, 2.7, 1.4 Hz, 1H), 7.98 (s, 1H), 7.48 (ddd, J = 8.4, 4.7, 0.8 Hz, 1H), 4.42 (d, J = 13.3 Hz, 1H), 4.00 (d, J = 14.0 Hz, 1H), 3.75-3.59 (m, 2H), 3.08 (t, J = 12.9 Hz, 1H), 2.79 (t, J = 12.8 Hz, 1H), 2.56 (td, J = 10.4, 5.1 Hz, 1H), 1.95-1.68 (m, 4H), 1.16 (t, J = 7.1 Hz, 3H) | IR (thin film) 1684 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA6 | | Yellow solid 142-143° C. | ESIMS 458 ([M + H]⁺) | (600 MHz, CDCl₃) δ 8.97 (d, J = 2.7 Hz, 1H), 8.64 (dd, J = 4.7, 1.4 Hz, 1H), 8.07 (ddd, J = 8.3, 2.6, 1.4 Hz, 1H), 7.98 (s, 1H), 7.48 (dd, J = 8.3, 4.7 Hz, 1H), 4.52 (d, J = 13.3 Hz, 1H), 3.82 (d, J = 13.7 Hz, 1H), 3.77-3.59 (m, 2H), 2.95 (t, J = 12.8 Hz, 1H), 2.51 (ddq, J = 18.7, 13.6, 9.8, 9.1 Hz, 6H), 1.87-1.66 (m, 4H), 1.15 (t, J = 7.2 Hz, 3H) | IR (thin film) 1646 cm⁻¹ |
| FA7 | | Yellow solid 160-161° C. | ESIMS 415 ([M + H]⁺) | (600 MHz, CDCl₃) δ 8.98 (d, J = 2.7 Hz, 1H), 8.64 (dd, J = 4.8, 1.4 Hz, 1H), 8.07 (ddd, J = 8.4, 2.7, 1.4 Hz, 1H), 7.99 (s, 1H), 7.52-7.43 (m, 1H), 4.50 (d, J = 13.4 Hz, 1H), 3.78 (d, J = 13.8 Hz, 1H), 3.74-3.63 (m, 2H), 2.96 (t, J = 12.8 Hz, 1H), 2.75-2.60 (m, 4H), 2.60-2.43 (m, 2H), 1.89-1.66 (m, 4H), 1.15 (t, J = 7.1 Hz, 3H) | IR (thin film) 1642 cm⁻¹ |
| FA8 | | White semi-solid | ESIMS 439 ([M + H]⁺) | (600 MHz, CDCl₃) δ 8.97 (dd, J = 2.8 Hz, 1H), 8.65 (ddd, J = 8.6, 4.3, 2.7, 1.4 Hz, 1H), 8.07 (ddd, J = 8.4, 2.7, 1.4 Hz, 1H), 7.98 (s, 1H), 7.73 (dt, J = 7.9, 1.9 Hz, 1H), 7.48 (dd, J = 8.4, 4.7 Hz, 1H), 7.35 (ddd, J = 8.0, 4.8, 1.0 Hz, 1H), 4.66-4.52 (m, 1H), 3.88-3.56 (m, 3H), 3.07-2.88 (m, 1H), 2.82-2.66 (m, 1H), 2.54 (td, J = 10.8, 5.2 Hz, 1H), 1.97-1.63 (m, 4H), 1.16 (t, J = 7.2 Hz, 3H) | IR (thin film) 1624 cm⁻¹ |
| FA9 | | Colorless oil | ESIMS 416 ([M + H]⁺) | (600 MHz, CDCl₃) δ 8.97 (dd, J = 7.2, 2.7 Hz, 1H), 8.65 (dt, J = 4.8, 1.6 Hz, 1H), 8.10-8.03 (m, 1H), 8.00 (d, J = 0.8 Hz, 1H), 7.48 (dddd, J = 9.0, 4.6, 3.3, 0.8 Hz, 1H), 4.04-3.62 (m, 5H), 3.62-3.53 (m, 1H), 3.03 (p, J = 7.7 Hz, 1H), 2.43-2.29 (m, 1H), 2.14-2.07 (m, 1H), 1.19-1.16 (m, 3H) Compound exists as a ~6:4 mixture of rotamers, only signals of major rotamer was reported. | IR (thin film) 1683 cm⁻¹ |

TABLE 3-continued

| No. | Formula | Appearance, Melting Point | Mass (m/z) | 1H NMR | 13C NMR, 19F NMR, IR |
|---|---|---|---|---|---|
| FA10 | (structure: 3-chloro-1-(pyridin-3-yl)-1H-pyrazole with N-ethyl amide linked to pyrrolidine N-acyl with CH2CH2CF3 chain) | White semi-solid | ESIMS 444 ([M + H]+) | (400 MHz, CDCl3) δ 8.97 (t, J = 3.1 Hz, 1H), 8.64 (ddd, J = 4.7, 3.1, 1.4 Hz, 1H), 8.09-8.01 (m, 1H), 8.00 (d, J = 2.2 Hz, 1H), 7.47 (ddd, J = 8.3, 5.0, 0.8 Hz, 1H), 3.86-3.48 (m, 5H), 3.39 (dt, J = 9.8, 7.6 Hz, 1H), 2.98 (p, J = 7.4 Hz, 1H), 2.62-2.38 (m, 4H), 2.14-2.02 (m, 1H), 1.99 (s, 1H), 1.29-1.10 (m, 3H) | IR (thin film) 1646 cm−1 |
| FA11 | (structure: pyrazole with N-ethyl amide to pyrrolidine N-acyl-CH2CH2CN) | Yellow semi-solid | ESIMS 401 ([M + H]+) | (600 MHz, CDCl3) δ 9.00-8.93 (m, 1H), 8.64 (td, J = 4.7, 1.4 Hz, 1H), 8.09-8.02 (m, 1H), 8.00 (d, J = 4.5 Hz, 1H), 7.47 (dddd, J = 8.4, 7.6, 4.8, 0.8 Hz, 1H), 3.83-3.47 (m, 4H), 3.38 (dt, J = 9.8, 7.6 Hz, 1H), 2.99 (p, J = 7.4 Hz, 1H), 2.64 (dddt, J = 45.4, 15.8, 13.2, 7.7 Hz, 4H), 2.42-2.33 (m, 1H), 2.12-2.03 (m, 1H), 2.03-1.94 (m, 1H), 1.24-1.12 (m, 3H) | IR (thin film) 1645 cm−1 |
| FA12 | (structure: pyrazole with N-ethyl amide to pyrrolidine N-acyl-pyridin-3-yl) | Colorless oil | ESIMS 425 ([M + H]+) | (600 MHz, CDCl3) δ 8.96 (d, J = 45.6 Hz, 1H), 8.81-8.72 (m, 1H), 8.65 (ddt, J = 7.9, 6.1, 3.0 Hz, 2H), 8.10-7.99 (m, 2H), 7.88-7.79 (m, 1H), 7.47 (dt, J = 8.3, 5.4 Hz, 1H), 7.40-7.31 (m, 1H), 3.88-3.53 (m, 5H), 3.44 (dt, J = 10.3, 7.5 Hz, 1H), 3.09 (p, J = 7.6 Hz, 1H), 2.04-1.96 (m, 1H), 1.19 (t, J = 7.2 Hz, 3H) Compounds exists as a mixture of two rotamers, only the signals of major rotamer was reported, one aliphatic proton not located. | IR (thin film) 1621 cm−1 |
| FA13 | (structure: pyrazole with N-ethyl amide to piperidine with Boc group) | White semi-solid | ESIMS 434 ([M + H]+) | (400 MHz, CDCl3) δ 9.05-8.89 (m, 1H), 8.59 (dd, J = 4.8, 1.5 Hz, 1H), 8.13 (s, 1H), 8.02 (ddd, J = 8.4, 2.6, 1.4 Hz, 1H), 7.43 (dd, J = 8.4, 4.8 Hz, 1H), 4.92-4.74 (m, 1H), 3.93-3.74 (m, 2H), 3.73-3.06 (m, 2H), 1.89 (d, J = 13.4 Hz, 1H), 1.80-1.52 (m, 5H), 1.50-1.26 (m, 9H), 1.15 (t, J = 7.1 Hz, 3H) | IR (thin film) 1670 cm−1 |

TABLE 3-continued

| No. | Formula | Appearance, Melting Point | Mass (m/z) | ¹H NMR | ¹³C NMR, ¹⁹F NMR, IR |
|---|---|---|---|---|---|
| FA14 | | Colorless oil | ESIMS 402 ([M + H]⁺) | (400 MHz, CDCl₃) δ 9.00-8.91 (m, 1H), 8.66 (dd, J = 4.8, 1.4 Hz, 1H), 8.04 (ddd, J = 8.3, 2.7, 1.5 Hz, 1H), 7.94 (s, 1H), 7.49 (ddd, J = 8.3, 4.8, 0.8 Hz, 1H), 4.70 (t, J = 8.0 Hz, 1H), 4.37-4.22 (m, 2H), 4.04 (t, J = 9.8 Hz, 1H), 3.75 (d, J = 7.7 Hz, 2H), 3.54 (tt, J = 9.0, 6.4 Hz, 1H), 1.19 (t, J = 7.2 Hz, 3H) | IR (thin film) 1693 cm⁻¹ |
| FA15 | | Colorless oil | ESIMS 430 ([M + H]⁺) | (400 MHz, CDCl₃) δ 8.95 (d, J = 2.7 Hz, 1H), 8.65 (dd, J = 4.8, 1.5 Hz, 1H), 8.04 (ddd, J = 8.4, 2.7, 1.4 Hz, 1H), 7.93 (s, 1H), 7.48 (ddd, J = 8.2, 4.8, 0.7 Hz, 1H), 4.47 (dd, J = 8.2, 6.0 Hz, 1H), 4.16-4.01 (m, 2H), 3.89 (t, J = 9.3 Hz, 1H), 3.74 (d, J = 7.8 Hz, 2H), 3.41 (tt, J = 8.9, 6.1 Hz, 1H), 2.51-2.38 (m, 2H), 2.36-2.23 (m, 2H), 1.18 (t, J = 7.2 Hz, 3H) | IR (thin film) 1655 cm⁻¹ |
| FA16 | | White solid 49-52° C. | ESIMS 387 ([M + H]⁺) | (400 MHz, CDCl₃) δ 8.99-8.92 (m, 1H), 8.65 (dd, J = 4.8, 1.4 Hz, 1H), 8.04 (ddd, J = 8.3, 2.7, 1.4 Hz, 1H), 7.93 (s, 1H), 7.48 (ddd, J = 8.3, 4.8, 0.8 Hz, 1H), 4.52-4.43 (m, 1H), 4.09 (q, J = 9.3, 8.6 Hz, 2H), 3.91 (t, J = 9.4 Hz, 1H), 3.74 (d, J = 7.7 Hz, 2H), 3.44 (tt, J = 8.9, 6.2 Hz, 1H), 2.75-2.56 (m, 2H), 2.48-2.38 (m, 2H), 1.18 (t, J = 7.2 Hz, 3H) | IR (thin film) 1655 cm⁻¹ |
| FA17 | | Colorless oil | ESIMS 387 ([M + H]⁺) | (400 MHz, CDCl₃) δ 8.95 (dd, J = 2.8, 0.8 Hz, 1H), 8.85-8.79 (m, 1H), 8.69 (dd, J = 4.8, 1.7 Hz, 1H), 8.65 (dd, J = 4.8, 2.7, 1.4 Hz, 1H), 8.04 (ddd, J = 8.3, 2.7, 1.4 Hz, 1H), 7.98-7.93 (m, 2H), 7.48 (ddd, J = 8.3, 4.8, 0.8 Hz, 1H), 7.37 (ddd, J = 7.9, 4.9, 0.9 Hz, 1H), 4.67 (t, J = 7.3 Hz, 1H), 4.25 (dd, J = 20.9, 12.1 Hz, 2H), 4.12 (d, J = 9.5 Hz, 1H), 3.81-3.66 (m, 2H), 3.51 (tt, J = 9.0, 6.3 Hz, 1H), 1.19 (t, J = 7.2 Hz, 3H) | IR (thin film) 1655 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA18 | | Yellow semi-solid | ESIMS 434 ([M + H]⁺) | (400 MHz, CDCl₃) δ 9.16-8.97 (m, 1H), 8.62 (dd, J = 4.8, 1.5 Hz, 1H), 8.20-8.07 (m, 2H), 7.49-7.38 (m, 1H), 4.26-3.86 (m, 3H), 3.80-3.17 (m, 3H), 3.03-2.54 (m, 2H), 2.35 (ddd, J = 14.9, 10.4, 4.0 Hz, 1H), 1.91-1.69 (m, 2H), 1.36 (s, 9H), 1.13 (t, J = 7.1 Hz, 3H) | IR (thin film) 1667 cm⁻¹ |
| FA19 | | Light yellow gum | ESIMS 446 ([M + H]⁺) | (400 MHz, CDCl₃) δ 8.95 (d, J = 2.7 Hz, 1H), 8.63 (dd, J = 4.8, 1.4 Hz, 1H), 8.04 (ddd, J = 8.3, 2.8, 1.4 Hz, 1H), 7.93 (d, J = 2.1 Hz, 1H), 7.46 (ddd, J = 8.3, 4.8, 0.8 Hz, 1H), 4.01 (t, J = 6.2 Hz, 2H), 3.71 (q, J = 7.2 Hz, 2H), 2.51 (dd, J = 8.0, 6.3 Hz, 2H), 2.36 (td, J = 7.1, 6.6, 5.7 Hz, 2H), 2.24-2.01 (m, 2H), 1.86 (q, J = 5.2, 4.6 Hz, 2H), 1.81 (s, 3H), 1.20-1.10 (m, 3H) | IR (thin film) 3092, 2935, 1663 cm⁻¹ |
| FA20 | | Light yellow gum | ESIMS 410 ([M + H]⁺) | (400 MHz, CDCl₃) δ 8.95 (dd, J = 2.7, 0.8 Hz, 1H), 8.62 (dd, J = 4.8, 1.5 Hz, 1H), 8.05 (ddt, J = 8.3, 2.7, 1.3 Hz, 1H), 7.95 (s, 1H), 7.52-7.40 (m, 1H), 4.51 (t, J = 5.8 Hz, 0.75H), 4.46 (t, J = 5.8 Hz, 0.25H), 4.39 (m, 0.75H), 4.34 (m, 0.25H), 4.00 (t, J = 6.1 Hz, 1.5H), 3.94 (s, 0.5H), 3.71 (q, J = 7.2 Hz, 2H), 2.57 (dd, J = 8.5, 7.0 Hz, 0.5H), 2.55-2.46 (m, 1.5H), 2.37 (dd, J = 8.0, 6.5 Hz, 2H), 1.85 (s, 0.9H), 1.80 (s, 2.1H), 1.77-1.62 (m, 4H), 1.16 (t, J = 7.2 Hz, 3H) | IR (thin film) 3092, 2964, 2932, 1663 cm⁻¹ |
| FA21 | | Colorless gum | ESIMS 440 ([M + H]⁺) | (400 MHz, CDCl₃) δ 9.02-8.87 (m, 1H), 8.63 (m, 1H), 7.94 (s, 0.3H), 7.93 (s, 0.7H), 7.51-7.37 (m, 1H), 4.00 (d, J = 6.0 Hz, 1.4H), 3.94 (d, J = 6.1 Hz, 0.6H), 3.71 (q, J = 7.1 Hz, 2H), 2.70-2.55 (m, 2H), 2.54-2.44 (m, 2H), 2.35 (m, 6H), 1.85 (s, 1H), 1.80 (s, 2H), 1.21-1.08 (m, 3H) | IR (thin film) 3092, 2933, 2870, 1664 cm⁻¹ |

| No. | Formula | Appearance, Melting Point | Mass (m/z) | ¹H NMR | ¹³C NMR, ¹⁹F NMR, IR |
|---|---|---|---|---|---|
| FA22 | | Light brown gum | ESIMS 495 ([M + H]⁺) | (400 MHz, CDCl₃) δ 9.04-8.92 (m, 1H), 8.73-8.52 (m, 2H), 8.06 (ddd, J = 8.3, 2.8, 1.4 Hz, 1H), 7.96 (s, 1H), 7.80 (d, J = 8.1 Hz, 1H), 7.71-7.55 (m, 1H), 7.46 (ddd, J = 8.3, 4.7, 0.8 Hz, 1H), 5.07 (s, 1.4H), 5.06 (s, 0.6H), 3.65 (q, J = 7.2 Hz, 2H), 2.62 (m, 0.3H), 2.50 (t, J = 7.0 Hz, 1.7H), 2.36 (td, J = 7.5, 7.0, 4.9 Hz, 2H), 1.86 (s, 2H), 1.85 (s, 1H), 1.18-1.14 (m, 1H), 1.12 (t, J = 7.2 Hz, 2H) | IR (thin film) 3091, 2975, 2933, 1664, 1585, 1487, 1441, 1459, 1401, 1428, 1377, 1333, 1305, 1266, 1174, 1130, 1084 cm⁻¹ |
| FA23 | | Light brown gum | ESIMS 474 ([M + H]⁺) | (400 MHz, CDCl₃) δ 9.07 (d, J = 2.7 Hz, 0.7H), 8.97 (d, J = 2.7 Hz, 0.3H), 8.61 (m, 1H), 8.35 (s, 0.7H), 8.13 (ddd, J = 8.4, 2.7, 1.5 Hz, 0.7H), 8.07 (s, 0.3H), 8.05 (dd, J = 2.7, 1.5 Hz, 0.3H), 7.46 (ddd, J = 8.3, 4.7, 0.8 Hz, 1H), 5.30 (s, 0.6H), 5.04 (s, 1.4H), 3.67 (q, J = 7.9, 7.1 Hz, 2H), 2.61 (t, J = 7.6 Hz, 0.6H), 2.51 (d, J = 6.6 Hz, 1.4H), 2.45 (d, J = 7.6 Hz, 0.6H), 2.36 (d, J = 6.8 Hz, 1.4H), 1.88 (d, J = 1.9 Hz, 0.9H), 1.85 (s, 2.1H), 1.41 (s, 6.3H), 1.39 (s, 2.7H), 1.14 (t, J = 7.2 Hz, 3H) | IR (thin film) 3095, 2974, 2934, 1668 cm⁻¹ |
| FA24 | | Light brown gum | ESIMS 529 ([M + H]⁺) | (400 MHz, CDCl₃) δ 9.01 (dd, J = 2.7, 0.7 Hz, 0.7H), 8.94-8.89 (m, 0.3H), 8.68 (dd, J = 2.0, 1.0 Hz, 0.7H), 8.63 (dd, J = 4.7, 1.5 Hz, 1.3H), 8.13 (s, 0.7H), 8.11-8.06 (m, 1H), 8.02 (ddd, J = 8.4, 2.8, 1.5 Hz, 0.3H), 7.92-7.84 (m, 0.7H), 7.81 (d, J = 2.0 Hz, 0.3H), 7.50-7.41 (m, 1H), 5.27 (s, 1.4H), 5.20 (s, 0.6H), 3.65 (q, J = 7.4 Hz, 2H), 2.63 (dd, J = 8.4, 6.9 Hz, 0.6H), 2.49 (t, J = 7.1 Hz, 1.4H), 2.46-2.38 (m, 0.6H), 2.33 (t, J = 7.1 Hz, 1.4H), 1.85 (s, 2.1H), 1.84 (s, 0.9H), 1.16 (t, J = 7.1 Hz, 0.9H), 1.12 (t, J = 7.2 Hz, 2.1H) | IR (thin film) 3090, 2974, 2934, 1664 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA25 | | Light brown gum | ESIMS 445 ([M + H]⁺) | (400 MHz, CDCl₃) δ 8.97 (td, J = 3.0, 1.5 Hz, 1H), 8.63 (dd, J = 4.7, 1.4 Hz, 1H), 8.07 (ddd, J = 8.3, 2.9, 1.4 Hz, 1H), 7.94 (s, 0.8H), 7.90 (s, 0.2H), 7.48 (ddd, J = 8.4, 4.8, 0.7 Hz, 1H), 4.70 (d, J = 7.4 Hz, 1.6H), 4.65 (s, 0.4H), 3.70 (q, J = 7.0 Hz, 2H), 2.57-2.46 (m, 2H), 2.42-2.34 (m, 2H), 2.33 (s, 0.6H), 2.30 (s, 2.4H), 2.20 (s, 2.4H), 1.83 (s, 0.6H), 1.76 (s, 3H), 1.20-1.10 (m, 3H) | IR (thin film) 3092, 2972, 2931, 1664 cm⁻¹ |
| FA26 | | Light yellow gum | ESIMS 514 ([M + H]⁺) | (400 MHz, CDCl₃) δ 9.05-8.86 (m, 1H), 8.62 (dd, J = 4.8, 1.5 Hz, 1H), 8.02 (ddd, J = 8.3, 2.7, 1.5 Hz, 1H), 7.80 (s, 1H), 7.45 (ddd, J = 8.3, 4.8, 0.8 Hz, 1H), 7.25 (m, 2H), 6.99 (dd, J = 5.1, 3.8 Hz, 1H), 4.04 (t, J = 6.0 Hz, 2H), 3.67 (m, 2H), 3.03 (dd, J = 8.4, 7.1 Hz, 2H), 2.42 (dd, J = 8.4, 7.2 Hz, 2H), 2.17-2.02 (m, 2H), 1.92-1.84 (m, 2H), 1.09 (t, J = 7.2 Hz, 3H) | IR (thin film) 3090, 2972, 2973, 1662 cm⁻¹ |
| FA27 | | Light yellow gum | ESIMS 514 ([M + H]⁺) | (400 MHz, CDCl₃) δ 8.90 (d, J = 2.6 Hz, 1H), 8.48 (d, J = 4.8 Hz, 1H), 8.01 (ddd, J = 8.3, 2.7, 1.4 Hz, 1H), 7.82 (s, 1H), 7.51-7.41 (m, 3H), 7.06 (dd, J = 5.2, 3.9 Hz, 1H), 4.22 (t, J = 6.1 Hz, 2H), 3.71 (q, J = 7.2 Hz, 2H), 3.12 (t, J = 7.1 Hz, 2H), 2.58-2.50 (m, 2H), 2.32-2.15 (m, 2H), 2.03-1.90 (m, 2H), 1.15 (t, J = 7.2 Hz, 3H) | IR (thin film) 3092, 2972, 2934, 1662 cm⁻¹ |
| FA28 | | Light brown gum | ESIMS 528 ([M + H]⁺) | (400 MHz, CDCl₃) δ 9.02-8.84 (m, 1H), 8.62 (dd, J = 4.7, 1.4 Hz, 1H), 8.02 (ddd, J = 8.4, 2.7, 1.4 Hz, 1H), 7.79 (s, 1H), 7.45 (ddd, J = 8.4, 4.8, 0.8 Hz, 1H), 7.24-7.19 (m, 2H), 6.99 (dd, J = 5.1, 3.7 Hz, 1H), 3.98 (t, J = 6.2 Hz, 2H), 3.66 (d, J = 7.8 Hz, 2H), 3.02 (t, J = 8.2, 7.2 Hz, 2H), 2.42 (t, J = 7.7 Hz, 2H), 2.09-1.95 (m, 2H), 1.64 (dt, J = 13.4, 6.5 Hz, 2H), 1.52 (m, 2H), 1.07 (t, J = 7.2 Hz, 3H) | IR (thin film) 3089, 2936, 2875, 1662 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA29 | | Light brown gum | ESIMS 528 ([M + H]⁺) | (400 MHz, CDCl₃) δ 9.02-8.84 (m, 1H), 8.62 (dd, J = 4.7, 1.4 Hz, 1H), 8.02 (ddd, J = 8.4, 2.7, 1.4 Hz, 1H), 7.79 (s, 1H), 7.45 (ddd, J = 8.4, 4.8, 0.8 Hz, 1H), 7.24-7.19 (m, 2H), 6.99 (dd, J = 5.1, 3.7 Hz, 1H), 3.98 (t, J = 6.2 Hz, 2H), 3.66 (d, J = 7.8 Hz, 2H), 3.02 (dd, J = 8.2, 7.2 Hz, 2H), 2.42 (t, J = 7.7 Hz, 2H), 2.09-1.95 (m, 2H), 1.64 (dt, J = 13.4, 6.5 Hz, 2H), 1.52 (m, 2H), 1.07 (t, J = 7.2 Hz, 3H) | IR (thin film) 3095, 2970, 2933, 1661 cm⁻¹ |
| FA30 | | Light brown gum | ESIMS 508 ([M + H]⁺) | (400 MHz, CDCl₃) δ 8.93 (d, J = 2.6 Hz, 1H), 8.62 (dd, J = 4.8, 1.4 Hz, 1H), 8.03 (ddd, J = 8.3, 2.7, 1.4 Hz, 1H), 7.81 (s, 1H), 7.45 (ddd, J = 8.3, 4.8, 0.8 Hz, 1H), 7.24 (m, 2H), 6.99 (dd, J = 5.1, 3.7 Hz, 1H), 4.02 (d, J = 6.3 Hz, 2H), 3.67 (m, 2H), 3.02 (dd, J = 8.4, 7.1 Hz, 2H), 2.64-2.48 (m, 2H), 2.42 (dd, J = 8.4, 7.2 Hz, 2H), 2.36-2.18 (m, 3H), 1.09 (t, J = 7.1 Hz, 3H) | IR (thin film) 3089, 2932, 1664 cm⁻¹ |
| FA31 | | Light brown gum | ESIMS 508 ([M + H]⁺) | (400 MHz, CDCl₃) δ 8.92-8.89 (m, 1H), 8.62 (dd, J = 4.7, 1.4 Hz, 1H), 8.01 (ddd, J = 8.3, 2.7, 1.5 Hz, 1H), 7.83 (s, 1H), 7.46 (ttd, J = 8.6, 4.9, 0.9 Hz, 3H), 7.05 (ddd, J = 5.1, 3.9 Hz, 1H), 4.21 (d, J = 6.2 Hz, 2H), 3.71 (q, J = 7.2 Hz, 2H), 3.07 (dd, J = 8.1, 6.6 Hz, 2H), 2.74-2.57 (m, 2H), 2.54 (dd, J = 8.2, 6.6 Hz, 2H), 2.50-2.36 (m, 3H), 1.31 (t, J = 7.1 Hz, 3H) | IR (thin film) 3089, 2933, 1664 cm⁻¹ |
| FA32 | | Yellow oil | ESIMS 376 ([M + H]⁺) | 1H NMR (500 MHz, Chloroform-d) δ 9.02 (d, J = 2.8 Hz, 1H), 8.60 (ttd, J = 4.9, 1.4 Hz, 1H), 8.01 (ddd, J = 8.4, 2.7, 1.5 Hz, 1H), 7.42 (ddd, J = 8.3, 4.8, 0.8 Hz, 1H), 5.25-5.10 (m, 1H), 4.08-3.68 (m, 3H), 3.67-3.56 (m, 1H), 2.02 (s, 3H), 1.98-1.68 (m, 4H), 1.51-1.34 (m, 2H), 1.14 (t, J = 7.1 Hz, 3H) | IR (thin film) 1633 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA33 | | Yellow oil | ESIMS 376 ([M + H]⁺) | 1H NMR (500 MHz, Chloroform-d) δ 9.02 (dd, J = 2.8, 0.8 Hz, 1H), 8.61 (dd, J = 4.8, 1.4 Hz, 1H), 8.15 (s, 1H), 8.07 (ddd, J = 8.4, 2.7, 1.5 Hz, 1H), 7.44 (ddd, J = 8.3, 4.8, 0.8 Hz, 1H), 3.69 (q, J = 7.2 Hz, 2H), 3.39 (t, J = 7.1 Hz, 2H), 3.24 (t, J = 6.7 Hz, 2H), 2.31 (t, J = 8.1 Hz, 2H), 2.18 (t, J = 6.7 Hz, 2H), 2.05-1.93 (m, 2H), 1.87 (p, J = 6.7 Hz, 2H), 1.15 (t, J = 7.2 Hz, 3H) | IR (thin film) 1665 cm⁻¹ |
| FA34 | | Yellow oil | ESIMS 378 ([M + H]⁺) | 1H NMR (500 MHz, Chloroform-d) δ 9.04 (dd, J = 2.7, 0.8 Hz, 1H), 8.61 (dd, J = 4.8, 1.4 Hz, 1H), 8.18 (s, 1H), 8.05 (ddd, J = 8.3, 2.7, 1.4 Hz, 1H), 7.44 (ddd, J = 8.4, 4.7, 0.8 Hz, 1H), 4.35-4.22 (m, 2H), 3.69 (q, J = 7.1 Hz, 2H), 3.59 (dd, J = 9.1, 7.0 Hz, 2H), 3.25 (t, J = 6.3 Hz, 2H), 2.23 (t, J = 6.3 Hz, 2H), 1.92 (s, 2H), 1.15 (t, J = 7.2 Hz, 3H) | IR (thin film) 1739, 1660 cm⁻¹ |
| FA35 | | Light brown gum | ESIMS 486 ([M + H]⁺) | (400 MHz, CDCl₃) δ 8.91 (dd, J = 6.0, 2.6 Hz, 1H), 8.62 (dd, J = 4.8, 1.4 Hz, 0.75H), 8.47 (dd, J = 4.8, 1.4 Hz, 0.25H), 8.01 (ddd, J = 8.3, 2.7, 1.4 Hz, 1H), 7.82 (d, J = 1.2 Hz, 1H), 7.45 (ddd, J = 8.4, 4.8, 0.8 Hz, 1H), 7.39-7.32 (m, 1H), 7.30 (dd, J = 5.1, 1.1 Hz, 1H), 7.12-6.90 (m, 1H), 4.52 (q, J = 8.6 Hz, 0.5H), 4.39 (q, J = 8.5 Hz, 1.5H), 3.78-3.60 (m, 2H), 3.14-3.02 (m, 2H), 2.54 (t, J = 7.3 Hz, 0.5H), 2.49-2.40 (m, 1.5H), 1.20 (t, J = 6.6 Hz, 1H), 1.12 (t, J = 7.2 Hz, 2H) | IR (thin film) 3091, 2974, 1660, 1154 cm⁻¹ |

| No. | Formula | Appearance, Melting Point | Mass (m/z) | $^1$H NMR | $^{13}$C NMR, $^{19}$F NMR, IR |
|---|---|---|---|---|---|
| FA36 | | Light brown gum | ESIMS 563 ([M + H]$^+$) | (400 MHz, CDCl$_3$) δ 8.97-8.89 (m, 1H), 8.67-8.58 (m, 2H), 8.03 (ddd, J = 8.3, 2.7, 1.4 Hz, 1H), 7.83 (s, 1H), 7.81-7.74 (m, 1H), 7.66-7.59 (m, 1H), 7.44 (ddd, J = 8.3, 4.8, 0.8 Hz, 1H), 7.28 (d, J = 1.1 Hz, 1H), 7.25 (d, J = 1.1 Hz, 1H), 6.99 (dd, J = 5.1, 3.7 Hz, 1H), 5.12 (s, 2H), 3.77-3.51 (m, 2H), 3.08-3.00 (m, 2H), 2.48-2.37 (m, 2H), 1.14-0.99 (m, 3H) | IR (thin film) 3086, 2972, 2932, 1662 cm$^{-1}$ |
| FA37 | | Light brown gum | ESIMS 563 ([M + H]$^+$) | (400 MHz, CDCl$_3$) δ 8.93 (d, J = 2.5 Hz, 1H), 8.73 (d, J = 2.0 Hz, 1H), 8.62 (dd, J = 4.8, 1.5 Hz, 1H), 8.03 (ddd, J = 8.3, 2.7, 1.4 Hz, 1H), 7.86 (s, 1H), 7.80 (m, 1H), 7.72-7.59 (m, 2H), 7.53-7.47 (m, 1H), 7.45 (ddd, J = 8.3, 4.7, 0.8 Hz, 1H), 7.07 (dd, J = 4.9, 4.1 Hz, 1H), 5.29 (d, J = 8.8 Hz, 2H), 3.67 (q, J = 7.1 Hz, 2H), 3.07 (t, J = 7.3 Hz, 2H), 2.58-2.39 (m, 2H), 1.18-1.01 (m, 3H) | IR (thin film) 3086, 2972, 2932, 1662 cm$^{-1}$ |
| FA38 | | Light brown gum | ESIMS 494 ([M + H]$^+$) | (400 MHz, CDCl$_3$) δ 8.97-8.87 (m, 1H), 8.61 (dd, J = 4.7, 1.4 Hz, 1H), 8.02 (ddd, J = 8.3, 2.7, 1.4 Hz, 1H), 7.83 (s, 1H), 7.44 (ddd, J = 8.3, 4.8, 0.8 Hz, 1H), 7.26 (m, 2H), 7.00 (dd, J = 5.1, 3.7 Hz, 1H), 4.13-3.93 (m, 2H), 3.68 (m, 2H), 3.03 (dd, J = 8.5, 7.1 Hz, 2H), 2.50-2.38 (m, 2H), 1.97-1.86 (m, 1H), 1.41 (dtd, J = 11.8, 7.8, 4.4 Hz, 1H), 1.14 (d, J = 4.7 Hz, 1H), 1.10 (t, J = 7.2 Hz, 3H) | IR (thin film) 3094, 2971, 2933, 1663 cm$^{-1}$ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA39 | | Light brown gum | ESIMS 494 ([M + H]⁺) | (400 MHz, CDCl₃) δ 8.91 (d, J = 2.6 Hz, 1H), 8.61 (dd, J = 4.7, 1.4 Hz, 1H), 8.02 (dd, J = 2.7, 1.5 Hz, 1H), 7.83 (s, 1H), 7.49-7.42 (m, 3H), 7.04 (dd, J = 5.1, 3.9 Hz, 1H), 4.25-4.16 (m, 2H), 3.71 (dd, J = 7.2, 3.6 Hz, 2H), 3.10-3.03 (m, 2H), 2.56 (t, J = 7.3 Hz, 2H), 2.07-1.92 (m, 1H), 1.48 (tdd, J = 11.9, 8.0, 4.5 Hz, 1H), 1.21 (dd, J = 13.0, 3.9 Hz, 1H), 1.15 (t, J = 7.2 Hz, 3H) | IR (thin film) 3095, 2970, 2931, 1662 cm⁻¹ |
| FA40 | | Light brown gum | ESIMS 510 ([M + H]⁺) | (400 MHz, CDCl₃) δ 8.95-8.89 (m, 1H), 8.63 (dd, J = 4.7, 1.5 Hz, 1H), 8.01 (ddd, J = 8.3, 2.8, 1.4 Hz, 1H), 7.60 (s, 1H), 7.45 (ddd, J = 8.4, 4.7, 0.8 Hz, 1H), 7.31 (d, J = 8.6 Hz, 2H), 7.20-7.10 (m, 2H), 4.97 (s, 2H), 3.67 (q, J = 7.1 Hz, 2H), 2.52 (dd, J = 7.9, 6.5 Hz, 2H), 2.36 (dd, J = 7.8, 6.5 Hz, 2H), 1.86 (s, 3H), 1.13 (t, J = 7.2 Hz, 3H) | IR (thin film) 3092, 2974, 2929, 1664 cm⁻¹ |
| FA41 | | White semi-solid | ESIMS 430 ([M + H]⁺) | (500 MHz, CDCl₃) δ 9.03 (s, 1H), 8.64 (td, J = 4.8, 1.4 Hz, 1H), 8.11-8.00 (m, 1H), 7.50-7.41 (m, 1H), 4.55-4.41 (m, 1H), 3.98-3.83 (m, 2H), 3.75-3.62 (m, 1H), 3.19-3.06 (m, 1H), 2.95 (t, J = 12.1 Hz, 1H), 2.56-2.39 (m, 1H), 1.97-1.73 (m, 3H), 1.47-1.34 (m, 1H), 1.16 (t, J = 7.2, 3H) Compound exists as two rotamers in 6:4 ratio. | IR (thin film) 1687, 1658 cm⁻¹ |
| FA42 | | White semi-solid | ESIMS 444 ([M + H]⁺) | (500 MHz, CDCl₃) δ 9.07 (d, J = 2.7 Hz, 1H), 8.64 (ddd, J = 11.6, 4.8, 1.4 Hz, 1H), 8.20-8.09 (m, 1H), 7.51-7.40 (m, 1H), 4.69-4.58 (m, 1H), 4.07-3.95 (m, 1H), 3.79-3.59 (m, 2H), 3.50-3.33 (m, 1H), 3.24-3.06 (m, 3H), 2.76 (dd, J = 13.1, 11.0 Hz, 1H), 2.46-2.31 (m, 1H), 1.97-1.79 (m, 2H), 1.42-1.26 (m, 1H), 1.14 (t, J = 7.2 Hz, 3H) Compound exists as two rotamers in 6:4 ratio. | IR (thin film) 1650 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA43 | | Yellow semi-solid | ESIMS 458 ([M + H]⁺) | (500 MHz, CDCl₃) δ 9.08 (s, 1H), 8.64 (ddd, J = 7.4, 4.7, 1.4 Hz, 1H), 8.12 (ddd, J = 8.3, 2.6, 1.5 Hz, 1H), 7.53-7.39 (m, 1H), 4.60 (d, J = 13.1 Hz, 1H), 4.02-3.92 (m, 1H), 3.72 (d, J = 15.3 Hz, 2H), 3.43 (s, 1H), 3.06 (td, J = 13.2, 2.9 Hz, 1H), 2.73 (t, J = 12.0 Hz, 1H), 2.56-2.27 (m, 5H), 1.88 (d, J = 9.0 Hz, 2H), 1.80 (ddd, J = 13.7, 3.4 Hz, 1H), 1.14 (t, J = 7.2 Hz, 3H) Compound exists as two rotamers in 2:1 ratio, only signals of major rotamer reported. | IR (thin film) 1646 cm⁻¹ |
| FA44 | | White semi-solid | ESIMS 415 ([M + H]⁺) | (500 MHz, CDCl₃) δ 9.08 (d, J = 2.8 Hz, 1H), 8.64 (ddd, J = 7.5, 4.7, 1.4 Hz, 1H), 8.18-8.05 (m, 1H), 7.52-7.41 (m, 1H), 4.59 (dd, J = 13.3, 3.7 Hz, 1H), 3.96 (s, 1H), 3.71-3.58 (m, 1H), 3.50-3.39 (m, 1H), 3.07 (td, J = 13.3, 2.9 Hz, 1H), 2.75 (dd, J = 13.0, 11.0 Hz, 1H), 2.71-2.49 (m, 5H), 2.42-2.31 (m, 1H), 1.97-1.77 (m, 2H), 1.34 (td, J = 12.6, 11.3, 6.1 Hz, 1H), 1.14 (t, J = 7.1 Hz, 3H) Compound exists as a mixture of two rotamers in 7:3 ratio, only signals of major isomer reported. | IR (thin film) 1643 cm⁻¹ |
| FA45 | | Yellow solid 52-54° C. | ESIMS 376 ([M + H]⁺) | (500 MHz, CDCl₃) δ 9.08 (d, J = 2.6 Hz, 1H), 8.63 (ddd, J = 15.1, 4.8, 1.4 Hz, 1H), 8.12 (ddd, J = 8.3, 2.6, 1.4 Hz, 1H), 7.58-7.40 (m, 1H), 4.62 (d, J = 13.0 Hz, 1H), 4.04-3.89 (m, 1H), 3.75-3.62 (m, 1H), 3.47-3.36 (m, 1H), 3.05 (td, J = 13.2, 2.9 Hz, 1H), 2.67 (t, J = 12.0 Hz, 1H), 2.37 (ddd, J = 15.1, 8.6, 3.9 Hz, 1H), 2.00 (s, 3H), 1.93-1.83 (m, 2H), 1.76 (dt, J = 13.4, 3.4 Hz, 1H), 1.42-1.23 (m, 1H), 1.13 (t, J = 7.2 Hz, 3H) Compound exists as a mixture of two rotamers in 7:3 ratio, only signals of major rotamer reported. | IR (thin film) 1643 cm⁻¹ |

TABLE 3-continued

| No. | Formula | Appearance, Melting Point | Mass (m/z) | ¹H NMR | ¹³C NMR, ¹⁹F NMR, IR |
|---|---|---|---|---|---|
| FA46 | (structure: 1-(pyridin-3-yl)-3-chloro-pyrazole with N-ethyl amide and hydroxyimino ketone) | Colorless oil | ESIMS 336 ([M+H]⁺) | (400 MHz, Benzene-$d_6$) δ 9.14 (s, 1H), 8.85-8.54 (m, 1H), 8.24 (dd, J = 4.7, 1.5 Hz, 1H), 7.60 (ddd, J = 8.4, 2.7, 1.4 Hz, 1H), 7.31 (s, 1H), 6.58 (ddd, J = 8.3, 4.8, 0.8 Hz, 1H), 3.61 (q, J = 7.1 Hz, 2H), 2.51 (t, J = 7.1 Hz, 2H), 2.36 (t, J = 7.1 Hz, 2H), 1.68 (s, 3H), 0.99 (t, J = 7.1 Hz, 3H) | ¹³C NMR (101 MHz, Benzene-$d_6$) δ 171.7, 156.2, 148.0, 140.9, 139.6, 135.8, 126.5, 125.7, 124.4, 123.8, 44.0, 31.3, 30.2, 14.1, 13.2 |
| FA47 | (structure: similar with hydroxyimino group, E/Z isomer) | Colorless oil | ESIMS 336 ([M+H]⁺) | (400 MHz, Benzene-$d_6$) δ 9.17 (s, 1H), 8.65 (d, J = 2.6 Hz, 1H), 8.19 (dd, J = 4.7, 1.5 Hz, 1H), 7.53 (ddd, J = 8.3, 2.7, 1.5 Hz, 1H), 7.02 (t, J = 1.1 Hz, 1H), 6.53 (ddd, J = 8.3, 4.7, 0.7 Hz, 1H), 3.58 (q, J = 7.1 Hz, 2H), 2.75 (t, J = 7.5 Hz, 2H), 2.40 (t, J = 7.5 Hz, 2H), 1.73 (s, 3H), 0.98 (t, J = 7.1 Hz, 3H) | ¹³C NMR (101 MHz, Benzene-$d_6$) δ 171.6, 157.2, 147.9, 140.8, 139.6, 135.7, 126.4, 125.8, 124.3, 123.7, 43.9, 30.0, 25.3, 20.3, 13.2 |
| FA48 | (structure: α-methyl aldehyde amide) | Yellow oil | ESIMS 321 ([M+H]⁺) | (400 MHz, CDCl₃) δ 9.72 (s, 1H), 9.04-8.97 (m, 1H), 8.68-8.58 (m, 1H), 8.06 (ddd, J = 8.4, 2.8, 1.5 Hz, 1H), 7.51-7.38 (m, 2H), 3.93 (d, J = 24.4 Hz, 2H), 3.15 (dd, J = 18.9, 10.1 Hz, 1H), 3.00-2.92 (m, 1H), 2.44 (dd, J = 18.8, 3.6 Hz, 1H), 1.15 (t, J = 7.1 Hz, 3H), 1.10 (d, J = 6.9 Hz, 3H) | |
| FA49 | (structure: O-(2-(2,2-difluorocyclopropyl)ethyl)oxime) | Colorless oil | | (400 MHz, Benzene-$d_6$) δ 8.76-8.58 (m, 1H), 8.29 (dd, J = 4.7, 1.5 Hz, 1H), 7.51 (ddd, J = 8.3, 2.8, 1.5 Hz, 1H), 6.97 (s, 1H), 6.58 (ddd, J = 8.3, 4.8, 0.8 Hz, 1H), 3.92 (t, J = 6.3 Hz, 2H), 3.60 (q, J = 7.1 Hz, 2H), 2.55 (dd, J = 8.7, 6.8 Hz, 2H), 2.40-2.33 (m, 3H), 1.67 (s, 3H), 1.62 (dd, J = 14.3, 7.0 Hz, 1H), 1.49-1.38 (m, 1H), 1.25 (ddq, J = 14.7, 11.3, 7.4 Hz, 1H), 1.00 (t, J = 7.1 Hz, 3H), 0.91 (dddd, J = 12.6, 11.4, 7.5, 4.1 Hz, 1H), 0.48 (dtd, J = 12.9, 7.5, 3.5 Hz, 1H) | ¹³C NMR (101 MHz, Benzene-$d_6$) δ 171.2, 155.8, 148.3, 140.9, 139.7, 135.6, 126.0, 125.4, 124.5, 123.6, 71.9, 44.0, 31.3, 30.3, 27.0, 27.0, 20.0 (t, J = 10.9 Hz), 15.7 (t, J = 10.8 Hz), 14.7, 13.3 ¹⁹F NMR (376 MHz, Benzene-$d_6$) δ -128.4 (d, J = 155.5 Hz), -143.9 (d, J = 155.6 Hz) |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| FA50 | | Colorless oil | | (400 MHz, Benzene-d$_6$) δ 8.66 (d, J = 2.7 Hz, 1H), 8.29 (dd, J = 4.7, 1.5 Hz, 1H), 7.53 (ddd, J = 8.3, 2.7, 1.5 Hz, 1H), 6.86 (s, 1H), 6.67-6.48 (m, 1H), 3.99-3.85 (m, 2H), 3.56 (q, J = 7.2 Hz, 2H), 2.74 (t, J = 7.7 Hz, 2H), 2.34 (t, J = 7.5 Hz, 2H), 1.76 (s, 3H), 1.61 (qd, J = 16.1, 14.5, 7.7 Hz, 1H), 1.50-1.36 (m, 1H), 1.23 (ddq, J = 14.7, 11.3, 7.4 Hz, 1H), 0.97 (t, J = 7.2 Hz, 3H), 0.94 0.78 (m, 1H), 0.44 (dtd, J = 12.8, 7.5, 3.5, 1H) | $^{13}$C NMR (101 MHz, Benzene-d$_6$) δ 171.2, 156.8, 148.4, 140.9, 139.6, 135.6, 126.0, 125.4, 124.3, 123.7, 72.0, 44.1, 34.9, 30.3, 26.9, 25.5, 20.2, 20.0 (t, J = 11.0 Hz), 15.6 (t, J = 10.9 Hz), 13.3 $^{19}$F NMR (376 MHz, Benzene-d$_6$) δ -128.3 (d, J = 155.4 Hz), -143.8 (d, J = 155.5 Hz) |
| FA51 | | Colorless oil | ESIMS 335 ([M + H]$^+$) | (400 MHz, CDCl$_3$) δ 9.02 (t, J = 2.1 Hz, 1H), 8.61 (dq, J = 4.6, 1.4 Hz, 1H), 8.33 (s, 1H), 8.05 (ddd, J = 8.4, 2.7, 1.5 Hz, 1H), 7.45 (ddd, J = 8.4, 4.7, 1.6 Hz, 1H), 4.00 (s, 1H), 3.35 (s, 1H), 3.14 (ddd, J = 18.3, 10.5, 2.2 Hz, 1H), 3.02-2.84 (m, 1H), 2.37 (ddd, J = 18.3, 3.5, 1.5 Hz, 1H), 2.13 (s, 3H), 1.15 (td, J = 7.2, 2.1 Hz, 3H), 1.06 (dd, J = 7.0, 2.0 Hz, 3H) | $^{13}$C NMR (101 MHz, CDCl$_3$) δ 208.0, 176.5, 148.4, 140.6, 140.2, 136.1, 135.7, 126.1, 124.0, 123.8, 48.2, 43.3, 32.0, 29.8, 17.6, 12.7 |
| FA52 | | Colorless oil | ESIMS 350 ([M + H]$^+$) | (400 MHz, CDCl$_3$) δ 9.45 (s, 1H), 8.88 (d, J = 2.6 Hz, 1H), 8.39 (d, J = 4.8 Hz, 1H), 8.18-7.97 (m, 2H), 7.33 (dd, J = 8.1, 5.2 Hz, 1H), 3.93 (s, 1H), 3.48 (s, 1H), 3.07 (dp, J = 8.6, 6.6 Hz, 1H), 2.52 (dd, J = 12.3, 6.1 Hz, 1H), 2.41 (dd, J = 12.3, 8.8 Hz, 1H), 1.84 (s, 3H), 1.22-1.07 (m, 6H) | $^{13}$C NMR (101 MHz, CDCl$_3$) δ 176.2, 157.4, 147.8, 140.8, 139.7, 135.9, 127.6, 126.5, 124.1, 123.6, 43.4, 34.4, 33.1, 21.8, 18.5, 13.1 |
| FA53 | | Colorless oil | ESIMS 350 ([M + H]$^+$) | (400 MHz, CDCl$_3$) δ 9.48 (s, 1H), 8.96 (d, J = 2.7 Hz, 1H), 8.56 (dd, J = 4.8, 1.4 Hz, 1H), 8.18 (s, 1H), 8.12 (ddd, J = 8.4, 2.8, 1.5 Hz, 1H), 7.43 (dd, J = 8.4, 4.8 Hz, 1H), 3.94-3.75 (m, 1H), 3.68-3.36 (m, 1H), 2.94-2.73 (m, 1H), 2.65 (dd, J = 15.1, 9.8 Hz, 1H), 2.24-2.10 (m, 1H), 1.79 (s, 3H), 1.11 (dt, J = 7.2, 3.7 Hz, 6H) | $^{13}$C NMR (101 MHz, CDCl$_3$) δ 176.63, 156.5, 148.0, 140.9, 139.6, 135.9, 127.4, 126.5, 124.3, 124.0, 43.5, 40.3, 34.6, 18.5, 14.6, 12.9 |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| FA54 | (structure: 3-chloro-1-(pyridin-3-yl)-1H-pyrazol-4-yl amide with N-ethyl and CH₃ branch bearing CH₂-CH=N-OH) | Colorless oil | ESIMS 336 ([M + H]⁺) | (400 MHz, Acetone-d₆) δ 9.09 (dd, J = 2.8, 0.8 Hz, 1H), 8.73 (s, 1H), 8.60 (dd, J = 4.8, 1.5 Hz, 1H), 8.22 (ddd, J = 8.3, 2.7, 1.4 Hz, 1H), 7.57 (ddd, J = 8.3, 4.7, 0.8 Hz, 1H), 7.42-7.13 (m, 1H), 3.85-3.65 (m, 1H), 3.55 (s, 2H), 2.83-2.67 (m, 1H), 2.45 (ddd, J = 14.9, 8.1, 5.3 Hz, 1H), 2.21-2.08 (m, 1H), 1.12 (t, J = 7.1 Hz, 3H), 1.06 (d, J = 6.8 Hz, 3H) | $^{13}$C NMR (101 MHz, Acetone-d₆) δ 210.0, 175.9, 149.1, 149.2, 148.9, 140.9, 140.9, 136.8, 129.4, 126.7, 125.0, 124.6, 44.2, 18.2, 13.3 |
| FA55 | (structure: similar pyrazole amide with =N-OH oxime, E/Z isomer) | Colorless oil | ESIMS 337 ([M + H]⁺) | (400 MHz, Acetone-d₆) δ 9.10 (d, J = 2.8 Hz, 1H), 8.80 (s, 1H), 8.59 (dd, J = 4.7, 1.5 Hz, 1H), 8.23 (ddd, J = 8.4, 2.7, 1.4 Hz, 1H), 7.69-7.52 (m, 1H), 6.62 (dd, J = 5.7, 4.9 Hz, 1H), 3.76 (s, 3H), 2.89-2.66 (m, 1H), 2.61-2.37 (m, 2H), 1.14 (t, J = 7.1 Hz, 3H), 1.08 (d, J = 6.8 Hz, 3H) | $^{13}$C NMR (101 MHz, Acetone-d₆) δ 209.9, 206.1, 176.0, 149.2, 149.1, 149.1, 141.0, 141.0, 140.8, 127.7, 126.7, 126.6, 124.9, 44.3, 17.4, 13.3 |
| FA56 | (structure: pyrazole amide with CH₂CH₂CH=N-OH chain) | Colorless oil | ESIMS 322 ([M + H]⁺) | (400 MHz, CDCl₃) δ 8.95 (dt, J = 2.8, 0.9 Hz, 1H), 8.61 (dd, J = 4.8, 1.4 Hz, 1H), 8.17-7.94 (m, 3H), 7.46 (ddd, J = 8.3, 4.6, 1.2 Hz, 2H), 6.80 (t, J = 5.5 Hz, 1H), 3.71 (qd, J = 7.2, 1.9 Hz, 2H), 3.48 (q, J = 7.0 Hz, 1H), 2.65 (td, J = 7.2, 5.5 Hz, 1H), 2.53 (td, J = 7.1, 5.2 Hz, 1H), 2.37 (td, J = 7.3, 2.7 Hz, 2H) | $^{13}$C NMR (101 MHz, CDCl₃) δ 171.7, 151.2, 150.8, 148.5, 139.9, 135.7, 126.5, 126.3, 124.2, 124.0, 44.0, 30.6, 25.2, 13.1 |
| FA57 | (structure: pyrazole amide with oxime-O-CH₂CH₂-difluorocyclopropyl group) | Colorless oil | ESIMS 454 ([M + H]⁺) | (400 MHz, CDCl₃) δ 8.95 (t, J = 2.6 Hz, 1H), 8.62 (dd, J = 4.7, 1.5 Hz, 1H), 8.08-8.00 (m, 2H), 7.46 (dd, J = 8.3, 4.7 Hz, 1H), 4.14-4.03 (m, 2H), 3.92 (s, 1H), 3.49 (s, 1H), 2.82 (p, J = 6.2 Hz, 1H), 2.63 (ddd, J = 15.0, 8.8, 6.0 Hz, 1H), 2.23-2.10 (m, 1H), 1.77 (s, 4H), 1.57 (ddtt, J = 18.6, 11.4, 7.4, 3.6 Hz, 1H), 1.46-1.34 (m, 1H), 1.26 (s, 1H), 1.15 (td, J = 7.2, 1.1 Hz, 3H), 1.09 (d, J = 6.8 Hz, 3H), 0.99-0.86 (m, 1H) | $^{19}$F NMR (376 MHz, CDCl₃) δ −128.46, −128.47, −128.87, −128.88, −143.76, −144.17 |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| FA58 | | Colorless oil | ESIMS 454 ([M + H]$^+$) | (400 MHz, CDCl$_3$) δ 8.97 (d, J = 2.6 Hz, 1H), 8.62 (dd, J = 4.8, 1.4 Hz, 1H), 8.11-7.99 (m, 1H), 7.88 (s, 1H), 7.51-7.40 (m, 1H), 3.97-3.50 (m, 4H), 2.94-2.85 (m, 2H), 2.51 (dd, J = 12.4, 6.2 Hz, 1H), 2.38 (t, J = 10.5 Hz, 1H), 1.83 (d, J = 1.6 Hz, 3H), 1.56 (s, 2H), 1.43-1.19 (m, 1H), 1.15 (t, J = 7.2 Hz, 3H), 1.11 (d, J = 6.9 Hz, 3H), 0.86-0.69 (m, 1H) | $^{19}$F NMR (376 MHz, CDCl$_3$) δ −128.58, −128.66, −129.00, −129.08, −143.70, −143.89, −144.11, −144.30 |
| FA59 | | Colorless oil | ESIMS 440 ([M + H]$^+$) | (400 MHz, CDCl$_3$) δ 8.95 (d, J = 2.7 Hz, 1H), 8.63 (dd, J = 4.7, 1.4 Hz, 1H), 8.10-8.00 (m, 2H), 7.46 (ddd, J = 8.3, 4.8, 0.8 Hz, 1H), 7.40-7.32 (m, 1H), 4.16-4.02 (m, 2H), 3.85 (s, 1H), 3.55 (s, 1H), 2.70 (d, J = 10.2 Hz, 1H), 2.56 (dddd, J = 14.2, 8.9, 5.3, 3.8 Hz, 1H), 2.27-2.11 (m, 1H), 1.95-1.65 (m, 2H), 1.63-1.50 (m, 1H), 1.39 (dddd, J = 12.6, 11.5, 7.5, 4.1 Hz, 1H), 1.18-1.11 (m, 6H), 1.00-0.80 (m, 1H) | $^{19}$F NMR (376 MHz, CDCl$_3$) δ −128.46, −128.87, −143.81, −144.22 |
| FA60 | | Colorless oil | ESIMS 441 ([M + H]$^+$) | (400 MHz, CDCl$_3$) δ 8.95 (t, J = 2.8 Hz, 1H), 8.63 (dt, J = 4.7, 1.4 Hz, 1H), 8.04 (ddd, J = 7.3, 2.1, 1.0 Hz, 1H), 7.51-7.43 (m, 1H), 7.36 (dd, J = 6.5, 5.4 Hz, 1H), 4.06 (t, J = 6.3 Hz, 2H), 3.96-3.40 (m, 4H), 2.75-2.63 (m, 1H), 2.62-2.40 (m, 1H), 2.29-2.12 (m, 1H), 1.90-1.64 (m, 1H), 1.57-1.45 (m, 1H), 1.45-1.21 (m, 1H), 1.15 (q, J = 7.1 Hz, 6H), 1.00-0.79 (m, 1H) | $^{19}$F NMR (376 MHz, CDCl$_3$) δ −128.46, −128.87, −143.81, −144.22 |

TABLE 3-continued

| No. | Formula | Appearance, Melting Point | Mass (m/z) | ¹H NMR | ¹³C NMR, ¹⁹F NMR, IR |
|---|---|---|---|---|---|
| FA61 | (structure: 3-chloro-1-(pyridin-3-yl)pyrazole with N-ethyl amide bearing O-N=CH-CH2-CH2-cyclopropyl(F,F) chain) | Colorless oil | ESIMS 426 ([M + H]⁺) | (400 MHz, CDCl₃) δ 9.05-8.86 (m, 1H), 8.63 (dd, J = 4.8, 1.5 Hz, 1H), 8.05 (ddd, J = 8.3, 2.8, 1.5 Hz, 1H), 7.95 (s, 1H), 7.51-7.37 (m, 2H), 6.72 (t, J = 5.4 Hz, 1H), 4.15-4.07 (m, 1H), 4.04 (t, J = 6.3 Hz, 1H), 3.71 (q, J = 7.2 Hz, 2H), 2.61 (td, J = 7.2, 5.4 Hz, 1H), 2.56-2.46 (m, 1H), 2.35 (q, J = 7.4 Hz, 2H), 1.89-1.65 (m, 1H), 1.55 (dddd, J = 18.7, 14.4, 7.2, 4.0 Hz, 1H), 1.38 (dddd, J = 12.6, 11.3, 7.5, 4.0 Hz, 1H), 1.16 (t, J = 7.2 Hz, 3H), 0.91 (ddq, J = 12.9, 7.5, 3.6 Hz, 1H) | ¹⁹F NMR (376 MHz, CDCl₃) δ −128.44, −128.45, −128.86, −128.86, −143.75, −143.92, −144.17, −144.34 |
| FA62 | (structure: 3-chloro-1-(pyridin-3-yl)pyrazole with N-ethyl amide bearing pyrrolidinone-CH2-CH2-cyclopropyl(F,F)) | Colorless oil | ESIMS 467 ([M + H]⁺) | (400 MHz, CDCl₃) δ 9.00 (dd, J = 2.6, 1.2 Hz, 1H), 8.61 (dt, J = 4.7, 1.5 Hz, 1H), 8.10-8.03 (m, 2H), 7.45 (dd, J = 8.3, 4.7 Hz, 1H), 3.85-3.54 (m, 2H), 3.45-3.16 (m, 4H), 2.37 (tt, J = 16.0, 8.3 Hz, 3H), 2.26-2.18 (m, 1H), 1.99 (dtd, J = 14.1, 7.1, 4.1 Hz, 1H), 1.82 (dt, J = 14.1, 7.3 Hz, 1H), 1.73-1.58 (m, 3H), 1.49-1.30 (m, 2H), 1.14 (td, J = 7.2, 1.3 Hz, 3H), 0.95-0.81 (m, 1H) | ¹⁹F NMR (376 MHz, CDCl₃) δ −128.49, −128.58, −128.91, −128.99, −143.43, −143.62, −143.85, −144.04 |
| FA63 | (structure: 3-chloro-1-(pyridin-3-yl)pyrazole with N-ethyl amide attached to CH2-pyrrolidinone-NH) | White semi-solid | ESIMS 348 ([M + H]⁺) | (400 MHz, CDCl₃) δ 8.95 (dd, J = 2.7, 0.7 Hz, 1H), 8.62 (dd, J = 4.8, 1.5 Hz, 1H), 8.03 (ddd, J = 8.3, 2.7, 1.4 Hz, 1H), 7.99 (s, 1H), 7.45 (ddd, J = 8.3, 4.8, 0.8 Hz, 1H), 5.69 (s, 1H), 3.71 (ddt, J = 38.0, 13.6, 7.4 Hz, 2H), 3.41-3.29 (m, 2H), 2.88 (qd, J = 9.4, 3.7 Hz, 1H), 2.73 (dd, J = 16.8, 3.7 Hz, 1H), 2.53 (dddd, J = 12.3, 9.0, 6.0, 3.3 Hz, 1H), 2.29-2.18 (m, 1H), 1.82 (dq, J = 12.7, 9.3 Hz, 1H), 1.16 (t, J = 12 Hz, 3H) | ¹³C NMR (101 MHz, CDCl₃) δ 179.13, 171.3, 148.6, 140.8, 140.1, 135.6, 126.6, 126.3, 124.1, 123.8, 43.9, 40.2, 37.6, 35.5, 29.3, 13.1 |

TABLE 3-continued

| No. | Formula | Appearance, Melting Point | Mass (m/z) | ¹H NMR | ¹³C NMR, ¹⁹F NMR, IR |
|---|---|---|---|---|---|
| FA64 | | Colorless oil | ESIMS 452 ([M + H]⁺) | (400 MHz, CDCl₃) δ 8.96 (td, J = 2.9, 0.7 Hz, 1H), 8.61 (dt, J = 4.7, 1.4 Hz, 1H), 8.14-8.01 (m, 2H), 7.45 (dddd, J = 8.3, 4.8, 1.5, 0.8 Hz, 1H), 3.76 (dt, J = 14.1, 7.0 Hz, 1H), 3.64 (dqd, J = 14.2, 7.2, 2.2 Hz, 1H), 3.50-3.19 (m, 4H), 2.94 (qt, J = 9.2, 3.4 Hz, 1H), 2.73 (dd, J = 16.8, 3.9 Hz, 1H), 2.50-2.37 (m, 1H), 1.80-1.58 (m, 4H), 1.56-1.29 (m, 2H), 1.16 (td, J = 7.1, 0.9 Hz, 3H), 1.00-0.81 (m, 1H) | ¹⁹F NMR (376 MHz, CDCl₃) δ −128.54, −128.71, −128.96, −129.12, −143.41, −143.59, −143.82, −144.00 |
| FA65 | | Colorless oil | ESIMS 430 ([M + H]⁺) | (400 MHz, CDCl₃) δ 8.96 (dd, J = 2.7, 0.7 Hz, 1H), 8.62 (dd, J = 4.8, 1.5 Hz, 1H), 8.09-8.01 (m, 2H), 7.46 (ddd, J = 8.3, 4.8, 0.8 Hz, 1H), 4.02-3.85 (m, 1H), 3.86-3.71 (m, 2H), 3.64 (dq, J = 14.0, 7.1 Hz, 1H), 3.48 (ddd, J = 11.3, 9.1, 6.8 Hz, 2H), 2.96 (qd, J = 9.2, 3.8 Hz, 1H), 2.73 (dd, J = 16.8, 3.9 Hz, 1H), 2.48 (dddd, J = 15.7, 9.2, 6.9, 2.6 Hz, 1H), 2.26 (dd, J = 16.9, 8.9 Hz, 1H), 1.79 (dq, J = 11.9, 9.3 Hz, 1H), 1.16 (t, J = 7.2 Hz, 3H) | ¹⁹F NMR (376 MHz, CDCl₃) δ −69.9 |
| FA66 | | Yellow oil | ESIMS 307 ([M + H]⁺) | (400 MHz, CDCl₃) δ 9.03-8.87 (m, 1H), 8.62 (dt, J = 4.0, 2.0 Hz, 1H), 8.04-7.99 (m, 2H), 7.51-7.39 (m, 1H), 3.73 (d, J = 7.5 Hz, 2H), 3.40 (s, 2H), 2.18 (s, 3H), 1.18 (t, J = 7.2 Hz, 3H) | IR (thin film) 1658 cm⁻¹ |

TABLE 3-continued

| No. | Formula | Appearance, Melting Point | Mass (m/z) | $^1$H NMR | $^{13}$C NMR, $^{19}$F NMR, IR |
|---|---|---|---|---|---|
| FA67 | | Colorless oil | ESIMS 417 ([M + H]$^+$) | (400 MHz, CDCl$_3$) δ 9.00 (dd, J = 2.7, 0.8 Hz, 1H), 8.62 (dd, J = 4.8, 1.4 Hz, 1H), 8.16 (s, 1H), 8.06 (ddd, J = 8.3, 2.7, 1.4 Hz, 1H), 7.45 (ddd, J = 8.3, 4.8, 0.8 Hz, 1H), 5.79 (ddt, J = 16.9, 10.2, 6.6 Hz, 1H), 5.08-4.88 (m, 2H), 3.73-3.62 (m, 2H), 3.56-3.50 (m, 2H), 3.42-3.34 (m, 2H), 2.50-2.29 (m, 3H), 2.16-2.02 (m, 3H), 1.94 (dddd, J = 13.7, 9.5, 6.9, 4.3 Hz, 1H), 1.64 (dq, J = 12.6, 8.6 Hz, 1H), 1.48-1.31 (m, 1H), 1.14 (t, J = 7.2 Hz, 3H) | $^{13}$C NMR (101 MHz, CDCl$_3$) δ 176.91, 170.9, 148.6, 140.6, 140.3, 137.9, 135.6, 127.1, 126.3, 124.0, 123.6, 115.1, 46.1, 43.9, 41.2, 39.1, 32.6, 31.3, 30.5, 25.2, 13.0 |
| FA68 | | Light brown oil | ESIMS 387 ([M + H]$^+$) | (400 MHz, DMSO-d$_6$) δ 9.06 (dd, J = 2.7, 0.7 Hz, 1H), 8.88 (s, 1H), 8.59 (dd, J = 4.7, 1.4 Hz, 1H), 8.21 (ddd, J = 8.3, 2.7, 1.4 Hz, 1H), 7.81 (d, J = 2.4 Hz, 1H), 7.59 (ddd, J = 8.4, 4.7, 0.7 Hz, 1H), 6.64 (d, J = 2.4 Hz, 1H), 4.41 (t, J = 6.6 Hz, 2H), 3.57 (d, J = 7.5 Hz, 2H), 2.72 (t, J = 6.7 Hz, 2H), 2.39 (s, 3H), 1.05 (t, J = 7.1 Hz, 3H) | IR (thin film) 3106, 2974, 1665 cm$^{-1}$ |
| FA69 | | Colorless oil | ESIMS 286 ([M]$^+$) | (400 MHz, Acetone-d$_6$) δ 9.09 (d, J = 2.5 Hz, 1H), 8.51 (dd, J = 5.3, 2.0 Hz, 2H), 8.19 (ddd, J = 8.3, 2.7, 1.5 Hz, 1H), 7.51 (ddd, J = 8.3, 4.7, 0.7 Hz, 1H), 3.14 (s, 3H), 2.71-2.63 (m, 2H), 2.36-2.30 (m, 2H), 2.28 (s, 3H), 2.09 (s, 3H) | $^{13}$C NMR (101 MHz, CDCl$_3$) δ 207.75, 172.6, 150.0, 141.3, 138.0, 134.8, 130.2, 128.7, 126.1, 125.5, 38.3, 37.1, 30.0, 27.6, 11.1 |
| FA70 | | Colorless oil | ESIMS 332 ([M]$^+$) | (400 MHz, CDCl$_3$) δ 8.77 (s, 1H), 8.42 (d, J = 2.5 Hz, 1H), 7.90 (s, 1H), 7.86 (dt, J = 9.4, 2.3 Hz, 1H), 3.66 (s, 2H), 2.48 (t, J = 6.9 Hz, 2H), 2.24 (s, 3H), 2.10 (s, 5H), 1.85 (p, J = 7.0 Hz, 2H), 1.13 (t, J = 7.2 Hz, 3H) | $^{19}$F NMR (376 MHz, CDCl$_3$) δ −121.0 |

TABLE 3-continued

| No. | Formula | Appearance, Melting Point | Mass (m/z) | ¹H NMR | ¹³C NMR, ¹⁹F NMR, IR |
|---|---|---|---|---|---|
| FA71 | (structure) | Tan solid 85-86° C. | ESIMS 330 ([M]⁺) | (400 MHz, CDCl₃) δ 8.96 (s, 1H), 8.46 (s, 1H), 8.10 (s, 1H), 8.02 (d, J = 9.2 Hz, 1H), 3.69 (s, 2H), 3.03 (p, J = 8.2 Hz, 1H), 2.56 (dd, J = 18.1, 9.0 Hz, 1H), 2.41 (m, 4H), 2.27 (s, 3H), 2.11 (m, 1H), 1.15 (t, J = 7.2 Hz, 3H) | ¹⁹F NMR (376 MHz, CDCl₃) δ −121.3 |
| FA72 | (structure) | White solid 117-120° C. | ESIMS 323 ([M + H]⁺) | (400 MHz, CDCl₃) δ 9.36 (s, 1H), 8.69 (d, J = 3.9 Hz, 1H), 8.46 (s, 1H), 8.40 (d, J = 8.4 Hz, 1H), 7.71 (dd, J = 8.2, 5.1 Hz, 1H), 4.50 (s, 2H), 3.72 (q, J = 7.1 Hz, 2H), 2.14 (s, 3H), 1.18 (t, J = 7.2 Hz, 3H) | |
| FA73 | (structure) | Off-white solid 73-75° C. | ESIMS 352 ([M + H]⁺) | (400 MHz, CDCl₃) δ 9.01 (s, 1H), 8.57 (s, 1H), 8.02 (s, 1H), 8.1 Hz, 1H), 7.51 (dd, J = 8.2, 4.8 Hz, 1H), 3.72 (s, 2H), 1.52 (s, 9H), 1.08 (t, J = 7.1 Hz, 3H) | |
| FA74 | (structure) | Yellow oil | ESIMS 405 ([M + H]⁺) | (400 MHz, CDCl₃) δ 8.99 (d, J = 2.5 Hz, 1H), 8.64 (dd, J = 4.7, 1.3 Hz, 1H), 8.17 (s, 1H), 8.03 (ddd, J = 8.3, 2.7, 1.4 Hz, 1H), 7.46 (dd, J = 8.3, 4.8 Hz, 1H), 5.11 (q, J = 6.5 Hz, 1H), 3.69 (d, J = 227.6 Hz, 2H), 3.27 (m, 2H), 1.42 (d, J = 6.8 Hz, 3H), 1.17 (t, J = 7.2 Hz, 3H) | ¹⁹F NMR (376 MHz, CDCl₃) δ −63.5 |
| FA75 | (structure) | Brown solid 96-97° C. | ESIMS 307 ([M + H]⁺) | (400 MHz, CDCl₃) δ 8.95 (d, J = 2.6 Hz, 1H), 8.61 (dd, J = 4.7, 1.4 Hz, 1H), 8.11 (s, 1H), 8.02 (ddd, J = 8.3, 2.7, 1.4 Hz, 1H), 7.44 (ddd, J = 8.3, 4.8, 0.6 Hz, 1H), 3.21 (s, 3H), 2.78 (t, J = 6.3 Hz, 2H), 2.41 (t, J = 6.3 Hz, 2H), 2.18 (s, 3H) | |

TABLE 3-continued

| No. | Formula | Appearance, Melting Point | Mass (m/z) | ¹H NMR | ¹³C NMR, ¹⁹F NMR, IR |
|---|---|---|---|---|---|
| FA76 | 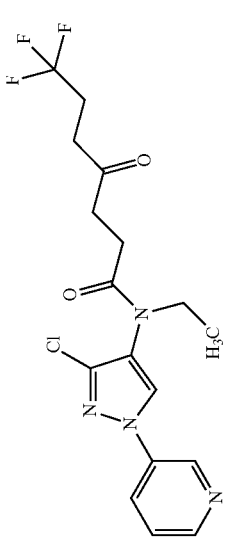 | Brown viscoul oil | HRMS-ESI [M + H]⁺ calcd for $C_{17}H_{19}ClF_3N_4O_2$, 403.1143; found, 403.1149 | (400 MHz, CDCl₃) δ 8.97 (d, J = 2.7 Hz, 1H), 8.63 (dd, J = 4.7, 1.4 Hz, 1H), 8.10-8.01 (multiple peaks, 2H), 7.46 (ddd, J = 8.3, 4.8, 0.7 Hz, 1H), 3.68 (q, J = 7.2 Hz, 2H), 2.84-2.70 (multiple peaks, 4H), 2.51-2.34 (multiple peaks, 4H), 1.15 (t, J = 7.2 Hz, 3H) | ¹⁹F NMR (376 MHz, CDCl₃) δ −66.6 IR (thin film) 1721, 1665 cm⁻¹ |
| FA77 | 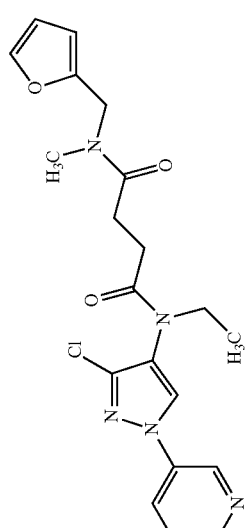 | Orange oil | HRMS-ESI [M + H]⁺ calcd for $C_{20}H_{23}ClN_5O_3$, 416.1484; found, 416.1489 | (400 MHz, CDCl₃) δ 8.97 (dt, J = 2.0, 0.9 Hz, 1H), 8.61 (dt, J = 4.8, 1.6 Hz, 1H), 8.11 (s, 1H), 8.03 (ddt, J = 8.3, 2.6, 1.2 Hz, 1H), 7.44 (dddd, J = 8.4, 4.8, 1.7, 0.8 Hz, 1H), 7.34 (ddd, J = 9.8, 1.9, 0.8 Hz, 1H), 6.31 (ddd, J = 9.4, 3.2, 1.9 Hz, 1H), 6.22 (ddd, J = 11.4, 3.2, 0.9 Hz, 1H), 4.51 (d, J = 20.2 Hz, 2H), 3.72 (qd, J = 7.1, 3.1 Hz, 2H), 3.03 (s, 1.7H, major), 2.92 (s, 1.3H, minor), 2.87-2.78 (m, 0.9H, minor), 2.73-2.64 (m, 1.1H, major), 2.51 (br s, 2H), 1.16 (td, J = 7.2, 1.7 Hz, 3H) | IR (thin film) 3090, 1648 cm⁻¹ |

TABLE 4

| No. | Structure | Prepared according to Example: |
|---|---|---|
| C1 | 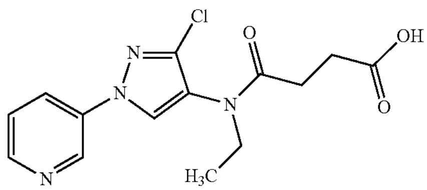 [SMILES: CCN(C(=O)CCC(=O)O)c1cn(-c2cccnc2)nc1Cl] | 3 |
| C2 | 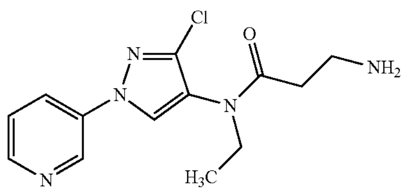 [SMILES: CCN(C(=O)CCN)c1cn(-c2cccnc2)nc1Cl] | 6 |
| C3 | 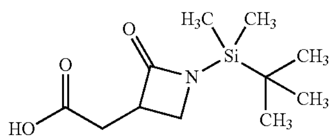 [SMILES: CC(C)(C)[Si](C)(C)N1CC(CC(=O)O)C1=O] | 12 |
| C4 | 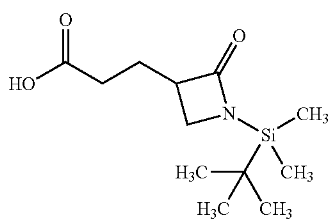 [SMILES: CC(C)(C)[Si](C)(C)N1CC(CCC(=O)O)C1=O] | 12 |
| C5 | 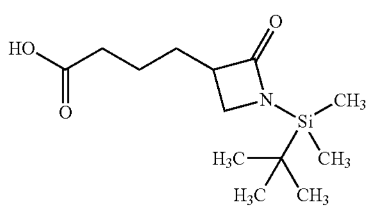 [SMILES: CC(C)(C)[Si](C)(C)N1CC(CCCC(=O)O)C1=O] | 12 |
| C6 | 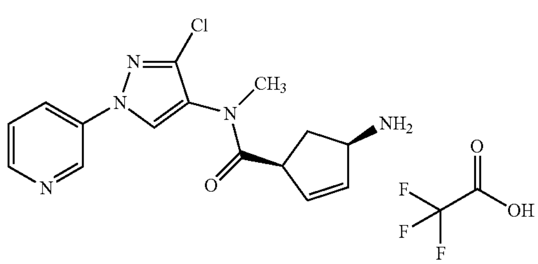 | 16 |
| C7 | 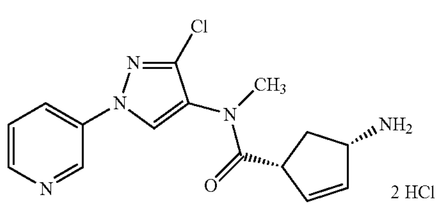 [SMILES: CN(C(=O)[C@H]1C=C[C@@H](N)C1)c1cn(-c2cccnc2)nc1Cl] | 18 |

TABLE 4-continued

| No. | Structure | Prepared according to Example: |
|---|---|---|
| C8 | ![structure] | 22 |
| C9 | ![structure] | 24 |
| C10 | ![structure] | 24 |
| C11 | ![structure] | 24 |
| C12 | ![structure] | 27 |
| C13 | ![structure] | 28 |
| C14 | ![structure] | 36 |

TABLE 4-continued
| No. | Structure | Prepared according to Example: |
|---|---|---|
| CA1 | 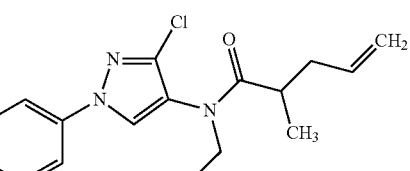 | 1 |
| CA2 | 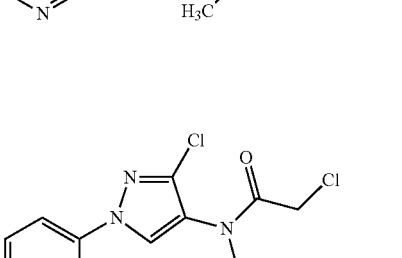 | 24 |
| CA3 | 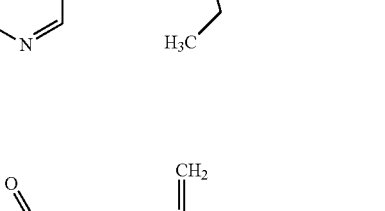 | 41 |
TABLE 5
| No. | Formula | May be prepared according to example |
|---|---|---|
| P1 |  | PE1 |
| P2 |  | PE1 |

TABLE 5-continued

| No. | Formula | May be prepared according to example |
|---|---|---|
| P3 | | PE1 |
| P4 | | PE1 |
| P5 | | PE1 |
| P6 | | PE1 |
| P7 | | PE1 |

TABLE 5-continued

| No. | Formula | May be prepared according to example |
|---|---|---|
| P8 | | PE2 |
| P10 | | PE2 |
| P11 | | PE2 |
| P12 | | PE2 |
| P13 | | PE2 |

TABLE 5-continued

| No. | Formula | May be prepared according to example |
|---|---|---|
| P14 | | PE2 |
| P15 | | PE2 |
| P16 | | PE3 |
| P17 | | PE3 |
| P18 | | PE2 |
| P19 | | PE2 |

TABLE 5-continued
| No. | Formula | May be prepared according to example |
|---|---|---|
| P20 | 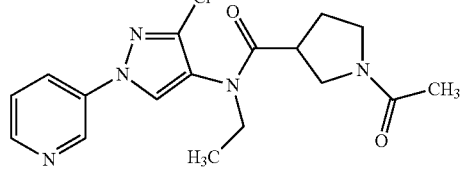 | PE3 |
| P21 | 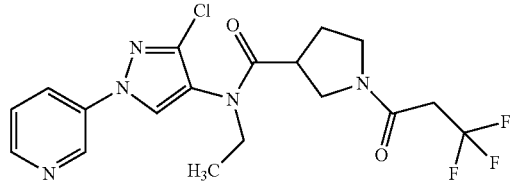 [SMILES: CCN(C(=O)C1CCN(C(=O)CC(F)(F)F)C1)c1cn(-c2cccnc2)nc1Cl] | PE3 |
| P22 | 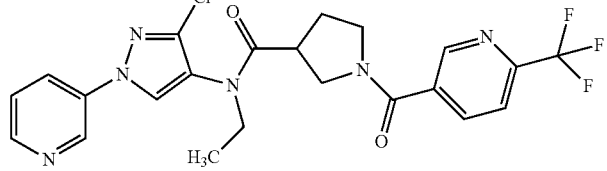 | PE3 |
| P23 | 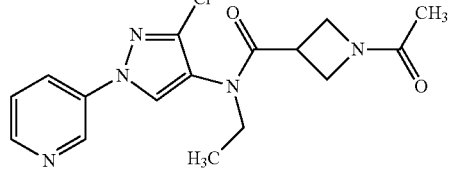 | PE3 |
| P24 | 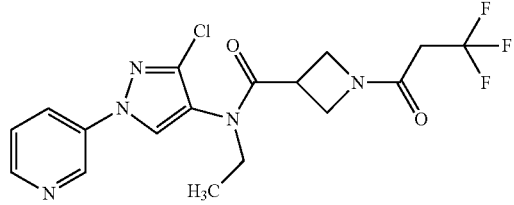 [SMILES: CCN(C(=O)C1CN(C(=O)CC(F)(F)F)C1)c1cn(-c2cccnc2)nc1Cl] | PE3 |
| P25 | 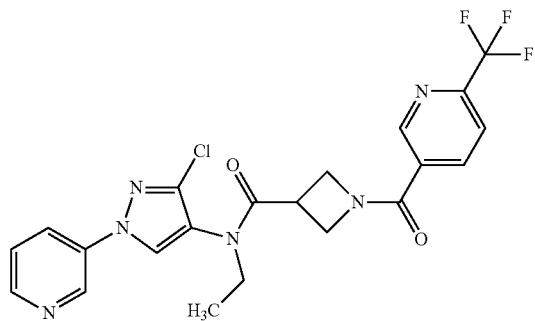 [SMILES: CCN(C(=O)C1CN(C(=O)c2ccc(C(F)(F)F)nc2)C1)c1cn(-c2cccnc2)nc1Cl] | PE3 |

TABLE 5-continued

| No. | Formula | May be prepared according to example |
|---|---|---|
| P26 | | PE4 |
| P27 | | PE4 |
| P28 | | PE3 |
| P29 | | PE3 |
| P30 | | PE3 |

TABLE 5-continued

| No. | Formula | May be prepared according to example |
|---|---|---|
| P31 | | PE3 |
| P32 | | PE3 |
| P33 | | PE3 |
| P34 | | PE4 |
| P35 | | PE4 |
| P36 | | PE4 |

TABLE 5-continued

| No. | Formula | May be prepared according to example |
|---|---|---|
| P37 | | PE4 |
| P38 | | PE5 |
| P39 | | PE5 |

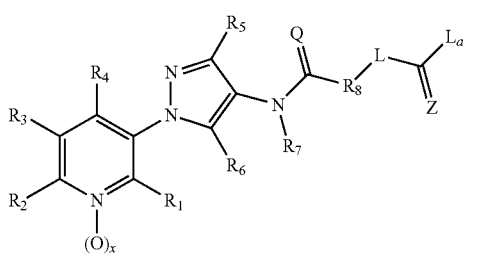

We claim:
1. A pesticidal composition, comprising a compound of formula I or any agriculturally acceptable salt thereof:

I wherein:
(a) $R_1$, $R_2$, and $R_4$ are independently selected from hydrogen, F, Cl, Br, I, substituted or unsubstituted $C_1$-$C_6$ alkyl, or substituted or unsubstituted $C_1$-$C_6$ haloalkyl,
wherein each said $R_1$, $R_2$, and $R_4$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_3$-$C_{10}$ cycloalkyl, or $C_3$-$C_{10}$ halocycloalkyl, (each of which that may be substituted, may optionally be substituted with $R_{10}$);
(b) $R_3$ is selected from hydrogen, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_1$-$C_6$ haloalkyl, substituted or unsubstituted $C_6$-$C_{20}$ aryl, substituted or unsubstituted C1-$C_{20}$ heterocyclyl, $OR_{10}$, $C(=X_1)R_{10}$, $C(=X_1)OR_{10}$, $C(=X_1)N(R_{10})_2$, $N(R_{10})_2$, $N(R_{10})C(=X_1)R_{10}$, $SR_{10}$, $S(O)_nOR_{10}$, or $R_{10}S(O)_nR_{10}$,
wherein each said $R_3$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, (each of which that may be substituted, may optionally be substituted with $R_{10}$);
(c) $R_5$ is selected from H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, $C_3$-$C_{10}$ cycloalkyl, substituted or unsubstituted $C_6$-$C_{20}$ aryl, substituted or unsubstituted $C_1$-$C_{20}$ heterocyclyl, $OR_{10}$, $C(=X_1)R_{10}$, $C(=X_1)OR_{10}$, $C(=X_1)N(R_{10})_2$, $N(R_{10})_2$, $N(R_{10})C(=X_1)R_{10}$, $SR_{10}$, $S(O)_nOR_{10}$, or $R_{10}S(O)_nR_{10}$,
wherein each said $R_5$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, (each of which that may be substituted, may optionally be substituted with $R_{10}$);

(d) $R_6$ is H, F, Cl, Br, I, substituted or unsubstituted $C_1$-$C_6$ alkyl, or $C_1$-$C_6$ haloalkyl, wherein each said $R_6$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, or $C_3$-$C_{10}$ halocycloalkenyl;

(e) $R_7$ is selected from hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ alkoxy, substituted or unsubstituted $C_3$-$C_{10}$ cycloalkyl, $C_1$-$C_6$ alkyl $C_2$-$C_6$ alkynyl wherein the alkyl and alkynyl is independently substituted or unsubstituted, substituted or unsubstituted $C_6$-$C_{20}$ aryl, substituted or unsubstituted $C_1$-$C_{20}$ heterocyclyl, $C_1$-$C_6$ alkyl $C_6$-$C_{20}$ aryl wherein the alkyl and aryl is independently substituted or unsubstituted), $C_1$-$C_6$ alkyl-($C_3$-$C_{10}$ cyclohaloalkyl) wherein the alkyl and cyclohaloalkyl is independently substituted or unsubstituted, or $C_1$-$C_6$ alkyl-($C_3$-$C_{10}$ cycloalkyl) wherein the alkyl and cycloalkyl is independently substituted or unsubstituted, wherein each said $R_7$, when substituted, has one or more substituents selected from F, Cl, Br, I, CN, $NO_2$, $C_1$-$C_6$ alkyl, $C_2$-$C_6$ alkenyl, $C_2$-$C_6$ alkynyl $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OR_{10}$, $S(O)_nOR_{10}$, $C_6$-$C_{20}$ aryl, or $C_1$-$C_{20}$ heterocyclyl, $R_{10}$ aryl, (each of which that may be substituted, may optionally be substituted with $R_{10}$);

(f) R8 is selected from substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl substituted or unsubstituted $C_3$-$C_{10}$ cycloalkenyl, substituted or unsubstituted $C_6$-$C_{20}$ aryl, or substituted or unsubstituted $C_1$-$C_{20}$ heterocyclyl, wherein each said $R_8$, when substituted, has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, oxo, $OR_{10}$, $S(O)_nR_{10}$, substituted or unsubstituted $C_6$-$C_{20}$ aryl, or substituted or unsubstituted $C_1$-$C_{20}$ heterocyclyl, (each of which, when substituted, is substituted with $R_{10}$);

(g) L is $N(R_9)$;

(h) $L_a$ is selected from $R_9$, $OR_9$, $N(R_9)_2$, $N(R_9)(R_{11})$, $N(R_9)(OR_{11})$, $N(R_9)C(=X_1)R_9$, $N(R_9)C(=X_1)(R_{11})$, $C(R_9)_3$, $C(R_9)(R_{11})(R_{12})$, or $SR_9$;

optionally L and $L_a$ are connected in a cyclic arrangement, which forms 3-8 membered heterocycles or carbocycles including L and $L_a$, wherein the cyclic arrangement contains none or at least one of O, S, or N heteroatoms, and the cyclic arrangement is unsubstituted or substituted, wherein, when substituted, the cyclic arrangement has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, $N(R_9)S(O)_n R_{11}$, oxo, $OR_9$, $S(O)_nR_{11}$, $S(O)R_9$, substituted or unsubstituted $C_6$-$C_{20}$ aryl, or substituted or unsubstituted $C_1$-$C_{20}$ heterocyclyl (each of which, when substituted, is substituted with $R_{10}$);

(i) $R_9$, $R_{11}$, $R_{12}$, and $R_{13}$ are independently selected from hydrogen, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_3$-$C_{10}$ cycloalkyl, substituted or unsubstituted $C_3$-$C_{10}$ halocycloalkyl, substituted or unsubstituted $C_3$-$C_{10}$ cycloalkenyl, substituted or unsubstituted $C_6$-$C_{20}$ aryl, or substituted or unsubstituted $C_1$-$C_{20}$ heterocyclyl, wherein each of said $R_9$, $R_{11}$, and $R_{12}$, when substituted, has one or more substituents selected from F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ haloalkyl, substituted or unsubstituted $C_2$-$C_6$ haloalkenyl, substituted or unsubstituted $C_1$-$C_6$ haloalkyloxy, substituted or unsubstituted $C_2$-$C_6$ haloalkenyloxy, substituted or unsubstituted $C_3$-$C_{10}$ cycloalkyl, substituted or unsubstituted $C_3$-$C_{10}$ cycloalkenyl, substituted or unsubstituted $C_3$-$C_{10}$ halocycloalkyl, substituted or unsubstituted $C_3$-$C_{10}$ halocycloalkenyl, oxo, $OR_{10}$ $C(=X_1)R_{10}$, $S(O)_nR_{10}$, substituted or unsubstituted $C_6$-$C_{20}$ aryl, or substituted or unsubstituted $C_1$-$C_{20}$ heterocyclyl, (each of which, when substituted, is substituted with $R_{10}$);

(j) $R_{10}$ is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, substituted or unsubstituted $S(O)_n C_1$-$C_6$ alkyl, or substituted or unsubstituted $N(C_1$-$C_6)$ alkyl)$_2$, wherein each said $R_{10}$, when substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nC_1$-$C_6$ alkyl, $S(O)_nOC_1$-$C_6$ alkyl, $C_6$-$C_{20}$ aryl, or $C_1$-$C_{20}$ heterocyclyl;

(k) Q is (each independently) O or S;

(l) Z is (each independently) O, S, $CH_2$, $NR_{13}$, or $NOR_{13}$;

(m) $X_1$ is (each independently) O or S;

(n) n is 0, 1, or 2; and (o) x is 0 or 1.

2. The composition of claim 1, comprising at least one compound of formula IA or IB

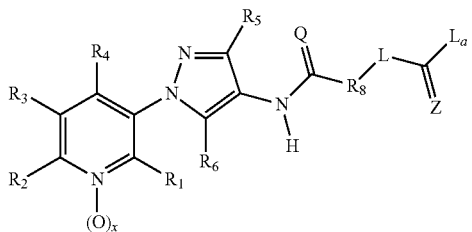

IA

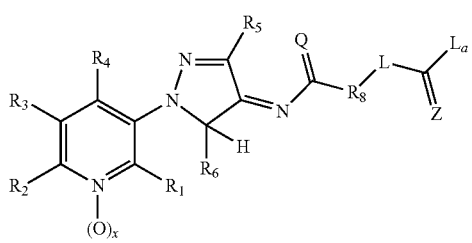

IB

3. The composition of claim 1, further comprising:
(a) one or more compounds having acaricidal, algicidal, avicidal, bactericidal, fungicidal, herbicidal, insecticidal, molluscicidal, nematicidal, rodenticidal, or virucidal properties; or
(b) one or more compounds that are antifeedants, bird repellents, chemosterilants, herbicide safeners, insect attractants, insect repellents, mammal repellents, mating disrupters, plant activators, plant growth regulators, or synergists; or
(c) both (a) and (b).

4. The composition of claim 1, further comprising one or more compounds selected from: (3-ethoxypropyl)mercury bromide, 1,2-dichloropropane, 1,3-dichloropropene, 1-methylcyclopropene, 1-naphthol, 2-(octylthio)ethanol, 2,3,5-triiodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, aciflurofen, aciflurofen-methyl, aciflurofen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chioranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlornidine, chlornitrofen, chlorobenzilate, chlorodinitronaphthalenes, chloroform, chloromebuform, chioromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencetpotassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdepallethrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flometoquin, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyradifurone, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, iofensulfuron, iofensulfuron-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron. TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, nifluridide, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropy)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium α-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium α-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyo fen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichioronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, trifopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid.

5. The composition of claim 1, further comprising an agriculturally acceptable carrier.

6. The composition of claim 1, wherein the compound is in the form of a pesticidally acceptable acid addition salt.

7. The composition of claim 1, wherein the compound is in the form of a salt derivative.

8. The composition of claim 1, wherein the compound is in the form a hydrate.

9. The composition of claim 1, wherein the compound is a resolved stereoisomer.

10. The composition of claim 1, wherein the compound is in the form a crystal polymorph.

11. The composition of claim 1, wherein the compound comprises a $^2H$ in place of $^1H$.

12. The composition of claim 1, wherein the compound comprises a $^{13}C$ in place of a $^{12}C$.

13. The composition of claim 1, further comprising a biopesticide.

14. The composition of claim 1, further comprising at least one of the following compounds:
   (a) 3-(4-chloro-2,6-dimethylphenyl)-4-hydroxy-8-oxa-1-azaspiro[4,5]dec-3-en-2-one;
   (b) 3-(4'-chloro-2,4-dimethyl[1,1'-biphenyl]-3-yl)-4-hydroxy-8-oxa-1-azaspiro[4,5]dec-3-en-2-one;
   (c) 4-[[(6-chloro-3-pyridinyl)methyl]methylamino]-2(5H)-furanone;
   (d) 4-[[(6-chloro-3-pyridinyl)methyl]cyclopropylamino]-2(5H)-furanone;
   (e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
   (f) 2-cyano-N-ethyl-4-fluoro-3-methoxy-benenesulfonamide;
   (g) 2-cyano-N-ethyl-3-methoxy-benzenesulfonamide;
   (h) 2-cyano-3-difluoromethoxy-N-ethyl-4-fluoro-benzenesulfonamide;
   (i) 2-cyano-3-fluoromethoxy-N-ethyl-benzenesulfonamide;
   (j) 2-cyano-6-fluoro-3-methoxy-N,N-dimethyl-benzenesulfonamide;
   (k) 2-cyano-N-ethyl-6-fluoro-3-methoxy-N-methyl-benzenesulfonamide;
   (l) 2-cyano-3-difluoromethoxy-N,N-dimethylbenzenesulfon-amide;
   (m) 3-(difluoromethyl)-N-[2-(3,3-dimethylbutyl)phenyl-1-methyl-1H-pyrazole-4-carboxamide;
   (n) N-ethyl-2,2-dimethylpropionamide-2-(2,6-dichloro-α,α,α-trifluoro-p-tolyl)hydrazone;
   (o) N-ethyl-2,2-dichloro-1-methylcyclopropane-carboxamide-2-(2,6-dichloro-α,α,α-trifluoro-p-tolyl)hydrazone nicotine;
   (p) O-{(E-)-[2-(4-chloro-phenyl)-2-cyano-1-(2-trifluoromethylphenyl)-vinyl]}S-methyl thiocarbonate;
   (q) (E)-N1-[(2-chloro-1,3-thiazol-5-ylmethyl)]-N2-cyano-N1-methylacetamidine;
   (r) 1-(6-chloropyridin-3-ylmethyl)-7-methyl-8-nitro-1,2,3,5,6,7-hexahydro-imidazo[1,2-a]pyridin-5-ol;
   (s) 4-[4-chlorophenyl-(2-butylidine-hydrazono)methyl)] phenyl mesylate; and
   (t) N-ethyl-2,2-dichloro-1-methylcyclopropanecarboxamide-2-(2,6-dichloro-α,α,α-trifluoro-p-tolyl)hydrazone.

15. The composition of claim 1, further comprising a compound having one or more of the following modes of action: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs).

16. The composition of claim 1, further comprising a seed.

17. The composition of claim 1, further comprising a seed that has been genetically modified to express one or more specialized traits.

18. The composition of to claim 1, wherein the composition is encapsulated inside, or placed on the surface of, a capsule.

19. The composition of claim 1, wherein the composition is encapsulated inside, or placed on the surface of, a capsule, wherein the capsule has a diameter of about 100 nanometers to about 900 nanometers, or about 10 microns to about 900 microns.

* * * * *